(12) United States Patent
Reich et al.

(10) Patent No.: US 9,802,921 B2
(45) Date of Patent: Oct. 31, 2017

(54) FLUOROMETHYL-SUBSTITUTED PYRROLE CARBOXAMIDES IV

(71) Applicant: Grünenthal GmbH, Aachen (DE)

(72) Inventors: Melanie Reich, Aachen (DE); Stefan Schunk, Aachen (DE); Florian Jakob, Aachen (DE); Henning Steinhagen, Schwalbach (DE); Nils Damann, Hürth (DE); Michael Haurand, Aachen (DE); Richard Hamlyn, Cambridgeshire (GB); Marc Rogers, Cambridgeshire (GB); Kathy MacKenzie, Hertfordshire (GB)

(73) Assignee: GRUENENTHAL GMBH, Aachen (DE)

( * ) Notice: Subject to any disclaimer, the term of this patent is extended or adjusted under 35 U.S.C. 154(b) by 0 days.

(21) Appl. No.: 15/182,054

(22) Filed: Jun. 14, 2016

(65) Prior Publication Data

US 2016/0297803 A1    Oct. 13, 2016

Related U.S. Application Data

(63) Continuation of application No. PCT/EP2014/003429, filed on Dec. 18, 2014.

(30) Foreign Application Priority Data

Dec. 19, 2013   (EP) ..................... 13005936

(51) Int. Cl.
| | | |
|---|---|---|
| *C07D 401/06* | (2006.01) | |
| *C07D 403/06* | (2006.01) | |
| *C07D 413/06* | (2006.01) | |
| *C07D 417/06* | (2006.01) | |
| *C07D 413/14* | (2006.01) | |
| *C07D 403/04* | (2006.01) | |
| *C07D 403/14* | (2006.01) | |

(52) U.S. Cl.
CPC ......... *C07D 403/06* (2013.01); *C07D 401/06* (2013.01); *C07D 403/04* (2013.01); *C07D 403/14* (2013.01); *C07D 413/06* (2013.01); *C07D 413/14* (2013.01); *C07D 417/06* (2013.01)

(58) Field of Classification Search
CPC .. C07D 401/06; C07D 403/06; C07D 413/06; C07D 417/06
See application file for complete search history.

(56) References Cited

U.S. PATENT DOCUMENTS

2013/0029962 A1   1/2013  Frank et al.

FOREIGN PATENT DOCUMENTS

| WO | 2007141039 A1 | 12/2007 |
| WO | 2012004604 A1 | 1/2012 |
| WO | 2014032801 A1 | 3/2014 |
| WO | 2015090600 A1 | 6/2015 |
| WO | 2015090603 A1 | 6/2015 |

OTHER PUBLICATIONS

Winters et al. (Bioorg. Med. Chem. Lett., 24 (2014), p. 2053-2056).*
Kubinyi (3D QSAR in Drug Design: Ligand-Protein Interactions and Molecular Similarity, vol. 2-3, Springer, 1998, 800 pages). pp. 243-244 provided.*
Wermuth, The Practice of Medicinal Chemsitry, 2d ed. (2003), 768 pages. Chs. 9-10 provided.*
A.R. Disanto, "Bioavailability and Bioequivalency Testing", Chapter 77, Gennaro (Ed), Remington's Pharmaceutical Sciences, 17th Ed., 1985.
A.M. Knevel, "Separation", Chapter 78, Gennaro (Ed), Remington's Pharmaceutical Sciences, 17th Ed., 1985.
G.B. Phillips, "Sterilization", Chapter 79, Gennaro (Ed), Remington's Pharmaceutical Sciences, 17th Ed., 1985.
F.P. Siegel, "Tonicity, Osmoticity, Osmolality, and Osmolarity", Chapter 80, Gennaro (Ed), Remington's Pharmaceutical Sciences, 17th Ed., 1985.
R.L. Giles, et al., "Plastic Packaging Materials", Chapter 81, Gennaro (Ed), Remington's Pharmaceutical Sciences, 17th Ed., 1985.
C.J. Lintner, "Stability of Pharmaceutical Products", Chapter 82, Gennaro (Ed), Remington's Pharmaceutical Sciences, 17th Ed., 1985.
C.R. Erskine, "Quality Assurance and Control", Chapter 83, Gennaro (Ed), Remington's Pharmaceutical Sciences, 17th Ed., 1985.
J.G. Nairn, "Solutions, Emulsions, Suspensions and Extractives", Chapter 84, Gennaro (Ed), Remington's Pharmaceutical Sciences, 17th Ed., 1985.
K.E. Avis, "Parenteral Preparations", Chapter 85, Gennaro (Ed), Remington's Pharmaceutical Sciences, 17th Ed., 1985.
S.J. Turco, et al., "Intravenous Admixtures", Chapter 86, Gennaro (Ed), Remington's Pharmaceutical Sciences, 17th Ed., 1985.
J.D. Mullins, "Ophthalmic Preparations", Chapter 87, Gennaro (Ed), Remington's Pharmaceutical Sciences, 17th Ed., 1985.
L.H. Block, "Medicated Applications", Chapter 88, Gennaro (Ed), Remington's Pharmaceutical Sciences, 17th Ed., 1985.
E.G. Ripple, "Powders", Chapter 89, Gennaro (Ed), Remington's Pharmaceutical Sciences, 17th Ed., 1985.
R.E. King, et al., "Oral Solid Dosage Forms", Chapter 90, Gennaro (Ed), Remington's Pharmaceutical Sciences, 17th Ed., 1985.
S.C. Porter, "Coating of Pharmaceutical Dosage Forms", Chapter 91, Gennaro (Ed), Remington's Pharmaceutical Sciences, 17th Ed., 1985.

(Continued)

*Primary Examiner* — Robert Havlin
(74) *Attorney, Agent, or Firm* — Norris McLaughlin & Marcus PA

(57) ABSTRACT

The invention relates to pyrrole carboxamides bearing a fluoromethyl-moiety as voltage gated calcium channel blockers, to pharmaceutical compositions containing these compounds and also to these compounds for use in the treatment and/or prophylaxis of pain and further diseases and/or disorders.

12 Claims, No Drawings

(56) References Cited

OTHER PUBLICATIONS

M.A. Longer, et al., "Sustained-Release Drug Delivery Systems", Chapter 92, Gennaro (Ed), Remington's Pharmaceutical Sciences, 17th Ed., 1985.
J.J.Sclarro, et al., "Aerosols", Chapter 93, Gennaro (Ed), Remington's Pharmaceutical Sciences, 17th Ed., 1985.
L.J. Ravin, "Prefomulation", Chapter 76, Gennaro (Ed), Remington's Pharmaceutical Sciences, 17th Ed., 1985.
International Search Report and Written Opinion of the international Searching Authority for corresponding application PCT/EP2014/003429 dated Feb. 12, 2015.
G. J. Bennett, et al., "A peripheral mononeuropathy in rat that produces disorders of pain sensation like those seen in man", Elsevier Science Publishers B.V., Pain vol. 33, pp. 87-107, 1988.
F. E. D'Amour, et al., "A Method for Determining Loss of Pain Sensation", Biologic Research Laboratory, Denver, pp. 74-79, 1941.
D. Dubuisson, et al., "The Formalin Test: A Quantitative Study of the Analgesic Effects of Morphine, Meperidine, and Brain Stem Stimulation in Rats and Cats", Elsevier/North-Holland Biomedical Press, Pain vol. 4, pp. 161-174, 1977.
S. H. Kim, et al., "An Experimental model for peripheral neuropathy produced by the segmental spinal nerve ligation in the rat", Elsevier Science Publishers B.V., Pain vol. 50, pp. 355-363, 1992.
G.P Miljanich, "Ziconotide: Neuronal Calcium Channel Blocker for Treating Severe Chronic Pain", Current Medicinal Chemistry, vol. 11, No. 23, pp. 3029-3040, 2004.
R. L. Rauck, MD., et al., "Intrathecal Ziconotide for Neuropathic Pain: A Review", World Institute of Pain, Pain Practice, vol. 9, Issue 5, pp. 327-337, 2009.
P. S. Staats, et al., "Intrathecal Ziconotide in the Treatment of Refractory Pain in Patients with Cancer or AIDS, A Randomized Controlled Trial", American Medical Association, JAMA vol. 291, No. 1, pp. 63-70, 2004.
S. Tyagarajan, et al., "A potent and selective indole N-type calcium channel (Cav2.2) blocker for the treatment of pain", Bioorganic & Medicinal Chemistry Letters, vol. 21, pp. 869-873, 2011.

* cited by examiner

FLUOROMETHYL-SUBSTITUTED PYRROLE CARBOXAMIDES IV

This application is a continuation of PCT International Patent Application No. PCT/EP2014/003429, filed Dec. 18, 2014, which claims foreign priority benefit of European Patent Application No. EP 13005936.3, filed Dec. 19, 2013, the disclosures of each of which patent applications are incorporated herein by reference.

FIELD OF THE INVENTION

The invention relates to substituted pyrrole-2-yl-carboxamides bearing a fluorinated methyl moiety in 5-position as voltage gated Ca-channel (CaV) blockers, to pharmaceutical compositions containing these compounds and also to these compounds for use in the treatment and/or prophylaxis of pain and further diseases and/or disorders.

BACKGROUND OF THE INVENTION

Ion channels are proteins that form pores in membranes of biological cells and control the flow of ions down their electrochemical gradient. They are involved in the regulation of a wide range of cellular functions in both excitable and nonexcitable cells and provide attractive therapeutic targets for the treatment of various diseases.

In the somatosensory context, CaV2.2 channels, specific cellular plasma membrane calcium channels that belong to a diverse superfamily of voltage-gated calcium channels (VGCCs), were demonstrated to play an important role in spinal nociceptive processing.

The critical role of CaV2.2 in pain processing was underlined by the clinical efficacy of the intrathecally delivered, selective CaV2.2 channel antagonist Ziconotide (SNX-111; Prialt™), a synthetic peptide derived from a ω-(omega)-conotoxin peptide (Miljanich, 2004, Curr. Med. Chem., 11(23), p. 3029-40; Staats et al., 2004, JAMA, 291(1), p. 63-70). Inthrathecal administration of Ziconotide is required in order to reach the ion channel in presynaptic terminals of sensory neurons in the spinal cord. Common side effects of Ziconotide include memory impairment, dizziness, nystagmus, speech disorder, nervousness, somnolence and abnormal gait (Rauck et al., 2009, Pain Pract., 9, p. 327-37), which have been attributed to the inhibition of CaV2.2 channels in the brain by Ziconotide.

Therefore, a demand remains for the development of orally available CaV2.2 calcium channel blockers that show the desired qualities and effectively block CaV2.2 calcium channels in the nociceptive signaling pathway.

1,4-disubstituted pyrrol-2-yl carboxylic acid amides are known from WO2007/141039 A1.

SUMMARY OF THE INVENTION

The present invention describes small molecule CaV2.2 channel blockers.

It was therefore an object of the invention to provide novel compounds, preferably having advantages over the prior-art compounds. The compounds should be suitable in particular as pharmacological active ingredients in pharmaceutical compositions, preferably in pharmaceutical compositions for the treatment and/or prophylaxis of disorders or diseases which are at least partially mediated by CaV2.2 calcium channels.

This object is achieved by the subject matter described herein.

It has surprisingly been found that the compounds of general formula (I), as given below, display outstanding affinity to CaV2.2 calcium channels and are therefore particularly suitable for the prophylaxis and/or treatment of disorders or diseases which are at least partially mediated by CaV2.2 calcium channels. A specific substitution in 5-position of the pyrrol ($R^4$) render these compounds particularly suitable for the purpose of the invention.

The present invention therefore relates to a compound of general formula (I),

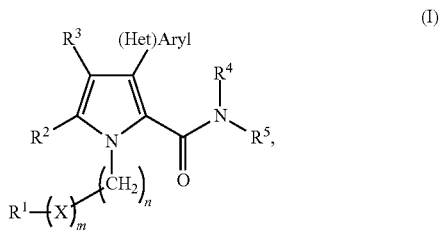

wherein
n represents 0, 1 or 2; m represents 0 or 1, with the proviso that n≥m;
X represents O, S, S(=O), S(=O)$_2$, NH or N(CH$_3$),
$R^1$ represents heteroaryl;
$R^2$ represents CH$_2$F; CHF$_2$ or CF$_3$;
$R^3$ represents H; C$_{1-6}$-alkyl; C$_{3-6}$-cycloalkyl; 3 to 7 membered heterocyclyl; OH; O—C$_{1-6}$-alkyl; NH$_2$; N(H)(C$_{1-6}$-alkyl); N(C$_{1-6}$-alkyl)$_2$ or SO$_2$(C$_{1-6}$-alkyl);
(Het)Aryl represents aryl or heteroaryl, each substituted by 0 or 1 or 2 or 3 substituents of the group consisting of $R^6$, $R^7$ and $R^8$,
wherein $R^6$, $R^7$ and $R^8$, are each independently of one another selected from the group consisting of F; Cl; Br; I; NO$_2$; CN; C$_{1-6}$-alkyl; CF$_3$; CF$_2$H; CFH$_2$; CF$_2$Cl; CFCl$_2$; C(=O)—H; C(=O)—C$_{1-6}$-alkyl; C(=O)—OH; C(=O)—O—C$_{1-6}$-alkyl; C(=O)—N(H)(OH); C(=O)—NH$_2$; C(=O)—N(H)(C$_{1-6}$-alkyl); C(=O)—N(C$_{1-6}$-alkyl)$_2$; C(=N—OH)—H; C(=N—OH)—C$_{1-6}$-alkyl; C(=N—O—C$_{1-6}$-alkyl)-H; C(=N—O—C$_{1-6}$-alkyl)-C$_{1-6}$-alkyl; OH; OCF$_3$; OCF$_2$H; OCFH$_2$; OCF$_2$Cl; OCFCl$_2$; O—C$_{1-6}$-alkyl; O—C(=O)—C$_{1-6}$-alkyl; O—C(=O)—O—C$_{1-6}$-alkyl; O—(C=O)—N(H)(C$_{1-6}$-alkyl); O—C(=O)—N(C$_{1-6}$-alkyl)$_2$; O—S(=O)$_2$—C$_{1-6}$-alkyl; O—S(=O)$_2$—OH; O—S(=O)$_2$—O—C$_{1-6}$-alkyl; O—S(=O)$_2$—NH$_2$; O—S(=O)$_2$—N(H)(C$_{1-6}$-alkyl); O—S(=O)$_2$—N(C$_{1-6}$-alkyl)$_2$; NH$_2$; N(H)(C$_{1-6}$-alkyl); N(C$_{1-6}$-alkyl)$_2$; N(H)—C(=O)—C$_{1-6}$-alkyl; N(H)—C(=O)—O—C$_{1-6}$-alkyl; N(H)—C(=O)—NH$_2$; N(H)—C(=O)—N(H)(C$_{1-6}$-alkyl); N(H)—C(=O)—N(C$_{1-6}$-alkyl)$_2$; N(C$_{1-6}$-alkyl)-C(=O)—C$_{1-6}$-alkyl; N(C$_{1-6}$-alkyl)-C(=O)—O—C$_{1-6}$-alkyl; N(C$_{1-6}$-alkyl)-C(=O)—NH$_2$; N(C$_{1-6}$-alkyl)-C(=O)—N(H)(C$_{1-6}$-alkyl); N(C$_{1-6}$-alkyl)-C(=O)—N(C$_{1-6}$-alkyl)$_2$; N(H)—S(=O)$_2$—OH; N(H)—S(=O)$_2$—C$_{1-6}$-alkyl; N(H)—S(=O)$_2$—O—C$_{1-6}$-alkyl; N(H)—S(=O)$_2$—NH$_2$; N(H)—S(=O)$_2$—N(H)(C$_{1-6}$-alkyl); N(H)—S(=O)$_2$N(C$_{1-6}$-alkyl)$_2$; N(C$_{1-6}$-alkyl)-S(=O)$_2$—OH; N(C$_{1-6}$-alkyl)-S(=O)$_2$—C$_{1-6}$-alkyl; N(C$_{1-6}$-alkyl)-S(=O)$_2$—O—C$_{1-6}$-alkyl; N(C$_{1-6}$-alkyl)-S(=O)$_2$—NH$_2$; N(C$_{1-6}$-alkyl)-S(=O)$_2$—N(H)(C$_{1-6}$-alkyl); N(C$_{1-6}$-alkyl)-S(=O)$_2$—N(C$_{1-6}$-alkyl)$_2$; SH; SCF$_3$; SCF$_2$H; SCFH$_2$; SCF$_2$Cl; SCFCl$_2$; S—C$_{1-6}$-alkyl; S(=O)—C$_{1-6}$-alkyl;

S(=O)$_2$—C$_{1-6}$-alkyl; S(=O)$_2$—OH; S(=O)$_2$—O—C$_{1-6}$-alkyl; S(=O)$_2$—NH$_2$; S(=O)$_2$—N(H)(C$_{1-6}$-alkyl); S(=O)$_2$—N(C$_{1-6}$-alkyl)$_2$, C$_{3-6}$-cycloalkyl or 3 to 7 membered heterocyclyl;

R$^4$ represents H or C$_{1-10}$-alkyl; and

R$^5$ represents H, C$_{1-10}$-alkyl; C$_{3-10}$-cycloalkyl; 3 to 10 membered heterocyclyl, aryl or heteroaryl; or C$_{3-10}$-cycloalkyl; 3 to 10 membered heterocyclyl, aryl or heteroaryl in each case connected via a C$_{1-8}$-alkylene group; or R$^4$ and R$^5$ together with the nitrogen atom connecting them form a 3 to 10 membered heterocyclyl;

wherein said C$_{1-6}$-alkyl, said C$_{1-10}$-alkyl and said C$_{1-8}$-alkylene in each case may be branched or unbranched and unsubstituted or mono- or poly-substituted;

and wherein said C$_{3-6}$-cycloalkyl, said C$_{3-10}$-cycloalkyl, said 3 to 7 membered heterocyclyl, said 3 to 10 membered heterocyclyl, said aryl and said heteroaryl in each case may be unsubstituted or mono- or polysubstituted;

optionally in the form of an individual stereoisomer or a mixture of stereoisomers, in the form of the free compound and/or a physiologically acceptable salt and/or a physiologically acceptable solvate thereof.

DETAILED DESCRIPTION

The term "single stereoisomer" preferably means in the sense of the present invention an individual enantiomer or diastereomer. The term "mixture of stereoisomers" means in the sense of this invention the racemate and mixtures of enantiomers and/or diastereomers in any mixing ratio.

The term "physiologically acceptable salt" preferably comprises in the sense of this invention a salt of at least one compound according to the present invention and at least one physiologically acceptable acid or base.

A physiologically acceptable salt of at least one compound according to the present invention and at least one physiologically acceptable acid preferably refers in the sense of this invention to a salt of at least one compound according to the present invention with at least one inorganic or organic acid which is physiologically acceptable—in particular when used in human beings and/or other mammals.

A physiologically acceptable salt of at least one compound according to the present invention and at least one physiologically acceptable base preferably refers in the sense of this invention to a salt of at least one compound according to the present invention as an anion with at least one preferably inorganic cation, which is physiologically acceptable in particular when used in human beings and/or other mammals.

The term "physiologically acceptable solvate" preferably comprises in the sense of this invention an adduct of one compound according to the present invention and/or a physiologically acceptable salt of at least one compound according to the present invention with distinct molecular equivalents of one solvent or more solvents. Examples of physiologically acceptable solvents are water, alkanols, esters, ethers or ketones.

The terms "C$_{1-6}$-alkyl" and "C$_{1-10}$-alkyl" preferably comprise in the sense of this invention acyclic saturated aliphatic hydrocarbon residues, which can be respectively branched or unbranched and can be unsubstituted or can be mono- or polysubstituted, e.g. mono-, di- or trisubstituted, and which contain 1 to 6 carbon atoms, i.e. 1, 2, 3, 4, 5 or 6 carbon atoms, or 1 to 10, i.e. 1, 2, 3, 4, 5, 6, 7, 8, 9 or 10 carbon atoms, respectively, i.e. C$_{1-6}$ alkyl and C$_{1-10}$ alkyl. Preferred C$_{1-6}$-alkyl groups are selected from the group consisting of methyl, ethyl, n-propyl, 2-propyl, n-butyl, isobutyl, sec.-butyl, tert.-butyl, n-pentyl, isopentyl, neopentyl, and n-hexyl. Preferred C$_{1-10}$-alkyl residues are selected from the group consisting of methyl, ethyl, n-propyl, 2-propyl, n-butyl, isobutyl, sec.-butyl, tert.-butyl, n-pentyl, isopentyl, neopentyl, n-hexyl, n-heptyl, n-octyl, n-nonyl, n-decanyl and isooctyl.

In relation to the terms "C$_{1-6}$-alkyl" and "C$_{1-10}$-alkyl", the term "monosubstituted" or "polysubstituted" such as di- or tri-substituted refers in the sense of this invention, with respect to the corresponding groups, to the single substitution or multiple substitution, e.g. disubstitution or trisubstitution, of one or more hydrogen atoms each independently of one another by at least one substituent. The term "polysubstituted" such as di- or tri-substituted with respect to polysubstituted groups such as di- or tri-substituted groups includes the polysubstitution of these groups either on different or on the same atoms, for example trisubstituted on the same carbon atom, as in the case of CF$_3$ or CH$_2$CF$_3$ or at various points, as in the case of CH(OH)—CH$_2$CH$_2$—CHCl$_2$. The multiple substitution can be carried out using the same or using different substituents.

The term "C$_{3-6}$-cycloalkyl" and "C$_{3-10}$-cycloalkyl" mean for the purposes of this invention cyclic aliphatic hydrocarbons containing 3, 4, 5 or 6 carbon atoms and 3, 4, 5, 6, 7, 8, 9 or 10 carbon atoms, respectively, wherein the hydrocarbons in each case can be saturated or unsaturated (but not aromatic), unsubstituted or mono- or polysubstituted. The cycloalkyl group can be bound to the respective superordinate general structure via any desired and possible ring member of the cycloalkyl group. The cycloalkyl group can also be condensed with further saturated, (partially) unsaturated, (hetero)cyclic, aromatic or heteroaromatic ring systems, i.e. with cycloalkyl, heterocyclyl, aryl or heteroaryl residues, which in each case can in turn be unsubstituted or mono- or polysubstituted. C$_{3-10}$-cycloalkyls can furthermore be singly or multiply bridged such as, for example, in the case of adamantyl, bicyclo[2.2.1]heptyl or bicyclo[2.2.2]octyl. Preferred C$_{3-10}$-cycloalkyl groups are selected from the group consisting of cyclopropyl, cyclobutyl, cyclopentyl, cyclohexyl, cycloheptyl, cyclooctyl, cyclononyl, cyclodecyl, adamantly, cyclopentenyl, cyclohexenyl, cycloheptenyl, cyclooctenyl,

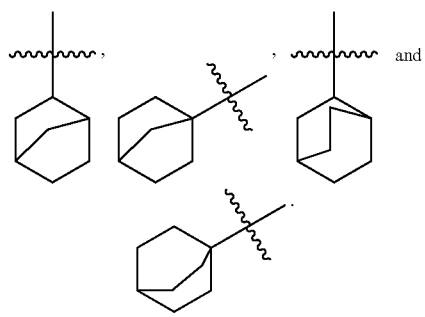

Preferred C$_{3-6}$-cycloalkyl groups are selected from the group consisting of cyclopropyl, cyclobutyl, cyclopentyl, cyclohexyl, cyclopentenyl and cyclo-hexenyl. Particularly preferred C$_{3-10}$-cycloalkyl groups and C$_{3-6}$-cycloalkyl groups are C$_{3-6}$-cycloalkyl groups such as cyclopropyl, cyclobutyl, cyclopentyl, cyclohexyl, cyclopentenyl and cyclohexenyl, in particular cyclopropyl.

The terms "3 to 7-membered heterocyclyl" and "3 to 10-membered heterocyclyl" mean for the purposes of this invention heterocycloaliphatic saturated or unsaturated (but not aromatic) residues having 3 to 7, i.e. 3, 4, 5, 6 or 7 ring members, and 3 to 10, i.e. 3, 4, 5, 6, 7, 8, 9 or 10 ring members, respectively, in which in each case at least one, if appropriate also two or three carbon atoms are replaced by a heteroatom or a heteroatom group each selected independently of one another from the group consisting of O, S, S(=O), S(=O)$_2$, N, NH and N($C_{1-6}$-alkyl) such as N(CH$_3$), wherein the ring members can be unsubstituted or mono- or polysubstituted. The cycloalkyl groups can also be condensed with further saturated or (partially) unsaturated cycloalkyl or heterocyclyl, aromatic or heteroaromatic ring systems, which in each case can in turn be unsubstituted or mono- or polysubstituted. The heterocyclyl group can be bound to the superordinate general structure via any desired and possible ring member of the heterocycloaliphatic residue if not indicated otherwise.

The term "aryl" means for the purpose of this invention aromatic hydrocarbons having 6 to 14, i.e. 6, 7, 8, 9, 10, 11, 12, 13 or 14 ring members, preferably having 6 to 10, i.e. 6, 7, 8, 9 or 10 ring members, including phenyls and naphthyls. Each aryl residue can be unsubstituted or mono- or polysubstituted, wherein the aryl substituents can be the same or different and in any desired and possible position of the aryl. The aryl can be bound to the superordinate general structure via any desired and possible ring member of the aryl residue. The aryl residues can also be condensed with further saturated or (partially) unsaturated cycloalkyl or heterocyclyl, aromatic or heteroaromatic ring systems, which can in turn be unsubstituted or mono- or polysubstituted. Examples of condensed aryl residues are benzodioxolanyl and benzodioxanyl. Preferably, aryl is selected from the group consisting of phenyl, 1-naphthyl, 2-naphthyl, fluorenyl and anthracenyl, each of which can be respectively unsubstituted or mono- or polysubstituted. A particularly preferred aryl is phenyl, unsubstituted or mono- or poly-substituted.

The term "heteroaryl" for the purpose of this invention represents a 5-, 6-, 8-, 9- or 10-membered cyclic aromatic residue containing at least 1, if appropriate also 2, 3, 4 or 5 heteroatoms, wherein the heteroatoms are each selected independently of one another from the group S, N and O and the heteroaryl residue can be unsubstituted or mono- or polysubstituted; in the case of substitution on the heteroaryl, the substituents can be the same or different and be in any desired and possible position of the heteroaryl. The binding to the superordinate general structure can be carried out via any desired and possible ring member of the heteroaryl residue if not indicated otherwise. The heteroaryl can also be part of a bi- or polycyclic system having up to 10 ring members, wherein the ring system can be formed with further saturated or (partially) unsaturated cycloalkyl or heterocyclyl, aromatic or hetero-aromatic ring systems, which can in turn be unsubstituted or mono- or polysubstituted. It is preferable for the heteroaryl residue to be selected from the group consisting of benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, furyl (furanyl), imidazolyl, imidazothiazolyl, indazolyl, indolizinyl, indolyl, isoquinolinyl, isoxazolyl, isothiazolyl, indolyl, naphthyridinyl, oxazolyl, oxadiazolyl, phenazinyl, phenothiazinyl, phthalazinyl, pyrazolyl, pyridyl (2-pyridyl, 3-pyridyl, 4-pyridyl), pyrrolyl, pyridazinyl, pyrimidinyl, pyrazinyl, purinyl, phenazinyl, thienyl (thiophenyl), triazolyl, tetrazolyl, thiazolyl, thiadiazolyl and triazinyl.

The terms "$C_{1-8}$-alkylene" and "$C_{2-6}$-alkylene" means in the sense of this invention a bivalent acyclic saturated, aliphatic hydrocarbon residue, which can be branched or unbranched and also unsubstituted or mono- or polysubstituted, which contain 1 to 8 carbon atoms or 2 to 6 carbon atoms respectively. Preferred $C_{1-8}$-alkylene groups are selected from the group consisting of CH$_2$, CH$_2$CH$_2$, CH(CH$_3$), CH$_2$CH$_2$CH$_2$, CH(CH$_3$)CH$_2$, CH(CH$_2$CH$_3$), CH$_2$(CH$_2$)$_2$CH$_2$, CH(CH$_3$)CH$_2$CH$_2$, CH$_2$CH(CH$_3$)CH$_2$, CH(CH$_3$)CH(CH$_3$), CH(CH$_2$CH$_3$)CH$_2$, C(CH$_3$)$_2$CH$_2$, CH(CH$_2$CH$_2$CH$_3$) and C(CH$_3$)(CH$_2$CH$_3$). Preferred $C_{2-6}$-alkylene groups are selected from the group consisting of CH$_2$CH$_2$, CH(CH$_3$), CH$_2$CH$_2$CH$_2$, CH(CH$_3$)CH$_2$, CH(CH$_2$CH$_3$), CH$_2$(CH$_2$)$_2$CH$_2$, CH(CH$_3$)CH$_2$CH$_2$, CH$_2$CH(CH$_3$)CH$_2$, CH(CH$_3$)CH(CH$_3$), CH(CH$_2$CH$_3$)CH$_2$, C(CH$_3$)$_2$CH$_2$, CH(CH$_2$CH$_2$CH$_3$) and C(CH$_3$)(CH$_2$CH$_3$).

In relation to the terms "$C_{1-6}$-alkyl", "$C_{1-10}$-alkyl", "$C_{1-6}$-alkylene", "$C_{3-6}$-cycloalkyl", "$C_{3-10}$-cycloalkyl", "3 to 7-membered heterocyclyl" and "3 to 10-membered heterocyclyl", the term "mono- or polysubstituted" refers in the sense of this invention, with respect to the corresponding residues or groups, to the single substitution or multiple substitution, e.g. disubstitution, trisubstitution, tetrasubstitution, or pentasubstitution, of one or more hydrogen atoms each independently of one another by at least one substituent selected from the group consisting of F; Cl; Br; I; NO$_2$; CN; =O; =NH; =N(OH); =N(O—$C_{1-6}$-alkyl); CF$_3$; CF$_2$H; CFH$_2$; CF$_2$Cl; CFCl$_2$; $C_{1-6}$-alkyl; ($C_{1-8}$-alkylene)-OH; C(=O)—H; C(=O)—$C_{1-6}$-alkyl; C(=O)—OH; C(=O)—O—$C_{1-6}$-alkyl; C(=O)—N(H)(OH); C(=O)—NH$_2$; C(=O)—N(H)($C_{1-6}$-alkyl); C(=O)—N($C_{1-6}$-alkyl)$_2$; C(=N—OH)—H; C(=N—OH)—$C_{1-6}$-alkyl; C(=N—O—$C_{1-6}$-alkyl)-H; C(=N—O—$C_{1-6}$-alkyl)-$C_{1-6}$-alkyl; OH; OCF$_3$; OCF$_2$H; OCFH$_2$; OCF$_2$Cl; OCFCl$_2$; O—$C_{1-6}$-alkyl; O—($C_{1-8}$-alkylene)-OH; O—($C_{1-8}$-alkylene)-O—$C_{1-6}$-alkyl; O—C(=O)—$C_{1-6}$-alkyl; O—C(=O)—O—$C_{1-6}$-alkyl; O—(C=O)—N(H)($C_{1-6}$-alkyl); O—C(=O)—N($C_{1-6}$-alkyl)$_2$; O—S(=O)$_2$—$C_{1-6}$-alkyl; O—S(=O)$_2$—OH; O—S(=O)$_2$—O—$C_{1-6}$-alkyl; O—S(=O)$_2$—NH$_2$; O—S(=O)$_2$—N(H)($C_{1-6}$-alkyl); O—S(=O)$_2$—N($C_{1-6}$-alkyl)$_2$; NH$_2$; N(H)($C_{1-6}$-alkyl); N($C_{1-6}$-alkyl)$_2$; N(H)—C(=O)—$C_{1-6}$-alkyl; N(H)—C(=O)—O—$C_{1-6}$-alkyl; N(H)—C(=O)—NH$_2$; N(H)—C(=O)—N(H)($C_{1-6}$-alkyl); N(H)—C(=O)—N($C_{1-6}$-alkyl)$_2$; N($C_{1-6}$-alkyl)-C(=O)—$C_{1-6}$-alkyl; N($C_{1-6}$-alkyl)-C(=O)—O—$C_{1-6}$-alkyl; N($C_{1-6}$-alkyl)-C(=O)—NH$_2$; N($C_{1-6}$-alkyl)-C(=O)—N(H)($C_{1-6}$-alkyl); N($C_{1-6}$-alkyl)-C(=O)—N($C_{1-6}$-alkyl)$_2$; N(H)—S(=O)$_2$—OH; N(H)—S(=O)$_2$—$C_{1-6}$-alkyl; N(H)—S(=O)$_2$—O—$C_{1-6}$-alkyl; N(H)—S(=O)$_2$—NH$_2$; N(H)—S(=O)$_2$—N(H)($C_{1-6}$-alkyl); N(H)—S(=O)$_2$—N($C_{1-6}$-alkyl)$_2$; N($C_{1-6}$-alkyl)-S(=O)$_2$—OH; N($C_{1-6}$-alkyl)-S(=O)$_2$—$C_{1-6}$-alkyl; N($C_{1-6}$-alkyl)-S(=O)$_2$—O—$C_{1-6}$-alkyl; N($C_{1-6}$-alkyl)-S(=O)$_2$—NH$_2$; N($C_{1-6}$-alkyl)-S(=O)$_2$—N(H)($C_{1-6}$-alkyl); N($C_{1-6}$-alkyl)-S(=O)$_2$—N($C_{1-6}$-alkyl)$_2$; SH; SCF$_3$; SCF$_2$H; SCFH$_2$; SCF$_2$Cl; SCFCl$_2$; S—$C_{1-6}$-alkyl; S(=O)—$C_{1-6}$-alkyl; S(=O)$_2$—$C_{1-6}$-alkyl; S(=O)$_2$—OH; S(=O)$_2$—O—$C_{1-6}$-alkyl; S(=O)$_2$—NH$_2$; S(=O)$_2$—N(H)($C_{1-6}$-alkyl); S(=O)$_2$—N($C_{1-6}$-alkyl)$_2$; $C_{3-6}$-cycloalkyl or 3 to 7 membered heterocyclyl. The term "polysubstituted" with respect to polysubstituted residues and groups includes the polysubstitution of these residues and groups either on different or on the same atoms, for example trisubstituted on the same carbon atom, as in the case of CF$_3$, CH$_2$CF$_3$ or 1,1-difluorocyclohexyl, or at various points, as in the case of CH(OH)—CHCl$_2$ or 1-chloro-3-fluorocyclohexyl. A substituent can if appropriate for its part in turn be mono- or polysubstituted. The multiple substitution can be carried out using the same or using different substituents.

Preferred substituents of "C$_{1-6}$-alkyl", "C$_{1-10}$-alkyl", "C$_{1-8}$-alkylene" and "C$_{2-6}$-alkylene" are selected from the group consisting of F; Cl; Br; I; NO$_2$; CF$_3$; CN; =O; =NH; C$_{1-6}$-alkyl; (C$_{1-8}$-alkylene)-OH; C(=O)—H; C(=O)—C$_{1-6}$-alkyl; C(=O)—OH; C(=O)—O—C$_{1-6}$-alkyl; C(=O)—NH$_2$; C(=O)—N(H)(C$_{1-6}$-alkyl); C(=O)—N(C$_{1-6}$-alkyl)$_2$; OH; O—C$_{1-6}$-alkyl; O—C(=O)—C$_{1-6}$-alkyl; O—(C$_{1-8}$-alkylene)-OH; O—(C$_{1-8}$-alkylene)-O—C$_{1-6}$-alkyl; OCF$_3$; NH$_2$; N(H)(C$_{1-6}$-alkyl); N(C$_{1-6}$-alkyl)$_2$; N(H)—C(=O)—C$_{1-6}$-alkyl; N(H)—S(=O)$_2$—C$_{1-6}$-alkyl; N(C$_{1-6}$-alkyl)-S(=O)$_2$—C$_{1-6}$-alkyl; N(H)—C(=O)—NH$_2$; N(H)—C(=O)—N(H)(C$_{1-6}$-alkyl); N(H)—C(=O)—N(C$_{1-6}$-alkyl)$_2$; N(H)—S(=O)$_2$—NH$_2$; N(H)—S(=O)$_2$—N(H)(C$_{1-6}$-alkyl); N(H)—S(=O)$_2$—N(C$_{1-6}$-alkyl)$_2$; N(C$_{1-6}$-alkyl)-S(=O)$_2$—NH$_2$; N(C$_{1-6}$-alkyl)-S(=O)$_2$—N(H)(C$_{1-6}$-alkyl); N(C$_{1-6}$-alkyl)-S(=O)$_2$—N(C$_{1-6}$-alkyl)$_2$; SH; SCF$_3$; S—C$_{1-6}$-alkyl; S(=O) C$_{1-6}$-alkyl; S(=O)$_2$OH; S(=O)$_2$O—C$_{1-6}$-alkyl and S(=O)$_2$—NH$_2$; S(=O)$_2$—N(H)(C$_{1-6}$-alkyl); and S(=O)$_2$—N(C$_{1-6}$-alkyl)$_2$.

Particularly preferred substituents of "C$_{1-6}$-alkyl", "C$_{1-10}$-alkyl", "C$_{1-8}$-alkylene" and "C$_{2-6}$-alkylene" are selected from the group consisting of F; Cl; Br; I; CF$_3$; C(=O)—NH$_2$; C(=O)—N(H)(C$_{1-6}$-alkyl); C(=O)—N(C$_{1-6}$-alkyl)$_2$; OH; O—C$_{1-6}$-alkyl; O—(C$_{1-8}$-alkylene)-OH; O—(C$_{1-8}$-alkylene)-O—C$_{1-6}$-alkyl; NH$_2$; N(H)(C$_{1-6}$-alkyl); N(C$_{1-6}$-alkyl)$_2$; N(H)—C(=O)—C$_{1-6}$-alkyl; N(H)—S(=O)$_2$—C$_{1-6}$-alkyl; N(C$_{1-6}$-alkyl)-S(=O)$_2$—C$_{1-6}$-alkyl; N(H)—S(=O)$_2$—NH$_2$; SH; S—C$_{1-6}$-alkyl; S(=O)$_2$ C$_{1-6}$-alkyl and S(=O)$_2$—N(H)(C$_{1-6}$-alkyl).

Preferred substituents of "C$_{3-6}$-cycloalkyl", "C$_{3-10}$-cycloalkyl", "3 to 7-membered heterocyclyl" and "3 to 10-membered heterocyclyl" are selected from the group consisting of F; Cl; Br; I; NO$_2$; CF$_3$; CN; =O; C$_{1-6}$-alkyl; C$_{3-6}$-cycloalkyl or 3 to 7 membered heterocyclyl; C$_{3-6}$-cycloalkyl or 3 to 7 membered hetero-cyclyl, each bridged via a C$_{1-8}$-alkylene; CHO; C(=O)—C$_{1-6}$-alkyl; CO$_2$H; C(=O)O—C$_{1-6}$-alkyl; CONH$_2$; C(=O)NH—C$_{1-6}$-alkyl; C(=O)N(C$_{1-6}$-alkyl)$_2$; OH; O—C$_{1-6}$-alkyl; OCF$_3$; O—(C$_{1-8}$-alkylene)-OH; O—(C$_{1-8}$-alkylene)-O—C$_{1-6}$-alkyl; O—C(=O)—C$_{1-6}$-alkyl; NH$_2$; NH—C$_{1-6}$-alkyl; N(C$_{1-6}$-alkyl)$_2$; NH—C(=O)—C$_{1-6}$-alkyl; SH; S—C$_{1-6}$-alkyl; SCF$_3$; S(=O)$_2$—C$_{1-6}$-alkyl; S(=O)$_2$OH; S(=O)$_2$O—C$_{1-6}$-alkyl and S(=O)$_2$—NH—C$_{1-6}$-alkyl.

In relation to the terms "aryl" and "heteroaryl", the term "mono- or polysubstituted" refers in the sense of this invention, with respect to the corresponding residues or groups, to the single substitution or multiple substitution, e.g. disubstitution, trisubstitution, tetrasubstitution, or pentasubstitution, of one or more hydrogen atoms each independently of one another by at least one substituent selected from the group consisting of F; Cl; Br; NO$_2$; CN; CF$_3$; CF$_2$H; CFH$_2$; CF$_2$Cl; CFCl$_2$; C$_{1-6}$-alkyl; C$_{3-6}$-cycloalkyl; 3 to 7 membered heterocyclyl; aryl; heteroaryl; aryl, heteroaryl, C$_{3-6}$-cycloalkyl or 3 to 7 membered hetero-cyclyl, each connected via a C$_{1-8}$-alkylene; C(=O)H; C(=O)—(C$_{1-6}$-alkyl); C(=O)—(C$_{3-6}$-cycloalkyl); C(=O)-(3 to 7 membered heterocyclyl); C(=O)-(aryl); C(=O)-(heteroaryl); C(=O)OH; C(=O)—O(C$_{1-6}$-alkyl); C(=O)—O(C$_{3-6}$-cycloalkyl); C(=O)—O(3 to 7 membered heterocyclyl); C(=O)—O(aryl); C(=O)—O(heteroaryl); C(=O)—NH$_2$; C(=O)—N(H)(C$_{1-6}$-alkyl); C(=O)—N(H)(C$_{3-6}$-cycloalkyl); C(=O)—N(H)(3 to 7 membered heterocycloalkyl); C(=O)—N(H)(aryl); C(=O)—N(H)(heteroaryl); C(=O)—N(C$_{1-6}$-alkyl)$_2$; C(=O)—N(C$_{1-6}$-alkyl)(C$_{3-6}$-cycloalkyl); C(=O)—N(C$_{1-6}$-alkyl)(3 to 7 membered heterocyclyl); C(=O)—N(C$_{1-6}$-alkyl)(aryl); C(=O)—N(C$_{1-6}$-alkyl)(heteroaryl); OH; =O; O—(C$_{1-6}$-alkyl); O—(C$_{3-6}$-cycloalkyl); O-(3 to 7 membered heterocyclyl); O-(aryl); O-(heteroaryl); OCF$_3$; OCF$_2$H; OCFH$_2$; OCF$_2$Cl; OCFCl$_2$; O—C(=O)—(C$_{1-6}$-alkyl); O—C(=O)—(C$_{3-6}$-cycloalkyl); O—C(=O)-(3 to 7 membered heterocyclyl); O—C(=O)-(aryl); C(=O)-(heteroaryl); O—C(=O)—NH$_2$; O—C(=O)—N(H)(C$_{1-6}$-alkyl); O—C(=O)—N(H)(C$_{3-6}$-cycloalkyl); O—C(=O)—N(H)(3 to 7 membered heterocyclyl); O—C(=O)—N(H)(aryl); O—C(=O)—N(H)(heteroaryl); O—C(=O)—N(C$_{1-6}$-alkyl)$_2$; O—C(=O)—N(C$_{1-6}$-alkyl)(C$_{3-6}$-cycloalkyl); O—C(=O)—N(C$_{1-6}$-alkyl)(3 to 7 membered heterocyclyl); O—C(=O)—N(C$_{1-6}$-alkyl)(aryl); O—C(=O)—N(C$_{1-6}$-alkyl)(heteroaryl); NH$_2$; N(H)(C$_{1-6}$-alkyl); N(H)(C$_{3-6}$-cycloalkyl); N(H)(3 to 7 membered heterocyclyl); N(H)(aryl); N(H)(heteroaryl); N(C$_{1-6}$-alkyl)$_2$; N(C$_{1-6}$-alkyl)(C$_{3-6}$-cycloalkyl); N(C$_{1-6}$-alkyl)(3 to 7 membered heterocyclyl); N(C$_{1-6}$-alkyl) (aryl); N(C$_{1-6}$-alkyl)(heteroaryl); N(H)—C(=O)—(C$_{1-6}$-alkyl); N(H)—C(=O)—(C$_{3-6}$-cycloalkyl); N(H)—C(=O)-(3 to 7 membered heterocyclyl); N(H)—C(=O)-(aryl); N(H)—C(=O)-(heteroaryl); N(C$_{1-6}$-alkyl)-C(=O)—(C$_{1-6}$-alkyl); N(C$_{1-6}$-alkyl)-C(=O)—(C$_{3-6}$-cycloalkyl); N(C$_{1-6}$-alkyl)-C(=O)-(3 to 7 membered heterocyclyl); N(C$_{1-6}$-alkyl)-C(=O)-(aryl); N(C$_{1-6}$-alkyl)-C(=O)-(heteroaryl); N(H)—S(=O)$_2$—(C$_{1-6}$-alkyl); N(H)—S(=O)$_2$—(C$_{3-6}$-cycloalkyl); N(H)—S(=O)$_2$-(3 to 7 membered heterocyclyl); N(H)—S(=O)$_2$-(aryl); N(H)—S(=O)$_2$-(heteroaryl); N(C$_{1-4}$-alkyl)-S(=O)$_2$—(C$_{1-6}$-alkyl); N(C$_{1-6}$-alkyl)-S(=O)$_2$—(C$_{3-6}$-cycloalkyl); N(C$_{1-6}$-alkyl)-S(=O)$_2$-(3 to 7 membered heterocyclyl); N(C$_{1-6}$-alkyl)-S(=O)$_2$-(aryl); N(C$_{1-6}$-alkyl)-S(=O)$_2$-(heteroaryl); N(H)—C(=O)—O(C$_{1-6}$-alkyl); N(H)—C(=O)—O(C$_{3-6}$-cycloalkyl); N(H)—C(=O)—O(3 to 7 membered heterocyclyl); N(H)—C(=O)—O(aryl); N(H)—C(=O)—O(heteroaryl); N(C$_{1-6}$-alkyl)-C(=O)—O(C$_{1-6}$-alkyl); N(C$_{1-6}$-alkyl)-C(=O)—O(C$_{3-6}$-cycloalkyl); N(C$_{1-6}$-alkyl)-C(=O)—O(3 to 7 membered heterocyclyl); N(C$_{1-6}$-alkyl)-C(=O)—O(aryl); N(C$_{1-6}$-alkyl)-C(=O)—O(heteroaryl); N(H)—C(=O)—NH$_2$; N(H)—C(=O)—N(H)(C$_{1-6}$-alkyl); N(H)—C(=O)—N(H)(C$_{3-6}$-cycloalkyl); N(H)—C(=O)—N(H)(3 to 7 membered heterocyclyl); N(H)—C(=O)—N(H)(aryl); N(H)—C(=O)—N(H)(heteroaryl); N(C$_{1-6}$-alkyl)-C(=O)—NH$_2$; N(C$_{1-6}$-alkyl)-C(=O)—N(H)(C$_{1-6}$-alkyl); N(C$_{1-6}$-alkyl)-C(=O)—N(H)(C$_{3-6}$-cycloalkyl); N(C$_{1-6}$-alkyl)-C(=O)—N(H)(3 to 7 membered heterocyclyl); N(C$_{1-6}$-alkyl)-C(=O)—N(H)(aryl); N(C$_{1-6}$-alkyl)-C(=O)—N(H)(heteroaryl); N(H)—C(=O)—N(C$_{1-6}$-alkyl)$_2$; N(H)—C(=O)—N(C$_{1-6}$-alkyl)(C$_{3-6}$-cycloalkyl); N(H)—C(=O)—N(C$_{1-6}$-alkyl)(3 to 7 membered heterocyclyl); N(H)—C(=O)—N(C$_{1-6}$-alkyl)(aryl); N(H)—C(=O)—N(C$_{1-6}$-alkyl) (heteroaryl); N(C$_{1-6}$-alkyl)-C(=O)—N(C$_{1-6}$-alkyl)$_2$; N(C$_{1-6}$-alkyl)-C(=O)—N(C$_{1-6}$-alkyl)(C$_{3-6}$-cycloalkyl); N(C$_{1-6}$-alkyl)-C(=O)—N(C$_{1-6}$-alkyl)(3 to 7 membered heterocyclyl); N(C$_{1-6}$-alkyl)-C(=O)—N(C$_{1-6}$-alkyl)(aryl); N(C$_{1-6}$-alkyl)-C(=O)—N(C$_{1-6}$-alkyl) heteroaryl); SH; S—(C$_{1-6}$-alkyl); S—(C$_{3-6}$-cycloalkyl); S-(3 to 7 membered heterocyclyl); S-(aryl); S-(heteroaryl); SCF$_3$; S(=O)$_2$OH; S(=O)—(C$_{1-6}$-alkyl); S(=O)—(C$_{3-6}$-cycloalkyl); S(=O)-(3 to 7 membered heterocyclyl); S(=O)-(aryl); S(=O)-(heteroaryl); S(=O)$_2$—(C$_{1-6}$-alkyl); S(=O)$_2$—(C$_{3-6}$-cycloalkyl); S(=O)$_2$-(3 to 7 membered heterocyclyl); S(=O)$_2$-(aryl); S(=O)$_2$-(heteroaryl); S(=O)$_2$—O(C$_{1-6}$-alkyl); S(=O)$_2$—O(C$_{3-6}$-cycloalkyl);

S(=O)₂—O(3 to 7 membered heterocyclyl); S(=O)₂—O (aryl); S(=O)₂—O(heteroaryl); S(=O)₂—N(H)(C₁₋₆-alkyl); S(=O)₂—N(H)(C₃₋₆-cycloalkyl); S(=O)₂—N(H)(3 to 7 membered heterocyclyl); S(=O)₂—N(H)(aryl); S(=O)₂—N(H)(heteroaryl); S(=O)₂—N(C₁₋₆-alkyl)₂; S(=O)₂—N(C₁₋₆-alkyl)(C₃₋₆-cycloalkyl); S(=O)₂—N(C₁₋₆-alkyl)(3 to 7 membered heterocyclyl); S(=O)₂—N(C₁₋₆-alkyl)-(aryl) and S(=O)₂—N(C₁₋₆-alkyl)(heteroaryl).

Preferred substituents of "aryl" and "heteroaryl" are selected from the group consisting of F; Cl; Br; NO₂; CN; CF₃; CF₂H; CFH₂; CF₂Cl; CFCl₂; C₁₋₆-alkyl; aryl; heteroaryl; C₃₋₆-cycloalkyl; 3 to 6 membered heterocyclyl; aryl, heteroaryl, C₃₋₆-cycloalkyl or 3 to 6 membered heterocycloaliphatic, each connected via a C₁₋₈-alkylene; C(=O)—H; C(=O)—C₁₋₆-alkyl; C(=O)aryl; C(=O)heteroaryl; C(=O)—OH; C(=O)—O—C₁₋₆-alkyl; C(=O)O-aryl; C(=O)O-heteroaryl; CO—NH₂; C(=O)—N(H)C₁₋₆-alkyl; C(=O)—N(C₁₋₆-alkyl)₂; C(=O)NH-aryl; C(=O)N(aryl)₂; C(=O)NH-heteroaryl; C(=O)N(heteroaryl)₂; C(=O)N(C₁₋₆-alkyl)(aryl); C(=O)N(C₁₋₆-alkyl)(heteroaryl); C(=O)N(heteroaryl)(aryl); OH; OCF₃; OCF₂H; OCFH₂; OCF₂Cl; OCFCl₂; O—C₁₋₆-alkyl; O-benzyl; O-aryl; O-heteroaryl; O—C(=O)—C₁₋₆-alkyl; O—C(=O) aryl; O—C(=O)heteroaryl; O—C(=O)—O—C₁₋₆-alkyl; O—(C=O)—N(H)C₁₋₆-alkyl; O—C(=O)—N(C₁₋₆-alkyl)₂; O—S(=O)₂—C₁₋₆-alkyl; O—S(=O)₂—OH; O—S(=O)₂—O—C₁₋₆-alkyl; O—S(=O)₂—NH₂; O—S(=O)₂—N(H)C₁₋₆-alkyl; O—S(=O)₂—N(C₁₋₆-alkyl)₂; NH₂; N(H)C₁₋₆-alkyl; N(C₁₋₆-alkyl)₂; N(H)—C(=O)—C₁₋₆-alkyl; N(H)—C(=O)-aryl; N(H)—C(=O)-heteroaryl; N(H)—C(=O)—O—C₁₋₆-alkyl; N(H)C(=O)—NH₂; N(H)—C(=O)—N(H)C₁₋₆-alkyl; N(H)—C(=O)—N(C₁₋₆-alkyl)₂; N(C₁₋₆-alkyl)-C(=O)C₁₋₆-alkyl; N(C₁₋₆-alkyl)-C(=O)—O—C₁₋₆-alkyl; N(C₁₋₆-alkyl)C(=O)—NH₂; N(C₁₋₆-alkyl)-C(=O)—N(H)C₁₋₆-alkyl; N(C₁₋₆-alkyl)-C(=O)—N(C₁₋₆-alkyl)₂; N(H)—S(=O)₂—OH; N(H)—S(=O)₂—C₁₋₆-alkyl; N(H)—S(=O)₂—O—C₁₋₆-alkyl; N(H)—S(=O)₂—NH₂; N(H)S(=O)₂—N(H)C₁₋₆-alkyl; N(H)—S(=O)₂—N(C₁₋₆-alkyl)₂; N(C₁₋₆-alkyl)-S(=O)₂—OH; N(C₁₋₆-alkyl)-S(=O)₂(C₁₋₆-alkyl); N(C₁₋₆-alkyl)-S(=O)₂—O(C₁₋₆-alkyl); N(C₁₋₆-alkyl)-S(=O)₂—NH₂; N(C₁₋₆-alkyl)-S(=O)₂—N(H)C₁₋₆-alkyl; N(C₁₋₆-alkyl)S(=O)₂—N(C₁₋₆-alkyl)₂; SH; SCF₃; SCF₂H; SCFH₂; SCF₂Cl; SCFCl₂; S—C₁₋₆-alkyl; S-benzyl; S-aryl; S-heteroaryl; S(=O)—C₁₋₆-alkyl; S(=O)₂—C₁₋₆-alkyl; S(=O)₂-aryl; S(=O)₂-heteroaryl; S(=O)₂—OH; S(=O)₂—OC₁₋₆-alkyl; S(=O)₂O-aryl; S(=O)₂O-heteroaryl; S(=O)₂—NH₂; S(=O)₂—N(H)C₁₋₆-alkyl, S(=O)₂—N(H)-aryl; S(=O)₂—N(H)-heteroaryl and S(=O)₂—N(C₁₋₆-alkyl)₂.

More preferred substituents of "aryl" and "heteroaryl" are selected from the group consisting of F; Cl; CF₃; CN; C₁₋₆-alkyl; C(=O)—OH; C(=O)—O—C₁₋₆-alkyl; CO—NH₂; C(=O)—N(H)C₁₋₆-alkyl; C(=O)—N(C₁₋₆-alkyl)₂; OH; O—C₁₋₆-alkyl; O—C(=O)—C₁₋₆-alkyl; OCF₃; OCHF₂; OCH₂F; NH₂; N(H)C₁₋₆-alkyl; N(C₁₋₆-alkyl)₂; N(H)—C(=O)—C₁₋₆-alkyl; N(C₁₋₆-alkyl)-C(=O)C₁₋₆-alkyl; N(H)—S(=O)₂—C₁₋₆-alkyl; N(C₁₋₆-alkyl)-S(=O)₂(C₁₋₆-alkyl); N(H)C(=O)NH₂; N(H)C(=O)—N(H)C₁₋₆-alkyl; N(H)—C(=O)—N(C₁₋₆-alkyl)₂; N(C₁₋₆-alkyl)-C(=O)—NH₂; N(C₁₋₆-alkyl)C(=O)—N(H)C₁₋₆-alkyl; N(C₁₋₆-alkyl)-C(=O)—N(C₁₋₆-alkyl)₂; S(=O)₂C₁₋₆-alkyl; S(=O)₂—NH₂; S(=O)₂—N(H)C₁₋₆-alkyl and S(=O)₂—N(C₁₋₆-alkyl)₂.

The compounds according to the invention are defined by substituents, for example by R¹, R² and R³ (1ˢᵗ generation substituents) which are for their part if appropriate themselves substituted (2ⁿᵈ generation substituents). Depending on the definition, these substituents of the substituents can for their part be resubstituted (3ʳᵈ generation substituents). If, for example, R¹ = a C₁₋₆-alkyl (1ˢᵗ generation substituent), then the C₁₋₆-alkyl can for its part be substituted, for example with a NH—C₁₋₆-alkyl (2ⁿᵈ generation substituent). This produces the functional group R¹=(C₁₋₆-alkyl-NH—C₁₋₆-alkyl). The NH—C₁₋₆-alkyl can then for its part be resubstituted, for example with Cl (3ʳᵈ generation substituent). Overall, this produces the functional group R¹=C₁₋₆-alkyl-NH—C₁₋₆-alkyl, wherein the C₁₋₆-alkyl of the NH—C₁₋₆-alkyl is substituted by Cl. However, in a preferred embodiment, the 3ʳᵈ generation substituents may not be resubstituted, i.e. there are then no 4ᵗʰ generation substituents. If a residue occurs multiply within a molecule, then this residue can have respectively different meanings for various substituents: if, for example, both R¹ and R² denote a 3 to 10 membered heterocyclyl, then the 3 to 10 membered heterocyclyl can e.g. represent morpholinyl for R¹ and can represent piperazinyl for R².

Within the scope of the present invention, the symbols

or ------ used in the formulae denotes a link of a corresponding residue to the respective superordinate general structure.

In one embodiment of the first aspect of the invention, the compound according to general formula (I) is characterized in that n represents 0 or 1. Preferably, n is 1.

In another embodiment of the first aspect of the invention, the compound according to general formula (I) is characterized in that m is 0.

In a preferred embodiment of the first aspect of the invention, the compound according to general formula (I) is characterized in that n is 1 and m is 0.

In another embodiment of the first aspect of the invention, the compound according to general formula (I) is characterized in that R¹ represents 5- or 6-membered heteroaryl, unsubstituted or mono- or polysubstituted by one or more substituents selected from the group consisting of F; Cl; Br; I; NO₂; CN; C₁₋₆-alkyl; CF₃; CF₂H; CFH₂; CF₂Cl; CFCl₂; C(=O)—H; C(=O)—C₁₋₆-alkyl; C(=O)—OH; C(=O)—O—C₁₋₆-alkyl; C(=O)—N(H)(OH); C(=O)—NH₂; C(=O)—N(H)(C₁₋₆-alkyl); C(=O)—N(C₁₋₆-alkyl)₂; C(=N—OH)—H; C(=N—OH)—C₁₋₆-alkyl; C(=N—O—C₁₋₆-alkyl)-H; C(=N—O—C₁₋₆-alkyl)-C₁₋₆-alkyl; OH; OCF₃; OCF₂H; OCFH₂; OCF₂Cl; OCFCl₂; O—C₁₋₆-alkyl; O—C(=O)—C₁₋₆-alkyl; O—C(=O)—O—C₁₋₆-alkyl; O—(C=O)—N(H)(C₁₋₆-alkyl); O—C(=O)—N(C₁₋₆-alkyl)₂; O—S(=O)₂—C₁₋₆-alkyl; O—S(=O)₂—OH; O—S(=O)₂—O—C₁₋₆-alkyl; O—S(=O)₂—NH₂; O—S(=O)₂—N(H)(C₁₋₆-alkyl); O—S(=O)₂—N(C₁₋₆-alkyl)₂; NH₂; N(H)(C₁₋₆-alkyl); N(C₁₋₆-alkyl)₂; N(H)—C(=O)—C₁₋₆-alkyl; N(H)—C(=O)—O—C₁₋₆-alkyl; N(H)—C(=O)—NH₂; N(H)—C(=O)—N(H)(C₁₋₆-alkyl); N(H)—C(=O)—N(C₁₋₆-alkyl)₂; N(C₁₋₆-alkyl)-C(=O)—C₁₋₆-alkyl; N(C₁₋₆-alkyl)-C(=O)—O—C₁₋₆-alkyl; N(C₁₋₆-alkyl)-C(=O)—NH₂; N(C₁₋₆-alkyl)-C(=O)—N(H)(C₁₋₆-alkyl); N(C₁₋₆-alkyl)-C(=O)—N(C₁₋₆-alkyl)₂; N(H)—S(=O)₂OH; N(H)—S(=O)₂—C₁₋₆-alkyl; N(H)—S(=O)₂—O—C₁₋₆-alkyl; N(H)—S(=O)₂—NH₂; N(H)—S(=O)₂—N(H)(C₁₋₆-alkyl); N(H)—S(=O)₂

N(C$_{1-6}$-alkyl)$_2$; N(C$_{1-6}$-alkyl)-S(=O)$_2$—OH; N(C$_{1-6}$-alkyl)-S(=O)$_2$—C$_{1-6}$-alkyl; N(C$_{1-6}$-alkyl)-S(=O)$_2$—O—C$_{1-6}$-alkyl; N(C$_{1-6}$-alkyl)-S(=O)$_2$—NH$_2$; N(C$_{1-6}$-alkyl)-S(=O)$_2$—N(H)(C$_{1-6}$-alkyl); N(C$_{1-6}$-alkyl)-S(=O)$_2$—N(C$_{1-6}$-alkyl)$_2$; SH; SCF$_3$; SCF$_2$H; SCFH$_2$; SCF$_2$Cl; SCFCl$_2$; S—C$_{1-6}$-alkyl; S(=O)—C$_{1-6}$-alkyl; S(=O)$_2$—C$_{1-6}$-alkyl; S(=O)$_2$—OH; S(=O)$_2$—O—C$_{1-6}$-alkyl; S(=O)$_2$—NH$_2$; S(=O)$_2$—N(H)(C$_{1-6}$-alkyl); S(=O)$_2$—N(C$_{1-6}$-alkyl)$_2$; C$_{3-6}$-cycloalkyl or 3 to 7 membered heterocyclyl, wherein each C$_{1-6}$-alkyl in each case may be branched or unbranched and in each case may be independently unsubstituted or mono- or poly-substituted and wherein each C$_{3-6}$-cycloalkyl or 3 to 7 membered heterocyclyl may in each case be independently unsubstituted or mono- or polysubstituted.

Preferably, the compound according to general formula (I) is characterized in that m is 0 and R$^1$ represents 5- or 6-membered heteroaryl, unsubstituted or mono- or polysubstituted by one or more substituents selected from the group consisting of F; Cl; Br; I; NO$_2$; CN; C$_{1-6}$-alkyl; CF$_3$; CF$_2$H; CFH$_2$; CF$_2$Cl; CFCl$_2$; C(=O)—H; C(=O)—C$_{1-6}$-alkyl; C(=O)—OH; C(=O)—O—C$_{1-6}$-alkyl; C(=O)—N(H)(OH); C(=O)—NH$_2$; C(=O)—N(H)(C$_{1-6}$-alkyl); C(=O)—N(C$_{1-6}$-alkyl)$_2$; C(=N—OH)—H; C(=N—OH)—C$_{1-6}$-alkyl; C(=N—O—C$_{1-6}$-alkyl)-H; C(=N—O—C$_{1-6}$-alkyl)-C$_{1-6}$-alkyl; OH; OCF$_3$; OCF$_2$H; OCFH$_2$; OCF$_2$Cl; OCFCl$_2$; O—C$_{1-6}$-alkyl; O—C(=O)—C$_{1-6}$-alkyl; O—C(=O)—O—C$_{1-6}$-alkyl; O—(C=O)—N(H)(C$_{1-6}$-alkyl); O—C(=O)—N(C$_{1-6}$-alkyl)$_2$; O—S(=O)$_2$—C$_{1-6}$-alkyl; O—S(=O)$_2$—OH; O—S(=O)$_2$—O—C$_{1-6}$-alkyl; O—S(=O)$_2$—NH$_2$; O—S(=O)$_2$—N(H)(C$_{1-6}$-alkyl); O—S(=O)$_2$—N(C$_{1-6}$-alkyl)$_2$; NH$_2$; N(H)(C$_{1-6}$-alkyl); N(C$_{1-6}$-alkyl)$_2$; N(H)—C(=O)—C$_{1-6}$-alkyl; N(H)—C(=O)—O—C$_{1-6}$-alkyl; N(H)—C(=O)—NH$_2$; N(H)—C(=O)—N(H)(C$_{1-6}$-alkyl); N(H)—C(=O)—N(C$_{1-6}$-alkyl)$_2$; N(C$_{1-6}$-alkyl)-C(=O)—C$_{1-6}$-alkyl; N(C$_{1-6}$-alkyl)-C(=O)—O—C$_{1-6}$-alkyl; N(C$_{1-6}$-alkyl)-C(=O)—NH$_2$; N(C$_{1-6}$-alkyl)-C(=O)—N(H)(C$_{1-6}$-alkyl); N(C$_{1-6}$-alkyl)-C(=O)—N(C$_{1-6}$-alkyl)$_2$; N(H)—S(=O)$_2$OH; N(H)—S(=O)$_2$—C$_{1-6}$-alkyl; N(H)—S(=O)$_2$—O—C$_{1-6}$-alkyl; N(H)—S(=O)$_2$—NH$_2$; N(H)—S(=O)$_2$—N(H)(C$_{1-6}$-alkyl); N(H)—S(=O)$_2$N(C$_{1-6}$-alkyl)$_2$; N(C$_{1-6}$-alkyl)-S(=O)$_2$—OH; N(C$_{1-6}$-alkyl)-S(=O)$_2$—C$_{1-6}$-alkyl; N(C$_{1-6}$-alkyl)-S(=O)$_2$—O—C$_{1-6}$-alkyl; N(C$_{1-6}$-alkyl)-S(=O)$_2$—NH$_2$; N(C$_{1-6}$-alkyl)-S(=O)$_2$—N(H)(C$_{1-6}$-alkyl); N(C$_{1-6}$-alkyl)-S(=O)$_2$—N(C$_{1-6}$-alkyl)$_2$; SH; SCF$_3$; SCF$_2$H; SCFH$_2$; SCF$_2$Cl; SCFCl$_2$; S—C$_{1-6}$-alkyl; S(=O)—C$_{1-6}$-alkyl; S(=O)$_2$—C$_{1-6}$-alkyl; S(=O)$_2$—OH; S(=O)$_2$—O—C$_{1-6}$-alkyl; S(=O)$_2$—NH$_2$; S(=O)$_2$—N(H)(C$_{1-6}$-alkyl); S(=O)$_2$—N(C$_{1-6}$- alkyl)$_2$; C$_{3-6}$-cycloalkyl or 3 to 7 membered heterocyclyl.

wherein each C$_{1-6}$-alkyl in each case may be branched or unbranched and in each case may be independently unsubstituted or mono- or poly-substituted and wherein each C$_{3-6}$-cycloalkyl or 3 to 7 membered heterocyclyl may in each case be independently unsubstituted or mono- or polysubstituted.

Preferably, the compound according to general formula (I) is characterized in that R$^1$ is selected from the group consisting of

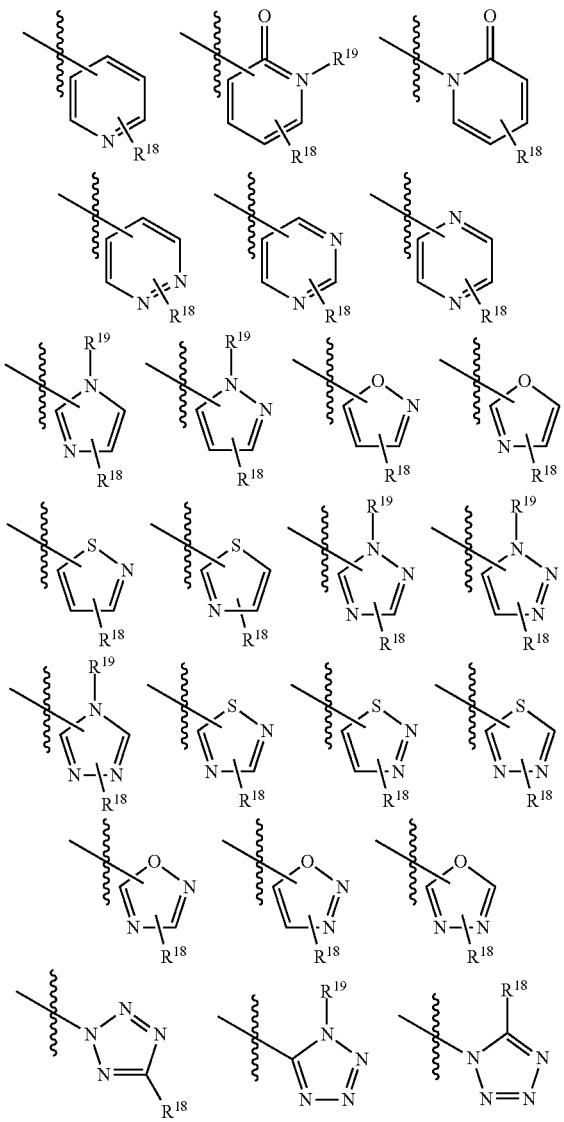

wherein

R$^{18}$ represents 0, 1, 2 or 3 substituents, selected from C$_{1-6}$-alkyl, CF$_3$, F, Cl, CN, OH, OCF$_3$, O—C$_{1-6}$-alkyl, SO$_2$—C$_{1-6}$-alkyl, NH$_2$, N(H)C$_{1-6}$-alkyl, N(C$_{1-6}$-alkyl)$_2$, 1-pyrrolidinyl, 1-piperidinyl, 4-methyl-piperidin-1-yl or 1-morpholinyl, and R$^{19}$ represents H or C$_{1-6}$-alkyl.

More preferably, the compound according to general formula (I) is characterized in that n is 1, m is 0 and R$^1$ is selected from the group consisting of

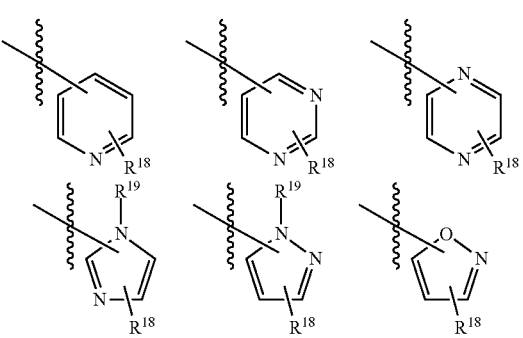

-continued

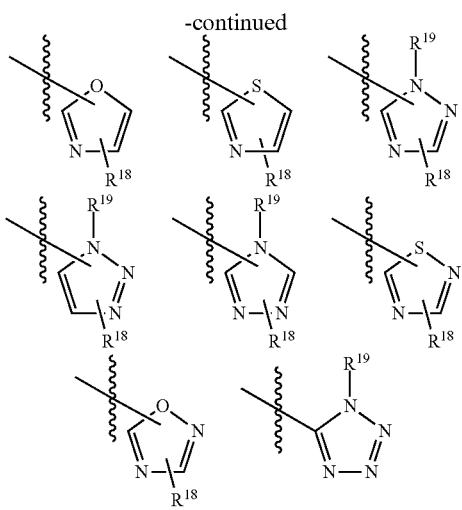

wherein

R$^{18}$ represents 0, 1, 2 or 3 substituents, selected from CH$_3$, CH$_2$CH$_3$, CH(CH$_3$)$_2$, CF$_3$, F, Cl, CN, OH, OCF$_3$, OCH$_3$, OCH$_2$CH$_3$, OCH(CH$_3$)$_2$, and R$^{19}$ represents H, CH$_3$, CH$_2$CH$_3$ or CH(CH$_3$)$_2$.

In another embodiment of the first aspect of the invention, the compound according to general formula (I) is characterized in that R$^2$ represents CH$_2$F, CHF$_2$ or CF$_3$. Preferably, R$^2$ represents CHF$_2$ or CF$_3$.

A particularly preferred compound according to formula (I) is characterized in that R$^2$ represents CF$_3$.

Another particularly preferred compound according to formula (I) is characterized in that R$^2$ represents CHF$_2$.

In a further embodiment of the first aspect of the invention, the compound according to general formula (I) is characterized in that R$^3$ represents H, C$_{1-6}$-alkyl, branched or unbranched, unsubstituted or mono- or poly-substituted, C$_{3-6}$-cycloalkyl or 3 to 7 membered heterocyclyl, in each case unsubstituted or mono- or polysubstituted; OH; O—C$_{1-6}$-alkyl; NH$_2$; N(H)—C$_{1-6}$-alkyl; N(C$_{1-6}$-alkyl)$_2$ or SO$_2$(—C$_{1-6}$-alkyl), wherein in each case C$_{1-6}$-alkyl may be branched or unbranched and may be unsubstituted or mono- or polysubstituted.

Preferably, R$^3$ is selected from the group consisting of H, methyl, ethyl, n-propyl, iso-propyl, n-butyl, sec-butyl, iso-butyl, tert-butyl, cyclopropyl, methoxy, ethoxy, methylsulfonyl, 2-oxetyl, 3-oxetyl, 2-tetrahydrofuranyl and 3-tetrahydrofuranyl.

More preferably, R$^3$ is selected from the group consisting of H, methyl, ethyl, iso-propyl and cyclopropyl. Even more preferably, R$^3$ represents H or methyl.

In a particularly preferred embodiment of the invention, the compound according to general formula (I) is characterized in that R$^3$ represents methyl (CH$_3$). In another particularly preferred embodiment of the invention, the compound according to general formula (I) is characterized in that R$^3$ represents H.

In another embodiment of the first aspect of the invention, the compound according to general formula (I) is characterized in that (Het)Aryl is selected from the group consisting of phenyl, naphthyl, pyrrol, furanyl, thienyl, pyrazolyl, imidazolyl, isoxazolyl, isothiazolyl, oxazolyl, thiazolyl, triazolyl, oxadiazolyl, thiadiazolyl, tetrazolyl, indolyl, benzofuranyl, benzothienyl, indazolyl, benzimidazolyl, benzoxazolyl, benzothiazolyl, benzotriazolyl, pyridinyl, pyrazinyl, pyrimidinyl, pyridazinyl, triazinyl, quinolinyl, isoquinolinyl, quinoxalinyl, quinazolinyl, cinnolinyl, 1,5-naphthyridinyl, 1,6-naphthyridinyl, 1,7-naphthyridinyl, 1,8-naphthyridinyl, 2,3-naphthyridinyl, 2,6-naphthyridinyl and 2,7-naphthyridinyl, each substituted by zero or one or two or three substituents of the group consisting of R$^6$, R$^7$ and R$^8$.

Particularly preferred compounds according to the invention are characterized in that the (Het)Aryl substituent is selected from aryl substituents. Therefore, in one preferred embodiment of the first aspect of the invention, the compound according to general formula (I) is characterized in that (Het)Aryl is selected from the group consisting of phenyl, 1-naphthyl or 2-naphthyl, each substituted by zero or one or two or three substituents of the group consisting of R$^6$, R$^7$ and R$^8$.

Also particularly preferred compounds according to the invention are characterized in that the (Het)Aryl substituent is selected from heteroaryl substituents. Therefore, in another preferred embodiment of the first aspect of the invention, the compound according to general formula (I) is characterized in that (Het)Aryl is selected from the group consisting of pyrrol, furanyl, thienyl, pyrazolyl, imidazolyl, isoxazolyl, isothiazolyl, oxazolyl, thiazolyl, triazolyl, oxadiazolyl, thiadiazolyl, tetrazolyl, indolyl, benzofuranyl, benzothienyl, indazolyl, benzimidazolyl, benzoxazolyl, benzothiazolyl, benzotriazolyl, pyridinyl, pyrazinyl, pyrimidinyl, pyridazinyl, triazinyl, quinolinyl, isoquinolinyl, quinoxalinyl, quinazolinyl, cinnolinyl, 1,5-naphthyridinyl, 1,6-naphthyridinyl, 1,7-naphthyridinyl, 1,8-naphthyridinyl, 2,3-naphthyridinyl, 2,6-naphthyridinyl and 2,7-naphthyridinyl, each substituted by zero or one or two or three substituents of the group consisting of R$^6$, R$^7$ and R$^8$.

Preferably, (Het)Aryl is selected from the group consisting of phenyl, pyrrol, pyrazolyl, imidazolyl, isoxazolyl, oxazolyl, thiazolyl, pyridinyl, pyrazinyl, pyrimidinyl and pyridazinyl, each substituted by zero or one or two or three substituents of the group consisting of R$^6$, R$^7$ and R$^8$.

More preferably, (Het)Aryl represents phenyl, substituted by zero or one or two or three substituents of the group consisting of R$^6$, R$^7$ and R$^8$.

In another embodiment of the first aspect of the invention, the compound according to general formula (I) is characterized in that R$^6$, R$^7$ and R$^8$ are independently selected from the group consisting of F; Cl; CN; C$_{1-6}$-alkyl; CF$_3$; CF$_2$H; CFH$_2$; OH; OCF$_3$; OCF$_2$H; OCFH$_2$; O—C$_{1-6}$-alkyl; O—C(═O)—C$_{1-6}$-alkyl; NH$_2$; N(H)(C$_{1-6}$-alkyl); N(C$_{1-6}$-alkyl)$_2$; SCF$_3$; S(═O)—C$_{1-6}$-alkyl; S(═O)$_2$—C$_{1-6}$-alkyl; S(═O)$_2$—OH; S(═O)$_2$—O—C$_{1-6}$-alkyl; S(═O)$_2$—NH$_2$; S(═O)$_2$—N(H)(C$_{1-6}$-alkyl); S(═O)$_2$—N(C$_{1-6}$-alkyl)$_2$; C$_{3-6}$-cycloalkyl or O—C$_{3-6}$-cycloalkyl, wherein in each case said C$_{1-6}$-alkyl may be branched or unbranched and wherein in each case said C$_{3-6}$-cycloalkyl may be unsubstituted or mono- or polysubstituted.

Preferably, R$^6$, R$^7$ and R$^8$ are each independently selected from the group consisting of F; Cl; CN; C$_{1-6}$-alkyl; CF$_3$; CF$_2$H; CFH$_2$; OH; OCF$_3$; OCF$_2$H; OCFH$_2$; O—C$_{1-6}$-alkyl; S(═O)—C$_{1-6}$-alkyl; S(═O)$_2$—C$_{1-6}$-alkyl; cyclopropyl and O-cyclopropyl.

More preferably, (Het)Aryl is selected from the group consisting of phenyl, pyrrol, pyrazolyl, imidazolyl, isoxazolyl, oxazolyl, thiazolyl, pyridinyl, pyrazinyl, pyrimidinyl and pyridazinyl, each substituted by zero or one or two or three substituents of the group consisting of R$^6$, R$^7$ and R$^8$, wherein R$^6$, R$^7$ and R$^8$ are each independently of one another selected from the group consisting of F; Cl; CN; C$_{1-6}$-alkyl; CF$_3$; CF$_2$H; CFH$_2$; OH; OCF$_3$; OCF$_2$H; OCFH$_2$; O—C$_{1-6}$-alkyl; O—C(═O)—C$_{1-6}$-alkyl; NH$_2$; N(H)(C$_{1-6}$-alkyl); N(C$_{1-6}$-alkyl)$_2$; SCF$_3$; S(═O)—C$_{1-6}$-alkyl; S(═O)$_2$—C$_{1-6}$- alkyl; S(=O)$_2$—OH; S(=O)$_2$—O—C$_{1-6}$-alkyl; S(=O)$_2$—NH$_2$; S(=O)$_2$—N(H)(C$_{1-6}$-alkyl); S(=O)$_2$—N(C$_{1-6}$-alkyl)$_2$; C$_{3-6}$-cycloalkyl or O—C$_{3-6}$-cycloalkyl, wherein in each case said C$_{1-6}$-alkyl may be branched or unbranched and wherein in each case said C$_{3-6}$-cycloalkyl may be unsubstituted or mono- or polysubstituted.

Even more preferably, (Het)Aryl is selected from the group consisting of phenyl, pyrrol, pyrazolyl, imidazolyl, isoxazolyl, oxazolyl, thiazolyl, pyridinyl, pyrazinyl, pyrimidinyl and pyridazinyl, each substituted by zero or one or two or three substituents of the group consisting of R$^6$, R$^7$ and R$^8$, wherein R$^6$, R$^7$ and R$^8$ are each independently of one another selected from the group consisting of F; Cl; CN; C$_{1-6}$-alkyl; CF$_3$; CF$_2$H; CFH$_2$; OH; OCF$_3$; OCF$_2$H; OCFH$_2$; O—C$_{1-6}$-alkyl; S(=O)—C$_{1-6}$-alkyl; S(=O)$_2$—C$_{1-6}$-alkyl; cyclopropyl and O-cyclopropyl.

Yet more preferably, (Het)Aryl is selected from the group consisting of phenyl, pyridin-2-yl, pyridin-3-yl, pyridin-4-yl, pyrazin-2-yl, pyrimidin-2-yl, pyrimidin-4-yl, pyrimidin-5-yl, pyridazin-3-yl, pyridazin-4-yl, pyrazol-3-yl, pyrazol-4-yl, pyrazol-5-yl, isoxazol-3-yl, isoxazol-4-yl, isoxazol-5-yl, oxazol-2-yl, oxazol-4-yl, oxazol-5-yl, thiazol-2-yl, thiazol-4-yl, thiazol-5-yl,
each substituted by zero or one or two substituents of the group consisting of R$^6$ and R$^7$, wherein R$^6$ and R$^7$ are each independently of one another selected from the group consisting of F; Cl; CN; CF$_3$; CH$_3$; OH; OCF$_3$; OCH$_3$; S(=O)CH$_3$; S(=O)$_2$CH$_3$; cyclopropyl and O-cyclopropyl.

Even more preferably, (Het)Aryl represents phenyl, substituted by zero or one or two substituents of the group consisting of R$^6$ and R$^7$, wherein R$^6$ and R$^7$ are each independently of one another selected from the group consisting of F; Cl; CN; CF$_3$; CH$_3$; OH; OCF$_3$; OCH$_3$; S(=O)CH$_3$; S(=O)$_2$CH$_3$; cyclopropyl and O-cyclopropyl.

Particularly preferred, (Het)Aryl is selected from the group consisting of phenyl, 2-fluoro-phenyl, 3-fluoro-phenyl, 4-fluoro-phenyl, 2-chloro-phenyl, 3-chloro-phenyl, 4-chloro-phenyl, 2-cyano-phenyl, 3-cyano-phenyl, 4-cyano-phenyl, 2-methoxy-phenyl, 3-methoxy-phenyl, 4-methoxy-phenyl, 2-methyl-phenyl, 3-methyl-phenyl, 4-methyl-phenyl, 2-trifluoromethyl-phenyl, 3-trifluoromethyl-phenyl, 4-trifluoromethyl-phenyl, 2,3-difluoro-phenyl, 2,4-difluoro-phenyl, 2,5-difluoro-phenyl, 2,6-difluoro-phenyl, 3,4-difluoro-phenyl, 3,5-difluoro-phenyl, 2,3-dichloro-phenyl, 2,4-dichloro-phenyl, 2,5-dichloro-phenyl, 2,6-dichloro-phenyl, 3,4-dichloro-phenyl, 3,5-dichloro-phenyl, 4-chloro-2-fluoro-phenyl, 3-chloro-2-fluoro-phenyl, 5-chloro-2-fluoro-phenyl, 6-chloro-2-fluoro-phenyl, 4-chloro-3-fluoro-phenyl, 2-chloro-3-fluoro-phenyl, 5-chloro-3-fluoro-phenyl, 6-chloro-3-fluoro-phenyl, 2-chloro-4-fluoro-phenyl, 3-chloro-4-fluoro-phenyl, 6-hydroxy-pyridin-3-yl, 3-fluoro-5-(trifluoromethyl)-pyridin-2-yl, 6-cyano-4-methyl-pyridin-3-yl, 6-chloro-4-methyl-pyridin-3-yl, 6-methoxy-4-methyl-pyridin-3-yl, 2-cyano-4-methyl-pyridin-5-yl, pyridin-2-yl, 3-fluoro-pyridin-2-yl, 4-fluoro-pyridin-2-yl, 5-fluoro-pyridin-2-yl, 6-fluoro-pyridin-2-yl, 3-chloro-pyridin-2-yl, 4-chloro-pyridin-2-yl, 5-chloro-pyridin-2-yl, 6-chloro-pyridin-2-yl, 3-cyano-pyridin-2-yl, 4-cyano-pyridin-2-yl, 5-cyano-pyridin-2-yl, 6-cyano-pyridin-2-yl, 3-methoxy-pyridin-2-yl, 4-methoxy-pyridin-2-yl, 5-methoxy-pyridin-2-yl, 6-methoxy-pyridin-2-yl, 3-methyl-pyridin-2-yl, 4-methyl-pyridin-2-yl, 5-methyl-pyridin-2-yl, 6-methyl-pyridin-2-yl, 3-trifluoromethyl-pyridin-2-yl, 4-trifluoromethyl-pyridin-2-yl, 5-trifluoromethyl-pyridin-2-yl, 6-trifluoromethyl-pyridin-2-yl, pyridin-3-yl, 2-fluoro-pyridin-3-yl, 4-fluoro-pyridin-3-yl, 5-fluoro-pyridin-3-yl, 6-fluoro-pyridin-3-yl, 2-chloro-pyridin-3-yl, 4-chloro-pyridin-3-yl, 5-chloro-pyridin-3-yl, 6-chloro-pyridin-3-yl, 2-cyano-pyridin-3-yl, 4-cyano-pyridin-3-yl, 5-cyano-pyridin-3-yl, 6-cyano-pyridin-3-yl, 2-methoxy-pyridin-3-yl, 4-methoxy-pyridin-3-yl, 5-methoxy-pyridin-3-yl, 6-methoxy-pyridin-3-yl, 2-methyl-pyridin-3-yl, 4-methyl-pyridin-3-yl, 5-methyl-pyridin-3-yl, 6-methyl-pyridin-3-yl, 2-trifluoromethyl-pyridin-3-yl, 4-trifluoromethyl-pyridin-3-yl, 5-trifluoromethyl-pyridin-3-yl, 6-trifluoromethyl-pyridin-3-yl, pyridin-4-yl, 2-fluoro-pyridin-4-yl, 3-fluoro-pyridin-4-yl, 2-chloro-pyridin-4-yl, 3-chloro-pyridin-4-yl, 2-cyano-pyridin-4-yl, 3-cyano-pyridin-4-yl, 2-methoxy-pyridin-4-yl, 3-methoxy-pyridin-4-yl, 2-methyl-pyridin-4-yl, 3-methyl-pyridin-4-yl, 2-trifluoromethyl-pyridin-4-yl, 3-trifluoromethyl-pyridin-4-yl, pyrimidin-2-yl, 4-fluoro-pyrimidin-2-yl, 4-chloro-pyrimidin-2-yl, 5-fluoro-pyrimidin-2-yl, 5-chloro-pyrimidin-2-yl, 4-methoxy-pyrimidin-2-yl, 4-methyl-pyrimidin-2-yl, 5-methoxy-pyrimidin-2-yl, 5-methyl-pyrimidin-2-yl, 4-trifluoromethyl-pyrimidin-2-yl, 4-cyano-pyrimidin-2-yl, 5-trifluoromethyl-pyrimidin-2-yl, 5-cyano-pyrimidin-2-yl, pyrimidin-4-yl, 2-fluoro-pyrimidin-4-yl, 2-chloro-pyrimidin-4-yl, 5-fluoro-pyrimidin-4-yl, 5-chloro-pyrimidin-4-yl, 6-fluoro-pyrimidin-4-yl, 6-chloro-pyrimidin-4-yl, 2-trifluoro-methyl-pyrimidin-4-yl, 2-cyano-pyrimidin-4-yl, 5-trifluoromethyl-pyrimidin-4-yl, 5-cyano-pyrimidin-4-yl, 6-trifluoromethyl-pyrimidin-4-yl, 6-cyano-pyrimidin-4-yl, 2-methyl-pyrimidin-4-yl, 2-methoxy-pyrimidin-4-yl, 5-methyl-pyrimidin-4-yl, 5-methoxy-pyrimidin-4-yl, 6-methyl-pyrimidin-4-yl, 6-methoxy-pyrimidin-4-yl, pyrimidin-5-yl, 2-fluoro-pyrimidin-5-yl, 2-chloro-pyrimidin-5-yl, 4-fluoro-pyrimidin-5-yl, 4-chloro-pyrimidin-5-yl, 2-methyl-pyrimidin-5-yl, 2-methoxy-pyrimidin-5-yl, 4-methyl-pyrimidin-5-yl, 4-methoxy-pyrimidin-5-yl, 2-trifluoromethyl-pyrimidin-5-yl, 2-cyano-pyrimidin-5-yl, 4-trifluoromethyl-pyrimidin-5-yl, 4-cyano-pyrimidin-5-yl, pyrazin-2-yl, 2-methoxy-pyrazin-2-yl, 5-methoxy-pyrazin-2-yl, 6-methoxy-pyrazin-2-yl, 2-methyl-pyrazin-2-yl, 5-methyl-pyrazin-2-yl, 6-methyl-pyrazin-2-yl, 2-fluoro-pyrazin-2-yl, 5-fluoro-pyrazin-2-yl, 6-fluoro-pyrazin-2-yl, 2-chloro-pyrazin-2-yl, 5-chloro-pyrazin-2-yl, 6-chloro-pyrazin-2-yl, 2-trifluoromethyl-pyrazin-2-yl, 5-trifluoromethyl-pyrazin-2-yl, 6-trifluoromethyl-pyrazin-2-yl, 2-cyano-pyrazin-2-yl, 5-cyano-pyrazin-2-yl, 6-cyano-pyrazin-2-yl, pyridazin-3-yl, 4-methoxy-pyridazin-3-yl, 5-methoxy-pyridazin-3-yl, 6-methoxy-pyridazin-3-yl, 4-methyl-pyridazin-3-yl, 5-methyl-pyridazin-3-yl, 6-methyl-pyridazin-3-yl, 4-fluoro-pyridazin-3-yl, 5-fluoro-pyridazin-3-yl, 6-fluoro-pyridazin-3-yl, 4-chloro-pyridazin-3-yl, 5-chloro-pyridazin-3-yl, 6-chloro-pyridazin-3-yl, 4-trifluoromethyl-pyridazin-3-yl, 5-trifluoromethyl-pyridazin-3-yl, 6-trifluoromethyl-pyridazin-3-yl, 4-cyano-pyridazin-3-yl, 5-cyano-pyridazin-3-yl, 6-cyano-pyridazin-3-yl, pyridazin-4-yl, 3-methoxy-pyridazin-4-yl, 5-methoxy-pyridazin-4-yl, 6-methoxy-pyridazin-4-yl, 3-methyl-pyridazin-4-yl, 5-methyl-pyridazin-4-yl, 6-methyl-pyridazin-4-yl, 3-fluoro-pyridazin-4-yl, 5-fluoro-pyridazin-4-yl, 6-fluoro-pyridazin-4-yl, 3-chloro-pyridazin-4-yl, 5-chloro-pyridazin-4-yl, 6-chloro-pyridazin-4-yl, 3-trifluoromethyl-pyridazin-4-yl, 5-trifluoromethyl-pyridazin-4-yl, 6-trifluoromethyl-pyridazin-4-yl, 3-cyano-pyridazin-4-yl, 5-cyano-pyridazin-4-yl, 6-cyano-pyridazin-4-yl, thiophen-2-yl, 1H-pyrazol-4-yl, 1-methyl-1H-pyrazol-4-yl, 5-trifluoromethyl-1-methyl-1H-pyrazol-4-yl, 3-trifluoromethyl-1-methyl-1H-pyrazol-4-yl, 1,5-dimethyl-1H-pyrazol-4-yl, 1,3-dimethyl-1H-pyrazol-4-yl, 1,3,5-trimethyl-1H-pyrazol-4-yl, 1H-pyrazol-3-yl, 1-methyl-1H-pyrazol-3-yl, 5-trifluoromethyl-1-methyl-1H-pyrazol-3-yl, 4-trifluoromethyl-1-methyl-1H-pyrazol-3-yl, 1,5-dimethyl-1H-pyrazol-3-yl, 1,4-dimethyl-1H-pyrazol-3-yl and 1,4,5-trimethyl-1H-pyrazol-3-yl.

Particularly preferred, (Het)Aryl is selected from the group consisting of phenyl, 2-fluoro-phenyl, 3-fluoro-phenyl, 4-fluoro-phenyl, 2-chloro-phenyl, 3-chloro-phenyl, 4-chloro-phenyl, 2,4-difluoro-phenyl, 3,4-difluoro-phenyl, 2,4-dichloro-phenyl, 3,4-dichloro-phenyl, 4-chloro-2-fluoro-phenyl, 4-chloro-3-fluoro-phenyl, 2-chloro-4-fluoro-phenyl and 3-chloro-4-fluoro-phenyl.

In another embodiment of the first aspect of the invention, the compound according to general formula (I) is characterized in that is a compound according to general formula (Ia),

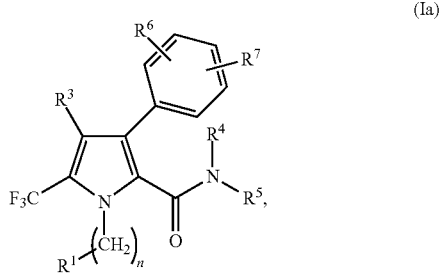

(Ia)

wherein $R^3$ represents H or $CH_3$ or cyclopropyl;

$R^6$ and $R^7$ are independently absent or are each independently of one another selected from the group consisting of F; Cl; CN; $C_{1-6}$-alkyl; $CF_3$; $CF_2H$; $CFH_2$; OH; $OCF_3$; $OCF_2H$; $OCFH_2$; O—$C_{1-6}$-alkyl; S(=O)—$C_{1-6}$-alkyl; S(=O)$_2$—$C_{1-6}$-alkyl; cyclopropyl and O-cyclopropyl.

In another embodiment of the first aspect of the invention, the compound according to general formula (I) is characterized in that $R^4$ represents H or $C_{1-6}$-alkyl, branched or unbranched and unsubstituted or substituted with 1, 2, 3, 4 or 5 substituents independently selected from the group consisting of OH, =O, O—$C_{1-6}$-alkyl, S(=O)—$C_{1-6}$-alkyl, S(=O)$_2$—$C_{1-6}$-alkyl, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, C(=O)—$NH_2$, C(=O)—N(H)($C_{1-6}$-alkyl), C(=O)—N($C_{1-6}$-alkyl)$_2$, C(=O)—O—$C_{1-6}$-alkyl; N(H—C(=O)—$C_{1-6}$-alkyl, and N($C_{1-6}$-alkyl)-C(=O)—$C_{1-6}$-alkyl; or $C_{3-6}$-cycloalkyl, unsubstituted or substituted with 1, 2, 3, 4 or 5 substituents independently selected from the group consisting of F, Cl, $CF_3$, =O, $OCF_3$; $C_{1-8}$-alkylen-OH, $C_{1-6}$-alkyl, OH, O—$C_{1-6}$-alkyl, S(=O)—$C_{1-6}$-alkyl, S(=O)$_2$—$C_{1-6}$-alkyl, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, C(=O)—$NH_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl, and N($C_{1-6}$-alkyl)-C(=O)—$C_{1-6}$-alkyl; wherein said $C_{3-6}$-cycloalkyl residue is optionally connected via a $C_{1-8}$-alkylene group, which in turn may be branched or unbranched and unsubstituted or substituted with 1, 2, 3, 4 or 5 substituents independently selected from the group consisting of F, Cl, $CF_3$, =O, $OCF_3$, OH, O—$C_{1-6}$-alkyl and $C_{1-8}$-alkylen-OH; or 3 to 7 membered heterocyclyl, which is unsubstituted or substituted with 1, 2, 3, 4 or 5 substituents independently selected from the group consisting of F, Cl, $CF_3$, =O, $OCF_3$; $C_{1-8}$-alkylen-OH, $C_{1-6}$-alkyl, OH, O—$C_{1-6}$-alkyl, S(=O)—$C_{1-6}$-alkyl, S(=O)$_2$—$C_{1-6}$-alkyl, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, C(=O)—$NH_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl, and N($C_{1-6}$-alkyl)-C(=O)—$C_{1-6}$-alkyl, wherein said 3 to 7 membered heterocyclyl is optionally connected via a $C_{1-8}$-alkylene group, which in turn may be branched or unbranched and unsubstituted or substituted with 1, 2, 3, 4 or 5 substituents independently selected from the group consisting of F, Cl, $CF_3$, =O, $OCF_3$, OH, O—$C_{1-6}$-alkyl and $C_{1-8}$-alkylen-OH.

More preferably, $R^4$ represents represents H or $C_{1-6}$-alkyl, branched or unbranched and unsubstituted or substituted with 1, 2, 3, 4 or 5 substituents independently selected from the group consisting of OH, =O, O—$C_{1-6}$-alkyl, S(=O)—$C_{1-6}$-alkyl, S(=O)$_2$—$C_{1-6}$-alkyl, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, C(=O)—$NH_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl, and N($C_{1-6}$-alkyl)-C(=O)—$C_{1-6}$-alkyl.

Still more preferably, $R^4$ represents represents H or $C_{1-6}$-alkyl. Particularly preferred, $R^4$ represents represents H, methyl, ethyl, iso-propyl or n-propyl.

In a preferred embodiment of the first aspect of the present invention, $R^4$ denotes methyl. In another preferred embodiment of the first aspect of the present invention, $R^4$ represents H.

In another embodiment of the first aspect of the invention, the compound according to general formula (I) is characterized in that $R^5$ represents H or $C_{1-6}$-alkyl, branched or unbranched and unsubstituted or substituted with 1, 2, 3, 4 or 5 substituents independently selected from the group consisting of F, Cl, $CF_3$, CN, OH, =O, $OCF_3$, O—$C_{1-6}$-alkyl, O—(C=O)$C_{1-6}$-alkyl, S(=O)—$C_{1-6}$-alkyl, S(=O)$_2$—$C_{1-6}$-alkyl, S(=O)$_2$—$NH_2$, S(=O)$_2$—N(H)$C_{1-6}$-alkyl, S(=O)$_2$—N($C_{1-6}$-alkyl)$_2$, $NH_2$, NH($C_{1-6}$-alkyl), N($C_{1-6}$-alkyl)$_2$, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, N(H)—C(=O)—$NH_2$, N(H)—C(=O)—N(H)($C_{1-6}$-alkyl), N(H)—C(=O)—N($C_{1-6}$-alkyl)$_2$, N(H)—C(=O)—O—$C_{1-6}$-alkyl; O—C(=O)—$NH_2$, O—C(=O)—N(H)($C_{1-6}$-alkyl), O—C(=O)—N($C_{1-6}$-alkyl)$_2$, C(=O)—$NH_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl, and N($C_{1-6}$-alkyl)-C(=O)—$C_{1-6}$-alkyl; or $C_{3-6}$-cycloalkyl, unsubstituted or substituted with 1, 2, 3, 4 or 5 substituents independently selected from the group consisting of F, Cl, CN, $CF_3$, =O, $OCF_3$, $C_{1-8}$-alkylen-OH, $C_{1-6}$-alkyl, OH, O—$C_{1-6}$-alkyl, O—(C=O)$C_{1-6}$-alkyl, S(=O)—$C_{1-6}$-alkyl, S(=O)$_2$—$C_{1-6}$-alkyl, S(=O)$_2$—$NH_2$, S(=O)$_2$—N(H)$C_{1-6}$-alkyl, S(=O)$_2$—N($C_{1-6}$-alkyl)$_2$, $NH_2$, NH($C_{1-6}$-alkyl), N($C_{1-6}$-alkyl)$_2$, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, N(H)—C(=O)—O—$C_{1-6}$-alkyl; O—C(=O)—$NH_2$, O—C(=O)—N(H)($C_{1-6}$-alkyl), O—C(=O)—N($C_{1-6}$-alkyl)$_2$, N(H)—C(=O)—$NH_2$, N(H)—C(=O)—N(H)($C_{1-6}$-alkyl), N(H)—C(=O)—N($C_{1-6}$-alkyl)$_2$, C(=O)—$NH_2$, C(=O)—N(H)($C_{1-6}$-alkyl), C(=O)—N($C_{1-6}$-alkyl)$_2$, C(=O)—O—

$C_{1-6}$-alkyl; N(H)—C(=O)—$C_{1-6}$-alkyl, and N($C_{1-6}$-alkyl)-C(=O)—$C_{1-6}$-alkyl; wherein said $C_{3-6}$-cycloalkyl is optionally connected via a $C_{1-8}$-alkylene group, which in turn may be branched or unbranched and unsubstituted or substituted with 1, 2, 3, 4 or 5 substituents independently selected from the group consisting of F, Cl, $CF_3$, =O, $OCF_3$, OH, O—$C_{1-6}$-alkyl and $C_{1-8}$-alkylen-OH; or 3 to 7 membered heterocyclyl, which is unsubstituted or substituted with 1, 2, 3, 4 or 5 substituents independently from one another selected from the group consisting of F, Cl, CN, $CF_3$, =O, $OCF_3$, $C_{1-6}$-alkylen-OH, $C_{1-6}$-alkyl, OH, O—$C_{1-6}$-alkyl, O—(C=O)$C_{1-6}$-alkyl, S(=O)—$C_{1-6}$-alkyl, $S(=O)_2$—$C_{1-6}$-alkyl, $S(=O)_2$—$NH_2$, $S(=O)_2$—N(H)$C_{1-6}$-alkyl, $S(=O)_2$—N($C_{1-6}$-alkyl)$_2$, $NH_2$, NH($C_{1-6}$-alkyl), N($C_{1-6}$-alkyl)$_2$, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, N(H)—C(=O)—O—$C_{1-6}$-alkyl; O—C(=O)—$NH_2$, O—C(=O)—N(H)($C_{1-6}$-alkyl), O—C(=O)—N($C_{1-6}$-alkyl)$_2$, N(H)—C(=O)—$NH_2$, N(H)—C(=O)—N(H)($C_{1-6}$-alkyl), N(H)—C(=O)—N($C_{1-6}$-alkyl)$_2$, (C=O)$C_{1-6}$-alkyl, C(=O)—$NH_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl, and N($C_{1-6}$-alkyl)-C(=O)—$C_{1-6}$-alkyl; wherein said 3 to 7 membered heterocyclyl is optionally connected via a $C_{1-8}$-alkylene group, which in turn may be branched or unbranched and unsubstituted or substituted with 1, 2, 3, 4 or 5 substituents independently selected from the group consisting of F, Cl, $CF_3$, =O, $OCF_3$, OH, O—$C_{1-6}$-alkyl and $C_{1-8}$-alkylen-OH; or aryl or heteroaryl, which is unsubstituted or substituted with 1, 2, 3, 4 or 5 substituents selected from the group consisting of F, Cl, CN, $CF_3$, $OCF_3$, $C_{1-8}$-alkylen-OH, $C_{1-6}$-alkyl, OH, O—$C_{1-6}$-alkyl, O—(C=O)$C_{1-6}$-alkyl, S(=O)—$C_{1-6}$-alkyl, $S(=O)_2$—$C_{1-6}$-alkyl, $S(=O)_2$—$NH_2$, $S(=O)_2$—N(H)$C_{1-6}$-alkyl, $S(=O)_2$—N($C_{1-6}$-alkyl)$_2$, $NH_2$, NH($C_{1-6}$-alkyl), N($C_{1-6}$-alkyl)$_2$, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, N(H)—C(=O)—O—$C_{1-6}$-alkyl; O—C(=O)—$NH_2$, O—C(=O)—N(H)($C_{1-6}$-alkyl), O—C(=O)—N($C_{1-6}$-alkyl)$_2$, N(H)—C(=O)—$NH_2$, N(H)—C(=O)—N(H)($C_{1-6}$-alkyl), N(H)—C(=O)—N($C_{1-6}$-alkyl)$_2$, C(=O)—$NH_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl, and N($C_{1-6}$-alkyl)-C(=O)—$C_{1-6}$-alkyl, wherein said aryl or heteroaryl is optionally connected via a $C_{1-8}$-alkylene group, which in turn may be branched or unbranched and unsubstituted or substituted with 1, 2, 3, 4 or 5 substituents independently from one another selected from the group consisting of F, Cl, $CF_3$, =O, $OCF_3$, OH, O—$C_{1-6}$-alkyl and $C_{1-8}$-alkylen-OH.

In another preferred embodiment of the first aspect of the invention, the compound according to general formula (I) is characterized in that $R^5$ represents $C_{3-6}$-cycloalkyl, which is unsubstituted or substituted with 1, 2, 3, 4 or 5 substituents independently from one another selected from the group consisting of F, Cl, $CF_3$, =O, $OCF_3$, OH, O—$C_{1-6}$-alkyl, $C_{1-8}$-alkylen-OH and $C_{1-6}$-alkyl; or 3 to 7 membered heterocyclyl, which contains 1 or 2 heteroatoms or heteroatom groups independently from one another selected from the group consisting of O, S, S(=O), $S(=O)_2$, NH and N—$C_{1-6}$-alkyl, and which is unsubstituted or substituted with 1, 2, 3, 4 or 5 substituents independently from one another selected from the group consisting of F, Cl, $CF_3$, $OCF_3$, CN, $C_{1-6}$-alkyl, $C_{1-8}$-alkylen-OH and O—$C_{1-6}$-alkyl; or aryl or heteroaryl, which contains at least one nitrogen atom, and wherein said aryl or heteroaryl is unsubstituted or substituted with 1, 2 or 3 substituents independently from one another selected from the group consisting of F, Cl, CN, $CF_3$, $OCF_3$, $C_{1-8}$-alkylen-OH, $C_{1-6}$-alkyl, OH, O—$C_{1-6}$-alkyl, $S(=O)_2$—$C_{1-6}$-alkyl, $S(=O)_2$—$NH_2$, $NH_2$, NH($C_{1-6}$-alkyl), N($C_{1-6}$-alkyl)$_2$, O—C(=O)—$NH_2$, C(=O)—$NH_2$, C(=O)—N(H)($C_{1-6}$-alkyl), C(=O)—N($C_{1-6}$-alkyl)$_2$, C(=O)—O—$C_{1-6}$-alkyl; or a part structure of general formula SF-III

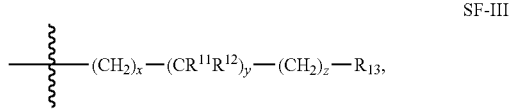

$$\xi\text{—}(CH_2)_x\text{—}(CR^{11}R^{12})_y\text{—}(CH_2)_z\text{—}R_{13},\quad \text{SF-III}$$

wherein x represents 0, 1 or 2; y represents 0, 1 or 2; z represents 0, 1 or 2;

on the condition that the sum of x, y and z is 1, 2, 3, 4, 5 or 6;

$R^{11}$ and $R^{12}$ are independently from one another selected from H or $C_{1-6}$-alkyl; or $R^{11}$ and $R^{12}$ together with the carbon atom connecting them form a $C_{3-6}$-cycloalkyl or a 3 to 7 membered heterocyclyl, which contains 1 or 2 heteroatoms or heteroatom groups independently from one another selected from the group consisting of O, S, S(=O), $S(=O)_2$, NH and N—$C_{1-6}$-alkyl, wherein said $C_{3-6}$-cycloalkyl or 3 to 7 membered heterocyclyl may be unsubstituted or substituted with 1, 2, 3, 4 or 5 substituents independently from one another selected from the group consisting of F, Cl, $CF_3$, $OCF_3$, CN, $C_{1-6}$-alkyl and O—$C_{1-6}$-alkyl;

$R^{13}$ is selected from the group consisting of

H, F, Cl, CN, OH, O—$C_{1-6}$-alkyl, O—(C=O)$C_{1-6}$-alkyl, S(=O)—$C_{1-6}$-alkyl, $S(=O)_2$—$C_{1-6}$-alkyl, $S(=O)_2$—$NH_2$, $S(=O)_2$—N(H)$C_{1-6}$-alkyl, $S(=O)_2$—N($C_{1-6}$-alkyl)$_2$, $NH_2$, NH($C_{1-6}$-alkyl), N($C_{1-6}$-alkyl)$_2$, N(H)—C(=O)—$C_{1-6}$-alkyl, N($C_{1-6}$-alkyl)-C(=O)—$C_{1-6}$-alkyl, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, C(=O)—$NH_2$, C(=O)—N(H)($C_{1-6}$-alkyl), C(=O)—N($C_{1-6}$-alkyl)$_2$, C(=O)—O—$C_{1-6}$-alkyl, N(H)—C(=O)—$NH_2$, N(H)—C(=O)—N(H)($C_{1-6}$-alkyl), N(H)—C(=O)—N($C_{1-6}$-alkyl)$_2$, N(H)—C(=O)—O—$C_{1-6}$-alkyl; O—C(=O)—$NH_2$, O—C(=O)—N(H)($C_{1-6}$-alkyl), O—C(=O)—N($C_{1-6}$-alkyl)$_2$;

or represents $C_{3-6}$-cycloalkyl, which is unsubstituted or substituted with 1, 2, 3, 4, or 5 substituents independently from one another selected from the group consisting of F, Cl, $CF_3$, =O, $OCF_3$, OH, O—$C_{1-6}$-alkyl, $C_{1-6}$-alkylen-OH and $C_{1-6}$-alkyl; or 3-7-membered heterocyclyl, which contains 1 or 2 heteroatoms or heteroatom groups independently from one another selected from the group consisting of O, S, S(=O), $S(=O)_2$, NH and N—$C_{1-6}$-alkyl, and which is unsubstituted or substituted with 1, 2, 3, 4 or 5 substituents independently from one another selected from the group consisting of F, Cl, $CF_3$, $OCF_3$, CN, $C_{1-6}$-alkyl and O—$C_{1-6}$-alkyl; or aryl or heteroaryl, which contains at least one nitrogen atom and wherein said aryl or heteroaryl is unsubstituted or substituted with 1, 2 or 3 substituents independently from one another selected from the group consisting of F, Cl, CN, $CF_3$, $OCF_3$, $C_{1-6}$-alkylen-OH, $C_{1-6}$-alkyl, OH, O—$C_{1-6}$- alkyl, S(=O)$_2$—C$_{1-6}$-alkyl, S(=O)$_2$—NH$_2$, NH$_2$, NH(C$_{1-6}$-alkyl), N(C$_{1-6}$-alkyl)$_2$, O—C(=O)—NH$_2$, C(=O)—NH$_2$, C(=O)—N(H)(C$_{1-6}$-alkyl), C(=O)—N(C$_{1-6}$-alkyl)$_2$, C(=O)—O—C$_{1-6}$-alkyl.

Preferred heteroaryl residues, which contain at least one nitrogen atom, are selected from pyridine, pyrimidine, pyrazine, pyridazine, triazine, quinoline, isoquinoline, phthalazine, naphtheridine, quinoxaline, quinazoline, indole, isoindole, pyrrole, imidazole, pyrazole, 1,2,3-triazole, 1,2,4-triazole, oxazole, isoxazole, thiazole, isothiazole, oxadiazole and thiadiazole. Preferred aryl residue is phenyl.

More preferably, R$^5$ represents a part structure of general formula SF-III,
wherein R$^{13}$ is selected from the group consisting of
H, F, Cl, CN, CF$_3$, OCF$_3$, O—C$_{1-6}$-alkylen-OH, C$_{1-8}$-alkylen-OH, C$_{1-6}$-alkyl, OH, O—C$_{1-6}$-alkyl, S(=O)—C$_{1-6}$-alkyl, S(=O)$_2$—C$_{1-6}$-alkyl, S(=O)$_2$—NH$_2$, S(=O)$_2$—N(H)C$_{1-6}$-alkyl, S(=O)$_2$—N(C$_{1-6}$-alkyl)$_2$, NH$_2$, NH(C$_{1-6}$-alkyl), N(C$_{1-6}$-alkyl)$_2$, N(H)—S(=O)—C$_{1-6}$-alkyl, N(C$_{1-6}$-alkyl)-S(=O)—C$_{1-6}$-alkyl, N(H)—S(=O)$_2$—C$_{1-6}$-alkyl, N(C$_{1-6}$-alkyl)-S(=O)$_2$—C$_{1-6}$-alkyl, N(H)—C(=O)—NH$_2$, N(H)—C(=O)—N(H)(C$_{1-6}$-alkyl), N(H)—C(=O)—N(C$_{1-6}$-alkyl)$_2$, C(=O)—NH$_2$, C(=O)—N(H)(C$_{1-6}$-alkyl), C(=O)—N(C$_{1-6}$-alkyl)$_2$, C(=O)—O—C$_{1-6}$-alkyl; N(H)—C(=O)—C$_{1-6}$-alkyl and N(C$_{1-6}$-alkyl)-C(=O)—C$_{1-6}$-alkyl.

Still more preferably, R$^5$ represents a part structure of general formula SF-III,
wherein R$^{13}$ is selected from the group consisting of H, OH, F, Cl, CN, S(=O)$_2$—C$_{1-6}$-alkyl, NH$_2$, N(H)—C(=O)—C$_{1-6}$-alkyl, N(H)—S(=O)$_2$—C$_{1-6}$-alkyl, O—C$_{1-6}$-alkyl, C(=O)—NH$_2$, C(=O)—N(H)(C$_{1-6}$-alkyl) and C(=O)—O—C$_{1-6}$-alkyl.

In a preferred embodiment of the invention, the general formula SF-III is selected from formulae SF-IIIa to SF-IIIo SF-IIIa
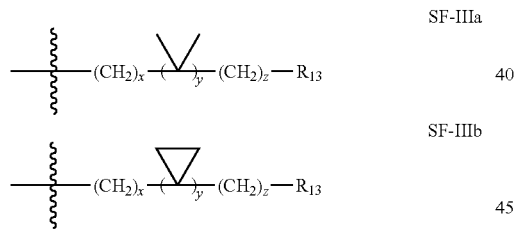

SF-IIIb

SF-IIIc

SF-IIId

SF-IIIe

SF-IIIf

SF-IIIg
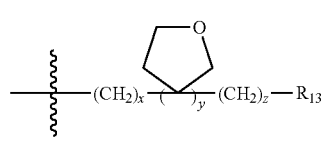

SF-IIIh
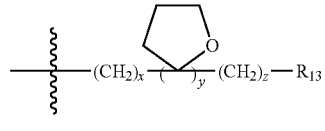

SF-IIIi
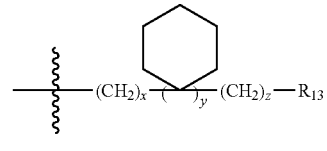

SF-IIIj
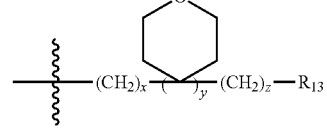

SF-IIIk

SF-IIIm
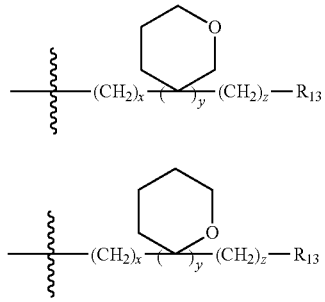

SF-IIIn

SF-IIIo
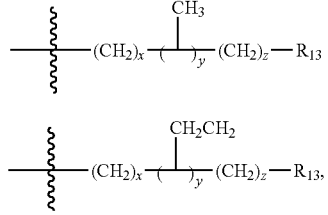

wherein
x represents 0, 1 or 2; y represents 0 or 1; z represents 0, 1 or 2; on the condition that the sum of x, y and z is 1, 2, 3, 4, 5 or 6.

Preferred are compounds according formula (I), that are characterized that R$^5$ is represented by any part structure the general formulae SF-IIIa to SF-IIIo, wherein x represents 1, y represents 0 and z represents 0.

Also preferred are compounds according formula (I), that are characterized that R$^5$ is represented by any part structure the general formulae SF-IIIa to SF-IIIo, wherein x represents 1, y represents 1 and z represents 0.

Also preferred are compounds according formula (I), that are characterized that R$^5$ is represented by any part structure the general formulae SF-IIIa to SF-IIIo, wherein x represents 0, y represents 1 and z represents 0.

Also preferred are compounds according formula (I), that are characterized that R$^5$ is represented by any part structure the general formulae SF-IIIa to SF-IIIo, wherein x represents 0, y represents 1 and z represents 1.

In a particularly preferred embodiment of the first aspect of the invention, the compound according to general formula (I) is characterized in that $R^5$ is selected from the group consisting of methyl, ethyl, 2-propyl (iso-propyl), 1-propyl (n-propyl), 1-butyl, 2-butyl, 2-methyl-propyl, 1,1-dimethyl-ethyl (tert-butyl), 1-pentyl, 2-pentyl, 3-pentyl, 2-methyl-butyl, 2,2-dimethyl-propyl (neo-pentyl), 1-hexyl, 2-hexyl, 3-hexyl, 3,3-dimethyl-butyl, cyclopropyl, cyclopropylmethyl, 2-cyclopropyl-ethyl, 1-cyclopropyl-ethyl as well as

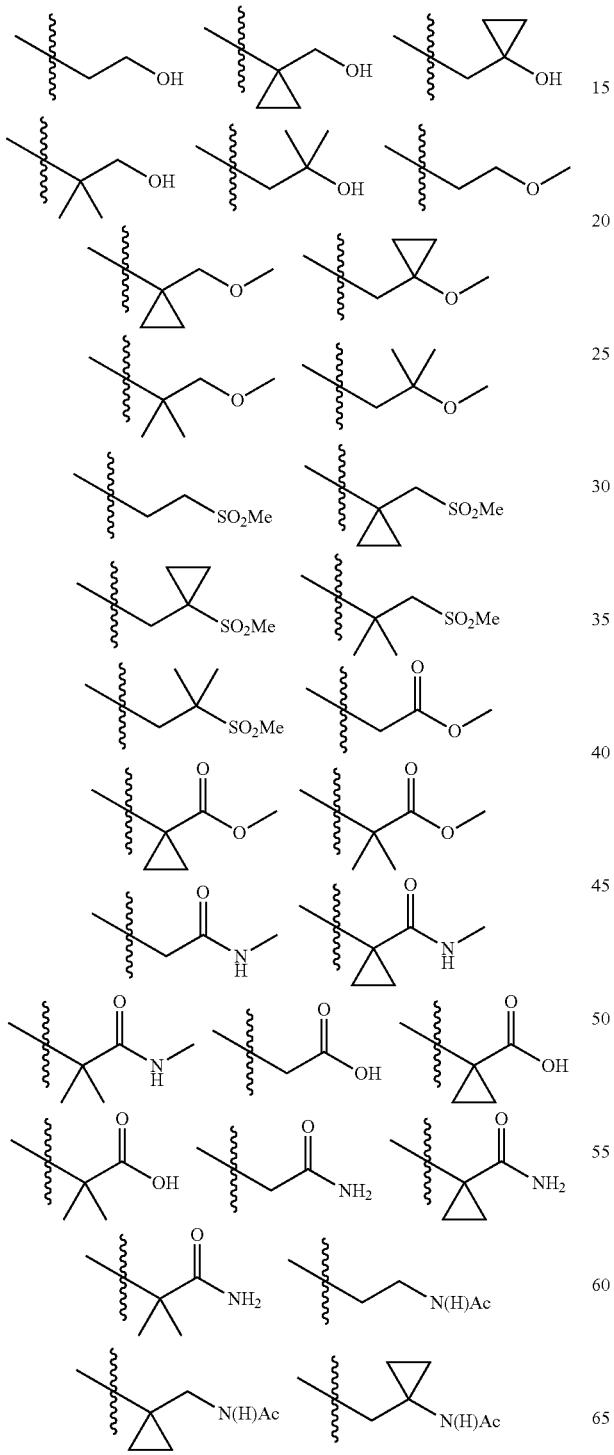
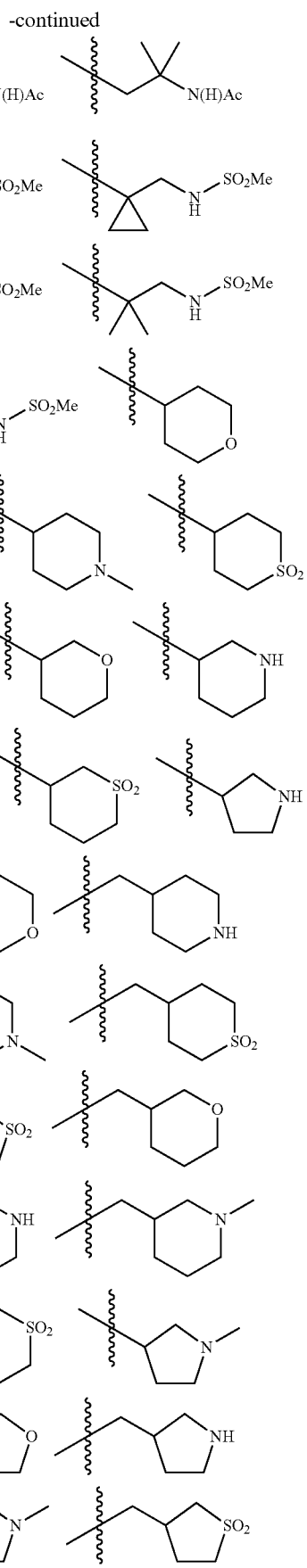

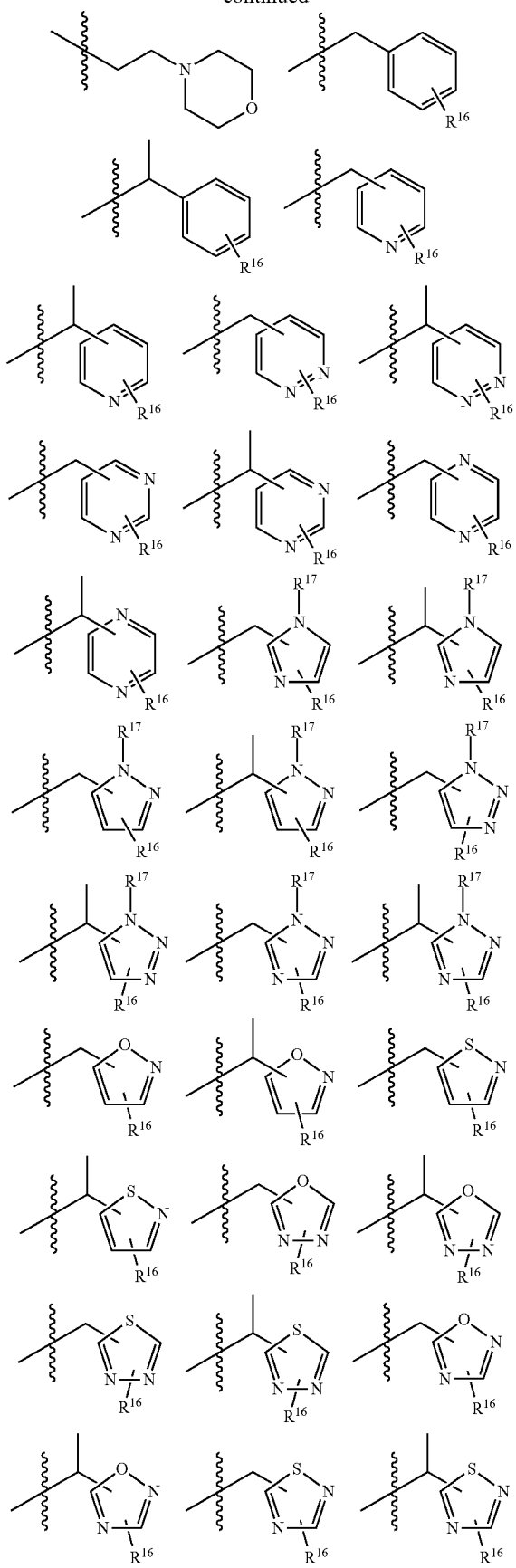

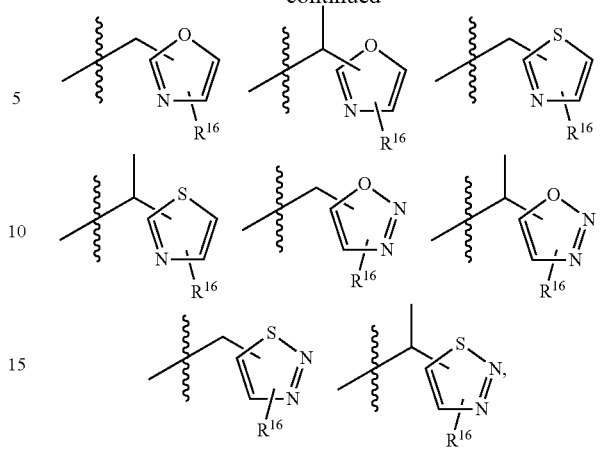

wherein
R$^{16}$ represents 1, 2 or 3 substituents, selected from C$_{1-6}$-alkyl, CF$_3$, F, Cl, CN, OH, OCF$_3$, O—C$_{1-6}$-alkyl, NH$_2$, N(H)C$_{1-6}$-alkyl, N(C$_{1-6}$-alkyl)$_2$, 1-pyrrolidinyl, 1-piperidinyl, 4-methyl-piperidin-1-yl or 1-morpholinyl, and R$^{17}$ represents H or C$_{1-6}$-alkyl.

In a particularly preferred embodiment, R$^4$ represents H or C$_{1-6}$-alkyl or benzyl and R$^5$ represents C$_{3-6}$-cycloalkyl, which is unsubstituted or substituted with 1, 2, 3, 4 or 5 substituents independently from one another selected from the group consisting of F, Cl, CF$_3$, =O, OCF$_3$, OH, O—C$_{1-6}$-alkyl, C$_{1-8}$-alkylen-OH and C$_{1-6}$-alkyl; or 3 to 7 membered heterocyclyl, which contains 1 or 2 heteroatoms or heteroatom groups independently from one another selected from the group consisting of O, S, S(=O), S(=O)$_2$, NH and N—C$_{1-6}$-alkyl, and which is unsubstituted or substituted with 1, 2, 3, 4 or 5 substituents independently from one another selected from the group consisting of F, Cl, CF$_3$, OCF$_3$, CN, C$_{1-6}$-alkyl, C$_{1-8}$-alkylen-OH and O—C$_{1-6}$-alkyl; or aryl or heteroaryl, which contains at least one nitrogen atom, and wherein said aryl or heteroaryl is unsubstituted or substituted with 1, 2 or 3 substituents independently from one another selected from the group consisting of F, Cl, CN, CF$_3$, OCF$_3$, C$_{1-8}$-alkylen-OH, C$_{1-6}$-alkyl, OH, O—C$_{1-6}$-alkyl, S(=O)$_2$—C$_{1-6}$-alkyl, S(=O)$_2$—NH$_2$, NH$_2$, NH(C$_{1-6}$-alkyl), N(C$_{1-6}$-alkyl)$_2$, O—C(=O)—NH$_2$, C(=O)—NH$_2$, C(=O)—N(H)(C$_{1-6}$-alkyl), C(=O)—N(C$_{1-6}$-alkyl)$_2$, C(=O)—O—C$_{1-6}$-alkyl; or a part structure of general formula SF-III

SF-III

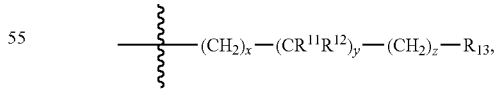

wherein
x represents 0, 1 or 2; y represents 0, 1 or 2; z represents 0, 1 or 2; on the condition that the sum of x, y and z is 1, 2, 3, 4, 5 or 6;
R$^{11}$ and R$^{12}$ are independently from one another selected from H or C$_{1-6}$-alkyl; or
R$^{11}$ and R$^{12}$ together with the carbon atom connecting them form a C$_{3-6}$-cycloalkyl or a 3 to 7 membered heterocyclyl, which contains 1 or 2 heteroatoms or heteroatom groups independently from one another selected from the group consisting of O, S, S(=O), S(=O)$_2$, NH and N—C$_{1-6}$-alkyl, wherein said C$_{3-6}$-cycloalkyl or 3 to 7 membered heterocyclyl may be unsubstituted or substituted with 1, 2, 3, 4 or 5 substituents independently from one another selected from the group consisting of F, Cl, CF$_3$, OCF$_3$, CN, C$_{1-6}$-alkyl and O—C$_{1-6}$-alkyl;

R$^{13}$ is selected from the group consisting of

H, F, Cl, CN, CF$_3$, OCF$_3$, C$_{1-8}$-alkylen-OH, C$_{1-6}$-alkyl, OH, O—C$_{1-6}$-alkyl, S(=O)—C$_{1-6}$-alkyl, S(=O)$_2$—C$_{1-6}$-alkyl, S(=O)$_2$—NH$_2$, S(=O)$_2$—N(H)C$_{1-6}$-alkyl, S(=O)$_2$—N(C$_{1-6}$-alkyl)$_2$, NH$_2$, NH(C$_{1-6}$-alkyl), N(C$_{1-6}$-alkyl)$_2$, N(H)—S(=O)—C$_{1-6}$-alkyl, N(C$_{1-6}$-alkyl)-S(=O)—C$_{1-6}$-alkyl, N(H)—S(=O)$_2$—C$_{1-6}$-alkyl, N(C$_{1-6}$-alkyl)-S(=O)$_2$—C$_{1-6}$-alkyl, N(H)—C(=O)—NH$_2$, N(H)—C(=O)—N(H)(C$_{1-6}$-alkyl), N(H)—C(=O)—N(C$_{1-6}$-alkyl)$_2$, C(=O)—NH$_2$, C(=O)—N(H)(C$_{1-6}$-alkyl), C(=O)—N(C$_{1-6}$-alkyl)$_2$, C(=O)—O—C$_{1-6}$-alkyl; N(H)—C(=O)—C$_{1-6}$-alkyl and N(C$_{1-6}$-alkyl)-C(=O)—C$_{1-6}$-alkyl, or represents C$_{3-6}$-cycloalkyl, which is unsubstituted or substituted with 1, 2, 3, 4, or 5 substituents independently from one another selected from the group consisting of F, Cl, CF$_3$, =O, OCF$_3$, OH, O—C$_{1-6}$-alkyl, C$_{1-8}$-alkylen-OH and C$_{1-6}$-alkyl; or 3 to 7 membered heterocyclyl, which contains 1 or 2 heteroatoms or heteroatom groups independently from one another selected from the group consisting of O, S, S(=O), S(=O)$_2$, NH and N—C$_{1-6}$-alkyl, and which is unsubstituted or substituted with 1, 2, 3, 4 or 5 substituents independently from one another selected from the group consisting of F, Cl, CF$_3$, OCF$_3$, CN, C$_{1-6}$-alkyl and O—C$_{1-6}$-alkyl; or aryl or heteroaryl, which contains at least one nitrogen atom, and wherein said aryl or heteroaryl is unsubstituted or substituted with 1, 2 or 3 substituents independently from one another selected from the group consisting of F, Cl, CN, CF$_3$, OCF$_3$, C$_{1-8}$-alkylen-OH, C$_{1-6}$-alkyl, OH, O—C$_{1-6}$-alkyl, S(=O)$_2$—C$_{1-6}$-alkyl, S(=O)$_2$—NH$_2$, NH$_2$, NH(C$_{1-6}$-alkyl), N(C$_{1-6}$-alkyl)$_2$, O—C(=O)—NH$_2$, C(=O)—NH$_2$, C(=O)—N(H)(C$_{1-6}$-alkyl), C(=O)—N(C$_{1-6}$-alkyl)$_2$, C(=O)—O—C$_{1-6}$-alkyl.

In another embodiment of the first aspect of the invention, the compound according to general formula (I) is characterized in that R$^4$ and R$^5$ together with the nitrogen atom connecting them form a 3 to 7 membered heterocyclyl, unsubstituted or substituted with 1, 2, 3, 4 or 5 substituents selected from the group consisting of F, Cl, CN, CF$_3$, =O, OH, C$_{1-6}$-alkyl, O—C$_{1-6}$-alkyl, C$_{1-6}$-alkylen-OH, OCF$_3$, SO$_2$(C$_{1-6}$-alkyl), SO$_2$NH$_2$, SO$_2$N(H)C$_{1-6}$-alkyl, SO$_2$N(C$_{1-6}$-alkyl)$_2$, C$_{1-6}$-alkylen-SO$_2$(C$_{1-6}$-alkyl), NH$_2$, NH(C$_{1-6}$-alkyl), N(C$_{1-6}$-alkyl)$_2$, (C=O)C$_{1-6}$-alkyl, C$_{3-6}$-cycloalkyl or 3 to 7 membered heterocyclyl, aryl, heteroaryl, O-aryl and O-heteroaryl, in each case unsubstituted or mono- or polysubstituted.

Preferably, R$^4$ and R$^5$ together with the nitrogen atom connecting them form a heterocyclyl selected from the group consisting of

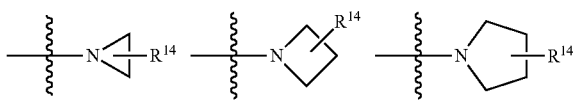

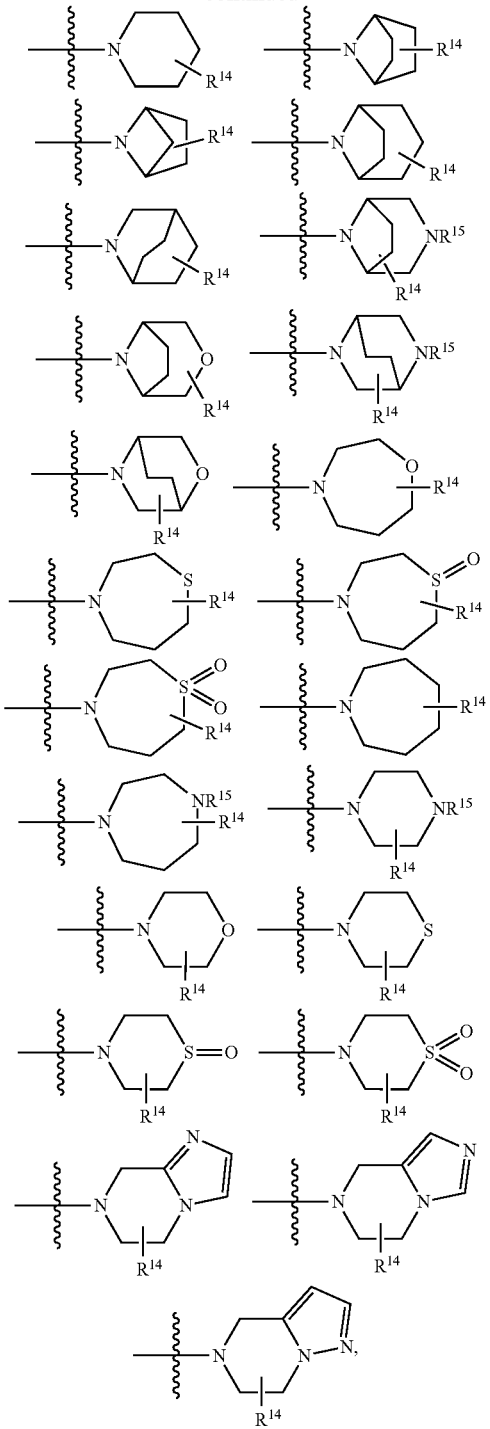

wherein

R$^{14}$ denotes 0, 1, 2, 3 or 4 substituents which are in each case independently of each other selected from the group consisting of F, Cl, CF$_3$, =O, OCF$_3$, OH, O—C$_{1-6}$-alkyl, C$_{1-8}$-alkylen-OH, SO$_2$(C$_{1-6}$-alkyl), C$_{1-8}$-alkylen-SO$_2$(C$_{1-6}$-alkyl), C$_{1-6}$-alkyl, aryl, heteroaryl, O-aryl and O-heteroaryl, wherein said aryl or said heteroaryl is unsubstituted or substituted with 1, 2, 3, 4 or 5 substituents independently from one another selected from the group consisting of F, Cl, CN, CF$_3$, OCF$_3$, C$_{1-6}$-alkylen-OH, C$_{1-6}$-alkyl, OH, O—C$_{1-6}$-alkyl, NH$_2$, NH(C$_{1-6}$-alkyl), N(C$_{1-6}$-alkyl)$_2$, N(H)—S (=O)$_2$—C$_{1-6}$-alkyl, C(=O)—NH$_2$ or C(=O)—N(H)(C$_{1-6}$-alkyl), C(=O)—N(C$_{1-6}$-alkyl)$_2$; or R$^{14}$ denotes at least two substituents, wherein two substituents R$^{14}$ stand together for a C$_{1-8}$-alkylen-group, substituted or unsubstituted, wherein optionally one or more C-atoms of the C$_{1-8}$-alkylen-group is replaced by a heteroatom or heteroatom group, selected of O, N—R$^{15}$, S, S(O) and S(O)$_2$, and wherein these two substituents R$^{14}$ are positioned at different carbon atoms of the heterocyclyl residue, so the C$_{1-8}$-alkylen-group represents a bridge to form a bicyclic heterocyclyl residue; or R$^{14}$ denotes at least two substituents, wherein two substituents R$^{14}$ stand together for a C$_{2-6}$-alkylen-group, substituted or unsubstituted, wherein optionally one or more C-atoms of the C$_{2-6}$-alkylen-group is replaced by a heteroatom or heteroatom group, selected from O, N—R$^{15}$, S, S(O) and S(O)$_2$, and wherein these two substituents R$^{14}$ are positioned at the same carbon atom of the heterocyclyl residue, so the C$_{2-6}$-alkylen-group forms a spiro-heterocyclyl residue;
and R$^{15}$ represents H, C$_{1-6}$-alkyl or (C=O)C$_{1-6}$-alkyl.

More preferably,

R$^4$ and R$^5$ together with the nitrogen atom connecting them form a heterocycloaliphatic residue selected from the group consisting of

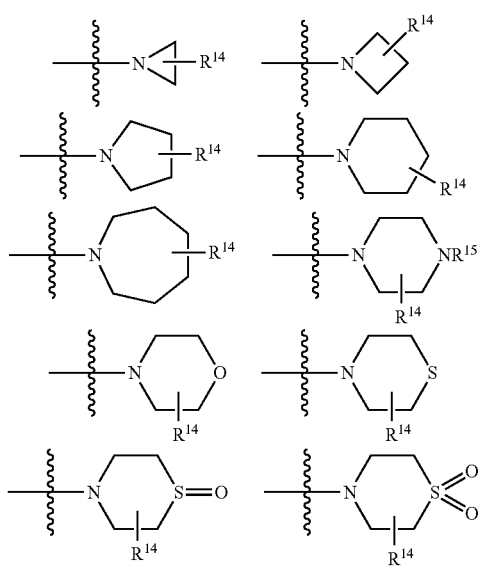

wherein

R$^{14}$ denotes 0, 1, 2, 3 or 4 substituents which are in each case independently of each other selected from the group consisting of F, Cl, CF$_3$, =O, OCF$_3$, OH, O—C$_{1-6}$-alkyl, C$_{1-6}$-alkylen-OH, C$_{1-6}$-alkylen-SO$_2$(C$_{1-6}$-alkyl), SO$_2$(C$_{1-6}$-alkyl), C$_{1-6}$-alkyl, aryl, heteroaryl, O-aryl and O-heteroaryl, wherein said aryl or said heteroaryl is unsubstituted or substituted with 1, 2 or 3 substituents independently from one another selected from the group consisting of F, Cl, CN, CF$_3$, OCF$_3$, C$_{1-6}$-alkylen-OH, C$_{1-6}$-alkyl, OH or O—C$_{1-6}$-alkyl;
or R$^{14}$ denotes at least two substituents, wherein two substituents R$^{14}$ stand together for a C$_{1-6}$-alkylen-group, substituted or unsubstituted, wherein optionally one or more C-atoms of the C$_{1-6}$-alkylen-group is replaced by a heteroatom or heteroatom group, selected of O, N—R$^{15}$, S, S(O) and S(O)$_2$, and wherein these two substituents R$^{14}$ are positioned at different carbon atoms of the heterocyclyl, so the C$_{1-6}$-alkylen-group represents a bridge to form a bicyclic heterocyclyl;
or R$^{14}$ denotes at least two substituents, wherein two substituents R$^{14}$ stand together for a C$_{2-6}$-alkylen-group, substituted or unsubstituted, wherein optionally one or more C-atoms of the C$_{2-6}$-alkylen-group is replaced by a heteroatom or heteroatom group, selected of O, N—R$^{15}$, S, S(O) and S(O)$_2$, and wherein these two substituents R$^{14}$ are positioned at the same carbon atom of the heterocyclyl, so the C$_{2-6}$-alkylen-group forms a spiro-heterocyclyl; and R$^{15}$ represents H, C$_{1-6}$-alkyl or (C=O)C$_{1-6}$-alkyl.

Most preferred,

R$^4$ and R$^5$ together with the nitrogen atom connecting them form a heterocycloaliphatic residue selected from the group consisting of

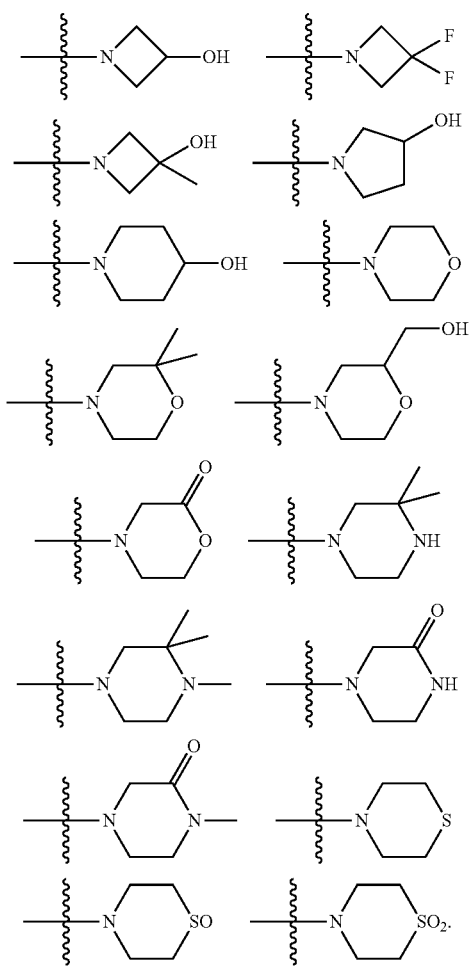

In another embodiment of the first aspect of the invention, the compound according to general formula (I) is characterized in that the compound of general formula (I) is a compound according to general formula (Ia),

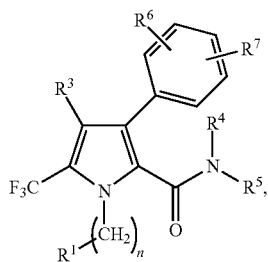

(Ia)

wherein
n is 1 and $R^1$ is selected from the group consisting of

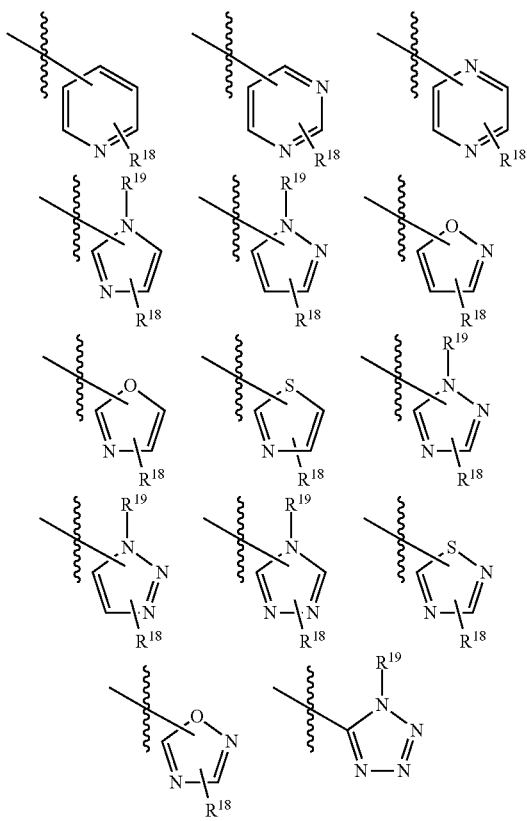

wherein
$R^{18}$ represents 0, 1, 2 or 3 substituents, selected from $CH_3$, $CH_2CH_3$, $CH(CH_3)_2$, $CF_3$, F, Cl, CN, OH, $OCF_3$, $OCH_3$, $OCH_2CH_3$, $OCH(CH_3)_2$, and $R^{19}$ represents H, $CH_3$, $CH_2CH_3$ or $CH(CH_3)_2$;

$R^3$ represents H or $CH_3$ or cyclopropyl;

$R^6$ and $R^7$ are independently absent or are each independently of one another selected from the group consisting of F; Cl; CN; $C_{1-6}$-alkyl; $CF_3$; $CF_2H$; $CFH_2$; OH; $OCF_3$; $OCF_2H$; $OCFH_2$ or O—$C_{1-6}$-alkyl;

$R^4$ represents H or $C_{1-6}$-alkyl or benzyl; and $R^5$ represents
$C_{3-6}$-cycloalkyl, which is unsubstituted or substituted with 1, 2, 3, 4 or 5 substituents independently from one another selected from the group consisting of F, Cl, $CF_3$, =O, $OCF_3$, OH, O—$C_{1-6}$-alkyl, $C_{1-6}$-alkylen-OH, $C_{1-6}$-alkyl, C(=O)—$NH_2$, C(=O)—N(H)($C_{1-6}$-alkyl) and C(=O)—$N(C_{1-6}$-alkyl$)_2$; or 5- or 6-membered heterocyclyl, which contains 1 or 2 heteroatoms or heteroatom groups independently from one another selected from the group consisting of O, S, S(=O), S(=O)$_2$, NH and N—$C_{1-6}$-alkyl, and which is unsubstituted or substituted with 1, 2, 3, 4 or 5 substituents independently from one another selected from the group consisting of F, Cl, $CF_3$, $OCF_3$, CN, $C_{1-6}$-alkyl, $C_{1-6}$-alkylen-OH and O—$C_{1-6}$-alkyl;

or a part structure of general formula SF-III

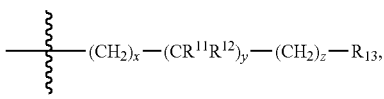

SF-III wherein
x represents 1 and y and z each represent 0 or x and y each represent 1 and z represents 0 or x and z each represent 1 and y represents 0 or x, y and z each represent 1;

$R^{11}$ and $R^{12}$ are independently from one another selected from H or $CH_3$;

$R^{13}$ is selected from the group consisting of
H, F, Cl, CN, OH, O—$C_{1-6}$-alkyl, O—(C=O)$C_{1-6}$-alkyl, S(=O)—$C_{1-6}$-alkyl, S(=O)$_2$—$C_{1-6}$-alkyl, $NH_2$, NH($C_{1-6}$-alkyl), N($C_{1-6}$-alkyl)$_2$, N(H)—C(=O)—$C_{1-6}$-alkyl, N(H)—S(=O)$_2$—$C_{1-6}$-alkyl, C(=O)—$NH_2$, C(=O)—N(H)($C_{1-6}$-alkyl), C(=O)—N($C_{1-6}$-alkyl)$_2$, N(H)—C(=O)—$NH_2$, N(H)—C(=O)—N(H)($C_{1-6}$-alkyl), N(H)—C(=O)—N($C_{1-6}$-alkyl)$_2$, or represents
$C_{3-6}$-cycloalkyl or
3-7-membered heterocyclyl, which contains 1 or 2 heteroatoms or heteroatom groups independently from one another selected from the group consisting of O, S, S(=O), S(=O)$_2$, NH and N—$C_{1-6}$-alkyl, and which is unsubstituted or substituted with 1, 2, 3, 4 or 5 substituents independently from one another selected from the group consisting of F, Cl, $CF_3$, $OCF_3$, CN, $C_{1-6}$-alkyl and O—$C_{1-6}$-alkyl; or phenyl or heteroaryl, selected from pyrrolyl, pyrazolyl, imidazolyl, oxazolyl, isoxazolyl, thiazolyl, isothiazolyl, pyridinyl, pyrazinyl, pyrimidinyl and pyridazinyl, in each unsubstituted or substituted with 1, 2 or 3 substituents independently from one another selected from the group consisting of F, Cl, CN, $CF_3$, $OCF_3$, $C_{1-6}$-alkylen-OH, $C_{1-6}$-alkyl, OH, O—$C_{1-6}$-alkyl, S(=O)$_2$—$C_{1-6}$-alkyl, S(=O)$_2$—$NH_2$, $NH_2$, NH($C_{1-6}$-alkyl), N($C_{1-6}$-alkyl)$_2$, O—C(=O)—$NH_2$, C(=O)—$NH_2$, C(=O)—N(H)($C_{1-6}$-alkyl), C(=O)—N($C_{1-6}$-alkyl)$_2$, C(=O)—O—$C_{1-6}$-alkyl;

or $R^4$ and $R^5$ together with the nitrogen atom connecting them form a heterocyclyl, selected from the group consisting of

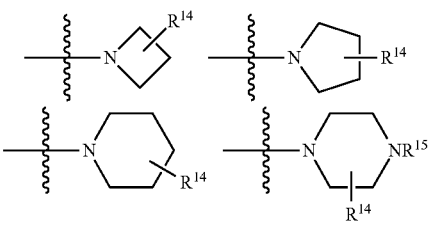

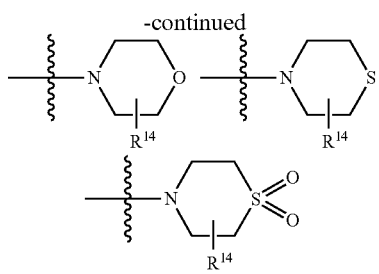

wherein

R$^{14}$ denotes 0, 1 or 2 substituents which are in each case independently of each other selected from the group consisting of F, Cl, CF$_3$, =O, OCF$_3$, OH, O—C$_{1-6}$-alkyl, C$_{1-6}$-alkylen-OH, C$_{1-6}$-alkylen-SO$_2$(C$_{1-6}$-alkyl), SO$_2$(C$_{1-6}$-alkyl), C$_{1-6}$-alkyl, aryl, heteroaryl, O-aryl and O-heteroaryl, wherein said aryl or said heteroaryl is unsubstituted or substituted with 1, 2 or 3 substituents independently from one another selected from the group consisting of F, Cl, CN, CF$_3$, OCF$_3$, C$_{1-6}$-alkylen-OH, C$_{1-6}$-alkyl, OH or O—C$_{1-6}$-alkyl;

and

R$^{15}$ represents H, C$_{1-6}$-alkyl or (C=O)C$_{1-6}$-alkyl.

In another preferred embodiment of the first aspect of the invention, the compound according to general formula (I) is characterized in that the compound of general formula (I) is a compound according to general formula (Ia), wherein n represents 0 or 1;

R$^1$ is selected from the group consisting of pyrrolyl, pyrazolyl, imidazolyl, oxazolyl (1,3-oxazolyl), isoxazolyl (1,2-oxazolyl), thiazolyl (1,3-thiazolyl), isothiazolyl (1,2-thiazolyl), 1,2,4-triazolyl, 1,2,3-triazolyl, tetrazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridinyl, pyridin-2-on-1-yl, pyrazinyl, pyrimidinyl, pyridazinyl, 1,2,3-triazinyl, 1,3,5-triazinyl and 1,2,4-triazinyl, in each case unsubstituted or mono- or polysubstituted by one or more substituents selected from F; Cl; CN; C$_{1-6}$-alkyl; CF$_3$; C(=O)—NH$_2$; C(=O)—N(H)(C$_{1-6}$-alkyl); C(=O)—N(C$_{1-6}$-alkyl)$_2$; OH; O—C$_{1-6}$-alkyl; NH$_2$; N(H)(C$_{1-6}$-alkyl); N(C$_{1-6}$-alkyl)$_2$; N(H)—C(=O)—C$_{1-6}$-alkyl; S(=O)—C$_{1-6}$-alkyl; S(=O)$_2$—C$_{1-6}$-alkyl or cyclopropyl, R$^3$ represents H or CH$_3$ or cyclopropyl;

R$^6$ and R$^7$ are independently absent or are each independently of one another selected from the group consisting of F; Cl; CN; C$_{1-6}$-alkyl; CF$_3$; CF$_2$H; CFH$_2$; OH; OCF$_3$; OCF$_2$H; OCFH$_2$ or O—C$_{1-6}$-alkyl;

R$^4$ represents H or C$_{1-6}$-alkyl; and

R$^5$ represents C$_{3-6}$-cycloalkyl, which is unsubstituted or substituted with 1, 2, 3, 4 or 5 substituents independently from one another selected from the group consisting of F, Cl, CF$_3$, =O, OCF$_3$, OH, O—C$_{1-6}$-alkyl, C$_{1-6}$-alkylen-OH, C$_{1-6}$-alkyl, C(=O)—NH$_2$, C(=O)—N(H)(C$_{1-6}$-alkyl) and C(=O)—N(C$_{1-6}$-alkyl)$_2$; or 5- or 6-membered heterocyclyl, which contains 1 or 2 heteroatoms or heteroatom groups independently from one another selected from the group consisting of O, S, S(=O), S(=O)$_2$, NH and N—C$_{1-6}$-alkyl, and which is unsubstituted or substituted with 1, 2, 3, 4 or 5 substituents independently from one another selected from the group consisting of F, Cl, CF$_3$, OCF$_3$, CN, C$_{1-6}$-alkyl, C$_{1-6}$-alkylen-OH and O—C$_{1-6}$-alkyl;

or a part structure of general formula SF-III

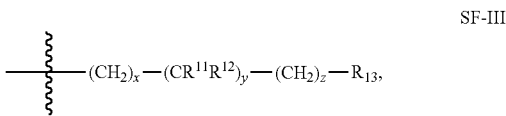

SF-III wherein x represents 1 and y and z each represent 0 or x and y each represent 1 and z represents 0 or x and z each represent 1 and y represents 0 or x, y and z each represent 1;

R$^{11}$ and R$^{12}$ are independently from one another selected from H or CH$_3$;

R$^{13}$ is selected from the group consisting of

H, F, Cl, CN, OH, O—C$_{1-6}$-alkyl, O—(C=O)C$_{1-6}$-alkyl, S(=O)—C$_{1-6}$-alkyl, S(=O)$_2$—C$_{1-6}$-alkyl, NH$_2$, NH(C$_{1-6}$-alkyl), N(C$_{1-6}$-alkyl)$_2$, N(H)—C(=O)—C$_{1-6}$-alkyl, N(H)—S(=O)$_2$—C$_{1-6}$-alkyl, C(=O)—NH$_2$, C(=O)—N(H)(C$_{1-6}$-alkyl), C(=O)—N(C$_{1-6}$-alkyl)$_2$, N(H)—C(=O)—NH$_2$, N(H)—C(=O)—N(H)(C$_{1-6}$-alkyl), N(H)—C(=O)—N(C$_{1-6}$-alkyl)$_2$, or represents C$_{3-6}$-cycloalkyl or 3-7-membered heterocyclyl, which contains 1 or 2 heteroatoms or heteroatom groups independently from one another selected from the group consisting of O, S, S(=O), S(=O)$_2$, NH and N—C$_{1-6}$-alkyl, and which is unsubstituted or substituted with 1, 2, 3, 4 or 5 substituents independently from one another selected from the group consisting of F, Cl, CF$_3$, OCF$_3$, CN, C$_{1-6}$-alkyl and O—C$_{1-6}$-alkyl; or phenyl or heteroaryl, selected from pyrrolyl, pyrazolyl, imidazolyl, oxazolyl, isoxazolyl, thiazolyl, isothiazolyl, pyridinyl, pyrazinyl, pyrimidinyl and pyridazinyl, in each unsubstituted or substituted with 1, 2 or 3 substituents independently from one another selected from the group consisting of F, Cl, CN, CF$_3$, OCF$_3$, C$_{1-6}$-alkylen-OH, C$_{1-6}$-alkyl, OH, O—C$_{1-6}$-alkyl, S(=O)$_2$—C$_{1-6}$-alkyl, S(=O)$_2$—NH$_2$, NH$_2$, NH(C$_{1-6}$-alkyl), N(C$_{1-6}$-alkyl)$_2$, O—C(=O)—NH$_2$, C(=O)—NH$_2$, C(=O)—N(H)(C$_{1-6}$-alkyl), C(=O)—N(C$_{1-6}$-alkyl)$_2$, C(=O)—O—C$_{1-6}$-alkyl;

or

R$^4$ and R$^5$ together with the nitrogen atom connecting them form a heterocyclyl, selected from the group consisting of

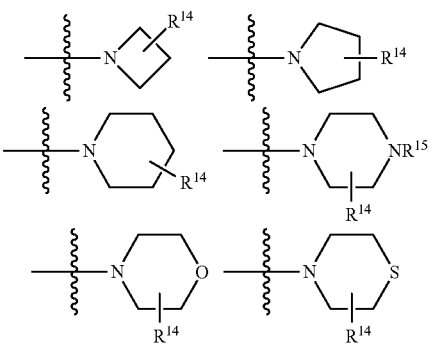

-continued

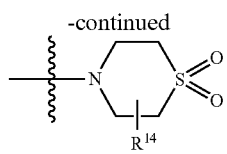

wherein
R$^{14}$ denotes 0, 1 or 2 substituents which are in each case independently of each other selected from the group consisting of F, Cl, CF$_3$, =O, OCF$_3$, OH, O—C$_{1-6}$-alkyl, C$_{1-6}$-alkylen-OH, C$_{1-6}$-alkylen-SO$_2$(C$_{1-6}$-alkyl), SO$_2$(C$_{1-6}$-alkyl) or C$_{1-6}$-alkyl;
and
R$^{15}$ represents H, C$_{1-6}$-alkyl or (C=O)C$_{1-6}$-alkyl.

In another particularly preferred embodiment of the first aspect of the invention, the compound according to general formula (I) is characterized in that
the compound of general formula (I) is a compound according to general formula (Ia),
wherein
n represents 0 or 1;
R$^1$ is selected from the group consisting of

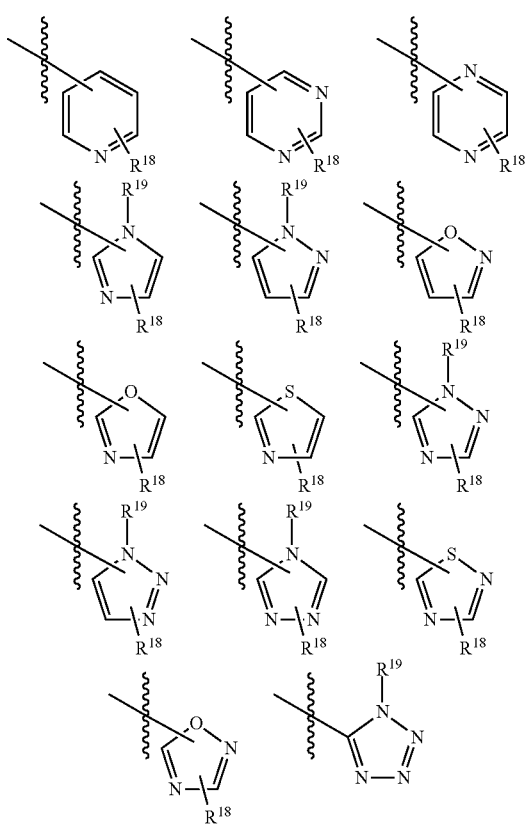

wherein
R$^{18}$ represents 0, 1, 2 or 3 substituents, selected from CH$_3$, CH$_2$CH$_3$, CH(CH$_3$)$_2$, CF$_3$, F, Cl, CN, OH, OCF$_3$, OCH$_3$, OCH$_2$CH$_3$, OCH(CH$_3$)$_2$,
and R$^{19}$ represents H, CH$_3$, CH$_2$CH$_3$ or CH(CH$_3$)$_2$;
R$^4$ represents H or CH$_3$; and
R$^5$ represents
ethyl, 2-propyl (iso-propyl), 1-propyl (n-propyl), 1-butyl, 2-butyl, 2-methyl-propyl, 1,1-dimethyl-ethyl (tert-butyl), 1-pentyl, 2-pentyl, 3-pentyl, 2-methyl-butyl, 2,2-dimethyl-propyl (neo-pentyl), 1-hexyl, 2-hexyl, 3-hexyl, 3,3-dimethyl-butyl, cyclopropyl, cyclopropylmethyl, 2-cyclopropyl-ethyl, 1-cyclopropyl-ethyl as well as

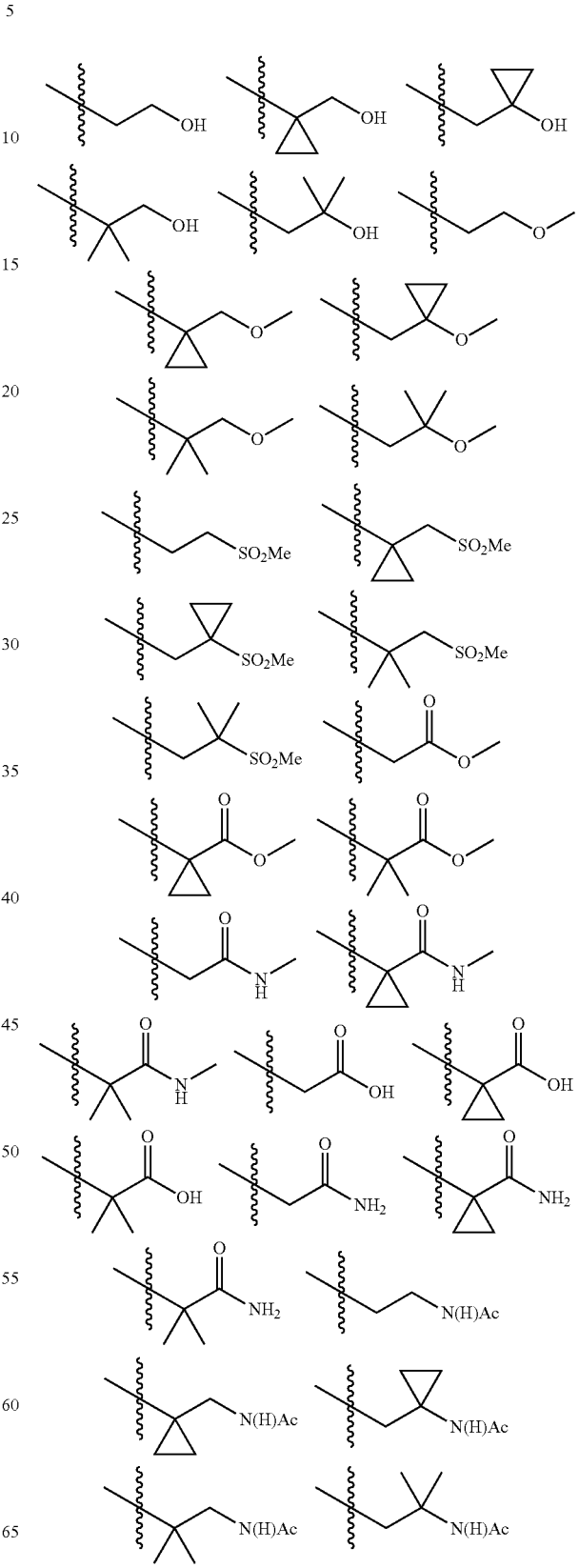

-continued

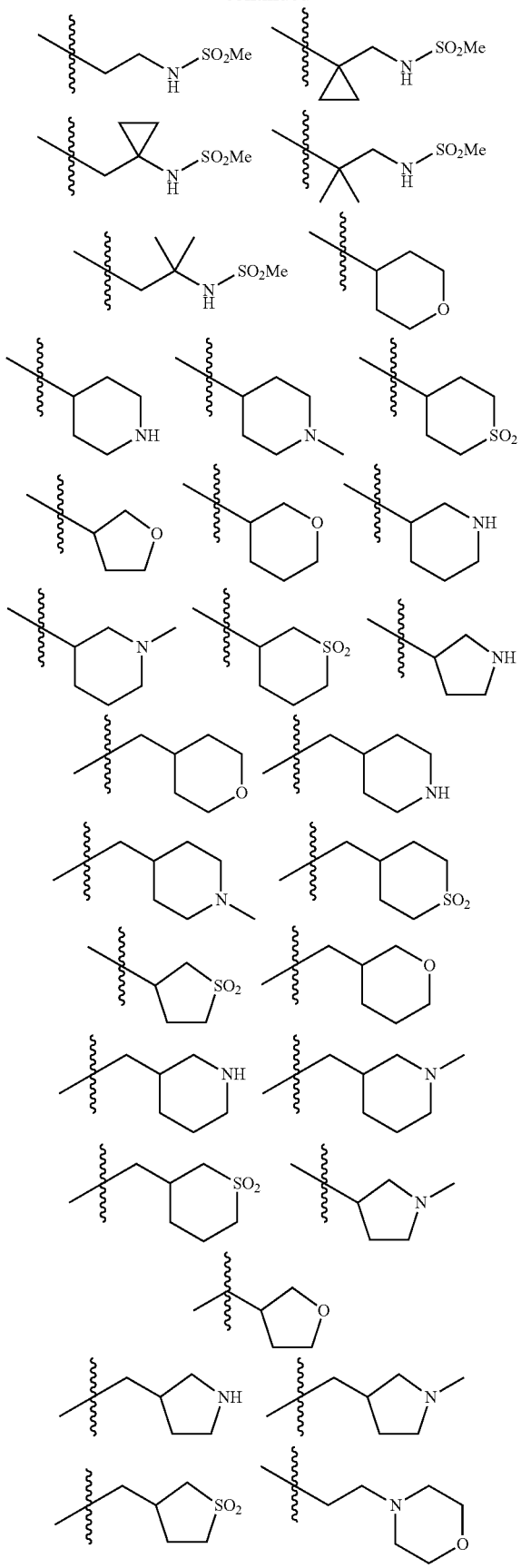

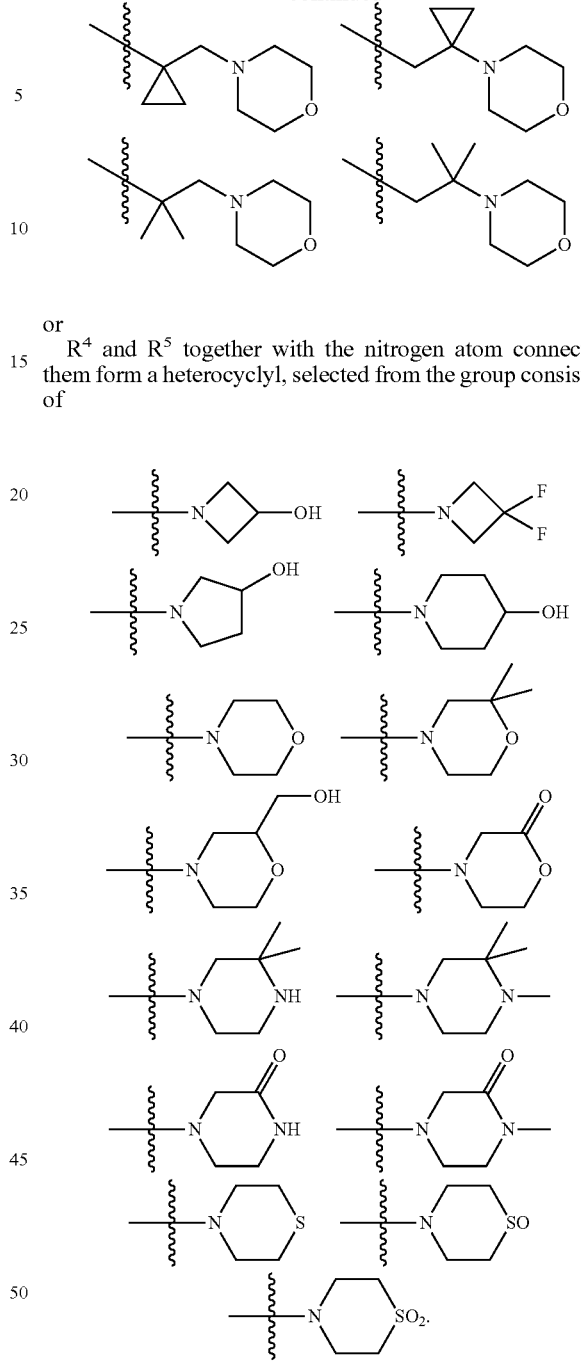

or
R⁴ and R⁵ together with the nitrogen atom connecting them form a heterocyclyl, selected from the group consisting of

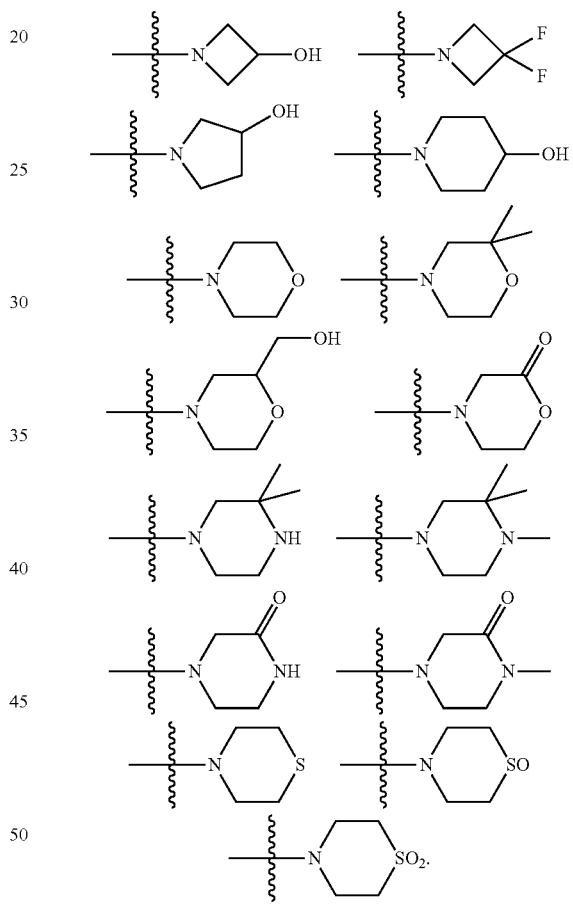

Particularly preferred compounds according to the invention are selected from the group consisting of 001  3-(4-Chlorophenyl)-1-[(3-ethyl-isoxazol-5-yl)-methyl]-N,4-dimethyl-N-(2-methylsulfonyl-ethyl)-5-(trifluoromethyl)-1H-pyrrole-2-carboxylic acid amide 002  3-(4-Chlorophenyl)-N,4-dimethyl-1-[(1-methyl-1H-imidazole-2-yl)-methyl]-N-(2-methylsulfonyl-ethyl)-5-(trifluoromethyl)-1H-pyrrole-2-carboxylic acid amide 003  3-(4-Chlorophenyl)-N,4-dimethyl-1-[(3-methyl-3H-imidazole-4-yl)-methyl]-N-(2-methylsulfonyl-ethyl)-5-(trifluoromethyl)-1H-pyrrole-2-carboxylic acid amide 004  N-Cyclopropyl-3-(4-fluorophenyl)-N-methyl-1-[(3-methyl-[1,2,4]oxadiazol-5-yl)-methyl]-5-(trifluoromethyl)-1H-pyrrole-2-carboxylic acid amide 005 N-(2-Carbamoyl-2-methyl-propyl)-3-(4-fluorophenyl)-N-methyl-1-[(3-methyl-[1,2,4]oxadiazol-5-yl)-methyl]-5-(trifluoromethyl)-1H-pyrrole-2-carboxylic acid amide 006 4-[3-(4-Fluorophenyl)-1-[(3-methyl-[1,2,4]oxadiazol-5-yl)-methyl]-5-(trifluoromethyl)-1H-pyrrole-2-carbonyl]-piperazin-2-one 007 [3-(4-Fluorophenyl)-1-[(3-methyl-[1,2,4]oxadiazol-5-yl)-methyl]-5-(trifluoromethyl)-1H-pyrrol-2-yl]-morpholin-4-yl-methanone 008 3-(4-Chlorophenyl)-N-(2,2-dimethyl-propyl)-N-methyl-1-[(2-methyl-2H-pyrazol-3-yl)-methyl]-5-(trifluoromethyl)-1H-pyrrole-2-carboxylic acid amide 009 3-(4-Chlorophenyl)-N-(2,2-dimethyl-propyl)-N-methyl-1-[(1-methyl-1H-[1,2,3]triazol-4-yl)-methyl]-5-(trifluoromethyl)-1H-pyrrole-2-carboxylic acid amide 010 3-(4-Chlorophenyl)-N-(2,2-dimethyl-propyl)-N-methyl-5-(trifluoromethyl)-1-[[3-(trifluoromethyl)-[1,2,4]oxadiazol-5-yl]-methyl]-1H-pyrrole-2-carboxylic acid amide 011 3-(4-Chlorophenyl)-N-(2,2-dimethyl-propyl)-N-methyl-1-[(3-methyl-[1,2,4]oxadiazol-5-yl)-methyl]-5-(trifluoromethyl)-1H-pyrrole-2-carboxylic acid amide 012 3-(4-Chlorophenyl)-N-(2,2-dimethyl-propyl)-N-methyl-1-[(5-methyl-[1,2,4]oxadiazol-3-yl)-methyl]-5-(trifluoromethyl)-1H-pyrrole-2-carboxylic acid amide 013 3-(4-Chlorophenyl)-N-(2,2-dimethyl-propyl)-N-methyl-1-[(1-methyl-1H-[1,2,4]triazol-3-yl)-methyl]-5-(trifluoromethyl)-1H-pyrrole-2-carboxylic acid amide 014 3-(4-Chlorophenyl)-N-(2,2-dimethyl-propyl)-N-methyl-1-[(5-methyl-[1,3,4]oxadiazol-2-yl)-methyl]-5-(trifluoromethyl)-1H-pyrrole-2-carboxylic acid amide 015 3-(4-Chlorophenyl)-N,4-dimethyl-1-[(3-methyl-[1,2,4]oxadiazol-5-yl)-methyl]-N-(2-methylsulfonyl-ethyl)-5-(trifluoromethyl)-1H-pyrrole-2-carboxylic acid amide 016 [3-(4-Chlorophenyl)-4-methyl-1-[(2-methyl-2H-pyrazol-3-yl)-methyl]-5-(trifluoromethyl)-1H-pyrrol-2-yl]-morpholin-4-yl-methanone 017 [3-(4-Chlorophenyl)-4-methyl-1-[(1-methyl-1H-[1,2,3]triazol-4-yl)-methyl]-5-(trifluoromethyl)-1H-pyrrol-2-yl]-morpholin-4-yl-methanone 018 [3-(4-Chlorophenyl)-4-methyl-1-[(3-methyl-[1,2,4]oxadiazol-5-yl)-methyl]-5-(trifluoromethyl)-1H-pyrrol-2-yl]-morpholin-4-yl-methanone 019 [3-(4-Chlorophenyl)-4-methyl-1-[(1-methyl-1H-[1,2,4]triazol-3-yl)-methyl]-5-(trifluoromethyl)-1H-pyrrol-2-yl]-morpholin-4-yl-methanone 020 3-(4-Chlorophenyl)-N,4-dimethyl-N-(2-methylsulfonyl-ethyl)-1-(1H-tetrazol-5-yl-methyl)-5-(trifluoromethyl)-1H-pyrrole-2-carboxylic acid amide 021 [3-(4-Chlorophenyl)-4-methyl-1-[(1-methyl-1H-imidazol-2-yl)-methyl]-5-(trifluoromethyl)-1H-pyrrol-2-yl]-(1,1-dioxo-[1,4]thiazinan-4-yl)-methanone 022 [3-(4-Chlorophenyl)-4-methyl-1-[(1-methyl-1H-imidazol-4-yl)-methyl]-5-(trifluoromethyl)-1H-pyrrol-2-yl]-(1,1-dioxo-[1,4]thiazinan-4-yl)-methanone 023 [3-(4-Chlorophenyl)-4-methyl-1-[(1-methyl-1H-pyrazol-4-yl)-methyl]-5-(trifluoromethyl)-1H-pyrrol-2-yl]-morpholin-4-yl-methanone 024 [3-(4-Chlorophenyl)-4-methyl-1-([1,3,4]thiadiazol-2-yl-methyl)-5-(trifluoromethyl)-1H-pyrrol-2-yl]-morpholin-4-yl-methanone 025 3-(4-Chlorophenyl)-N-(2,2-dimethyl-propyl)-N-methyl-1-[(1-methyl-1H-imidazole-2-yl)-methyl]-5-(trifluoromethyl)-1H-pyrrole-2-carboxylic acid amide 026 3-(4-Chlorophenyl)-N-(2,2-dimethyl-propyl)-N-methyl-1-[(3-methyl-3H-imidazole-4-yl)-methyl]-5-(trifluoromethyl)-1H-pyrrole-2-carboxylic acid amide 027 3-(4-Chlorophenyl)-N-(2,2-dimethyl-propyl)-N-methyl-1-[(4-methyl-4H-[1,2,4]triazol-3-yl)-methyl]-5-(trifluoromethyl)-1H-pyrrole-2-carboxylic acid amide 028 [3-(4-Chlorophenyl)-1-[(5-chloro-pyridin-3-yl)-methyl]-4-methyl-5-(trifluoromethyl)-1H-pyrrol-2-yl]-morpholin-4-yl-methanone 029 3-(4-Chlorophenyl)-N-(2,2-dimethyl-propyl)-1-[(5-fluoro-pyridin-2-yl)-methyl]-N-methyl-5-(trifluoromethyl)-1H-pyrrole-2-carboxylic acid amide 030 3-(4-Chlorophenyl)-N-(2,2-dimethyl-propyl)-N-methyl-1-[(5-methyl-pyrazin-2-yl)-methyl]-5-(trifluoromethyl)-1H-pyrrole-2-carboxylic acid amide 031 (2,2-Dimethyl-morpholin-4-yl)-[3-(4-fluorophenyl)-1-(pyrimidin-2-yl-methyl)-5-(trifluoromethyl)-1H-pyrrol-2-yl]-methanone 032 N-Cyclopropyl-3-(4-fluorophenyl)-1-(pyrimidin-2-yl-methyl)-5-(trifluoromethyl)-1H-pyrrole-2-carboxylic acid amide 033 3-(4-Chlorophenyl)-N-(2,2-dimethyl-propyl)-N-methyl-5-(trifluoromethyl)-1-[[2-(trifluoromethyl)-pyrimidin-4-yl]-methyl]-1H-pyrrole-2-carboxylic acid amide 034 3-(4-Chlorophenyl)-N-(2,2-dimethyl-propyl)-N-methyl-1-[(2-methyl-pyrimidin-5-yl)-methyl]-5-(trifluoromethyl)-1H-pyrrole-2-carboxylic acid amide 035 3-(4-Chlorophenyl)-N-(2,2-dimethyl-propyl)-N-methyl-1-[(5-methyl-pyrimidin-2-yl)-methyl]-5-(trifluoromethyl)-1H-pyrrole-2-carboxylic acid amide 036 3-(4-Chlorophenyl)-N-(2,2-dimethyl-propyl)-N-methyl-1-[(4-methyl-pyrimidin-2-yl)-methyl]-5-(trifluoromethyl)-1H-pyrrole-2-carboxylic acid amide 037 3-(4-Chlorophenyl)-N-(2,2-dimethyl-propyl)-N-methyl-1-(pyrimidin-2-yl-methyl)-5-(trifluoromethyl)-1H-pyrrole-2-carboxylic acid amide 038 3-(4-Chlorophenyl)-1-[(5-fluoro-pyridin-2-yl)-methyl]-N,4-dimethyl-N-(2-methylsulfonyl-ethyl)-5-(trifluoromethyl)-1H-pyrrole-2-carboxylic acid amide 039 3-(4-Chlorophenyl)-N,4-dimethyl-N-(2-methylsulfonyl-ethyl)-1-(pyrimidin-2-yl-methyl)-5-(trifluoromethyl)-1H-pyrrole-2-carboxylic acid amide 040 [3-(4-Chlorophenyl)-4-methyl-1-(pyrimidin-2-yl-methyl)-5-(trifluoromethyl)-1H-pyrrol-2-yl]-(2,2-dimethyl-morpholin-4-yl)-methanone 041 [3-(4-Chlorophenyl)-1-[(6-methoxy-pyridin-2-yl)-methyl]-4-methyl-5-(trifluoromethyl)-1H-pyrrol-2-yl]-morpholin-4-yl-methanone 042 [3-(4-Chlorophenyl)-4-methyl-1-[(5-methyl-pyrazin-2-yl)-methyl]-5-(trifluoromethyl)-1H-pyrrol-2-yl]-morpholin-4-yl-methanone 043 [3-(4-Chlorophenyl)-4-methyl-1-[(2-methyl-pyrimidin-5-yl)-methyl]-5-(trifluoromethyl)-1H-pyrrol-2-yl]-morpholin-4-yl-methanone 044 [3-(4-Chlorophenyl)-1-[(5-fluoro-pyridin-2-yl)-methyl]-4-methyl-5-(trifluoromethyl)-1H-pyrrol-2-yl]-morpholin-4-yl-methanone 045 [3-(4-Chlorophenyl)-4-methyl-1-[(5-methyl-pyrimidin-2-yl)-methyl]-5-(trifluoromethyl)-1H-pyrrol-2-yl]-morpholin-4-yl-methanone 046 [3-(4-Chlorophenyl)-4-methyl-1-[(4-methyl-pyrimidin-2-yl)-methyl]-5-(trifluoromethyl)-1H-pyrrol-2-yl]-morpholin-4-yl-methanone 047 [3-(4-Chlorophenyl)-4-methyl-1-(pyrimidin-2-yl-methyl)-5-(trifluoromethyl)-1H-pyrrol-2-yl]-morpholin-4-yl-methanone 048 3-(4-Chlorophenyl)-N-cyclopropyl-4-methyl-1-(pyrimidin-2-yl-methyl)-5-(trifluoromethyl)-1H-pyrrole-2-carboxylic acid amide 049 3-(4-Chlorophenyl)-N-(2,2-dimethyl-propyl)-N,4-dimethyl-1-pyrazin-2-yl-5-(trifluoromethyl)-1H-pyrrole-2-carboxylic acid amide
050 [3-(4-Chlorophenyl)-4-methyl-1-pyrazin-2-yl-5-(trifluoromethyl)-1H-pyrrol-2-yl]-(3,3-difluoro-azetidin-1-yl)-methanone
051 [3-(4-Chlorophenyl)-4-methyl-1-pyrazin-2-yl-5-(trifluoromethyl)-1H-pyrrol-2-yl]-(3-hydroxy-3-methyl-azetidin-1-yl)-methanone
052 [3-(4-Chlorophenyl)-4-methyl-1-(pyrimidin-5-yl-methyl)-5-(trifluoromethyl)-1H-pyrrol-2-yl]-morpholin-4-yl-methanone
053 3-[[3-(4-Chlorophenyl)-4-methyl-2-(morpholine-4-carbonyl)-5-(trifluoromethyl)-1H-pyrrol-1-yl]-methyl]-1H-pyridin-2-one
054 6-[[3-(4-Chlorophenyl)-4-methyl-2-(morpholine-4-carbonyl)-5-(trifluoromethyl)-1H-pyrrol-1-yl]-methyl]-1H-pyridin-2-one
055 1-[2-[3-(4-Chlorophenyl)-4-methyl-2-(morpholine-4-carbonyl)-5-(trifluoromethyl)-1H-pyrrol-1-yl]-ethyl]-1H-pyridin-2-one
056 1-[[3-(4-Chlorophenyl)-4-methyl-2-(morpholine-4-carbonyl)-5-(trifluoromethyl)-1H-pyrrol-1-yl]-methyl]-1H-pyridin-2-one
060 [3-(4-Chlorophenyl)-4-methyl-1-(1H-[1,2,4]triazol-3-yl-methyl)-5-(trifluoromethyl)-1H-pyrrol-2-yl]-morpholin-4-yl-methanone
061 3-(4-Chlorophenyl)-N-isopropyl-N,4-dimethyl-1-(pyrimidin-2-yl-methyl)-5-(trifluoromethyl)-1H-pyrrole-2-carboxylic acid amide
062 [3-(4-Chloro-2-fluoro-phenyl)-4-methyl-1-(pyrimidin-2-yl-methyl)-5-(trifluoromethyl)-1H-pyrrol-2-yl]-morpholin-4-yl-methanone
063 3-(4-Chloro-2-fluoro-phenyl)-N-cyclopropyl-N,4-dimethyl-1-(pyrimidin-2-yl-methyl)-5-(trifluoromethyl)-1H-pyrrole-2-carboxylic acid amide
064 3-(4-Chloro-2-fluoro-phenyl)-N-isopropyl-N,4-dimethyl-1-(pyrimidin-2-yl-methyl)-5-(trifluoromethyl)-1H-pyrrole-2-carboxylic acid amide
065 3-(4-Fluorophenyl)-N-isopropyl-N-methyl-1-[(3-methyl-[1,2,4]oxadiazol-5-yl)-methyl]-5-(trifluoromethyl)-1H-pyrrole-2-carboxylic acid amide
066 3-(4-Chloro-2-fluoro-phenyl)-N,4-dimethyl-N-[(5-methyl-isoxazol-3-yl)-methyl]-1-(pyrimidin-2-yl-methyl)-5-(trifluoromethyl)-1H-pyrrole-2-carboxylic acid amide
067 3-(4-Chlorophenyl)-N-isopropyl-N,4-dimethyl-1-[(3-methyl-isoxazol-5-yl)-methyl]-5-(trifluoromethyl)-1H-pyrrole-2-carboxylic acid amide
068 3-(4-Chlorophenyl)-N-isopropyl-N,4-dimethyl-1-[(5-methyl-isoxazol-3-yl)-methyl]-5-(trifluoromethyl)-1H-pyrrole-2-carboxylic acid amide
069 3-(4-Chlorophenyl)-N-isopropyl-N,4-dimethyl-1-([1,3,4]thiadiazol-2-yl-methyl)-5-(trifluoromethyl)-1H-pyrrole-2-carboxylic acid amide
optionally in the form of a single stereoisomer or a mixture of stereoisomers, in the form of the free compound and/or a physiologically acceptable salt or solvate thereof.

Furthermore, preference may be given to compounds according to the invention that cause at least a 50% inhibition, which is present at a concentration of 3 µM, in a fluorescent assay for CaV2.2 channels with HEK293 cells in which human CaV2.2 channels were stably expressed at a concentration of less 3 µM, preferably less than 1000 nM, particularly preferably less than 300 nM, most particularly preferably less than 100 nM, even more preferably less than 75 nM, additionally preferably less than 50 nM, most preferably less than 10 nM.

In the process, the $Ca^{2+}$ influx is quantified in the FLIPR assay with the aid of a $Ca^{2+}$-sensitive dye (type Fluo-4, Molecular Probes Europe BV, Leiden, the Netherlands) in a fluorescent imaging plate reader (FLIPR 3, Molecular Devices, Sunnyvale, USA), as described hereinafter.

The compounds according to the invention and corresponding stereoisomers and also the respective corresponding acids, bases, salts and solvates are suitable for the treatment and/or prophylaxis of one or more disorders and/or diseases selected from the group consisting of pain, preferably pain selected from the group consisting of acute pain, chronic pain, visceral pain, headache pain, inflammatory pain and mixed pain; stroke (the neuronal damage resulting from head trauma); mood disorders; epilepsy; schizophrenia, and neurodegenerative disorders.

The present invention further relates to a compound according to the present invention for CaV2.2 calcium channel regulation, preferably for use in CaV2.2 calcium channel blockage.

The present invention therefore further relates to a compound according to the present invention for the prophylaxis and/or treatment of disorders and/or diseases which are mediated, at least in part, at least in part, by CaV2.2 channels.

The term "disorders and/or diseases which are mediated, at least in part, by CaV2.2 channels", is intended to include each of or all of the disease states.

The substances according to the invention hence act, for example, on CaV2.2 channels relevant in connection with various diseases, so that they are suitable as a pharmacologically active compound in pharmaceutical compositions.

The compounds according to the first aspect of the present invention and the corresponding stereoisomers and the respective salts and solvates are toxicologically safe and are therefore suitable as pharmacologically active ingredients in pharmaceutical compositions.

In another aspect of the present invention, the invention therefore also provides pharmaceutical compositions, containing at least one compound according to the invention and optionally one or more suitable, pharmaceutically compatible auxiliaries and/or, if appropriate, one or more further pharmacologically active compounds.

The pharmaceutical composition according to the invention is suitable for administration to adults and children, including toddlers and babies.

The pharmaceutical composition according to the invention may be found as a liquid, semisolid or solid pharmaceutical form, for example in the form of injection solutions, drops, juices, syrups, sprays, suspensions, tablets, patches, capsules, plasters, suppositories, ointments, creams, lotions, gels, emulsions, aerosols or in multiparticulate form, for example in the form of pellets or granules, if appropriate pressed into tablets, decanted in capsules or suspended in a liquid, and also be administered as much.

In addition to at least one compound according to the invention, if appropriate in the form of one of its pure stereoisomers, in particular enantiomers or diastereomers, its racemate or in the form of mixtures of the stereoisomers, in particular the enantiomers or diastereomers, in any desired mixing ratio, or if appropriate in the form of a corresponding salt or respectively in the form of a corresponding solvate, the pharmaceutical composition according to the invention conventionally contains further physiologically compatible pharmaceutical auxiliaries which can for example be selected from the group consisting of excipients, fillers, solvents, diluents, surface-active substances, dyes, preservatives, blasting agents, slip additives, lubricants, aromas and binders.

The selection of the physiologically compatible auxiliaries and also the amounts thereof to be used depend on whether the pharmaceutical composition is to be applied orally, subcutaneously, parenterally, intravenously, intraperitoneally, intradermally, intramuscularly, intranasally, buccally, rectally or locally, for example to infections of the skin, the mucous membranes and of the eyes. Preparations in the form of tablets, dragées, capsules, granules, pellets, drops, juices and syrups are preferably suitable for oral application; solutions, suspensions, easily reconstitutable dry preparations and also sprays are preferably suitable for parenteral, topical and inhalative application. The compounds according to the invention used in the pharmaceutical composition according to the invention in a repository in dissolved form or in a plaster, agents promoting skin penetration being added if appropriate, are suitable percutaneous application preparations. Orally or percutaneously applicable preparation forms can release the respective compound according to the invention also in a delayed manner.

The pharmaceutical compositions according to the invention are prepared with the aid of conventional means, devices, methods and process known in the art, such as are described for example in "Remington's Pharmaceutical Sciences", A. R. Gennaro (Editor), $17^{th}$ edition, Mack Publishing Company, Easton, Pa., 1985, in particular in Part 8, Chapters 76 to 93. The corresponding description is introduced herewith by way of reference and forms part of the disclosure. The amount to be administered to the patient of the respective compounds according to the invention of the above-indicated general formula I may vary and is for example dependent on the patient's weight or age and also on the type of application, the indication and the severity of the disorder. Conventionally 0.001 to 100 mg/kg, preferably 0.05 to 75 mg/kg, particularly preferably 0.05 to 50 mg of at least one such compound according to the invention are applied per kg of the patient's body weight.

CaV2.2 channels are believed to be involved in a variety of diseases or disorders in mammals such as humans. These include pain (e.g.; acute pain, chronic pain, visceral pain, headache pain, inflammatory pain, mixed pain), stroke (the neuronal damage resulting from head trauma), epilepsy, mood disorders, schizophrenia, neurodegenerative disorders.

Another embodiment of the present invention is at least one compound according the present invention for the treatment and/or prophylaxis of one or more disorders selected from the group consisting of pain, preferably pain selected from the group consisting of acute pain, chronic pain, visceral pain, headache pain, inflammatory pain and mixed pain; stroke (the neuronal damage resulting from head trauma); mood disorders; epilepsy; schizophrenia, and neurodegenerative disorders.

Another embodiment of the present invention is at least one compound according to the present invention for the treatment and/or prophylaxis of pain, in particular acute pain and/or chronic pain and/or visceral pain and/or headache pain and/or inflammatory pain and/or mixed pain.

Acute pain according to the invention might include nociceptive pain and post-operative or surgical pain. Chronic pain according to the invention might include peripheral neuropathic pain such as post-herpetic neuralgia, traumatic nerve injury, nerve compression or entrapment, small fibre neuropathy, diabetic neuropathy, neuropathic cancer pain, failed back surgery Syndrome, trigeminal neuralgia, phantom limb pain; neuroma pain, complex regional pain syndrome, chronic arthritic pain and related neuralgias, and pain associated with cancer, chemotherapy, HIV and HIV treatment-induced neuropathy; central neuropathic pain such as multiple sclerosis related pain, Parkinson disease related pain, post-stroke pain, post-traumatic spinal cord injury pain, and pain in dementia; musculoskeletal pain such as osteoarthritic pain and fibromyalgia syndrome. In treating osteoarthritic pain, joint mobility will also improve as the underlying chronic pain is reduced. Thus, at least one compound for treatment of osteoarthritic pain inherently will also improve joint mobility in patients suffering from osteoarthritis. Visceral pain according to the invention might include interstitial cystitis, irritable bowel syndrome, Crohn's disease and chronic pelvic pain syndrome. Inflammatory pain according to the invention might include rheumatoid arthritis and endometriosis. Headachepain according to the invention might include migraine, cluster headache, tension headache syndrome, facial pain and headache caused by other diseases. Mixed pain according to the invention might include lower back pain, neck and shoulder pain, burning mouth syndrome and complex regional pain syndrome.

In another embodiment of the invention, at least one compound according to the present invention is particularly suitable for the treatment and/or prophylaxis of mood disorders.

Mood disorders according to the invention might include anxiety disorder, social anxiety disorder, panic disorder, specific phobias, for example, specific animal phobias, social phobias, obsessive-compulsive disorder, agoraphobia, post-traumatic stress syndrome, addiction (including dependence, withdrawal and/or relapse of medication, including opioids, but also drugs such as cocaine, opioids, alcohol and nicotine), generalised anxiety disorders, single episodic or recurrent major depressive disorders and dysthymic disorders, or bipolar disorders, for example, bipolar I disorder, bipolar II disorder and cyclothymic disorder.

In another embodiment of the invention, at least one compound according to the present invention is particularly suitable for the treatment and/or prophylaxis of epilepsy.

Epilepsy according to the invention might include partial seizures such as temporal lobe epilepsy, absence seizures generalized seizures, and tonic/clonic seizures.

In yet another embodiment of the invention, at least one compound according to the present invention is particularly suitable for the treatment and/or prophylaxis of neurodegenerative disorders.

Neurodegenerative disorders according to the invention might include Parkinson's disease, Alzheimer's disease, multiple sclerosis, neuropathies, Huntington's disease, presbycusis and amyotrophic lateral sclerosis (ALS).

Particularly preferably, at least one compound according to the present invention is suitable for the treatment and/or prophylaxis of one or more disorders and/or diseases selected from the group consisting of pain, preferably of pain selected from the group consisting of acute pain, chronic pain, visceral pain, headache pain, inflammatory pain and mixed pain; migraine; depression; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; medication dependency; misuse of medication; withdrawal symptoms in medication dependency;

development of tolerance to medication, preferably development of tolerance to natural or synthetic opioids; drug dependency; misuse of drugs; withdrawal symptoms in drug dependency; alcohol dependency; misuse of alcohol and withdrawal symptoms in alcohol dependency.

Most particularly preferably, at least one compound according to the present invention according to the invention is suitable for the treatment and/or prophylaxis of pain, preferably of pain selected from the group consisting of acute pain, chronic pain, visceral pain, headache pain, inflammatory pain and mixed pain.

The present invention further relates to a compound according to the present invention and one or more additional pharmaceutically active agents for use in the prophylaxis and/or treatment of disorders and/or diseases which are mediated, at least in part, at least in part, by CaV2.2 channels.

In particular, the present invention therefore further relates to a compound according to the present invention and one or more additional pharmaceutically active agents for the prophylaxis and/or treatment of disorders and/or diseases selected from the group consisting of pain, preferably pain selected from the group consisting of acute pain, chronic pain, visceral pain, headache pain, inflammatory pain and mixed pain; stroke (the neuronal damage resulting from head trauma); mood disorders; epilepsy; schizophrenia, and neurodegenerative disorders.

Most particularly preferred is a compound according to the present invention one or more additional pharmaceutically active agents for the prophylaxis and/or treatment of pain, preferably of pain selected from the group consisting of acute pain, chronic pain, visceral pain, headache pain, inflammatory pain and mixed pain.

Additional pharmaceutically active agents in the treatment of pain may include, for example, i) opiate agonists or antagonists, ii) calcium channel antagonists, iii) 5HT receptor agonists or antagonists, iv) sodium channel antagonists, v) NMDA receptor agonists or antagonists, vi) COX-2 selective inhibitors, vii) NKI antagonists, viii) non-steroidal anti-inflammatory drugs ("NSAID"), ix) selective serotonin reuptake inhibitors ("SSRI") and/or selective serotonin and norepinephrine reuptake inhibitors ("SSNRI"), x) tricyclic antidepressant drugs, xi) norepinephrine modulators, xii) lithium, xiii) valproate, xiv) neurontin (gabapentin), xv) pregabalin.

Additional pharmaceutically active agents in the treatment of depression or anxiety can include other anti-depressant or anti-anxiety agents, such as norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), adrenoreceptor antagonists, atypical anti-depressants, benzodiazepines, 5-HT1 A agonists or antagonists, especially 5-HT1A partial agonists, neurokinin 1 receptor antagonists, corticotropin releasing factor (CRF) antagonists, and pharmaceutically acceptable salts thereof.

Another embodiment of the present invention therefore relates to use of at least one compound according to the present invention for the preparation of a pharmaceutical composition for the treatment and/or prophylaxis of one or more disorders or diseases, particularly selected from the group consisting of pain, preferably pain selected from the group consisting of acute pain, chronic pain, visceral pain, headache pain, inflammatory pain and mixed pain; stroke; mood disorders; epilepsy; schizophrenia, and neurodegenerative disorders.

Another aspect of the present invention is a method of treatment and/or prophylaxis of disorders and/or diseases in a mammal, preferably of disorders and/or diseases selected from the group consisting of pain, preferably pain selected from the group consisting of acute pain, chronic pain, visceral pain, headache pain, inflammatory pain and mixed pain; stroke; mood disorders; epilepsy; schizophrenia, and neurodegenerative disorders, which comprises administering an effective amount of at least one compound according to the present invention to the mammal.

Another embodiment of the present invention is a method for CaV2.2 calcium channel regulation, preferably for use in CaV2.2 calcium channel blockage, and, further, a method of treatment and/or prophylaxis of disorders and/or diseases, which are mediated, at least in part, by CaV2.2 channels, in a mammal, preferably of disorders and/or diseases selected from the group consisting of pain, preferably pain selected from the group consisting of acute pain, chronic pain, visceral pain, headache pain, inflammatory pain and mixed pain; stroke; mood disorders; epilepsy; schizophrenia, and neurodegenerative disorders, which comprises administering an effective amount of at least one compound according to the present invention to the mammal.

All preferred embodiments of the first aspect of the invention are preferred vice versa for the other aspects and embodiments.

The effectiveness against pain can be shown, for example, in the Bennett or Chung model (Bennett, G. J. and Xie, Y. K., A peripheral mononeuropathy in rat that produces disorders of pain sensation like those seen in man, Pain 1988, 33(1), 87-107; Kim, S. H. and Chung, J. M., An experimental model for peripheral neuropathy produced by segmental spinal nerve ligation in the rat, Pain 1992, 50(3), 355-363), by tail flick experiments (e.g. according to D'Amour and Smith (J. Pharm. Exp. Ther. 72, 74 79 (1941)) or by the formalin test (e.g. according to D. Dubuisson et al., Pain 1977, 4, 161-174).

EXAMPLES

The compounds according to the invention can be prepared in the manner described below. The following examples further illustrate the invention but are not to be construed as limiting its scope. All starting materials which are not explicitly described were either commercially available (the details of suppliers such as for example Acros, Avocado, Aldrich, Apollo, Bachem, Fluka, FluoroChem, Lancaster, Manchester Organics, MatrixScientific, Maybridge, Merck, Rovathin, Sigma, TCI, Oakwood, etc. can be found in the Symyx® Available Chemicals Database of MDL, San Ramon, US or the SciFinder® Database of the ACS, Washington D.C., US, respectively, for example) or the synthesis thereof has already been described precisely in the specialist literature (experimental guidelines can be found in the Reaxys® Database of Elsevier, Amsterdam, NL or the SciFinder® Database of the ACS, Washington D.C., US, repspectively, for example) or can be prepared using the conventional methods known to the person skilled in the art.

The stationary phase used for the column chromatography was silica gel 60 (0.04-0.063 mm) from E. Merck, Darmstadt. The reactions were, if necessary, carried out under an inert amosphere (mostly nitrogen).

The yields of the compounds prepared are not optimized. The mixing ratios of solvents are usually stated in the volume/volume ratio. The reactions were, if necessary, carried out under an inert amosphere (mostly $N_2$). The number of equivalents of reagents and the amounts of solvents employed as well as the reaction temperatures and times can vary slightly between different reactions carried out by the same (general) method. The work-up and purification methods were adapted according to the characteristic properties of each compound and can vary slightly for analogous/general methods.

All the intermediate products and exemplary compounds were analytically characterized by means of $^1$H-NMR spectroscopy. In addition, mass spectrometry tests (MS, m/z for [M+H]$^+$) were carried out for all the exemplary compounds and selected intermediate products.

The indication "equivalents" ("eq." or "eq" or "equiv.") means molar equivalents, "RT" or "rt" means room temperature T (23±7° C.), "M" are indications of concentration in mol/l, "aq." means aqueous, "sat." means saturated, "sol." means solution, "conc." means concentrated. The mixing ratios of solvents are usually stated in the volume/volume ratio.

Boc=tert-butyloxycarbonyl; BOP—Cl=bis(2-oxo-3-oxazolidinyl)phosphinic chloride; d=day(s); DBU=1,8-Diazabicyclo[5.4.0]undec-7-ene; DCM=dichloromethane; DIAD=diisopropyl azodicarboxylate; DIPEA=N,N-diisopropylethylamine; DMAP=4-(N,N-dimethylamino)pyridine; DMF=N,N-dimethylformamid; DMSO=dimethylsulfoxide; EDCl=N-(3-dimethylaminopropyl)-N'-ethyl-carbodiimide hydrochloride; Et$_2$O=diethyl ether; EtOAc=ethylacetate; EtOH=ethanol; h=hour(s); HATU=O-(7-azabenzotriazol-1-yl)N,N,N',N'-tetramethyluroniunn hexafluorophosphate; HOBt=1-hydroxybenzotriazole hydrate; MeCN=acetonitrile; MeI=iodomethane; MeOH=methanol; min=minute(s); MS=mesylate; PPh$_3$=triphenylphosphine; i-Pr$_2$O=diisopropyl ether; i-PrOH=isopropanol; TBD=1,5,7-triazabicyclo[4.4.0]dec-5-ene; tert=tertiary; THF=tetrahydrofuran; TLC=thin layer chromatography.

1. Synthesis of Example Compounds

1.1 Synthesis of Carboxylic Acid Building Blocks (ACI)

1.1.1 3-(4-Chlorophenyl)-4-methyl-1-(pyrimidin-2-yl)methyl)-5-(trifluoromethyl)-1H-pyrrole-2-carboxylic acid (ACI-1)

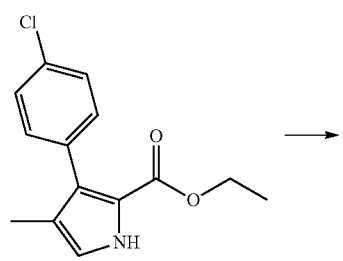

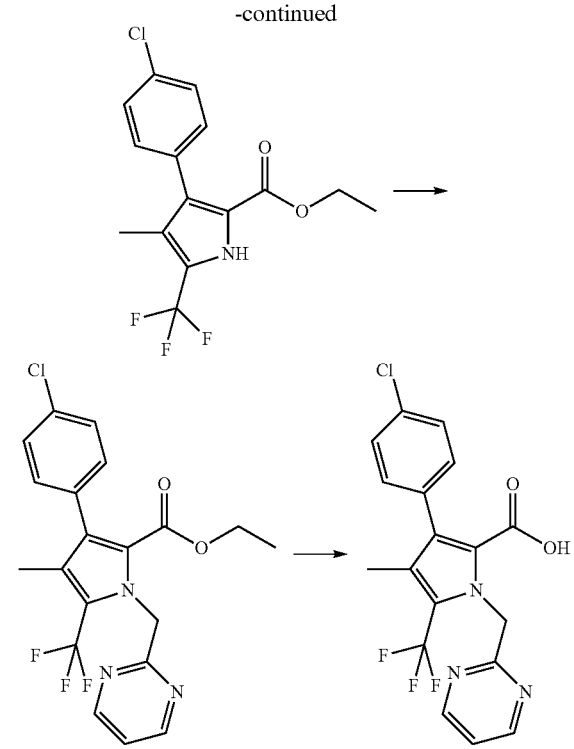

Step 1: Ethyl 3-(4-chlorophenyl)-4-methyl-5-(trifluoromethyl)-1H-pyrrole-2-carboxylate The reaction was performed under nitrogen. A solution of ethyl 3-(4-chlorophenyl)-4-methyl-1H-pyrrole-2-carboxylate [step 2, PY-1] (5.69 g, 21.6 mmol) in DMF (100 mL) was prepared, powdered FeSO$_4$.7H$_2$O (3.60 g, 13.0 mmol) was added, followed by trifluoromethanesulfonyl chloride (4.59 mL, 43.2 mmol). An ice/H$_2$O bath was applied. Subsequently, 35% aqueous H$_2$O$_2$ (5.67 mL, 64.7 mmol) was added dropwise over 45 min. The mixture was stirred at 10° C. for 40 min. The reaction mixture was poured out in ice/H$_2$O (500 mL) and stirred for 20 min. The solid was filtered off, washed with H$_2$O (3×50 mL) and dried. The residue was mixed with heptane (10 mL), adding DCM (around 30 mL) and warming was necessary to dissolve all material. Crystals were formed on cooling to RT. The volume was reduced at 600 mbar/40° C. to around 25 mL. The resulting clear solution was cooled to RT slowly. The crystals were filtered off and washed with heptane/i-Pr$_2$O (1:1, 20 mL). The crystals were air-dried to result in 2.09 g (28%) of the desired product as off-white crystals. The combination of filtrates was concentrated in vacuo and dissolved in warm DCM (10 mL), EtOAc (2 mL) was added. Cooling to RT resulted in a solution, which was used for flash chromatography (silica, heptane/EtOAc, 9:1) to arrive at 1.63 g (23%) of the desired product as a white solid. An impure fraction from chromatography was triturated with heptane (10 mL). Filtration and air-drying provided 0.53 g (7%) of the desired product as an off-white powder.

Step 2: Ethyl 3-(4-chlorophenyl)-4-methyl-1-(pyrimidin-2-ylmethyl)-5-(trifluoromethyl)-1H-pyrrole-2-carboxylate Ethyl 3-(4-chlorophenyl)-4-methyl-5-(trifluoromethyl)-1H-pyrrole-2-carboxylate (150 mg, 0.430 mmol) and PPh$_3$ (130 mg, 0.494 mmol) were combined with dry THF (0.2 mL), some warming resulted in a solution. DIAD (96 µL, 0.494 mmol) was added, the reaction mixture was stirred at RT for 10 min. In this period, the reaction mixture solidified. The vial was immersed in an ultrasound bath for 20 min to result in a viscous but stirrable slurry. Pyrimidin-2-yl-methanol (54 µL, 0.60 mmol) was added portion-wise in three portions of 18 µL, with 10 min between every addition. The reaction mixture was stirred at RT for 2 h. Extra reagents were added: PPh₃ (130 mg, 0.494 mmol) and DIAD (96 µL, 0.494 mmol). The reaction mixture was stirred at RT for 10 min. Pyrimidin-2-yl-methanol (54 µL, 0.60 mmol) was added in one portion. The reaction mixture was stirred at RT overnight. Addition of EtOAc (0.4 mL) and warming resulted in a clear solution, which was mixed with heptane (6 mL, 1 mL portions) to result in a precipitate. Filtration provided a residue and a filtrate. The residue was discarded. The filtrate was concentrated in vacuo, dissolved in heptane/DCM (1:1, 1 mL) and used for flash chromatography (silica, gradient heptane/EtOAc, 98:2→80:20) to arrive at 140 mg (77%) of the desired product as a colourless oil.

Step 3: 3-(4-Chlorophenyl)-4-methyl-1-(pyrimidin-2-ylmethyl)-5-(trifluoromethyl)-1H-pyrrole-2-carboxylic acid (ACI-1)

To a solution of ethyl 3-(4-chlorophenyl)-4-methyl-1-(pyrimidin-2-ylmethyl)-5-(trifluoromethyl)-1H-pyrrole-2-carboxylate (103 mg, 0.243 mmol) in EtOH (0.50 mL) was added a solution of LiOH H₂O (20 mg, 0.486 mmol) in H₂O (0.50 mL). The reaction mixture was stirred at RT for 4 d. A solution of LiOHH₂O (10 mg, 0.243 mmol) in H₂O (0.20 mL) was added. The reaction mixture was stirred at RT for 2 d. A flow of N₂ was applied, the volume was reduced to ca. 0.5 mL. The resulting mixture was partitioned between aqueous 1M KHSO₄ (6 mL) and EtOAc (10 mL). The layers were separated, the organic layer was dried (brine and Na₂SO₄) and concentrated in vacuo to yield 95 mg (99%) of the desired product as a white solid.

1.1.2 3-(4-Fluorophenyl)-1-(pyrimidin-2-ylmethyl)-5-(trifluoromethyl)-1H-pyrrole-2-carboxylic acid (ACI-2)

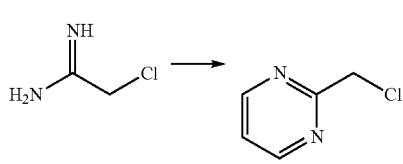 [SMILES: N=C(N)CCl ; ClCc1ncccn1]

Step A: 2-(Chloromethyl)pyrimidine

A suspension of Chloroacetamidine HCl (5 g, 38.76 mmol) in 1,1,3,3-tetramethoxy propane (12.5 mL) was heated at 100° C. for 16 h. Reaction mixture was diluted with H₂O (50 mL), the pH adjusted to ~8 using NaHCO₃ and extracted with DCM (2×50 mL). The organic layer was washed with brine (50 mL), then 4N Dioxane-HCl (2 mL) was added to the organic layer and stirred for 10 min. The organic layer was dried (Na₂SO₄), filtered and evaporated in vacuo to give the crude product (10 g) which was employed in the next step without further purification.

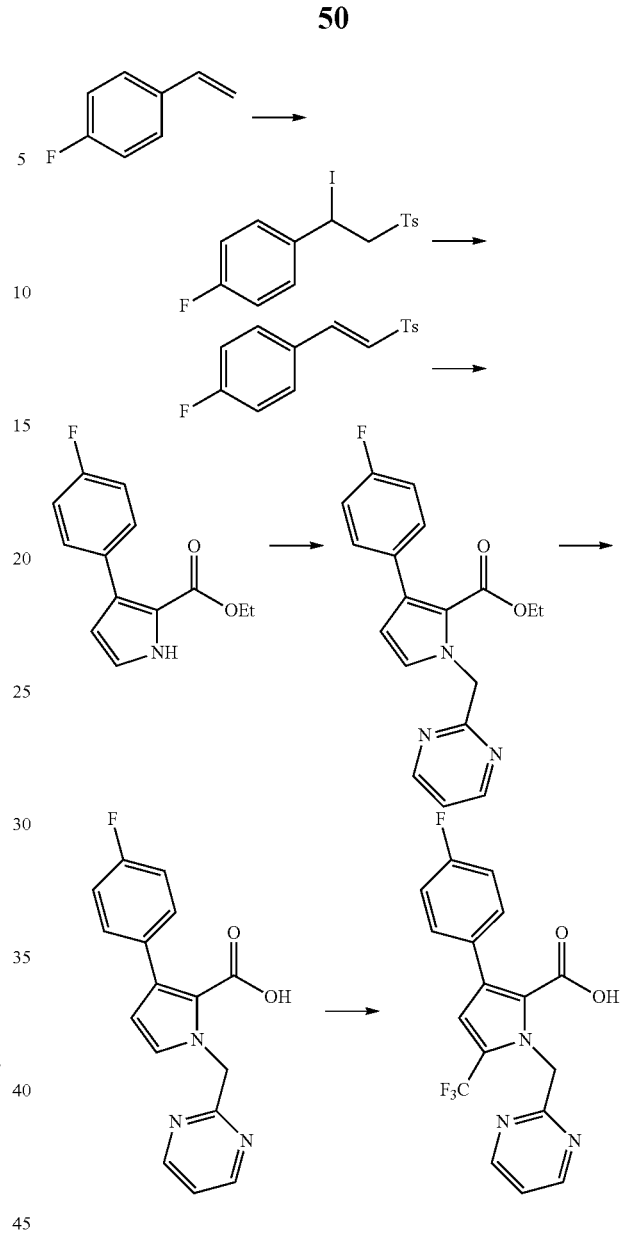

Step 1: 1-Fluoro-4-(1-iodo-2-tosylethyl)benzene

4-Fluorostyrene (10.5 g, 85.96 mmol) and ammonium ceric nitrate (94.25 g, 171.93 mmol) were added successively to a suspension of sodium p-toluenesulfinate (22.95 g, 128.93 mmol) and NaI (19.3 g, 128.95 mmol) in MeCN (400 mL) under Ar atmosphere at RT and stirred for 12 h. The reaction mixture was concentrated in vacuo and the residue was partitioned between H₂O (300 mL) and DCM (250 mL). The layers were separated and the aqueous phase was extracted with DCM (2×250 mL). The combined organic layer was washed with aqueous Na₂S₂O₃ (500 mL), brine (500 mL), dried over anhydrous Na₂SO₄, filtered and concentrated to give the crude product (21 g). The crude product was taken as such for next step without further purification.

Step 2: (E)-1-Fluoro-4-(2-tosylvinyl)benzene

Triethylamine (14.46 mL, 103.94 mmol) was added to a solution of 1-fluoro-4-(1-iodo-2-tosylethyl)-benzene (21 g, 51.9 mmol) in MeCN (210 mL) and stirred for 1 h at RT. The reaction mixture was concentrated under reduced pressure to obtain solid which was dissolved in dichloromethane (200 mL). The organic layer was washed successively with 1M KHSO₄ (500 mL), H₂O (500 mL), brine solution (500 mL); dried over anhydrous Na₂SO₄, filtered and concentrated to give the crude product. This was purified by column chromatography [silica gel (100-200 mesh; EtOAc: petroleum ether=1:9%)] to give 8.9 g of the desired compound (62%) as a white solid.

Step 3: Ethyl 3-(4-fluorophenyl)-1H-pyrrole-2-carboxylate

NaH (60% in mineral oil; 1.54 g, 38.68 mmol) was added portion wise to a solution of (E)-1-fluoro-4-(2-tosylvinyl) benzene (8.9 g, 32.23 mmol) and ethyl isocyanoacetate (3.85 mL, 35.46 mmol) in THF (200 mL) at 0° C. and the reaction mixture then stirred at RT for 2 h. EtOH (20 mL) was added and the solvents were evaporated to give a residue. The residue was partitioned between EtOAc (200 mL) and brine (200 mL) and the layers were separated. The organic layer was washed with H₂O (200 mL), dried (Na₂SO₄), filtered and concentrated to give the crude product. This was purified by column chromatography (neutral alumina; EtOAc: petroleum ether=2:8%) to give 5 g of the desired product (66%).

Step 4: Ethyl 3-(4-fluorophenyl)-1-(pyrimidin-2-ylmethyl)-1H-pyrrole-2-carboxylate Cs₂CO₃ (27.9 g, 85.8 mmol) was added to a stirred solution of ethyl 3-(4-fluorophenyl)-1H-pyrrole-2-carboxylate (2.5 g, 10.7 mmol) and 2-(chloromethyl)pyrimidine (Step A) (10 g crude) in MeCN (25 mL) at RT. The resulting reaction mixture was stirred at RT for 16 h. The reaction mixture was concentrated to give the residue, the residue was diluted with EtOAc (20 mL) and washed with H₂O (50 mL). The organic layer was washed with brine (50 mL), then dried (Na₂SO₄), filtered and evaporated the solvent under vacuo to give crude product which was purified by column chromatography (neutral alumina), the product was eluted by 10% EtOAc in petroleum ether to give the desired product (2 g, 57%) as a white solid.

Step 5: 3-(4-Fluorophenyl)-1-(pyrimidin-2-ylmethyl)-1H-pyrrole-2-carboxylic acid LiOH (7.2 g) was added to a stirred solution of ethyl 3-(4-fluorophenyl)-1-(pyrimidin-2-ylmethyl)-1H-pyrrole-2-carboxylate (7 g, 21.53 mmol) in EtOH (60 mL), THF (30 mL) and H₂O (10 mL) at RT. The resulting reaction mixture was stirred at 70° C. for 16 h. The reaction mixture was concentrated to give the residue which was diluted with H₂O (10 mL) and acidified with 6N HCl (pH~2). The precipitated solid was filtered and dried to give the desired product (5 g, 78%) as an off-white solid.

Step 6: 3-(4-Fluorophenyl)-1-(pyrimidin-2-ylmethyl)-5-(trifluoromethyl)-1H-pyrrole-2-carboxylic acid (ACI-2)

CF₃I gas (6 g) was bubbled through the solution of 3-(4-fluorophenyl)-1-(pyrimidin-2-ylmethyl)-1H-pyrrole-2-carboxylic acid (3 g, 10.1 mmol) in DMSO (30 mL) and FeSO₄.7H₂O (1.68 g, 6.06 mmol) at RT for 5 min. 30% aqueous H₂O₂ (6.8 mL, 60.6 mmol) was added at 0° C. and stirred at RT for 16 h, diluted with H₂O (100 mL) and extracted with Et₂O (3×50 mL). The combined organic layers was successively washed with H₂O (100 mL), brine (100 mL), dried (Na₂SO₄) and concentrated in vacuo to get the crude product, which was purified by column chromatography (silica gel; 100-200 mesh); the product was eluted by 70% EtOAc in petroleum ether to give crude product. The crude product was washed with pentane to give the desired product (0.85 g, 23%) as an off white solid.

1.1.3 3-(4-Fluorophenyl)-1-((3-methyl-1,2,4-oxadiazol-5-yl)methyl)-5-(trifluoromethyl)-1H-pyrrole-2-carboxylic acid (ACI-3)

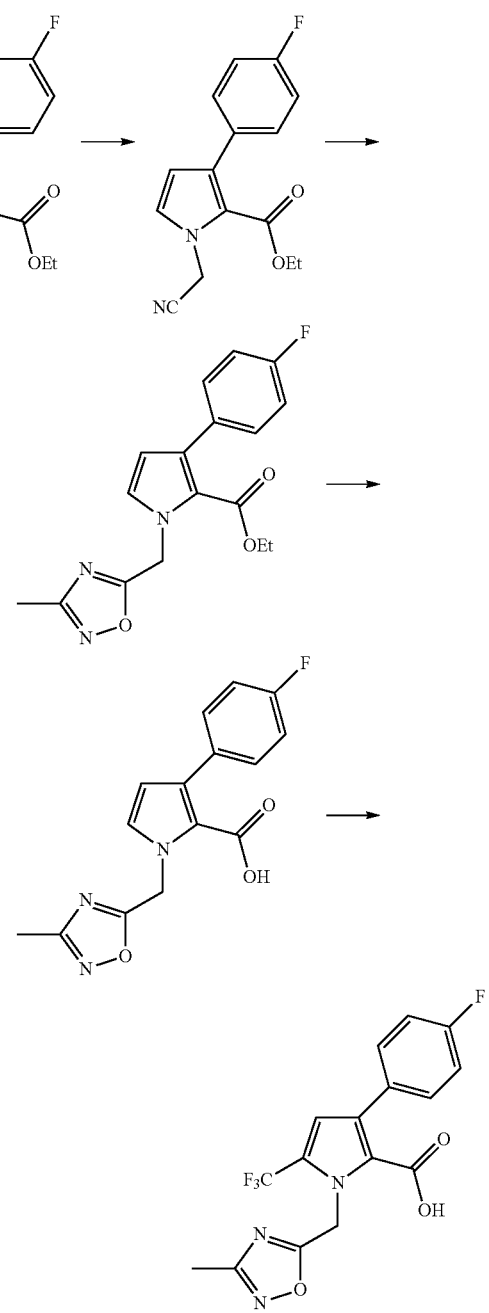

Step 1: Ethyl 1-(cyanomethyl)-3-(4-fluorophenyl)-1H-pyrrole-2-carboxylate

NaH (60%; 8.23 g, 205.09 mmol) was added to a solution of ethyl 3-(4-fluorophenyl)-1H-pyrrole-2-carboxylate (40 g, 171.6 mmol) in DMF (400 mL) at 0° C. under $N_2$ atmosphere and stirred for 15 min. Chloroacetonitrile (13 mL, 205.7 mmol) was added at the same temperature and the reaction mixture was allowed to warm to RT and stirred at for 16 h. The reaction mixture was quenched with $H_2O$ (500 mL) and the resulting precipitate was filtered and dried to give the desired product (46 g, 52%) as an off-white solid. (TLC system: $Et_2O$-petroleum ether; 1:9; Rf: 0.3).

Step 2: Ethyl 3-(4-fluorophenyl)-1-((3-methyl-1,2,4-oxadiazol-5-yl)methyl)-1H-pyrrole-2-carboxylate (E)-N'-hydroxy acetimidamide (7.34 g, 99.26 mmol) was added to a solution of ethyl 1-(cyanomethyl)-3-(4-fluorophenyl)-1H-pyrrole-2-carboxylate (18 g, 66.16 mmol) and anhydrous $ZnCl_2$ (13.5 mg, 99.26 mmol) in EtOAc (180 mL) and THF (40 mL) at RT. The resulting reaction mixture was heated at 90° C. for 20 h. Concentration in vacuo gave a residue, which was diluted with $H_2O$ (200 mL) and extracted with EtOAc (2×100 mL). The combined organic layer was washed with brine (200 mL), dried ($Na_2SO_4$), filtered and evaporated in vacuo to give crude. Purification by column chromatography (silica gel; 100-200 mesh) by eluting with 12-15% EtOAc in petroleum ether gave the desired product (4 g, 18%) as an off-white solid (TLC system: 30% EtOAc-petroleum ether; Rf: 0.6).

Step 3: 3-(4-fluorophenyl)-1-((3-methyl-1,2,4-oxadiazol-5-yl)methyl)-1H-pyrrole-2-carboxylic acid LiOH (0.764 g, 18.23 mmol) was added to a solution of ethyl 3-(4-fluorophenyl)-1-((3-methyl-1,2,4-oxadiazol-5-yl)methyl)-1H-pyrrole-2-carboxylate (4 g, 112.15 mmol) in THF-EtOH-$H_2O$ (6:3:1; 40 mL), at RT. The resulting reaction mixture was stirred at 50° C. for 48 h. The reaction mixture was concentrated to give residue. The residue was diluted with $H_2O$ (10 mL) and acidified (pH~5) with 6NHCl at 0° C. The aqueous layer was extracted with EtOAc (2×100 mL). The combined organic layer was washed with brine (200 mL), then dried ($Na_2SO_4$), filtered and evaporated the solvent in vacuoto give crude. Purification by flash column chromatography (silica gel; 60-120 mesh); the product eluted with 40%-100% petroleum ether in EtOAc to give the desired product (2.2 g, 60%) as an off-white solid (TLC system: 50% EtOAc-petroleum ether; Rf: 0.4).

Step 4: 3-(4-fluorophenyl)-1-((3-methyl-1,2,4-oxadiazol-5-yl)methyl)-5-(trifluoromethyl)-1H-pyrrole-2-carboxylicacid $CF_3I$ gas (10 g) was bubbled through the solution of 3-(4-fluorophenyl)-1-((3-methyl-1,2,4-oxadiazol-5-yl)methyl)-1H-pyrrole-2-carboxylic acid (4.5 g, 14.95 mmol) in DMSO (45 mL) and $FeSO_4.7H_2O$ (2.49 g, 8.97 mmol) at RT for 5 min. 30% aqueous $H_2O_2$ (10 mL, 89.7 mmol) was added at 0° C. and mixture stirred at RT for 16 h, diluted with $H_2O$ (100 mL) and extracted with $Et_2O$ (3×50 mL). The combined organic layer was successively washed with $H_2O$ (150 mL), brine (150 mL), dried ($Na_2SO_4$) and concentrated in vacuo to get the crude, which was purified by column chromatography (silica gel; 100-200 mesh). The product was eluted by 20-25% EtOAc in petroleum ether to give the desired product ACI-3 (0.9 g, 17%) as an off-white solid (TLC system: 50% EtOAc-petroleum ether; Rf: 0.2).

1.1.4 3-(4-Chloro-2-fluorophenyl)-4-methyl-5-(trifluoromethyl)-1H-pyrrole-2-carboxylic acid (ACI-4)

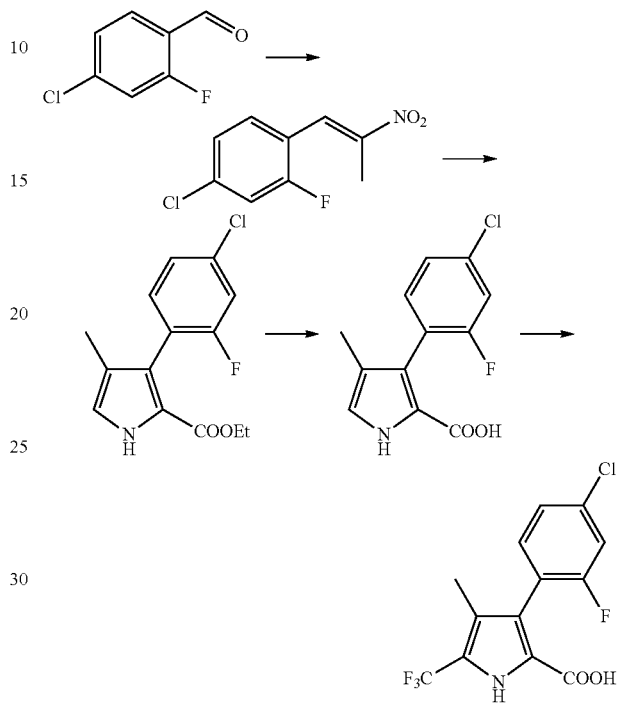

Step 1: (E)-4-Chloro-2-fluoro-1-(2-nitroprop-1-enyl)benzene

4-Chloro-2-fluorobenzaldehyde (25 g, 157.6 mmol), nitroethane (12.43 mL, 173.35 mmol), trimethyl orthoformate (38 mL, 346.62 mmol), methylamine HCl (8.3 g, 122.9 mmol) and potassium acetate (10.8 g, 98.14 mmol) in MeOH (125 mL) was heated at reflux for 18 h. The reaction mixture was cooled to RT and diluted with $H_2O$ (200 mL) and extracted with $Et_2O$ (3×100 mL). The combined organic layer was successively washed with $H_2O$ (200 mL), brine (200 mL), dried ($Na_2SO_4$), filtered and concentrated. The residue upon trituration with MeOH (30 mL) gave yellow solid. It was filtered off and washed with chilled MeOH (25 mL) to afford 15 g (44%) of the desired product as a yellow solid. (TLC system: EtOAc:Petroleum ether; 1:9; Rf: 0.56).

Step 2: Ethyl-3-(4-chloro-2-fluorophenyl)-4-methyl 1H-pyrrole-2-carboxylate (E)-4-Chloro-2-fluoro-1-(2-nitroprop-1-enyl)benzene (15 g, 215 mmol) in THF (100 mL) was treated with ethyl isocyanoacetate (9.6 mL, 88.35 mmol) and DBU (6.97 mL, 88.31 mmol) at 0° C. The reaction mixture was stirred for 2 h at RT. The reaction mixture was partitioned between EtOAc (100 mL) and $H_2O$ (200 mL). The organic layer was successively washed with $H_2O$ (2×200 mL), brine (200 mL), dried ($Na_2SO_4$) and concentrated in vacuo. The residue upon purification by column chromatography (silica gel; 100-200 mesh); the pure product eluted with 5% EtOAc in petroleum ether to give the desired product (10.5 g, 53%) as an off-white solid. (TLC system: 10% EtOAc-Petroleum ether; 1:9; Rf: 0.48).

Step 3 and 4: 3-(4-Chloro-2-fluorophenyl)-4-methyl-5-trifluoromethyl pyrrole-2-carboxylic acid 8M NaOH solution (60 mL) was added to a solution of ethyl-3-(4-chloro-2-fluorophenyl)-4-methyl 1H-pyrrole-2-carboxylate (5 g, 21.35 mmol) in EtOH (60 mL) and the whole heated at reflux overnight. The mixture was evaporated in vacuo and the residue diluted with $H_2O$ (60 mL) and washed once with EtOAc (100 mL). The aqueous layer was then acidified with 6N HCl to pH~4. The resulting precipitate was filtered and washed thoroughly with $H_2O$ and dried at 50° C. in vacuo to give 4 g (80%) of the desired acid, which was used for next step as it is.

$CF_3I$ gas (8 g, 40.8 mmol) was bubbled into a solution of the above acid (4 g, 15.8 mmol) in 40 mL DMSO and $FeSO_4.7H_2O$ (2.63 g, 9.48 mmol) at RT. The whole was cooled to 0° C. and 30% $H_2O_2$ (10.7 mL, 94.86 mmol) was added dropwise. The mixture was warmed to RT and stirred for 3 h. It was then quenched into $H_2O$ (100 mL) and extracted with EtOAc (3×100 mL). The combined organic layer was washed successively with $H_2O$, brine, dried ($Na_2SO_4$) and concentrated to dryness in vacuo. The residue was purified by flash column chromatography (silica gel; 60-120 mesh) and the compound eluted with 20% EtOAc in petroleum ether to give 2.4 g (47.3%) of 3-(4-chloro-2-fluorophenyl)-4-methyl-5-(trifluoromethyl)-1H-pyrrole-2-carboxylic acid as off white solid [TLC: 30% EtOAc in petroleum ether; $R_f$=0.3]

1.2 Synthesis of Pyrrole Building Blocks (PY)

1.2.1 (3-(4-Chlorophenyl)-4-methyl-1H-pyrrol-2-yl)(morpholino)methanone (PY-1)

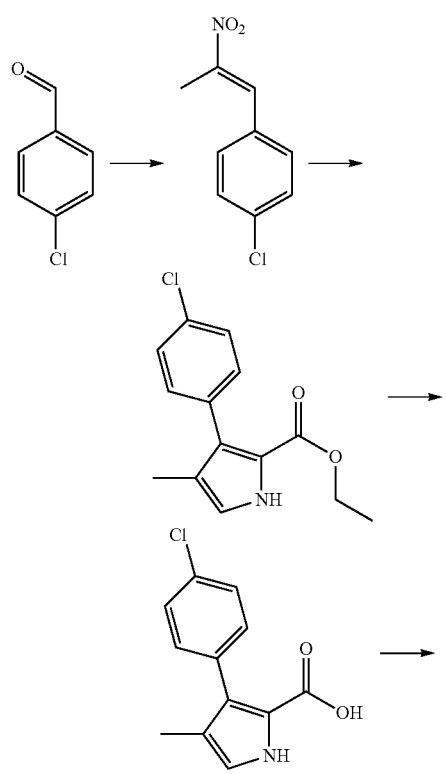

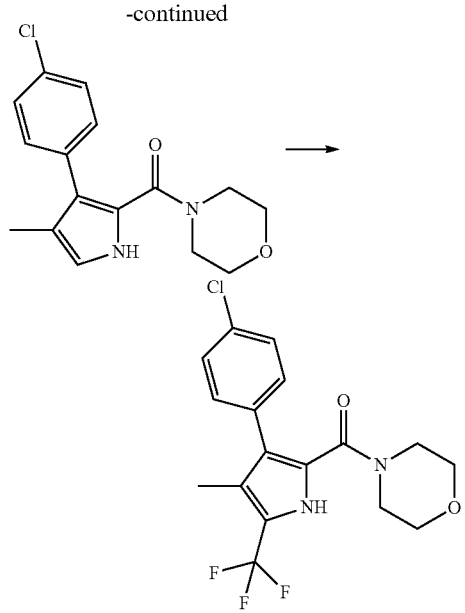

Step 1: (E)-1-Chloro-4-(2-nitroprop-1-en-1-yl)benzene

A solution of 4-chlorobenzaldehyde (58.5 g, 416 mmol), nitroethane (90 mL, 1249 mmol) and piperidine (8.22 mL, 83 mmol) in toluene (400 mL) was stirred at reflux (Dean-Stark) for 4 h. The mixture was left standing at RT overnight. The solvent was removed under reduced pressure and the residue recrystallised from absolute EtOH to furnish 51.81 g (63%) of the desired product.

Step 2: Ethyl 3-(4-chlorophenyl)-4-methyl-1H-pyrrole-2-carboxylate

To a suspension of (E)-1-chloro-4-(2-nitroprop-1-en-1-yl) benzene (11.6 g, 58.7 mmol) and ethyl 2-isocyanoacetate (7.0 g, 62 mmol) in dry THF (30 mL) and i-PrOH (30 mL) was added 2.6 mmol TBD/g polystyrene (24.8 g, 64.4 mmol). The reaction mixture was stirred at RT overnight. The suspension was filtered, the residue washed with i-PrOH/THF (1/1, v/v, 40 mL), followed by EtOH (ca. 20 mL). The combined filtrate was evaporated under reduced pressure, to furnish 16.95 g ('109%') of the desired product.

Step 3: 3-(4-Chlorophenyl)-4-methyl-1H-pyrrole-2-carboxylic acid

To a solution of ethyl 3-(4-chlorophenyl)-4-methyl-1H-pyrrole-2-carboxylate (16.95 g, max. 58.7 mmol) in absolute EtOH (30 mL) and THF (30 mL) was added $H_2O$ (30 mL) and NaOH (51.4 g, 1.285 mol) and the reaction mixture was stirred at reflux for 90 min and left standing at RT overnight. The reaction mixture was concentrated in vacuo. Upon cooling on an ice-bath, ice (250 mL) was added followed by the dropwise addition of aqueous 6 M HCl (250 mL). After stirring at 0° C. for 2 h, the suspension was filtered and the residue washed with $H_2O$ (2×50 mL). The product was dried on a filter overnight to obtain 12.30 g (89% over two steps) of the desired product.

Step 4: (3-(4-Chlorophenyl)-4-methyl-1H-pyrrol-2-yl)(morpholino)methanone

A suspension of 3-(4-chlorophenyl)-4-methyl-1H-pyrrole-2-carboxylic acid (7.23 g, 30.7 mmol) and morpholine (6.68 mL, 77 mmol) in DCM (100 mL) was cooled to 0° C. EDCl (7.65 g, 39.9 mmol) was added followed by HOAt (3.76 g, 27.6 mmol). The reaction mixture was stirred at RT overnight. DCM (100 mL) was added and the mixture was extracted with aqueous 1 M $KHSO_4$ (3×200 mL), saturated aqueous $NaHCO_3$ (1×200 mL), brine (200 mL), dried ($Na_2SO_4$) and evaporated under reduced pressure, to give 7.91 g (85%) of the desired product.

Step 5: (3-(4-Chlorophenyl)-4-methyl-5-(trifluoromethyl)-1H-pyrrol-2-yl)(morpholino)methanone (PY-1)

Trifluoromethanesulfonyl chloride (0.522 mL, 4.92 mmol) was added to a solution of (3-(4-chloro-phenyl)-4-methyl-1H-pyrrol-2-yl)(morpholino)methanone (1.00 g, 3.28 mmol) in dry DMF (30 mL). At 0° C., $FeSO_4.7H_2O$ (0.365 g, 1.312 mmol) was added followed by the dropwise addition of 30% aq. $H_2O_2$ (0.670 mL, 6.56 mmol). After 1 h, the reaction mixture was added to ice/$H_2O$ (100 mL) and stirred vigorously for 15 min. Filtration was attempted, but not successful. The mixture was extracted with EtOAc (2×100 mL). The combined organic layers were extracted with brine (2×100 mL), dried ($Na_2SO_4$) and left standing overnight. The suspension was filtered and the filtrate evaporated under reduced pressure. The product was combined with the batch of crude product described below and purified. Trifluoromethanesulfonyl chloride (4.60 mL, 43.4 mmol) was added to a solution of (3-(4-chlorophenyl)-4-methyl-1H-pyrrol-2-yl)(morpholino)methanone (6.62 g, 21.72 mmol) in dry DMF (200 mL). At 0° C., $FeSO_4.7H_2O$ (3.62 g, 13.03 mmol) was added followed by the dropwise addition of 30% aq. $H_2O_2$ (6.66 mL, 65.2 mmol). After 30 min, the reaction mixture was added to ice/$H_2O$ (500 mL) and stirred vigorously for 15 min. Filtration was attempted, but not successful. The mixture was extracted with EtOAc (3×200 mL). The combined organic layer was extracted with brine (2×100 mL), dried ($Na_2SO_4$), evaporated under reduced pressure and co-evaporated with toluene (2×). The resulting batch of crude product was combined with the crude batch described above and purified by column chromatography (silica, heptane/EtOAc, 4:1→3:1→2:1→1:1), to afford 6.03 g (65%) of the desired product.

1.2.2 3-(4-Chlorophenyl)-N-methyl-N-neopentyl-5-(trifluoromethyl)-1H-pyrrole-2-carboxamide (PY-2)

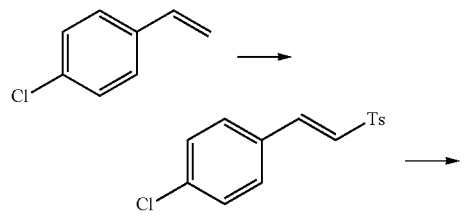

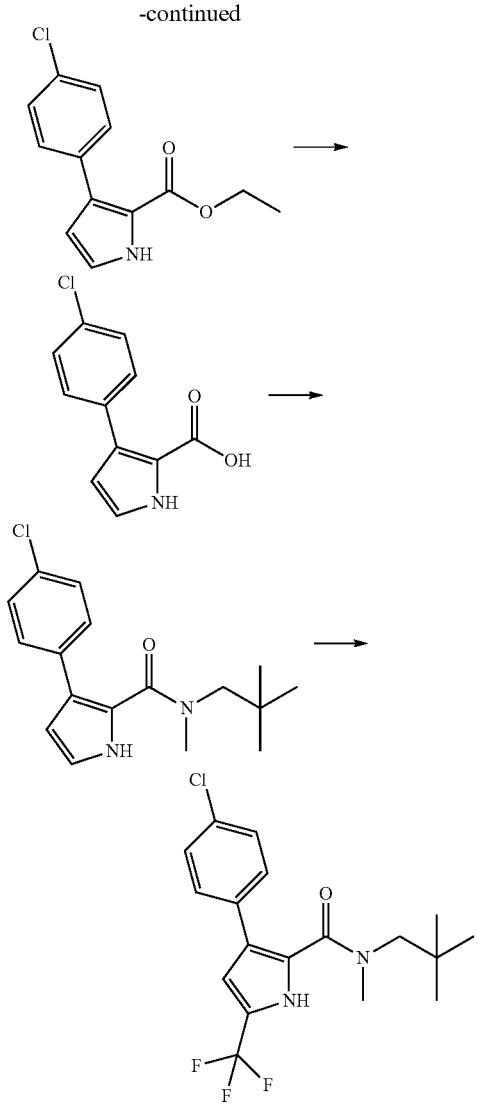

Step 1: (E)-1-Chloro-4-(2-tosylvinyl)benzene

To a suspension of sodium 4-methylbenzenesulfinate (68.7 g, 386 mmol) in DMSO (350 mL) was added acetic acid (350 mL). Subsequently, KI (61.1 g, 368 mmol), 2,2'-bypyridine (5.48 g, 35.1 mmol), CuI (6.68 g, 35.1 mmol) and 4-chlorostyrene (40.7 mL, 317 mmol) were added. The reaction mixture was directly warmed to 100° C. with a preheated oil bath and stirred at this temperature overnight. The reaction mixture was allowed to cool to RT and then poured into ice-water (1.4 L). The formed suspension was stirred for 0.5 h and the precipitate was filtered, washed with $H_2O$ (3×700 mL) and a small amount of i-$Pr_2O$ (2×). The precipitate was dissolved in hot toluene (1 L), filtered and the remaining impurities were washed with hot toluene (2×). The combined filtrate was left standing to crystallize. The crystals were washed with toluene (2×) and dried on filter to give the desired product (37.07 g). The mother liquor was concentrated and crystallized (i-PrOH) to give extra product (21.54 g). The crystals were combined (58.61 g, 63%).

Step 2: Ethyl 3-(4-chlorophenyl)-1H-pyrrole-2-carboxylate

During a period of 30 min a solution of ethyl 2-isocyanoacetate (25.0 g, 221 mmol) and (E)-1-chloro-4-(2-tosylvinyl)benzene (58.6 g, 200 mmol) in dry THF (200 mL) and dry DMF (200 mL) was added to a suspension of 60% NaH in mineral oil (9.61 g, 240 mmol) in dry THF (400 mL) while cooling with a water bath. The reaction mixture was stirred for 2 h, then quenched with saturated aqueous NH$_4$Cl (400 mL) and concentrated to a smaller volume. The residue was extracted with toluene (1 L). The organic layer was washed with saturated aqueous NaHCO$_3$ (400 mL) and brine (2×400 mL), dried (Na$_2$SO$_4$) and concentrated. The residue was dissolved in hot Et$_2$O, filtered and the filtrate was concentrated. The residue was subjected to column chromatography (silica, toluene/acetone, 99:1) giving two fractions. The first fraction was pure product (18.2 g) and the second fraction was purified further by crystallization (MeCN/H$_2$O) to give the desired product (1.93 g). The mother liquor was concentrated and crystallization (MeCN/H$_2$O/EtOH) of the residue gave also product (1.37 g). The combined yield of the desired product was 21.5 g (43%).

Step 3: 3-(4-Chlorophenyl)-1H-pyrrole-2-carboxylic acid

To a suspension of ethyl 3-(4-chlorophenyl)-1H-pyrrole-2-carboxylate (20.1 g, 80.0 mmol) in EtOH (80 mL) and H$_2$O (80 mL) was added LiOHH$_2$O (16.9 g, 402 mmol) and the reaction mixture was stirred at 80° C. overnight. Extra LiOHH$_2$O (6.76 g, 161 mmol) was added and the reaction mixture was stirred at 100° C. for 3 h. The reaction mixture was concentrated to a smaller volume and extra H$_2$O was added. The reaction mixture was stirred at 100° C. for 2 h and at RT over the weekend. The reaction mixture was acidified with aqueous 1M KHSO$_4$ while cooling with an ice-bath. The formed precipitate was filtered off, washed with H$_2$O (2×) and dried on filter overnight. The residue was suspended in EtOH (200 mL) and H$_2$O (200 mL) and LiOHH$_2$O (33.8 g, 805 mmol) was added. The reaction mixture was stirred at reflux overnight, allowed to cool to RT and concentrated. The reaction mixture was acidified with aqueous 1M KHSO$_4$ while cooling with an ice-bath. The formed precipitate was filtered, washed with H$_2$O (2×) and dried on filter overnight. The product was dissolved in EtOAc, dried (Na$_2$SO$_4$) and concentrated to give impure product (14.8 g, 52% pure, 43%).

Step 4: 3-(4-Chlorophenyl)-N-methyl-N-neopentyl-1H-pyrrole-2-carboxamide

To 3-(4-chlorophenyl)-1H-pyrrole-2-carboxylic acid (14.8 g, 52% pure, 34.7 mmol) in dry DME (200 mL) was added DIPEA (25 mL, 143 mmol), N,2,2-trimethylpropan-1-amine hydrochloride AMN-1 (7.17 g, 52.1 mmol) and BOP—Cl (10.6 g, 41.7 mmol). The reaction mixture was stirred at reflux temperature for 1 h. The reaction mixture was diluted with EtOAc (1 L), washed with aqueous 1M KHSO$_4$ and saturated aqueous NaHCO$_3$, dried (Na$_2$SO$_4$) and concentrated. The residue was stirred in i-Pr$_2$O for 10 min and the solids were filtered off. Crystallisation (EtOAc) of the residue and its subsequent mother liquor gave the desired product (7.45 g, 70%).

Step 5: 3-(4-Chlorophenyl)-N-methyl-N-neopentyl-5-(trifluoromethyl)-1H-pyrrole-2-carboxamide K$_2$HPO$_4$ (1.71 g, 9.84 mmol) was added to a solution of 3-(4-chlorophenyl)-N-methyl-N-neopentyl-1H-pyrrole-2-carboxamide (1.00 g, 3.28 mmol) in dry DMF (30 mL) and Ar was bubbled through the reaction mixture for 15 min. Dichlorotris(1,10-phenanthroline)rutheniunn(II) hydrate (0.118 g, 0.164 mmol) and trifluoromethanesulfonyl chloride (0.522 mL, 4.92 mmol) were added and the suspension was irradiated by a light bulb (E27-23W, 4000K, 165 mA) overnight. Extra trifluoromethanesulfonyl chloride (0.522 mL, 4.92 mmol) was added to the reaction mixture and the suspension was irradiated by a light bulb for another 4 h. The reaction mixture was poured into ice-cold water, stirred for 10 min. and the precipitate was filtered off. The precipitate was washed with H$_2$O (2×) and dried on filter. The residue was first purified by column chromatography (silica, heptane/EtOAc, 3:1) and then by crystallisation (i-Pr$_2$O/heptane) to give the desired product (400 mg, 33%). The mother liquor was concentrated and crystallisation (i-Pr$_2$O/heptane) of the residue gave extra product (69 mg, 6%). Total yield: 469 mg (39%).

1.2.3 3-(4-Chlorophenyl)-N,4-dimethyl-N-(2-(methylsulfonyl)ethyl)-5-(trifluoromethyl)-1H-pyrrole-2-carboxamide (PY-3)

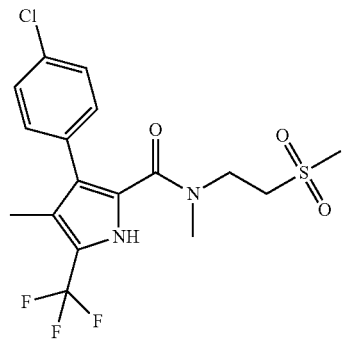

The synthesis of PY-3 was carried out in analogy to PY-1.

1.2.4 (3-(4-chlorophenyl)-4-methyl-5-(trifluoromethyl)-1H-pyrrol-2-yl)(1,1-dioxidothiomorpholino)methanone (PY-4)

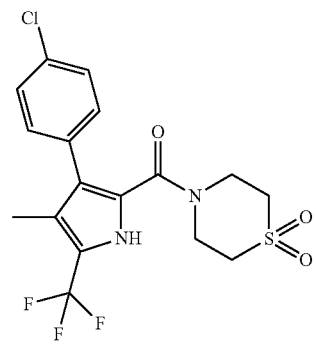 [SMILES: Cc1c(C(F)(F)F)[nH]c(C(=O)N2CCS(=O)(=O)CC2)c1-c1ccc(Cl)cc1]

The synthesis of PY-4 was carried out in analogy to PY-1.

1.2.5 3-(4-chlorophenyl)-N,4-dimethyl-N-(2-(methylthio)ethyl)-5-(trifluoromethyl)-1H-pyrrole-2-carboxamide (PY-5)

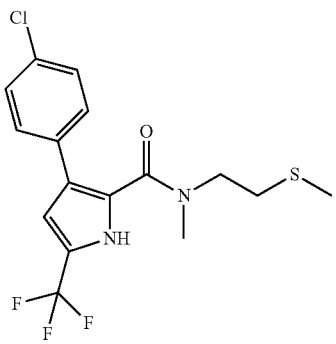 [SMILES: CSCCN(C)C(=O)c1[nH]c(C(F)(F)F)cc1-c1ccc(Cl)cc1]

The synthesis of PY-5 was carried out in analogy to PY-1.

1.3 Synthesis of Alcohol Building Blocks (AOH)

1.3.1 (1-Methyl-1H-1,2,3-triazol-4-yl)methanol (AOH-1)

The reaction was performed under $N_2$ atmosphere. To a suspension of 1-methyl-1H-1,2,3-triazole-4-carboxylic acid (400 mg, 3.15 mmol) in dry THF (7 mL) was dropwise added 2.4 M $LiAlH_4$ in THF (2.88 mL, 6.92 mmol) and the reaction mixture was stirred overnight. The reaction mixture was quenched with a solution of $H_2O$/THF (1:1) and stirred for 10 min, after which $Na_2SO_4$ was added. The suspension was stirred for 1 h, filtered, washed with EtOAc and the filtrate was concentrated. The residue was purified by flash chromatography (silica, gradient DCM/MeOH, 1:0→9:1) to give the desired product (235 mg, 66%).

1.3.2 (5-Chloropyridin-3-yl)methanol (AOH-2)

5-Chloronicotinic acid (1 g, 6.35 mmol) was dissolved in dry THF (20 mL) in a $N_2$ flushed flask and 1 M $BH_3$ in THF (25.4 mL, 25.4 mmol) was added via a syringe at 0° C. The mixture was stirred at RT for 72 h. The reaction mixture was cooled in an ice bath and aqueous saturated $K_2CO_3$ (50 mL) was added cautiously. The organic solvent was removed in vacuo and the residue was extracted with EtOAc (2×50 mL). The combined organic layers were washed with saturated aqueous $NaHCO_3$ (2×25 mL) and brine (2×25 mL) before drying on $Na_2SO_4$ and concentration in vacuo to give a colorless oil. The product was purified using column chromatography (silica, heptane/EtOAc, 1:1) to give the desired product (285 mg, 31%) as a yellow oil which partially solidified upon standing.

1.3.3 1-(Hydroxymethyl)pyridin-2(1H)-one (AOH-3)

Paraformaldehyde (83 mg, 2.76 mmol) was added to pyridin-2-ol (250 mg, 2.63 mmol) and the mixture was stirred at 100° C. for 30 min. The reaction mixture was 'concentrated' and used as such in the next step.

1.4 Synthesis of Mesylate (MS), Bromomethyl (BM) and Chloromethyl (CM) Building Blocks

1.4.1 (3-Methyl-1,2,4-oxadiazol-5-yl)methyl methanesulfonate (MS-1)

To a solution of (3-methyl-1,2,4-oxadiazol-5-yl)methanol (300 mg, 2.63 mmol) and $Et_3N$ (0.550 mL, 3.94 mmol) in DCM (5 mL) was added methanesulfonyl chloride (0.246 mL, 3.16 mmol) while cooling with an ice-bath. The reaction mixture was stirred for 2 h while cooling with an ice-bath. The reaction mixture was acidified with aqueous 1M $KHSO_4$ and the organic layer was separated and concentrated. The residue was purified by flash column chromatography (silica, gradient heptane/EtOAc, 93:7→30:70) to yield the desired product (412 mg, 82%).

1.4.2 4-(Bromomethyl)-1-methyl-1H-pyrazole (BM-1)

To a stirred solution of (1-methyl-1H-pyrazol-4-yl)methanol (1.5 g, 13.39 mmol) in glacial acetic acid (7.5 mL) was added 33% HBr in acetic acid (18 mL, 66.96 mmol) and the mixture was refluxed for 5 h. The solvent was removed under reduced pressure. The residue was crystallised from DCM and $Et_2O$ to afford pure desired product (1.4 g, 60%) as a light brown solid.

1.4.3 2-(Bromomethyl)-1,3,4-thiadiazole (BM-2)

To a stirred solution of (1,3,4-thiadiazol-2-yl)methanol (0.8 g, 6.89 mmol) in DCM (70 mL) $PBr_3$ (3.4 mL, 34.40 mmol) was added at 0° C. and the mixture was stirred for 3 h at RT. The reaction was cooled at 0° C., quenched with ice-water, extracted with EtOAc (3×20 mL). The organic layer was washed with saturated brine, dried over anhydrous $Na_2SO_4$, evaporated under reduced pressure to get crude product which was purified column chromatography to afford desired product (0.630 g, 52%) as a brown solid.

1.4.4 5-(Chloromethyl)pyrimidine (CM-1)

To a solution of pyrimidin-5-ylmethanol (0.5 g, 4.54 mmol), and DMAP (0.830 g, 6.81 mmol) in DCM was added tosylchloride (1.0 g, 5.45 mmol, 1.2 eq.) at 0° C. and the reaction mixture was stirred for 2 h. After completion of the reaction (TLC), the reaction mixture was concentrated under reduced pressure. The residue was diluted with EtOAc, washed with $H_2O$, brine, dried over anhydrous $Na_2SO_4$ and the solvent was evaporated under reduced pressure. The crude product was purified by column chromatography to afford desired compound (0.2 g, 34%) as a colourless liquid.

1.5 Synthesis of Amine Building Blocks (AMN)

1.5.1 N,2,2-Trimethylpropan-1-amine hydrochloride (AMN-1)

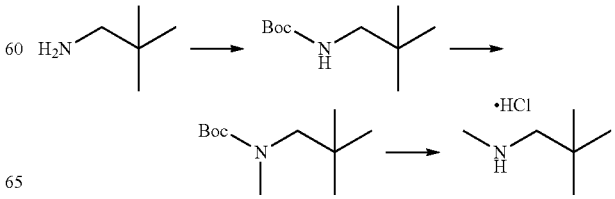

Step 1: tert-Butyl neopentylcarbamate

To a solution of 2,2-dimethylpropan-1-amine (17.90 g, 205 mmol) in DCM (150 mL) was dropwise added a solution of Boc$_2$O (44.8 g, 205 mmol) in DCM (50 mL) at 0° C. After complete addition, stirring was continued at RT overnight. The solvent was removed under reduced pressure and the residue co-evaporated with DCM (3×). EtOAc (250 mL) was added and the mixture was washed with H$_2$O (2×250 mL). The organic layer was dried (Na$_2$SO$_4$) and evaporated under reduced pressure, to give 36.98 g (96%) of the desired product.

Step 2: tert-Butyl methyl(neopentyl)carbamate

A solution of tert-butyl neopentylcarbamate (37.0 g, 198 mmol) in dry DMF (100 mL) was added to a suspension of 60% NaH in mineral oil (15.8 g, 395 mmol) in dry DMF (200 mL) under N$_2$ atmosphere in 10 min and the reaction mixture was stirred for 1 h. To the reaction mixture was added MeI (30.9 mL, 494 mmol) in 10 min while cooling with an ice-bath and the reaction mixture was stirred at RT overnight. The reaction mixture was quenched with ice/H$_2$O (600 mL) and extracted with Et$_2$O (1 L). The organic layer was washed with brine, dried (Na$_2$SO$_4$) and concentrated to result in the desired product (45.6 g, '115%').

Step 3: N,2,2-Trimethylpropan-1-amine hydrochloride (AMN-1)

To a solution of tert-butyl methyl(neopentyl)carbamate (45.6 g, max. 198 mmol) in dry 1,4-dioxane (200 mL) was dropwise added 4M HCl in dioxane (200 mL, 800 mmol) and the reaction mixture was stirred overnight. The reaction mixture was concentrated and stirred in Et$_2$O for 1 d. The product was filtered under a nitrogen stream, washed with a small amount of Et$_2$O (2×) and dried on filter for 10 min yielding the desired product (26.0 g, 95% over two steps).

1.6 Pyrrole Derivatives According to Formula (I)

General Method for Synthesis of Pyrrole Derivatives According to Formula (I):
General Procedure 1 (GP-1):

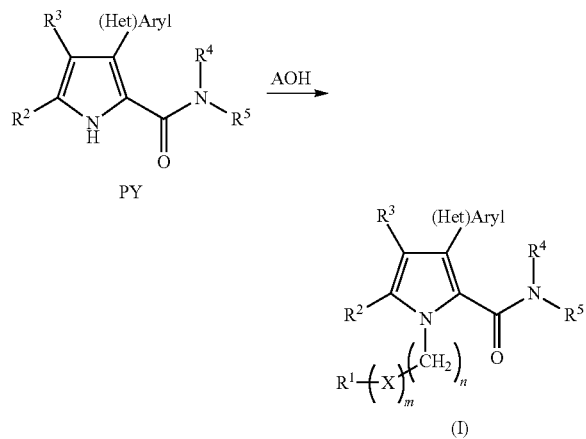

Pyrrole PY (1 eq), PPh$_3$ (1.15 eq) and alcohol AOH (1.25 eq) were dissolved in dry THF at RT. To the solution was added DIAD (1.1 eq), at RT or 0° C., and the reaction mixture was stirred for 1 h to 5 d at temperatures between RT and 70° C. In some cases the order of addition was changed and the alcohol was added last, after DIAD. Also, in some cases it was necessary to add extra reagent (up to 3×PPh$_3$, DIAD, alcohol AOH). The reaction mixture was either (a) evaporated in vacuo or (b) diluted with EtOAc and saturated aqueous NaHCO$_3$, the aqueous layer extracted with EtOAc and the combined organic layers washed with saturated aqueous NaHCO$_3$ and brine, dried and the solvent evaporated. The crude product was purified by flash chromatography (silica) and in some cases preparative LCMS or reversed phase chromatography.

General Procedure 2A (GP-2A):

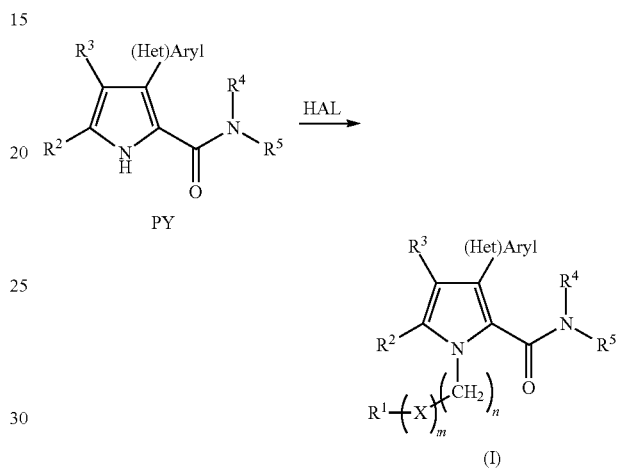

To a solution of pyrrole PY(1 eq) in dry DMF, Cs$_2$CO$_3$ (2 eq) and chloride HAL (or corresponding hydrochloride salt) (1.05 eq) were added and the reaction mixture was stirred between RT and 70° C., optionally in a sealed vessel, for 18 h and 3 d. If necessary, additional HAL was added. The reaction mixture was poured out in H$_2$O or saturated aqueous NaHCO$_3$ and extracted with EtOAc. Subsequently, the organic layer was washed with brine (2×) and dried over Na$_2$SO$_4$. The solvent was removed under reduced pressure and the residue purified using flash chromatography (silica) and in some cases preparative LCMS or reversed phase chromatography.

General Procedure 2B (GP-2B):
NaH (5 to 10 eq) was added to a solution of pyrrole PY(1 eq) in dry THF and stirred at RT for 90 min. Chloride HAL (or corresponding hydrochloride salt) (2 eq) were added and the reaction mixture was stirred between RT and 80° C. for 18 h. If necessary, additional HAL was added. The reaction mixture was poured out in H$_2$O or saturated aqueous NaHCO$_3$ and extracted with EtOAc. Subsequently, the organic layer was washed with brine (2×) and dried over Na$_2$SO$_4$. The solvent was removed under reduced pressure and the residue purified using flash chromatography (silica) and in some cases preparative LCMS or reversed phase chromatography.

General Procedure 2B (GP-2B):
Pyrrole PY(1 eq) was dissolved in dry MeCN. K$_2$CO$_3$ (2 eq) was added, followed by chloride HAL (1.2 eq). The reaction mixture was stirred at 80° C. overnight. Addition of silica was followed by filtration, and the residue was washed with EtOAc. The combined filtrates were concentrated in vacuo, dissolved in DCM (1 mL) and used for flash chromatography (silica). If required a second purification with preparative TLC was carried out.

General Procedure 3 (GP-3):

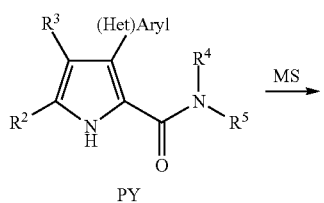

PY

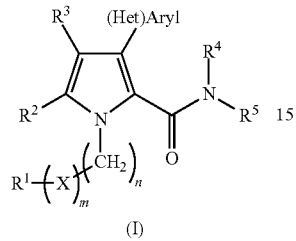

(I)

To a solution of pyrrole PY (1 eq) 0.322 mmol) in dry THF was added KOt-Bu (1-2 eq) and the reaction mixture was stirred for 10 min. Mesylate MS (1.3 eq) was added and the reaction mixture was stirred at RT overnight. If necessary, an extra portion of mesylate MS (0.65 eq) and KOt-Bu (1 eq) were added and stirring was continued overnight. The reaction mixture was concentrated in vacuo, the residue was acidified with aqueous 0.5 M $KHSO_4$ and the product was extracted with EtOAc (10 mL). The organic layer was washed with $H_2O$ (5 mL), saturated aqueous $NaHCO_3$ (5 mL) and brine (2×5 mL), dried ($Na_2SO_4$), filtered and concentrated. Purification was performed by flash column chromatography (silica).

General Procedure 4A (GP-4A):

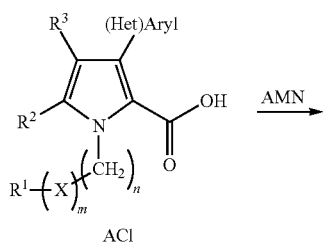

ACI

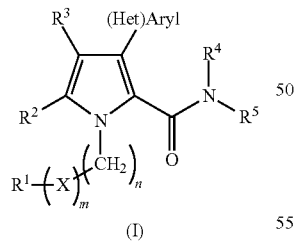

(I)

Carboxylic acid ACI (1 eq.) and amine AMN (1 eq.) were dissolved in DMF and DIPEA (3 eq.) were added. The mixture was cooled to −40° C. by an MeCN/dry ice bath and BOP—Cl (2 eq.) was added. The reaction mixture was stirred at −50° C. to −30° C. for 8 h and allowed to slowly warm to RT. To the reaction mixture was added aqueous 1M $KHSO_4$, followed by $H_2O$ and EtOAc to result in a clear two phase system. The layers were separated, the organic layer was washed with aqueous 1M $KHSO_4$ and saturated aqueous $NaHCO_3$, followed by drying with brine and $Na_2SO_4$. Concentration in vacuo was followed by purification by flash chromatography (silica). Lyophilisation resulted in the desired product.

General Procedure 4B (GP-4B):

Carboxylic acid ACI (1 eq) was dissolved in dry DMF by heating. At RT, amine AMN (2 eq) was added to the solution. The mixture was stirred at RT for 10 min, 50% T3P in DMF (2.2 eq) was added dropwise in 5 portions with time intervals of 10 min. The water-bath was applied during the addition. The reaction mixture was stirred at RT overnight. If necessary, more 50% T3P in DMF (1.3 eq) was added dropwise in 3 portions with time intervals of 10 min. A water-bath was applied during the addition. A little dry DMF was added. The reaction mixture was stirred at RT overnight and mixed with aqueous 1M $KHSO_4$, some ice and EtOAc to result in a clear two phase system. The layers were separated, the organic layer was washed with $H_2O$ and saturated aqueous $NaHCO_3$, followed by drying (brine and $Na_2SO_4$). Concentration in vacuo was followed by purification by flash chromatography (silica). If necessary the product was purified further by preparative TLC or reverse phase chromatography. Concentration in vacua or lyophilisation provided the desired product.

General Procedure 4C (GP-4C):

To a cooled (0° C.) stirred solution of carboxylic acid ACI (1 eq.) and DIPEA (2-4 eq.) in DCM was added EDCl (1.2 eq.), followed by HOBt (0.2 eq.) and stirring was continued for 15 min at RT before cooling again to 0° C. Amine AMN [or the corresponding hydrochloride salt] (1 eq.) was added and the solution was allowed to warm to RT and stir for 12-72 h. The reaction mixture was washed with saturated aqueous $NaHCO_3$ and concentrated in vacuo. The crude product was purified by flash column chromatography.

General Procedure 5 (GP-5):

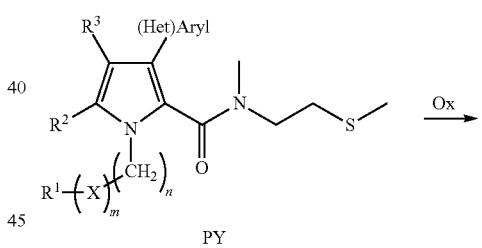

PY

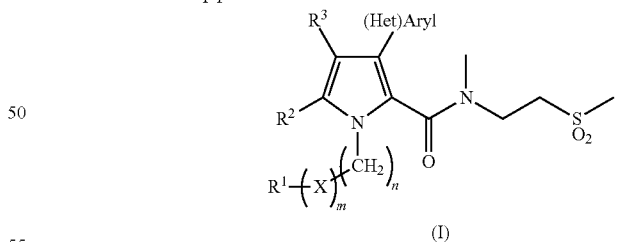

(I)

Oxone (2 equiv.) was added to a solution of Pyrrole PY (1 eq.) in MeOH and $H_2O$. The reaction was stirred at RT for 1 h. The reaction mixture was concentrated in vacuo and saturated aqueous $K_2CO_3$ was added and extracted with EtOAc, combined and followed by drying with $Na_2SO_4$. Concentration in vacuo was followed by purification by flash chromatography (silica).

Analytical Data:

*Material and Methods for LC/MS Analytics*: Hardware: Coupled Agilent 1290 Infinity UHPLC-TOF System; *LC-Module*: MTP-Handler: Agilent, Model BenchCel 2R; Themostatic Control Autoinjector: Agilent, Modell G4226A; Column oven: Agilent, Model G1316C; DAD: Agilent, Model G4212A; Binary Pump: Agilent, Model G4220A; *Time Of Flight Mass Spectrometer*: Agilent 6224; Ion source: Dual ESI; Column: Supplier: Waters; Type: Acquity UPLC HSS T3 1.8 μm (Part No. 186003538); Dimensions: 2.1×50 mm; Eluents: Eluent A: H$_2$O from Millipore Ultrapure water System: Milli-Q Integral 3+0.1% Formic acid; Eluent B: MeCN, Merck KGaA: LiChrosolv Hypergrade for LC-MS (1.00029.9010)+0.1% Formic acid; Formic acid: Merck KGaA: Suprapure 98-100% (1.11670.1000); LC-Method: Flow: 2.5 mL/min; Runtime: 1.2 min; Gradient: Start 2% B, 1 min 100% B, 1.09 min 100% B, 1.11 min 2% B, 1.2 min 2% B Stop; Columntemperature: 80° C.; UV: 190-400 nm; MS-Method: Ion Polarity: Positive; Gas Temperature: 325° C.; Gas Flow: 10 mL/min

TABLE

Synthesis and analytical data of pyrrole derivatives according to formula (I):

| Ex.-No. | Structure | Name | Synthesis according to (yield) | Mass | Mass Found | UV254-purity |
|---|---|---|---|---|---|---|
| 001 | 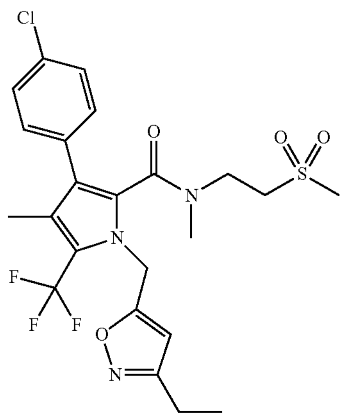 | 3-(4-Chlorophenyl)-1-[(3-ethyl-isoxazol-5-yl)-methyl]-N,4-dimethyl-N-(2-methylsulfonyl-ethyl)-5-(trifluoromethyl)-1H-pyrrole-2-carboxylic acid amide | GP-1 from PY-3 (75%) | 531.98 | Yes | 100 |
| 002 | 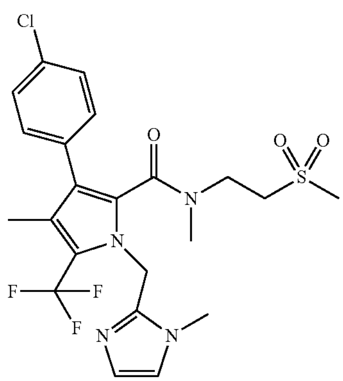 | 3-(4-Chlorophenyl)-N,4-dimethyl-1-[(1-methyl-1H-imidazol-2-yl)-methyl]-N-(2-methylsulfonyl-ethyl)-5-(trifluoromethyl)-1H-pyrrole-2-carboxylic acid amide | GP-2B from PY-5 (19%) followed by GP-5 (43%) | 516.96 | Yes | 100 |
| 003 | 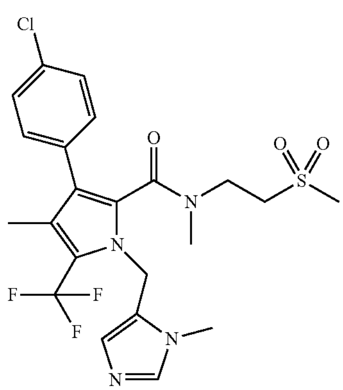 | 3-(4-Chlorophenyl)-N,4-dimethyl-1-[(3-methyl-3H-imidazol-4-yl)-methyl]-N-(2-methylsulfonyl-ethyl)-5-(trifluoromethyl)-1H-pyrrole-2-carboxylic acid amide | GP-2B from PY-5 (15%) followed by GP-5 (79%) | 516.96 | Yes | 100 |

TABLE-continued

Synthesis and analytical data of pyrrole derivatives according to formula (I):

| Ex.-No. | Structure | Name | Synthesis according to (yield) | Mass | Mass Found | UV254-purity |
|---|---|---|---|---|---|---|
| 004 | 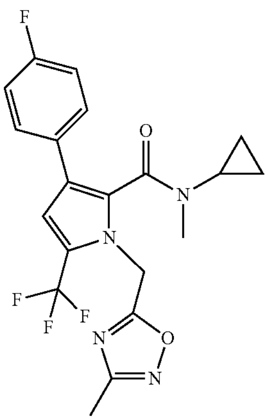 [SMILES: Cc1noc(Cn2c(C(F)(F)F)cc(-c3ccc(F)cc3)c2C(=O)N(C)C2CC2)n1] | N-Cyclopropyl-3-(4-fluorophenyl)-N-methyl-1-[(3-methyl-[1,2,4]oxadiazol-5-yl)-methyl]-5-(trifluoromethyl)-1H-pyrrole-2-carboxylic acid amide | See below | 422.38 | Yes | 93 |
| 005 | 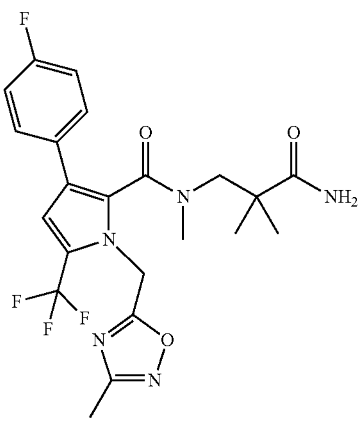 [SMILES: Cc1noc(Cn2c(C(F)(F)F)cc(-c3ccc(F)cc3)c2C(=O)N(C)CC(C)(C)C(N)=O)n1] | N-(2-Carbamoyl-2-methyl-propyl)-3-(4-fluorophenyl)-N-methyl-1-[(3-methyl-[1,2,4]oxadiazol-5-yl)-methyl]-5-(trifluoromethyl)-1H-pyrrole-2-carboxylic acid amide | See below | 481.44 | Yes | 93 |
| 006 | 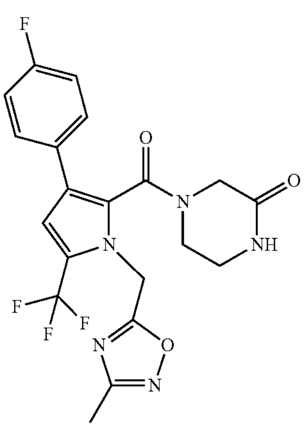 [SMILES: Cc1noc(Cn2c(C(F)(F)F)cc(-c3ccc(F)cc3)c2C(=O)N2CCNC(=O)C2)n1] | 4-[3-(4-Fluorophenyl)-1-[(3-methyl-[1,2,4]oxadiazol-5-yl)-methyl]-5-(trifluoromethyl)-1H-pyrrole-2-carbonyl]-piperazin-2-one | See below | 451.37 | Yes | 95 |

TABLE-continued

Synthesis and analytical data of pyrrole derivatives according to formula (I):

| Ex.-No. | Structure | Name | Synthesis according to (yield) | Mass | Mass Found | UV254-purity |
|---|---|---|---|---|---|---|
| 007 | 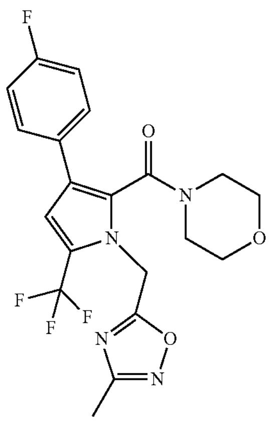 [SMILES: Cc1noc(Cn2c(C(F)(F)F)cc(-c3ccc(F)cc3)c2C(=O)N2CCOCC2)n1] | [3-(4-Fluorophenyl)-1-[(3-methyl-[1,2,4]oxadiazol-5-yl)-methyl]-5-(trifluoro-methyl)-1H-pyrrol-2-yl]-morpholin-4-yl-methanone | See below | 438.37 | Yes | 92 |
| 008 | 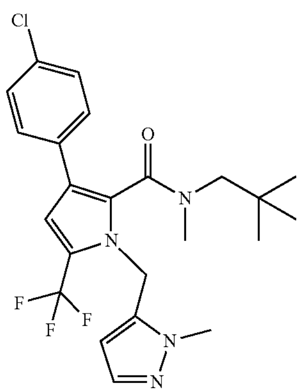 [SMILES: CN(CC(C)(C)C)C(=O)c1c(-c2ccc(Cl)cc2)cc(C(F)(F)F)n1Cc1ccnn1C] | 3-(4-Chlorophenyl)-N-(2,2-dimethyl-propyl)-N-methyl-1-[(2-methyl-2H-pyrazol-3-yl)-methyl]-5-(trifluoromethyl)-1H-pyrrole-2-carboxylic acid amide | GP-1 from PY-2 (36%) | 466.93 | Yes | 100 |
| 009 | 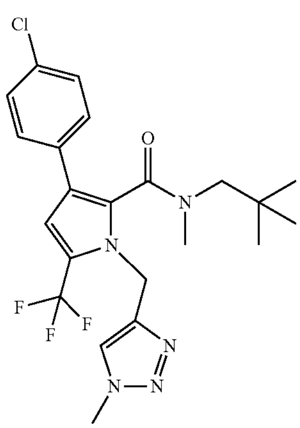 [SMILES: CN(CC(C)(C)C)C(=O)c1c(-c2ccc(Cl)cc2)cc(C(F)(F)F)n1Cc1cn(C)nn1] | 3-(4-Chlorophenyl)-N-(2,2-dimethyl-propyl)-N-methyl-1-[(1-methyl-1H-[1,2,3]triazol-4-yl)-methyl]-5-(trifluoromethyl)-1H-pyrrole-2-carboxylic acid amide | GP-1 from PY-2 & AOH-1 (45%) | 467.92 | Yes | 100 |

TABLE-continued

Synthesis and analytical data of pyrrole derivatives according to formula (I):

| Ex.-No. | Structure | Name | Synthesis according to (yield) | Mass | Mass Found | UV254-purity |
|---|---|---|---|---|---|---|
| 010 | 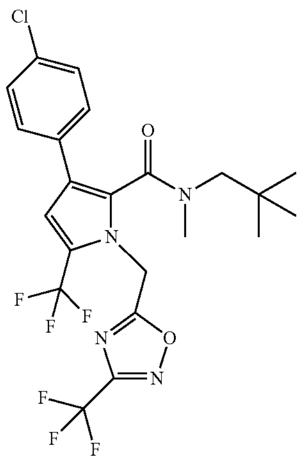 [SMILES: CN(CC(C)(C)C)C(=O)c1c(-c2ccc(Cl)cc2)cc(C(F)(F)F)n1Cc1nc(C(F)(F)F)no1] | 3-(4-Chlorophenyl)-N-(2,2-dimethyl-propyl)-N-methyl-5-(trifluoromethyl)-1-[[3-(trifluoromethyl)-[1,2,4]oxadiazol-5-yl]-methyl]-1H-pyrrole-2-carboxylic acid amide | GP-2A from PY-2 (42%) | 522.87 | Yes | 100 |
| 011 | 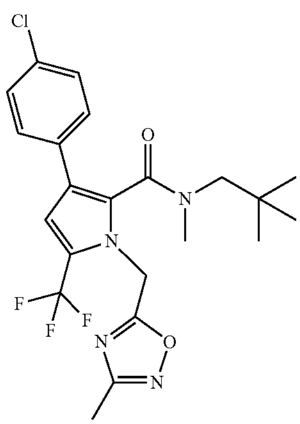 [SMILES: Cc1noc(Cn2c(C(F)(F)F)cc(-c3ccc(Cl)cc3)c2C(=O)N(C)CC(C)(C)C)n1] | 3-(4-Chlorophenyl)-N-(2,2-dimethyl-propyl)-N-methyl-1-[(3-methyl-[1,2,4]oxadiazol-5-yl)-methyl]-5-(trifluoromethyl)-1H-pyrrole-2-carboxylic acid amide | GP-3 from PY-2 & MS-1 (57%) | 468.90 | Yes | 99 |
| 012 | 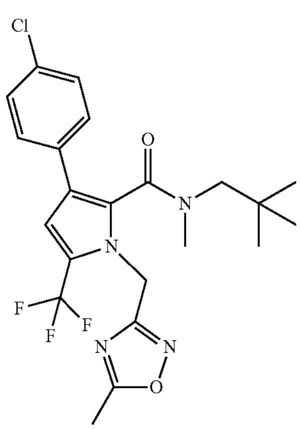 [SMILES: Cc1nc(Cn2c(C(F)(F)F)cc(-c3ccc(Cl)cc3)c2C(=O)N(C)CC(C)(C)C)no1] | 3-(4-Chlorophenyl)-N-(2,2-dimethyl-propyl)-N-methyl-1-[(5-methyl-[1,2,4]oxadiazol-3-yl)-methyl]-5-(trifluoromethyl)-1H-pyrrole-2-carboxylic acid amide | GP-2A from PY-2 (50%) | 468.90 | Yes | 100 |

| Ex.-No. | Structure | Name | Synthesis according to (yield) | Mass | Mass Found | UV254-purity |
|---|---|---|---|---|---|---|
| 013 | 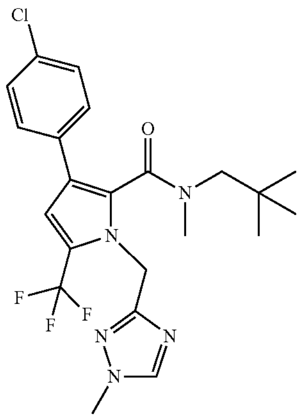 [SMILES: CN(CC(C)(C)C)C(=O)c1c(-c2ccc(Cl)cc2)cc(C(F)(F)F)n1Cc1ncn(C)n1] | 3-(4-Chlorophenyl)-N-(2,2-dimethyl-propyl)-N-methyl-1-[(1-methyl-1H-[1,2,4]triazol-3-yl)-methyl]-5-(trifluoromethyl)-1H-pyrrole-2-carboxylic acid amide | GP-1 from PY-2 (45%) | 467.92 | Yes | 100 |
| 014 | 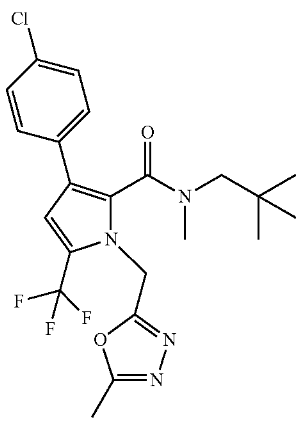 [SMILES: Cc1nnc(Cn2c(C(F)(F)F)cc(-c3ccc(Cl)cc3)c2C(=O)N(C)CC(C)(C)C)o1] | 3-(4-Chlorophenyl)-N-(2,2-dimethyl-propyl)-N-methyl-1-[(5-methyl-[1,3,4]oxadiazol-2-yl)-methyl]-5-(trifluoromethyl)-1H-pyrrole-2-carboxylic acid amide | GP-2A from PY-2 (80%) | 468.90 | Yes | 100 |
| 015 | 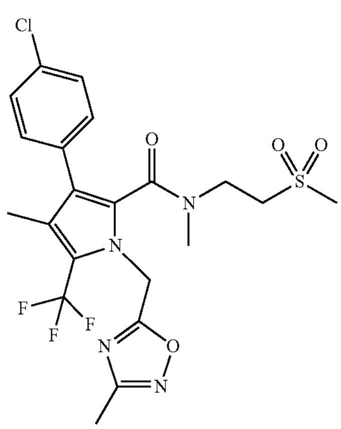 | 3-(4-Chlorophenyl)-N,4-dimethyl-1-[(3-methyl-[1,2,4]oxadiazol-5-yl)-methyl]-N-(2-methylsulfonyl-ethyl)-5-(trifluoromethyl)-1H-pyrrole-2-carboxylic acid amide | GP-1 from PY-3 (52%) | 518.94 | Yes | 100 |

TABLE-continued

Synthesis and analytical data of pyrrole derivatives according to formula (I):

| Ex.-No. | Structure | Name | Synthesis according to (yield) | Mass | Mass Found | UV254-purity |
|---|---|---|---|---|---|---|
| 016 | 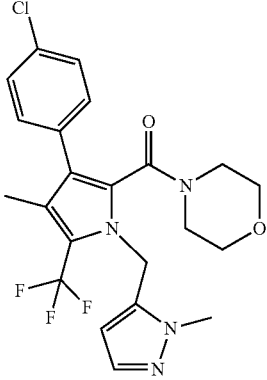 [SMILES: Cc1c(-c2ccc(Cl)cc2)c(C(=O)N2CCOCC2)n(Cc2ccnn2C)c1C(F)(F)F] | [3-(4-Chlorophenyl)-4-methyl-1-[(2-methyl-2H-pyrazol-3-yl)-methyl]-5-(trifluoromethyl)-1H-pyrrol-2-yl]-morpholin-4-yl-methanone | GP-1 from PY-1 (48%) | 466.88 | Yes | 100 |
| 017 | 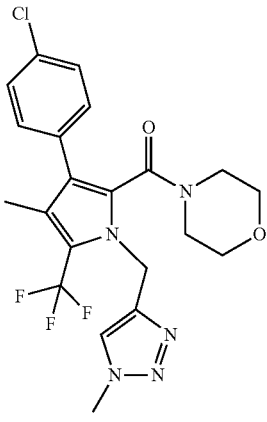 [SMILES: Cc1c(-c2ccc(Cl)cc2)c(C(=O)N2CCOCC2)n(Cc2cn(C)nn2)c1C(F)(F)F] | [3-(4-Chlorophenyl)-4-methyl-1-[(1-methyl-1H-[1,2,3]triazol-4-yl)-methyl]-5-(trifluoromethyl)-1H-pyrrol-2-yl]-morpholin-4-yl-methanone | GP-1 from PY-1 & AOH-1 (11%) | 467.87 | Yes | 98 |
| 018 | 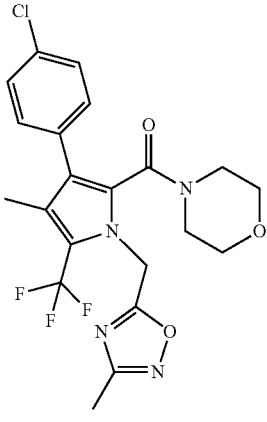 [SMILES: Cc1noc(Cn2c(C(=O)N3CCOCC3)c(-c3ccc(Cl)cc3)c(C)c2C(F)(F)F)n1] | [3-(4-Chlorophenyl)-4-methyl-1-[(3-methyl-[1,2,4]oxadiazol-5-yl)-methyl]-5-(trifluoromethyl)-1H-pyrrol-2-yl]-morpholin-4-yl-methanone | GP-3 from PY-1 & MS-1 (78%) | 468.86 | Yes | 100 |

TABLE-continued

Synthesis and analytical data of pyrrole derivatives according to formula (I):

| Ex.-No. | Structure | Name | Synthesis according to (yield) | Mass | Mass Found | UV254-purity |
|---|---|---|---|---|---|---|
| 019 | 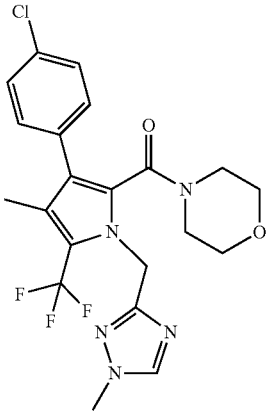 [SMILES: Cc1c(-c2ccc(Cl)cc2)c(C(=O)N2CCOCC2)n(Cc2ncn(C)n2)c1C(F)(F)F] | [3-(4-Chlorophenyl)-4-methyl-1-[(1-methyl-1H-[1,2,4]triazol-3-yl)-methyl]-5-(trifluoromethyl)-1H-pyrrol-2-yl]-morpholin-4-yl-methanone | GP-2A from PY-1 (57%) | 467.87 | Yes | 100 |
| 020 | 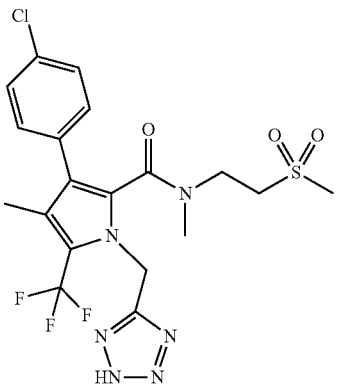 | 3-(4-Chlorophenyl)-N,4-dimethyl-N-(2-methyl-sulfonyl-ethyl)-1-(1H-tetrazol-5-yl-methyl)-5-(trifluoromethyl)-1H-pyrrole-2-carboxylic acid amide | | 504.91 | Yes | 100 |
| 021 | 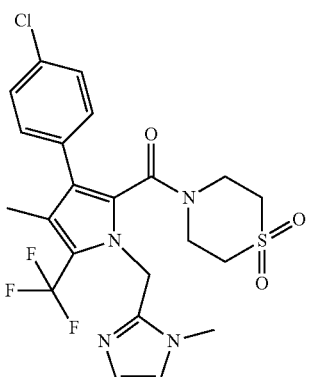 | [3-(4-Chlorophenyl)-4-methyl-1-[(1-methyl-1H-imidazol-2-yl)-methyl]-5-(trifluoromethyl)-1H-pyrrol-2-yl]-(1,1-dioxo-[1,4]thiazinan-4-yl)-methanone | GP-2B from PY-4 (26%) | 514.95 | Yes | 100 |

TABLE-continued

Synthesis and analytical data of pyrrole derivatives according to formula (I):

| Ex.-No. | Structure | Name | Synthesis according to (yield) | Mass | Mass Found | UV254-purity |
|---|---|---|---|---|---|---|
| 022 | 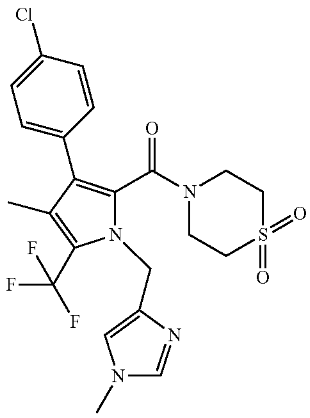 [SMILES: Cc1c(-c2ccc(Cl)cc2)c(C(=O)N2CCS(=O)(=O)CC2)n(Cc2cn(C)cn2)c1C(F)(F)F] | [3-(4-Chlorophenyl)-4-methyl-1-[(1-methyl-1H-imidazol-4-yl)-methyl]-5-(trifluoromethyl)-1H-pyrrol-2-yl]-(1,1-dioxo-[1,4]thiazinan-4-yl)-methanone | GP-2B from PY-4 (23%) | 514.95 | Yes | 100 |
| 023 | 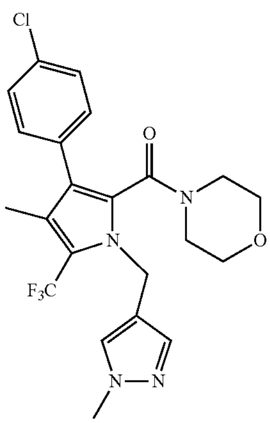 [SMILES: Cc1c(-c2ccc(Cl)cc2)c(C(=O)N2CCOCC2)n(Cc2cnn(C)c2)c1C(F)(F)F] | [3-(4-Chlorophenyl)-4-methyl-1-[(1-methyl-1H-pyrazol-4-yl)-methyl]-5-(trifluoromethyl)-1H-pyrrol-2-yl]-morpholin-4-yl-methanone | See below | 466.89 | Yes | 95 |
| 024 | 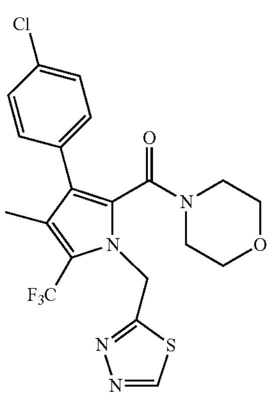 [SMILES: Cc1c(-c2ccc(Cl)cc2)c(C(=O)N2CCOCC2)n(Cc2nncs2)c1C(F)(F)F] | [3-(4-Chlorophenyl)-4-methyl-1-([1,3,4]thiadiazol-2-yl-methyl)-5-(trifluoromethyl)-1H-pyrrol-2-yl]-morpholin-4-yl-methanone | See below | 470.90 | Yes | 98 |

TABLE-continued

Synthesis and analytical data of pyrrole derivatives according to formula (I):

| Ex.-No. | Structure | Name | Synthesis according to (yield) | Mass | Mass Found | UV254-purity |
|---|---|---|---|---|---|---|
| 025 | 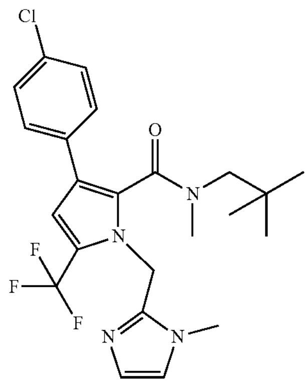 [SMILES: CN(CC(C)(C)C)C(=O)c1c(-c2ccc(Cl)cc2)cc(C(F)(F)F)n1Cc1nccn1C] | 3-(4-Chlorophenyl)-N-(2,2-dimethyl-propyl)-N-methyl-1-[(1-methyl-1H-imidazol-2-yl)-methyl]-5-(trifluoromethyl)-1H-pyrrole-2-carboxylic acid amide | GP-2B from PY-2 (37%) | 466.93 | Yes | 100 |
| 026 | 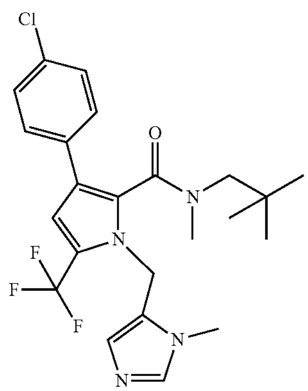 [SMILES: CN(CC(C)(C)C)C(=O)c1c(-c2ccc(Cl)cc2)cc(C(F)(F)F)n1Cc1cncn1C] | 3-(4-Chlorophenyl)-N-(2,2-dimethyl-propyl)-N-methyl-1-[(3-methyl-3H-imidazol-4-yl)-methyl]-5-(trifluoromethyl)-1H-pyrrole-2-carboxylic acid amide | GP-2B from PY-2 (31%) | 466.93 | Yes | 100 |
| 027 | 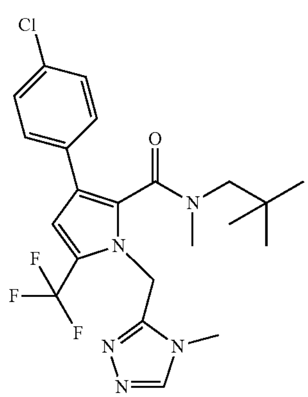 [SMILES: CN(CC(C)(C)C)C(=O)c1c(-c2ccc(Cl)cc2)cc(C(F)(F)F)n1Cc1nncn1C] | 3-(4-Chlorophenyl)-N-(2,2-dimethyl-propyl)-N-methyl-1-[(4-methyl-4H-[1,2,4]triazol-3-yl)-methyl]-5-(trifluoromethyl)-1H-pyrrole-2-carboxylic acid amide | GP-2B from PY-2 (13%) | 467.92 | Yes | 100 |

TABLE-continued

Synthesis and analytical data of pyrrole derivatives according to formula (I):

| Ex.-No. | Structure | Name | Synthesis according to (yield) | Mass | Mass Found | UV254-purity |
|---------|-----------|------|-------------------------------|------|------------|--------------|
| 028 | 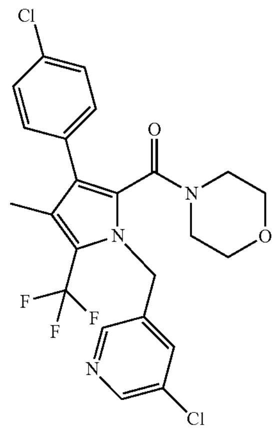 [SMILES: Cc1c(-c2ccc(Cl)cc2)c(C(=O)N2CCOCC2)n(Cc2cncc(Cl)c2)c1C(F)(F)F] | [3-(4-Chlorophenyl)-1-[(5-chloro-pyridin-3-yl)-methyl]-4-methyl-5-(trifluoromethyl)-1H-pyrrol-2-yl]-morpholin-4-yl-methanone | GP-1 from PY-1 & AOH-2 (21%) | 498.33 | Yes | 99 |
| 029 | 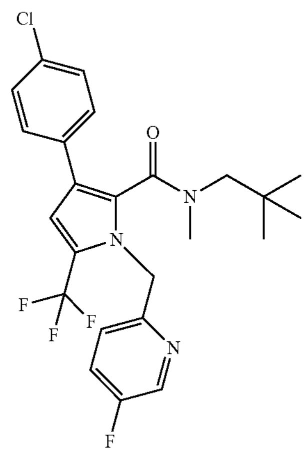 [SMILES: CN(CC(C)(C)C)C(=O)c1c(-c2ccc(Cl)cc2)cc(C(F)(F)F)n1Cc1ccc(F)cn1] | 3-(4-Chlorophenyl)-N-(2,2-dimethyl-propyl)-1-[(5-fluoro-pyridin-2-yl)-methyl]-N-methyl-5-(trifluoromethyl)-1H-pyrrole-2-carboxylic acid amide | GP-2A from PY-2 (59%) | 481.91 | Yes | 100 |
| 030 | 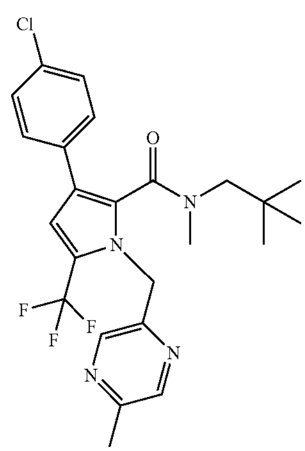 [SMILES: Cc1cnc(Cn2c(C(F)(F)F)cc(-c3ccc(Cl)cc3)c2C(=O)N(C)CC(C)(C)C)cn1] | 3-(4-Chlorophenyl)-N-(2,2-dimethyl-propyl)-N-methyl-1-[(5-methyl-pyrazin-2-yl)-methyl]-5-(trifluoromethyl)-1H-pyrrole-2-carboxylic acid amide | GP-2A from PY-2 (66%) | 478.94 | Yes | 100 |

TABLE-continued

Synthesis and analytical data of pyrrole derivatives according to formula (I):

| Ex.-No. | Structure | Name | Synthesis according to (yield) | Mass | Mass Found | UV254-purity |
|---|---|---|---|---|---|---|
| 031 | 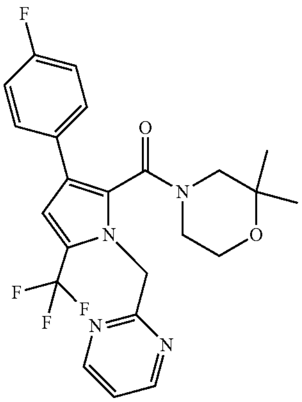 [SMILES: CC1(C)CN(C(=O)c2c(-c3ccc(F)cc3)cc(C(F)(F)F)n2Cc2ncccn2)CCO1] | (2,2-Dimethyl-morpholin-4-yl)-[3-(4-fluorophenyl)-1-(pyrimidin-2-yl-methyl)-5-(trifluoromethyl)-1H-pyrrol-2-yl]-methanone | GP-4C from ACI-2 (12%) | 462.44 | Yes | 91 |
| 032 | 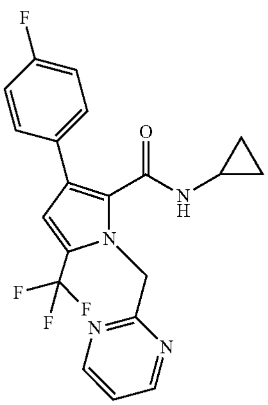 [SMILES: O=C(NC1CC1)c1c(-c2ccc(F)cc2)cc(C(F)(F)F)n1Cc1ncccn1] | N-Cyclopropyl-3-(4-fluorophenyl)-1-(pyrimidin-2-yl-methyl)-5-(trifluoromethyl)-1H-pyrrole-2-carboxylic acid amide | GP-4C from ACI-2 (36%) | 404.36 | Yes | 96 |
| 033 | 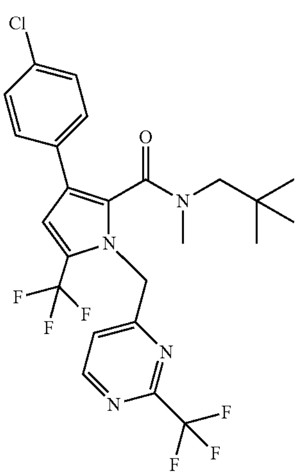 [SMILES: CN(CC(C)(C)C)C(=O)c1c(-c2ccc(Cl)cc2)cc(C(F)(F)F)n1Cc1ccnc(C(F)(F)F)n1] | 3-(4-Chlorophenyl)-N-(2,2-dimethyl-propyl)-N-methyl-5-(trifluoromethyl)-1-[[2-(trifluoromethyl)-pyrimidin-4-yl]-methyl]-1H-pyrrole-2-carboxylic acid amide | GP-2A from PY-2 (15%) | 532.91 | Yes | 100 |

TABLE-continued

Synthesis and analytical data of pyrrole derivatives according to formula (I):

| Ex.-No. | Structure | Name | Synthesis according to (yield) | Mass | Mass Found | UV254-purity |
|---|---|---|---|---|---|---|
| 034 | 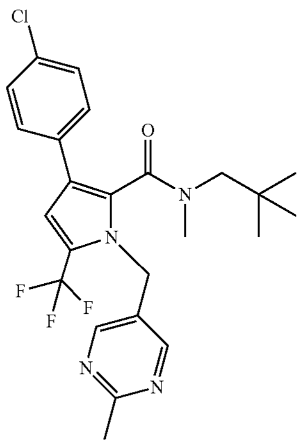 [SMILES: Cc1ncc(Cn2c(C(F)(F)F)cc(-c3ccc(Cl)cc3)c2C(=O)N(C)CC(C)(C)C)cn1] | 3-(4-Chlorophenyl)-N-(2,2-dimethyl-propyl)-N-methyl-1-[(2-methyl-pyrimidin-5-yl)-methyl]-5-(trifluoromethyl)-1H-pyrrole-2-carboxylic acid amide | GP-1 from PY-1 (59%) | 478.94 | Yes | 92 |
| 035 | 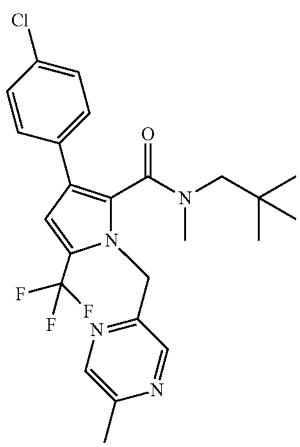 [SMILES: Cc1cnc(Cn2c(C(F)(F)F)cc(-c3ccc(Cl)cc3)c2C(=O)N(C)CC(C)(C)C)cn1] | 3-(4-Chlorophenyl)-N-(2,2-dimethyl-propyl)-N-methyl-1-[(5-methyl-pyrimidin-2-yl)-methyl]-5-(trifluoromethyl)-1H-pyrrole-2-carboxylic acid amide | GP-2A from PY-2 (80%) | 478.94 | Yes | 95 |
| 036 | 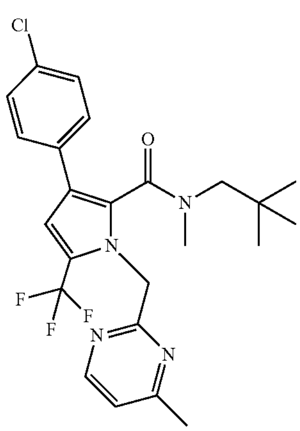 [SMILES: Cc1ccnc(Cn2c(C(F)(F)F)cc(-c3ccc(Cl)cc3)c2C(=O)N(C)CC(C)(C)C)n1] | 3-(4-Chlorophenyl)-N-(2,2-dimethyl-propyl)-N-methyl-1-[(4-methyl-pyrimidin-2-yl)-methyl]-5-(trifluoromethyl)-1H-pyrrole-2-carboxylic acid amide | GP-1 from PY-2 (59%) | 478.94 | Yes | 100 |

TABLE-continued

Synthesis and analytical data of pyrrole derivatives according to formula (I):

| Ex.-No. | Structure | Name | Synthesis according to (yield) | Mass | Mass Found | UV254-purity |
|---|---|---|---|---|---|---|
| 037 | 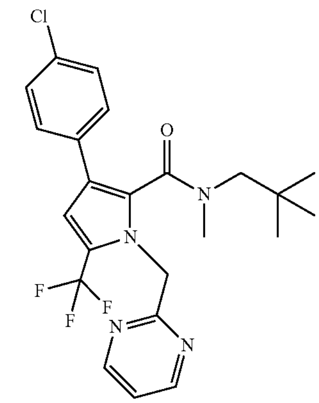 [SMILES: CN(CC(C)(C)C)C(=O)c1c(-c2ccc(Cl)cc2)cc(C(F)(F)F)n1Cc1ncccn1] | 3-(4-Chlorophenyl)-N-(2,2-dimethyl-propyl)-N-methyl-1-(pyrimidin-2-yl-methyl)-5-(trifluoro-methyl)-1H-pyrrole-2-carboxylic acid amide | GP-1 from PY-2 (59%) | 464.91 | Yes | 100 |
| 038 | 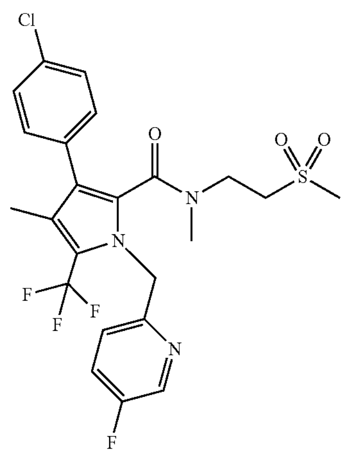 | 3-(4-Chlorophenyl)-1-[(5-fluoro-pyridin-2-yl)-methyl]-N,4-dimethyl-N-(2-methylsulfonyl-ethyl)-5-(trifluoromethyl)-1H-pyrrole-2-carboxylic acid amide | GP-2A from PY-3 (59%) | 531.95 | Yes | 100 |
| 039 | 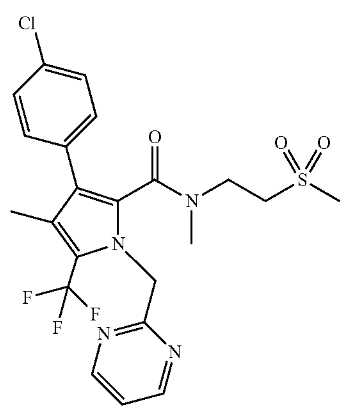 | 3-(4-Chlorophenyl)-N,4-dimethyl-N-(2-methylsulfonyl-ethyl)-1-(pyrimidin-2-yl-methyl)-5-(trifluoromethyl)-1H-pyrrole-2-carboxylic acid amide | GP-1 from PY-3 (74%) | 514.95 | Yes | 100 |

TABLE-continued

Synthesis and analytical data of pyrrole derivatives according to formula (I):

| Ex.-No. | Structure | Name | Synthesis according to (yield) | Mass | Mass Found | UV254-purity |
|---|---|---|---|---|---|---|
| 040 | 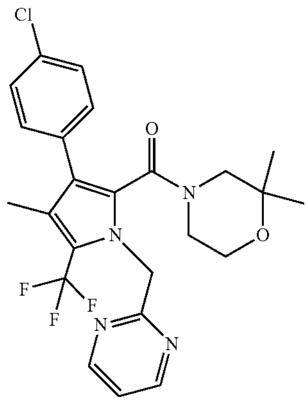 | [3-(4-Chlorophenyl)-4-methyl-1-(pyrimidin-2-yl-methyl)-5-(trifluoro-methyl)-1H-pyrrol-2-yl]-(2,2-dimethyl-morpholin-4-yl)-methanone | GP-4A from ACI-1 (50%) | 492.92 | Yes | 100 |
| 041 | 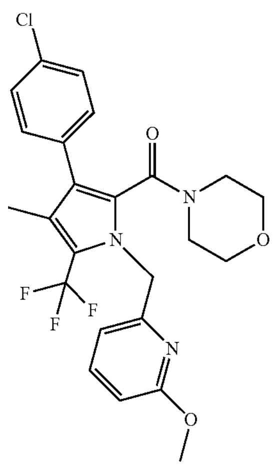 [SMILES: COc1cccc(Cn2c(C(=O)N3CCOCC3)c(-c3ccc(Cl)cc3)c(C)c2C(F)(F)F)n1] | [3-(4-Chlorophenyl)-1-[(6-methoxy-pyridin-2-yl)-methyl]-4-methyl-5-(trifluoromethyl)-1H-pyrrol-2-yl]-morpholin-4-yl-methanone | GP-1 from PY-1 (73%) | 493.91 | Yes | 99 |
| 042 | 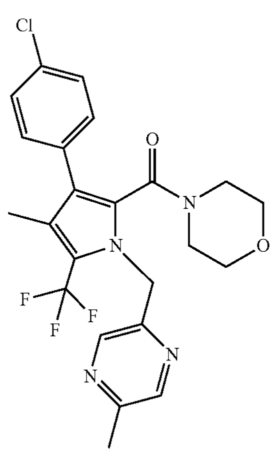 [SMILES: Cc1cnc(Cn2c(C(=O)N3CCOCC3)c(-c3ccc(Cl)cc3)c(C)c2C(F)(F)F)cn1] | [3-(4-Chlorophenyl)-4-methyl-1-[(5-methyl-pyrazin-2-yl)-methyl]-5-(trifluoromethyl)-1H-pyrrol-2-yl]-morpholin-4-yl-methanone | GP-2A from PY-1 (44%) | 478.90 | Yes | 100 |

TABLE-continued

Synthesis and analytical data of pyrrole derivatives according to formula (I):

| Ex.-No. | Structure | Name | Synthesis according to (yield) | Mass | Mass Found | UV254-purity |
|---------|-----------|------|-------------------------------|------|------------|--------------|
| 043 | 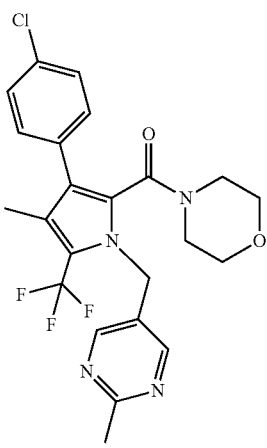 [SMILES: Cc1ncc(Cn2c(C(=O)N3CCOCC3)c(-c3ccc(Cl)cc3)c(C)c2C(F)(F)F)cn1] | [3-(4-Chlorophenyl)-4-methyl-1-[(2-methyl-pyrimidin-5-yl)-methyl]-5-(trifluoromethyl)-1H-pyrrol-2-yl]-morpholin-4-yl-methanone | GP-1 from PY-1 (65%) | 478.90 | Yes | 94 |
| 044 | 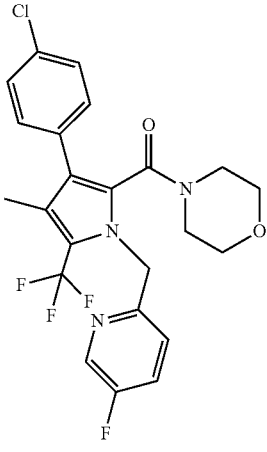 [SMILES: Cc1c(-c2ccc(Cl)cc2)c(C(=O)N2CCOCC2)n(Cc2ccc(F)cn2)c1C(F)(F)F] | [3-(4-Chlorophenyl)-1-[(5-fluoro-pyridin-2-yl)-methyl]-4-methyl-5-(trifluoromethyl)-1H-pyrrol-2-yl]-morpholin-4-yl-methanone | GP-2A from PY-1 (54%) | 481.87 | Yes | 100 |
| 045 | 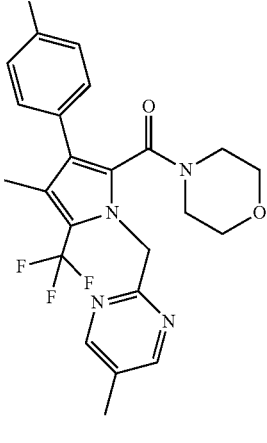 | [3-(4-Chlorophenyl)-4-methyl-1-[(5-methyl-pyrimidin-2-yl)-methyl]-5-(trifluoromethyl)-1-pyrrol-2-yl]-morpholin-4-yl-methanone | GP-2A from PY-1 (57%) | 478.90 | Yes | 100 |

| Ex.-No. | Structure | Name | Synthesis according to (yield) | Mass | Mass Found | UV254-purity |
|---|---|---|---|---|---|---|
| 046 | 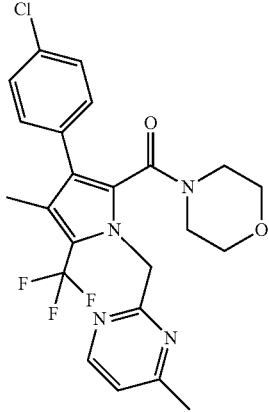 [SMILES: Cc1ccnc(Cn2c(C(=O)N3CCOCC3)c(-c3ccc(Cl)cc3)c(C)c2C(F)(F)F)n1] | [3-(4-Chlorophenyl)-4-methyl-1-[(4-methyl-pyrimidin-2-yl)-methyl]-5-(trifluoromethyl)-1H-pyrrol-2-yl]-morpholin-4-yl-methanone | GP-2B from PY-1 (25%) | 478.90 | Yes | 99 |
| 047 | 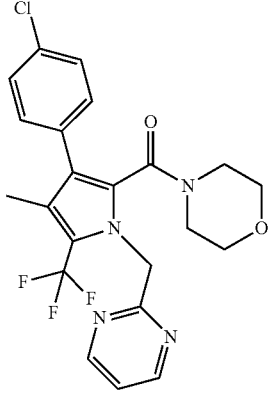 [SMILES: Cc1c(-c2ccc(Cl)cc2)c(C(=O)N2CCOCC2)n(Cc2ncccn2)c1C(F)(F)F] | [3-(4-Chlorophenyl)-4-methyl-1-(pyrimidin-2-yl-methyl)-5-(trifluoro-methyl)-1H-pyrrol-2-yl]-morpholin-4-yl-methanone | GP-1 from PY-1 (49%) | 464.87 | Yes | 100 |
| 048 | 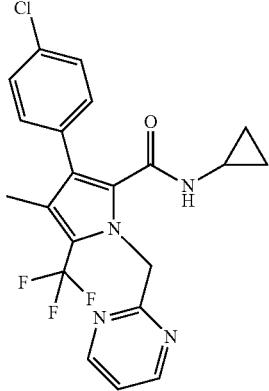 [SMILES: Cc1c(-c2ccc(Cl)cc2)c(C(=O)NC2CC2)n(Cc2ncccn2)c1C(F)(F)F] | 3-(4-Chlorophenyl)-N-cyclopropyl-4-methyl-1-(pyrimidin-2-yl-methyl)-5-(trifluoromethyl)-1H-pyrrole-2-carboxylic acid amide | GP-4B from ACI-1 (38%) | 434.84 | Yes | 98 |

TABLE-continued

Synthesis and analytical data of pyrrole derivatives according to formula (I):

| Ex.-No. | Structure | Name | Synthesis according to (yield) | Mass | Mass Found | UV254-purity |
|---|---|---|---|---|---|---|
| 049 | 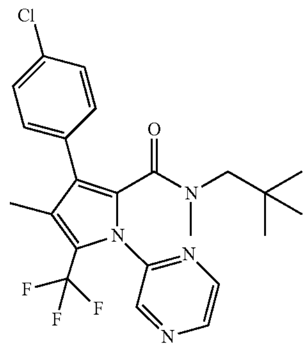 [SMILES: Cc1c(-c2ccc(Cl)cc2)c(C(=O)N(C)CC(C)(C)C)n(-c2cnccn2)c1C(F)(F)F] | 3-(4-Chlorophenyl)-N-(2,2-dimethyl-propyl)-N,4-dimethyl-1-pyrazin-2-yl-5-(trifluoromethyl)-1H-pyrrole-2-carboxylic acid amide | See below | 464.91 | Yes | 100 |
| 050 | 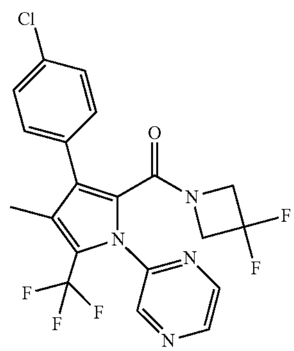 [SMILES: Cc1c(-c2ccc(Cl)cc2)c(C(=O)N2CC(F)(F)C2)n(-c2cnccn2)c1C(F)(F)F] | [3-(4-Chlorophenyl)-4-methyl-1-pyrazin-2-yl-5-(trifluoromethyl)-1H-pyrrol-2-yl]-(3,3-difluoro-azetidin-1-yl)-methanone | See below | 456.77 | Yes | 100 |
| 051 | 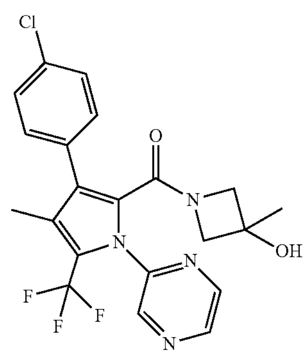 | [3-(4-Chlorophenyl)-4-methyl-1-pyrazin-2-yl-5-(trifluoromethyl)-1H-pyrrol-2-yl]-(3-hydroxy-3-methyl-azetidin-1-yl)-methanone | See below | 450.84 | Yes | 100 |
| 052 | 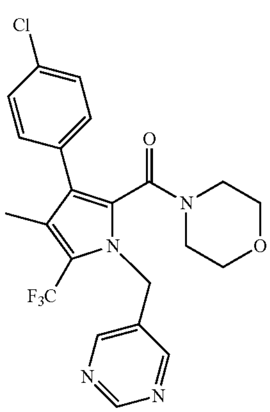 [SMILES: Cc1c(-c2ccc(Cl)cc2)c(C(=O)N2CCOCC2)n(Cc2cncnc2)c1C(F)(F)F] | [3-(4-Chlorophenyl)-4-methyl-1-(pyrimidin-5-yl-methyl)-5-(trifluoro-methyl)-1H-pyrrol-2-yl]-morpholin-4-yl-methanone | See below | 464.87 | Yes | 98 |

TABLE-continued

Synthesis and analytical data of pyrrole derivatives according to formula (I):

| Ex.-No. | Structure | Name | Synthesis according to (yield) | Mass | Mass Found | UV254-purity |
|---|---|---|---|---|---|---|
| 053 | 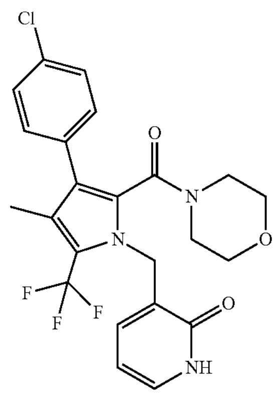 [SMILES: Cc1c(-c2ccc(Cl)cc2)c(C(=O)N2CCOCC2)n(Cc2ccc[nH]c2=O)c1C(F)(F)F] | 3-[[3-(4-Chlorophenyl)-4-methyl-2-(morpholine-4-carbonyl)-5-(trifluoromethyl)-1H-pyrrol-1-yl]-methyl]-1H-pyridin-2-one | GP-1 from PY-1 (4%) | 479.88 | Yes | 100 |
| 054 | 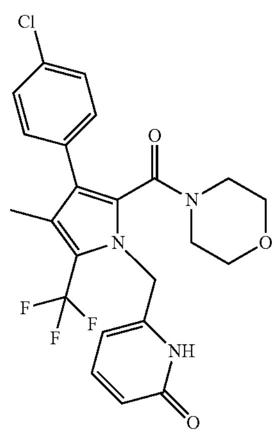 [SMILES: Cc1c(-c2ccc(Cl)cc2)c(C(=O)N2CCOCC2)n(Cc2cccc(=O)[nH]2)c1C(F)(F)F] | 6-[[3-(4-Chlorophenyl)-4-methyl-2-(morpholine-4-carbonyl)-5-(trifluoromethyl)-1H-pyrrol-1-yl]-methyl]-1H-pyridin-2-one | GP-1 from PY-1 (33%) | 479.88 | Yes | 97 |
| 055 | 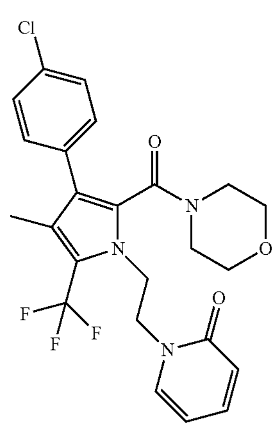 [SMILES: Cc1c(-c2ccc(Cl)cc2)c(C(=O)N2CCOCC2)n(CCn2ccccc2=O)c1C(F)(F)F] | 1-[2-[3-(4-Chlorophenyl)-4-methyl-2-(morpholine-4-carbonyl)-5-(trifluoromethyl)-1H-pyrrol-1-yl]-ethyl]-1H-pyridin-2-one | GP-1 from PY-1 (49%) | 493.91 | Yes | 99 |

TABLE-continued

Synthesis and analytical data of pyrrole derivatives according to formula (I):

| Ex.-No. | Structure | Name | Synthesis according to (yield) | Mass | Mass Found | UV254-purity |
|---|---|---|---|---|---|---|
| 056 | 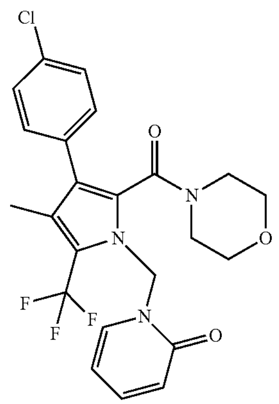 [SMILES: Cc1c(-c2ccc(Cl)cc2)c(C(=O)N2CCOCC2)n(Cn2ccccc2=O)c1C(F)(F)F] | 1-[[3-(4-Chlorophenyl)-4-methyl-2-(morpholine-4-carbonyl)-5-(trifluoromethyl)-1H-pyrrol-1-yl]-methyl]-1H-pyridin-2-one | GP-1 from PY-1 & AOH-3 (28%) | 479.88 | Yes | 99 |
| 060 | 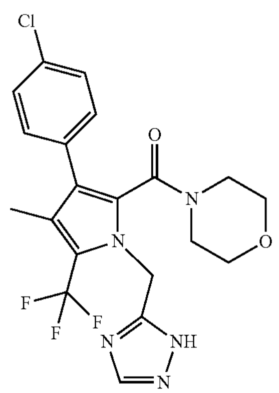 [SMILES: Cc1c(-c2ccc(Cl)cc2)c(C(=O)N2CCOCC2)n(Cc2ncn[nH]2)c1C(F)(F)F] | [3-(4-Chlorophenyl)-4-methyl-1-(1H-[1,2,4]triazol-3-yl-methyl)-5-(trifluoromethyl)-1H-pyrrol-2-yl]-morpholin-4-yl-methanone | See below | 453.85 | Yes | 95 |
| 061 | 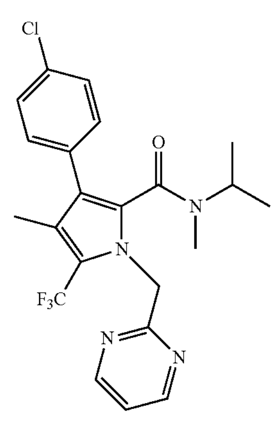 [SMILES: Cc1c(-c2ccc(Cl)cc2)c(C(=O)N(C)C(C)C)n(Cc2ncccn2)c1C(F)(F)F] | 3-(4-Chlorophenyl)-N-isopropyl-N,4-dimethyl-1-(pyrimidin-2-yl-methyl)-5-(trifluoromethyl)-1H-pyrrole-2-carboxylic acid amide | GP-4B from ACI-1 (4%) | 450.88 | Yes | 96 |

TABLE-continued

Synthesis and analytical data of pyrrole derivatives according to formula (I):

| Ex.-No. | Structure | Name | Synthesis according to (yield) | Mass | Mass Found | UV254-purity |
|---|---|---|---|---|---|---|
| 062 | 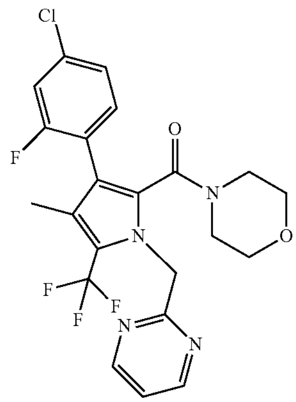 [SMILES: Cc1c(-c2ccc(Cl)cc2F)c(C(=O)N2CCOCC2)n(Cc2ncccn2)c1C(F)(F)F] | [3-(4-Chloro-2-fluoro-phenyl)-4-methyl-1-(pyrimidin-2-yl-methyl)-5-(trifluoromethyl)-1H-pyrrol-2-yl]-morpholin-4-yl-methanone | See below | 482.86 | Yes | 95 |
| 063 | 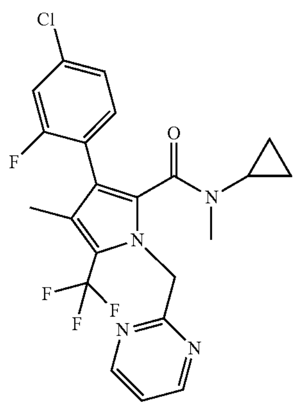 [SMILES: Cc1c(-c2ccc(Cl)cc2F)c(C(=O)N(C)C2CC2)n(Cc2ncccn2)c1C(F)(F)F] | 3-(4-Chloro-2-fluoro-phenyl)-N-cyclopropyl-N,4-dimethyl-1-(pyrimidin-2-yl-methyl)-5-(trifluoromethyl)-1H-pyrrole-2-carboxylic acid amide | See below | 466.86 | Yes | 95 |
| 064 | 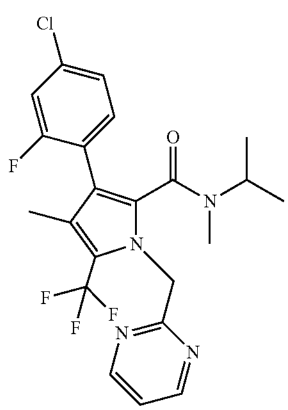 [SMILES: Cc1c(-c2ccc(Cl)cc2F)c(C(=O)N(C)C(C)C)n(Cc2ncccn2)c1C(F)(F)F] | 3-(4-Chloro-2-fluoro-phenyl)-N-isopropyl-N,4-dimethyl-1-(pyrimidin-2-yl-methyl)-5-(trifluoromethyl)-1H-pyrrole-2-carboxylic acid amide | See below | 468.88 | Yes | 92 |

TABLE-continued

Synthesis and analytical data of pyrrole derivatives according to formula (I):

| Ex.-No. | Structure | Name | Synthesis according to (yield) | Mass | Mass Found | UV254-purity |
|---|---|---|---|---|---|---|
| 065 | 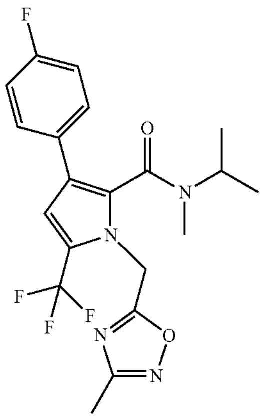 [SMILES: Cc1noc(Cn2c(C(F)(F)F)cc(-c3ccc(F)cc3)c2C(=O)N(C)C(C)C)n1] | 3-(4-Fluorophenyl)-N-isopropyl-N-methyl-1-[(3-methyl-[1,2,4]oxadiazol-5-yl)-methyl]-5-(trifluoromethyl)-1H-pyrrole-2-carboxylic acid amide | See below | 424.39 | Yes | 95 |
| 066 | 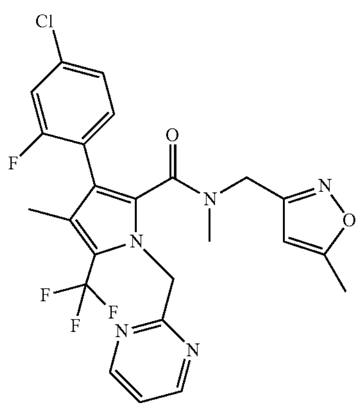 [SMILES: Cc1cc(CN(C)C(=O)c2c(-c3ccc(Cl)cc3F)c(C)c(C(F)(F)F)n2Cc2ncccn2)no1] | 3-(4-Chloro-2-fluoro-phenyl)-N,4-dimethyl-N-[(5-methyl-isoxazol-3-yl)-methyl]-1-(pyrimidin-2-yl-methyl)-5-(trifluoromethyl)-1H-pyrrole-2-carboxylic acid amide | See below | 521.89 | Yes | 91 |
| 067 | 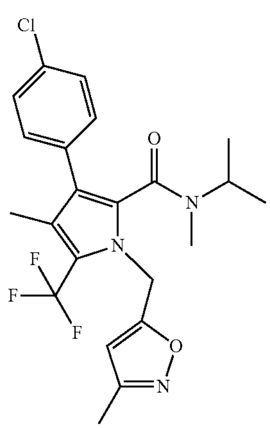 [SMILES: Cc1cc(Cn2c(C(=O)N(C)C(C)C)c(-c3ccc(Cl)cc3)c(C)c2C(F)(F)F)on1] | 3-(4-Chlorophenyl)-N-isopropyl-N,4-dimethyl-1-[(3-methyl-isoxazol-5-yl)-methyl]-5-(trifluoromethyl)-1H-pyrrole-2-carboxylic acid amide | See below | 453.89 | Yes | 97 |

TABLE-continued

Synthesis and analytical data of pyrrole derivatives according to formula (I):

| Ex.-No. | Structure | Name | Synthesis according to (yield) | Mass | Mass Found | UV254-purity |
|---|---|---|---|---|---|---|
| 068 | 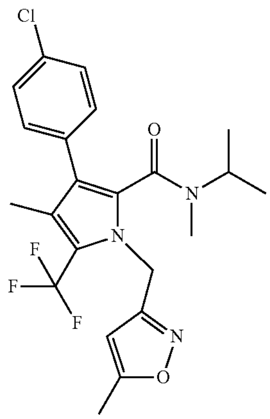 [SMILES: Cc1cc(Cn2c(C(=O)N(C)C(C)C)c(-c3ccc(Cl)cc3)c(C)c2C(F)(F)F)no1] | 3-(4-Chlorophenyl)-N-isopropyl-N,4-dimethyl-1-[(5-methyl-isoxazol-3-yl)-methyl]-5-(trifluoro-methyl)-1H-pyrrole-2-carboxylic acid amide | See below | 453.90 | Yes | 98 |
| 069 | 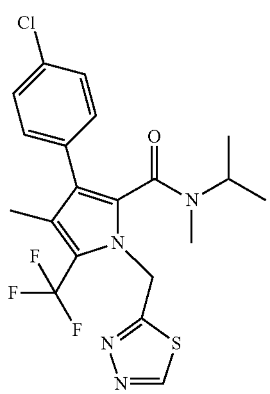 [SMILES: Cc1c(-c2ccc(Cl)cc2)c(C(=O)N(C)C(C)C)n(Cc2nncs2)c1C(F)(F)F] | 3-(4-Chlorophenyl)-N-isopropyl-N,4-dimethyl-1-([1,3,4]thiadiazol-2-yl-methyl)-5-(trifluoro-methyl)-1H-pyrrole-2-carboxylic acid amide | See below | 456.91 | Yes | 98 |

3-(4-Chlorophenyl)-N-(2,2-dimethyl-propyl)-N,4-dimethyl-1-pyrazin-2-yl-5-(trifluoromethyl)-1H-pyrrole-2-carboxylic acid amide (Example 049)

-continued

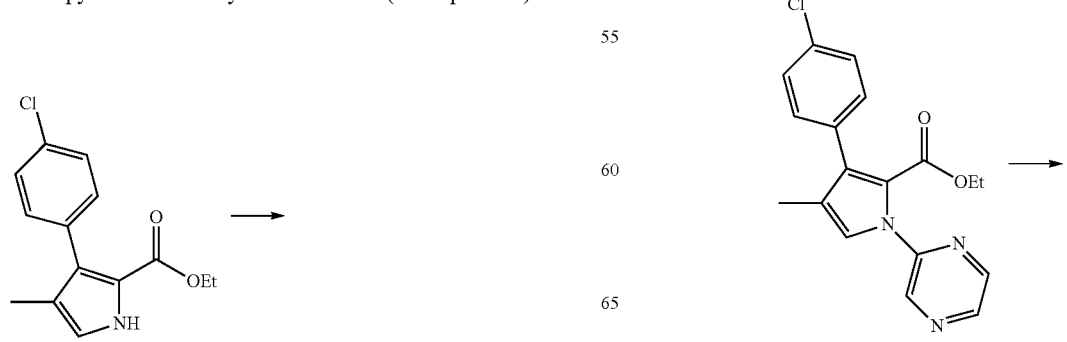

-continued

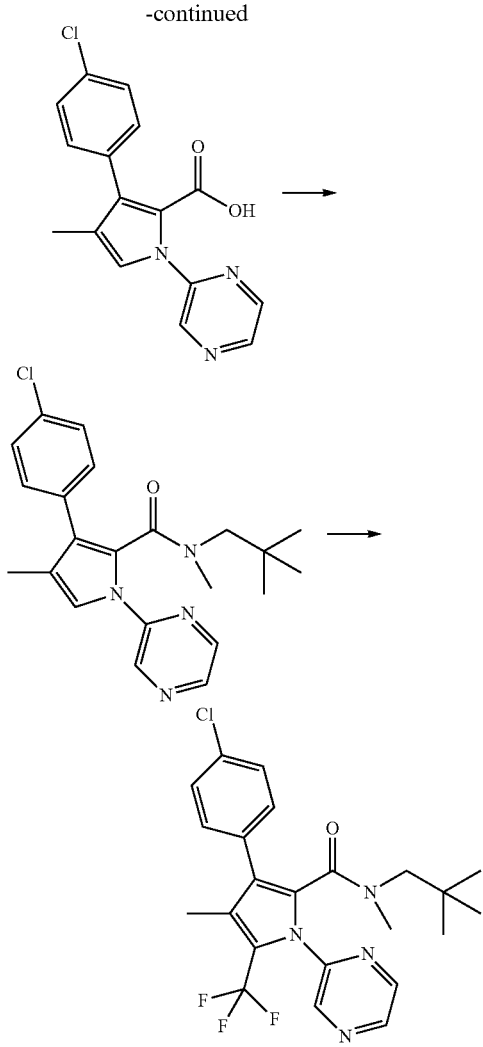

Step 1: Ethyl 3-(4-chlorophenyl)-4-methyl-1-(pyrazin-2-yl)-1H-pyrrole-2-carboxylate A 20 mL microwave vial was charged with 2-iodopyrazine (22 mmol), ethyl 3-(4-chlorophenyl)-4-methyl-1H-pyrrole-2-carboxylate (5.7 mmol), CuI (0.57 mmol), potassium phosphate tribasic (12 mmol), N,N'-dimethylethylendiamine (1.1 mmol) and NMP (47 mmol) and the reaction mixture heated to 140° C. for 2 h. The reaction mixture was diluted with EtOAc and $H_2O$, filtered and organic phase washed with $H_2O$ and 1M HCl. The organic layers were dried over $Na_2SO_4$ followed by concentration in vacuo. The crude product was purified by flash chromatography (silica) to afford 1.8 g (93%) of the desired product as yellow solid.

Step 2: 3-(4-Chlorophenyl)-4-methyl-1-(pyrazin-2-yl)-1H-pyrrole-2-carboxylic acid 6M NaOH (60 mmol) was added to (Ethyl 3-(4-chlorophenyl)-4-methyl-1-(pyrazin-2-yl)-1H-pyrrole-2-carboxylate (3 mmol) dissolved in THF and MeOH (1:1). The reaction mixture was heated to reflux for 2 h, allowed to cool and the acidified with 5M aq. HCl. The reaction mixture was concentrated in-vacuo, then extracted with EtOAc, combined organics were washed with $H_2O$, dried over $Na_2SO_4$ filtered and concentrated in-vacuo to yield the desired product (90%) as purple solid.

Step 3: 3-(4-chlorophenyl)-N,4-dimethyl-N-neopentyl-1-(pyrazin-2-yl)-1H-pyrrole-2-carboxamide Microwave vials were charged with 3-(4-chlorophenyl)-4-methyl-1-(pyrazin-2-yl)-1H-pyrrole-2-carboxylic acid (150 mg), N,N-bis(2-oxo-3-oxazolidinyl)phosphonic chloride (263 mg), N,2,2-trimethylpropane-1-amine hydrochloride (105 mg), DIPEA (0.42 ml) and DCM (1 ml), stirred and heated to 100° C. for 1 h. Subsequently the reaction mixture was diluted with DCM, washed with sat. aq. $NaHCO_3$, concentrated in-vacuo and purified by flash chromatography (silica) to afford the desired product (188 mg).

Step 4: 3-(4-Chlorophenyl)-N-(2,2-dimethyl-propyl)-N,4-dimethyl-1-pyrazin-2-yl-5-(trifluoromethyl)-1H-pyrrole-2-carboxylic acid amide 3-(4-Chlorophenyl)-N,4-dimethyl-N-neopentyl-1-(pyrazin-2-yl)-1H-pyrrole-2-carboxamide (0.47 mmol) followed by sodium trifluoromethanesulfinate (3 eq.), DMSO (1800 μL) and $H_2O$ (800 μL) were added to a microwave tube, stirred vigorously and cooled to 0° C. via ice/water bath. tert-Butyl hydroperoxide (70 mass %) in $H_2O$ (5 eq.) was added dropwise and the reaction mixture stirred vigorously. DCM (1800 μL) was added and reaction mixture stirred at RT for 18 h. The reaction mixture was quenched with 100 ml sat. sodium metabisufite (aq) and extracted 2×100 ml DCM. Organics were combined, dried over $MgSO_4$, filtered and reduced under vacuum to residue. Purification via preparative HPLC using 30-95% MeCN/$H_2O$ (0.1% Ammonia aq.) gave the desired product in 48%.

[3-(4-Chlorophenyl)-4-methyl-1-pyrazin-2-yl-5-(trifluoromethyl)-1H-pyrrol-2-yl]-(3,3-difluoro-azetidin-1-yl)-methanone (Example 050)

Title compound has been prepared in analogy to example 049 but utilizing the respective amine. Step 4 yielded the desired product in 35%.

[3-(4-Chlorophenyl)-4-methyl-1-pyrazin-2-yl-5-(trifluoromethyl)-1H-pyrrol-2-yl]-(3-hydroxy-3-methyl-azetidin-1-yl)-methanone (Example 051)

Title compound has been prepared in analogy to example 049 but utilizing the respective amine. Step 4 yielded the desired product in 41%.

[3-(4-Chlorophenyl)-4-methyl-1-1H-[1,2,4]triazol-3-yl-methyl)-5-(trifluoromethyl)-1H-pyrrol-2-yl]-morpholin-4-yl-methanone (Example 060)

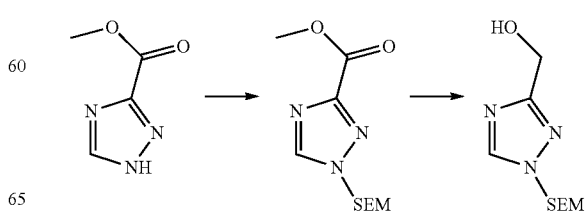

Step A: Methyl 1-((2-(trimethylsilyl)ethoxy)methyl)-1H-1,2,4-triazole-3-carboxylate A suspension of 60% NaH in mineral oil (0.585 g, 14.63 mmol) in dry DMF (15 mL) was cooled to 0° C. A solution of methyl 1H-1,2,4-triazole-3-carboxylate (1.86 g, 14.63 mmol) in dry DMF (40 mL) was added dropwise and stirring at 0° C. was continued for 30 min, SEM-Cl (2.60 mL, 14.63 mmol) was added dropwise and the reaction mixture was stirred at 0° C. for 30 min and then at RT for 1 h. The mixture was poured onto ice/H$_2$O (150 mL) and extracted with Et$_2$O (3×150 mL). Organic layers were combined, dried (Na$_2$SO$_4$) and evaporated under reduced pressure. The crude product was co-evaporated with toluene (3×). The product was purified by flash chromatography (silica, heptane/EtOAc, 4:1), to give 1.612 g (43%) of the title compound compound.

Step B: (1-((2-(Trimethylsilyl)ethoxy)methyl)-1H-1,2,4-triazol-3-yl)methanol At 0° C., 2M LiBH$_4$ in THF (3.03 mL, 6.07 mmol) was added dropwise to a solution of methyl 1-((2-(trimethylsilyl)ethoxy)methyl)-1H-1,2,4-triazole-3-carboxylate (1.562 g, 6.07 mmol) in dry THF (15 mL). The reaction mixture was stirred at RT for 30 min and Na$_2$SO$_4$.10H$_2$O/Na$_2$SO$_4$ was added. The mixture was left stirring at RT for 3 h and filtered over Na$_2$SO$_4$. The residue was washed with DCM and the combined filtrate was evaporated under reduced pressure, to afford 1.44 g (72%, purity: 70%) of the title compound.

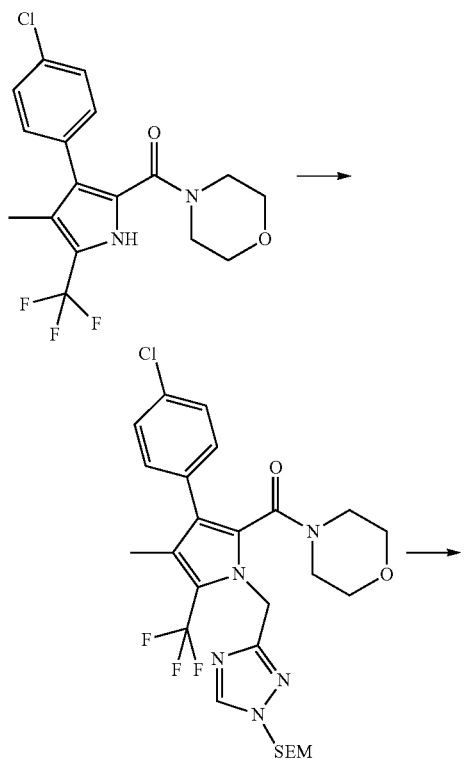

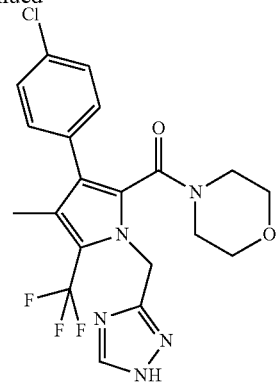

Step 1: (3-(4-Chlorophenyl)-4-methyl-5-(trifluoromethyl)-1-((1-((2-(trimethylsilyl)ethoxy)methyl)-1H-1,2,4-triazol-3-yl)methyl)-1H-pyrrol-2-yl)(morpholino)methanone A solution of (3-(4-Chlorophenyl)-4-methyl-1H-pyrrol-2-yl)(morpholino)methanone (PY-1) (250 mg, 0.671 mmol) in dry THF (0.5 mL) was cooled to 0° C., PPh$_3$ (176 mg, 0.671 mmol) was added followed by the dropwise addition of DIAD (0.130 mL, 0.671 mmol). After 10 min, a solution of step B product (154 mg, 0.47 mmol) in dry THF (0.5 mL) was added dropwise and the reaction mixture was stirred at RT. After 1 h, the mixture was cooled, PPh$_3$ (176 mg, 0.671 mmol) was added followed by the dropwise addition of DIAD (0.130 mL, 0.671 mmol), 10 min later step B product (154 mg, 0.47 mmol) in dry THF (0.5 mL) was added dropwise and stirring was continued at RT overnight. After cooling to 0° C., more PPh$_3$ (176 mg, 0.671 mmol) was added followed by the dropwise addition of DIAD (0.130 mL, 0.671 mmol), 10 min later more step B product (154 mg, 0.47 mmol) in dry THF (0.5 mL) was added dropwise and stirring was continued at room temperature for 6 h. The mixture was cooled to 0° C., more PPh$_3$ (176 mg, 0.671 mmol) was added followed by the dropwise addition of DIAD (0.130 mL, 0.671 mmol), 10 min later step B product (154 mg, 0.47 mmol) in dry THF (0.5 mL) was dropwise added and stirring was continued at RT for 2 d. The solvent was removed under reduced pressure. The product was purified by flash chromatography (silica, gradient heptane/EtOAc, 1:0→1:1) to give a TLC-pure and a TLC-impure batch. The TLC-impure was subjected again to flash chromatography (silica, gradient heptane/EtOAc, 1:0→1:1) to give another TLC-pure batch. Both batches of TLC-pure product were combined and purified further by reversed phase chromatography (C$_{18}$, H$_2$O/MeCN/HCO$_2$H) to remove alkylated DIAD. The solvent was removed by freeze-drying, to furnish 97 mg (25%) of the title compound.

Step 2: [3-(4-Chlorophenyl)-4-methyl-1-(1H-[1,2,4]triazol-3-yl-methyl)-5-(trifluoromethyl)-1H-pyrrol-2-yl]-morpholin-4-yl-methanone To a solution of (3-(4-chlorophenyl)-4-methyl-5-(trifluoromethyl)-1-((1-((2-(trimethylsilyl)ethoxy)methyl)-1H-1,2,4-triazol-3-yl)methyl)-1H-pyrrol-2-yl)(morpholino)methanone (97 mg, 0.166 mmol) in DCM (5 mL) was dropwise added TFA (5 mL). The reaction mixture was stirred at RT for 1 h. The solvent was removed under reduced pressure and the residue co-evaporated with DCM (3×). EtOAc (10 mL) and saturated aqueous NaHCO$_3$ (10 mL) were added. The organic layer was washed with more saturated aqueous NaHCO$_3$ (2×10 mL), dried (Na$_2$SO$_4$) and evaporated to dryness. The product was purified by flash chromatography (silica, gradient heptane/EtOAc, 2:1→1:2), to give 49 mg (65%) of title compound.

N-Cyclopropyl-3-(4-fluorophenyl)-N-methyl-1-[(3-methyl-[1,2,4]oxadiazol-5-yl)-methyl]-5-(trifluoromethyl)-1H-pyrrole-2-carboxylic acid amide (Example 004)

N-(2-Carbamoyl-2-methyl-propyl)-3-(4-fluorophenyl)-N-methyl-1-[(3-methyl-[1,2,4]oxadiazol-5-yl)-methyl]-5-(trifluoromethyl)-1H-pyrrole-2-carboxylic acid amide (Example 005)

4-[3-(4-Fluorophenyl)-1-[(3-methyl-[1,2,4]oxadiazol-5-yl)-methyl]-5-(trifluoromethyl)-1H-pyrrole-2-carbonyl]-piperazin-2-one (Example 006)

[3-(4-Fluorophenyl)-1-[(3-methyl-[1,2,4]oxadiazol-5-yl)-methyl]-5-(trifluoromethyl)-1H-pyrrol-2-yl]-morpholin-4-yl-methanone (Example 007)

General Procedure: A solution of the respective amine in DMF (1 mL) was added to a stirred solution of ACI-3 in DMF (1 mL, dry) at −40° C., and then DIPEA (5 eq) was added and stirred for 5 min. Finally BOP—Cl (1.2-1.5 eq) was added and then warmed to RT and stirred for 16 h. The reaction mixture was diluted with H$_2$O (20 mL) and Et$_2$O (50 mL). The organic layer was separated and washed with brine (20 mL), then dried (Na$_2$SO$_4$), filtered and evaporated in vacuo to give crude. The crude was purified by flash column chromatography (silica gel 100-200 mesh; 40-50% EtOAc in petroleum ether) to obtain corresponding pure products of 004, 005, 006 & 007, as solids.

| ACI-3 | Amine (Qty., mmol) | Structure | Qty., % yield Nature | Ex.-No. |
|---|---|---|---|---|
| 0.25 g, 0.67 mmol | 0.2 mL, 2.04 | —HN▷ | 80 mg, 32% Off-white solid | 004 |
| 0.2 g, 0.54 mmol | 0.13 g, 0.81 | HN–C(CH$_3$)$_2$–C(O)NH$_2$ | 90 mg, 34% White solid | 005 |
| 0.15 g, 0.40 mmol | 0.061 g, 0.60 | piperazinone | 90 mg, 50% white solid | 006 |
| 0.3 g, 0.81 mmol | 0.10 mL, 1.21 | morpholine | 120 mg, 34% Pale yellow solid | 007 |

(3-(4-chlorophenyl)-4-methyl-1-((1-methyl-1H-pyrazol-4-yl)methyl)-5-(trifluoromethyl)-1H-pyrrol-2-yl)(morpholino)methanone (Example 023)

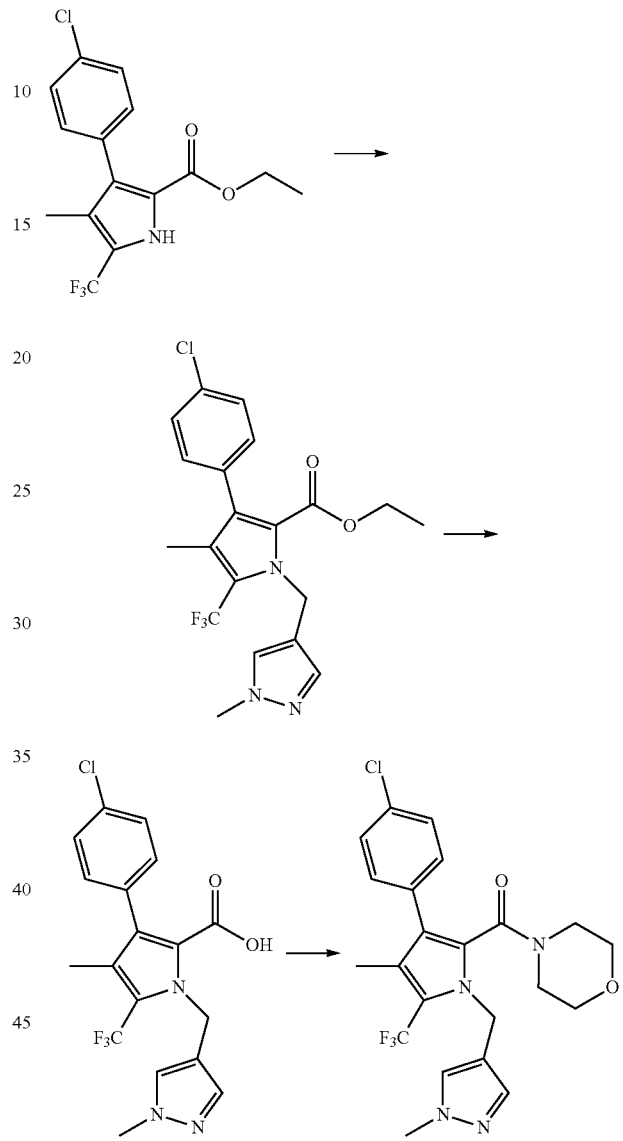

Step 1: Ethyl 3-(4-chlorophenyl)-4-methyl-1-((1-methyl-1H-pyrazol-4-yl)methyl)-5-(trifluoromethyl)-1H-pyrrole-2-carboxylate To a stirred solution of ethyl 3-(4-chlorophenyl)-4-methyl-5-(trifluoromethyl)-1H-pyrrole-2-carboxylate (0.5 g, 1.51 mmol) in MeCN (15 mL), K$_2$CO$_3$ (0.41 g, 3.02 mmol) was added along with 4-(bromomethyl)-1-methyl-1H-pyrazole (0.29 g, 1.72 mmol) and the mixture was heated up to 80° C. for 12 h. The reaction mixture was cooled to RT, diluted with EtOAc, washed with H$_2$O, brine and finally dried over anhydrous Na$_2$SO$_4$. The crude product was purified by column chromatography to afford desired product (0.37 g, 57.72%) as a brown liquid.

Step 2: 3-(4-Chlorophenyl)-4-methyl-1-((1-methyl-1H-pyrazol-4-yl)methyl)-5-(trifluoromethyl)-1H-pyrrole-2-carboxylic acid To a stirred solution of ethyl 3-(4-chlorophenyl)-4-methyl-1-((1-methyl-1H-pyrazol-4-yl)methyl)-5-(trifluoromethyl)-1H-pyrrole-2-carboxylate (0.36 g, 0.84 mmol) in THF: MeOH: H₂O (16 mL, 2:1:1) LiOH (0.355 g, 8.4 mmol) was added and the mixture was stirred for 12 h. The reaction mixture was distilled under reduced pressure, diluted with H₂O, acidified with 1N HCl, extracted with EtOAc (30 mL×2), the organic layer was washed with saturated brine, dried over anhydrous Na₂SO₄ and concentrated under reduced pressure to afford desired product (0.310 g, 92%) as a white solid

Step 3: (3-(4-Chlorophenyl)-4-methyl-1-((1-methyl-1H-pyrazol-4-yl)methyl)-5-(trifluoromethyl)-1H-pyrrol-2-yl)(morpholino)methanone To a stirred solution of 3-(4-chlorophenyl)-4-methyl-1-((1-methyl-1H-pyrazol-4-yl)methyl)-5-(trifluoromethyl)-1H-pyrrole-2-carboxylic acid (0.25 g, 0.629 mmol) in DMF (5 mL). DIPEA (0.274 mL, 1.57 mmol) and morpholine (0.065 g, 0.755 mmol) were added. The mixture was stirred for 10 min and then HATU (0.287 g, 0.755 mmol, 1.2 eq) was added and the mixture was stirred for further 2 h. DMF was evaporated under reduced pressure and the residue was purified by column chromatography to afford desired product (0.120 g, 51.19%) as a white solid.

(1-((1,3,4-thiadiazol-2-yl)methyl)-3-(4-chlorophenyl)-4-methyl-5-(trifluoromethyl)-1H-pyrrol-2-yl)(morpholino)methanone (Example 024)

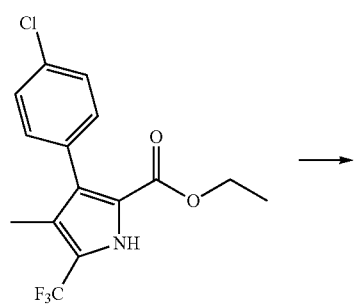

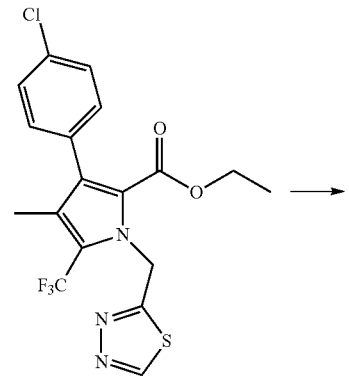

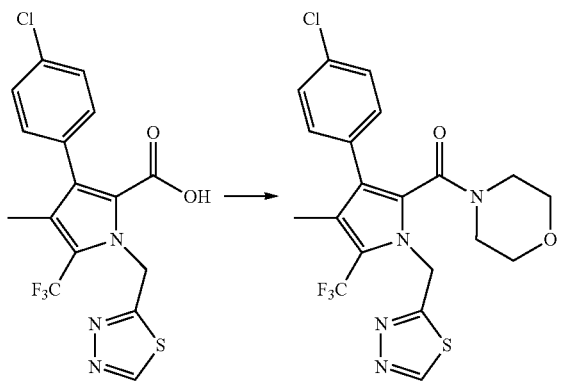

Step 1: Ethyl 1-((1,3,4-thiadiazol-2-yl)methyl)-3-(4-chlorophenyl)-4-methyl-5-(trifluoromethyl)-1H-pyrrole-2-carboxylate To a stirred solution of ethyl 3-(4-chlorophenyl)-4-methyl-5-(trifluoromethyl)-1H-pyrrole-2-carboxylate (0.5 g, 1.51 mmol) in MeCN (15 mL), K₂CO₃ (0.41 g, 3.02 mmol) was added along with 2-(bromomethyl)-1,3,4-thiadiazole (0.324 g, 1.81 mmol) and the mixture was heated up to 80° C. for 12 h. The reaction mixture was cooled to RT, diluted with EtOAc, washed with H₂O, brine and finally to afford desired product (0.38 g, 58.64%) as a brown liquid.

Step 2: 1-((1,3,4-Thiadiazol-2-yl)methyl)-3-(4-chlorophenyl)-4-methyl-5-(trifluoromethyl)-1H-pyrrole-2-carboxylic acid To a stirred solution of ethyl 1-((1,3,4-thiadiazol-2-yl)methyl)-3-(4-chlorophenyl)-4-methyl-5-(trifluoromethyl)-1H-pyrrole-2-carboxylate (0.38 g, 0.88 mmol) in THF: MeOH: H₂O (16 mL, 2:1:1) LiOH (0.372 g, 8.8 mmol) was added and the mixture was stirred for 12 h. The reaction mixture was distilled under reduced pressure, diluted with H₂O, acidified with 1N HCl, extracted with EtOAc (2×30 mL), organic layer was washed with saturated brine, dried over anhydrous Na₂SO₄ and concentrated under reduced pressure to afford desired product (0.265 g, 74.64%) as an off white solid.

Step 3: (1-((1,3,4-thiadiazol-2-yl)methyl)-3-(4-chlorophenyl)-4-methyl-5-(trifluoromethyl)-1H-pyrrol-2-yl)(morpholino)methanone To a stirred solution of 1-((1,3,4-thiadiazol-2-yl)methyl)-3-(4-chlorophenyl)-4-methyl-5-(trifluoromethyl)-1H-pyrrole-2-carboxylic acid (0.265 g, 0.66 mmol) in DMF (5 mL), DIPEA (0.28 mL, 1.65 mmol) and morpholine (0.057 g, 0.795 mmol) were added and the mixture was stirred for 10 min. Then HATU (0.251 g, 0.795 mmol) was added and the mixture was stirred for further 2 h. DMF was evaporated under reduced pressure and the residue was purified by column chromatography to afford desired compound (0.180 g, 58%) as an off white solid.

(3-(4-chlorophenyl)-4-methyl-1-(pyrimidin-5-ylmethyl)-5-(trifluoromethyl)-1H-pyrrol-2-yl)(morpholino)methanone (Example 052)

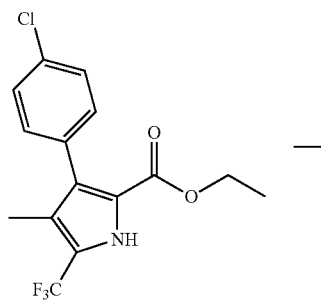

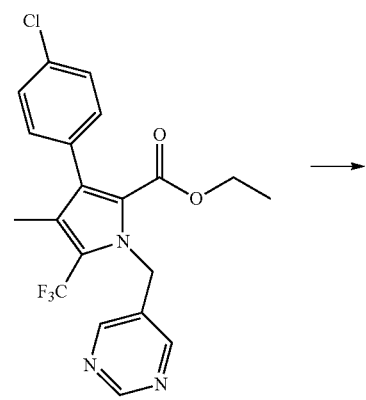

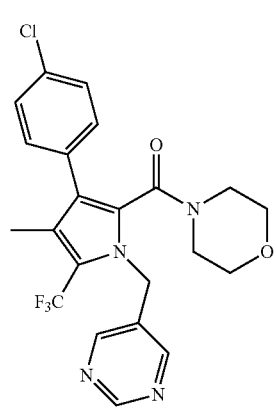

Step 1: ethyl 3-(4-chlorophenyl)-4-methyl-1-(pyrimidin-5-ylmethyl)-5-(trifluoromethyl)-1H-pyrrole-2-carboxylate To a solution of ethyl 3-(4-chlorophenyl)-4-methyl-5-(trifluoromethyl)-1H-pyrrole-2-carboxylate (0.15 g, 0.453 mmol) in MeCN (8 mL), $K_2CO_3$ (0.125 g, 0.906 mmol) was added along with 5-(chloromethyl)-pyrimidine (0.063 g, 0.498 mmol) and the mixture was heated up to 80° C. for 5 h. The reaction mixture was cooled to RT, diluted with EtOAc (50 mL), washed with $H_2O$, brine and finally dried over anhydrous $Na_2SO_4$. The residue was purified by column chromatography to afford desired compound (0.13 g, 68%) as a colourless liquid.

Step 2: 3-(4-chlorophenyl)-4-methyl-1-(pyrimidin-5-ylmethyl)-5-(trifluoromethyl)-1H-pyrrole-2-carboxylic acid To a solution of ethyl 3-(4-chlorophenyl)-4-methyl-1-(pyrimidin-5-ylmethyl)-5-(trifluoromethyl)-1H-pyrrole-2-carboxylate (0.13 g, 0.307 mmol) in THF: MeOH: $H_2O$ (8 mL, 2:1:1). LiOH (0.064 g, 1.53 mmol) was added and the mixture was stirred for 2 h. The reaction mixture was distilled under reduced pressure, diluted with $H_2O$, acidified with 1N HCl, extracted with EtOAc (2×30 mL), combined organic organic layers were washed with saturated brine, dried over anhydrous $Na_2SO_4$ and concentrated under reduced pressure to afford desired compound (0.12 g, 99%) as a white solid.

Step 3: (3-(4-chlorophenyl)-4-methyl-1-(pyrimidin-5-ylmethyl)-5-(trifluoromethyl)-1H-pyrrol-2-yl)-(morpholino)methanone To a solution of 3-(4-chlorophenyl)-4-methyl-1-(pyrimidin-5-ylmethyl)-5-(trifluoromethyl)-1H-pyrrole-2-carboxylic acid (0.12 g, 0.303 mmol) in DMF (5 mL) was added DIPEA (0.2 mL, 1.757 mmol) and morpholine (0.031 g, 0.364 mmol) and the mixture was stirred for 10 min. HATU (0.138 g, 0.364 mmol, 1.2 eq) was added and the mixture was stirred for further 2 h. The reaction mixture was diluted with $H_2O$ and extracted with EtOAc. The combined organic layers were washed with $H_2O$, brine, dried over anhydrous $Na_2SO_4$ and evaporated under reduced pressure. The residue was purified by column chromatography to afford desired compound (0.060 g, 42%) as a white solid.

[3-(4-Chloro-2-fluoro-phenyl)-4-methyl-1-(pyrimidin-2-yl-methyl)-5-(trifluoromethyl)-1H-pyrrol-2-yl]-morpholin-4-yl-methanone (Example 062)

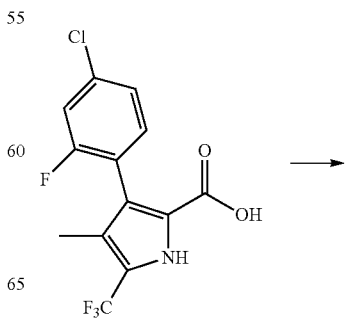

give the desired product (0.1 g, 27%) as a white solid (TLC system: 30% EtOAc-petroleum ether; Rf: 0.3).

3-(4-Chloro-2-fluoro-phenyl)-N-cyclopropyl-N,4-dimethyl-1-(pyrimidin-2-yl-methyl)-5-(trifluoromethyl)-1H-pyrrole-2-carboxylic acid amide (Example 063)

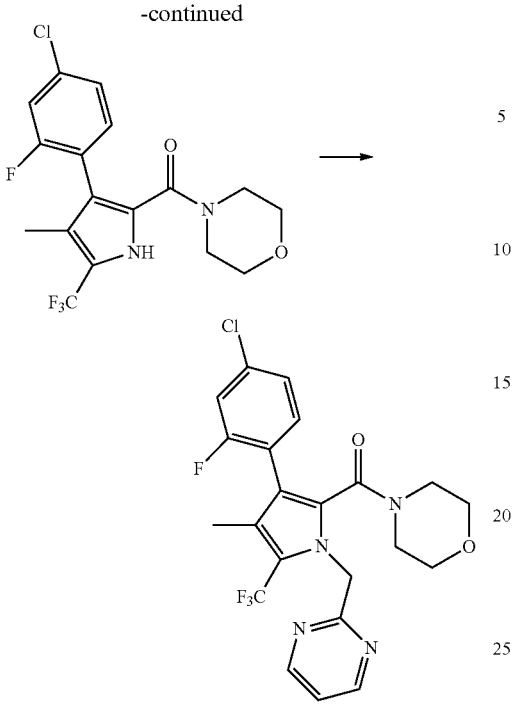

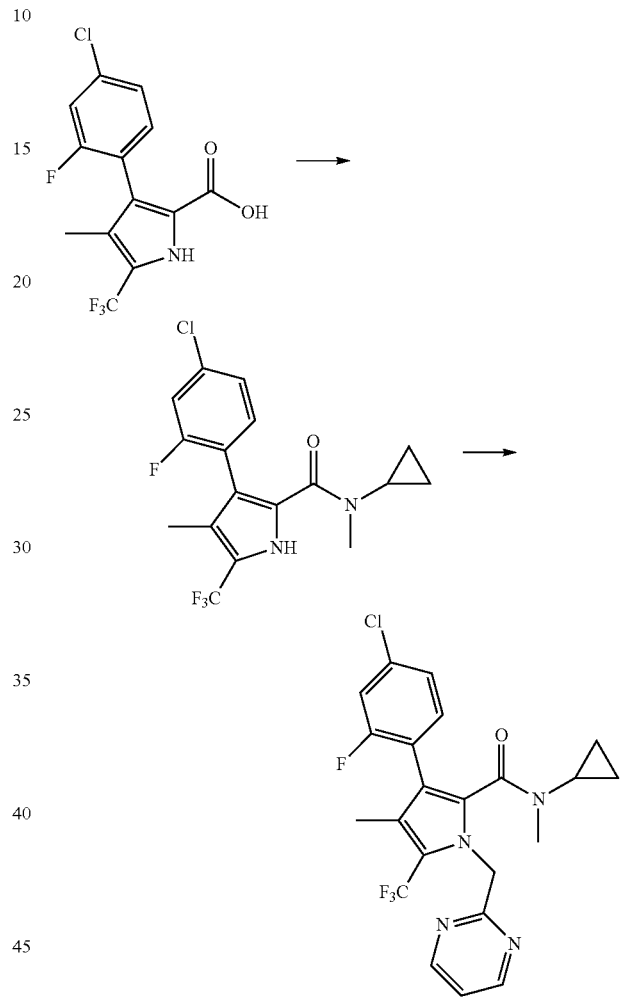

Step 1: 3-(4-Chloro-2-fluorophenyl)-4-methyl-5-(trifluoromethyl)-1H-pyrrole-2-yl)(morpholino)-methanone EDCl (0.238 g, 1.24 mmol), HOBt (0.126 g, 0.932 mmol), and DMAP (0.015 g, 0.122 mmol) were successively added to a solution of 3-(4-chloro-2-fluorophenyl)-4-methyl-5-(trifluoromethyl)-1H-pyrrole-2-carboxylic acid (200 mg, 0.62 mmol) in DCM (10 mL) at 0° C. After stirring for 10 min, a solution of morpholine (0.108 g, 1.23 mmol) in DCM (0.5 mL) was added drop-wise at the same temperature and stirred at RT for 16 h. The whole was diluted with H₂O (10 mL) and extracted with DCM (2×20 mL). The combined organic layer was successively washed with H₂O (20 mL), brine (20 mL), dried (Na₂SO₄) and concentrated in vacuo to get the crude, which was purified by column chromatography (silica gel; 60-120 mesh); eluting with 15-20% EtOAc in petroleum ether to give semi solid. The crude was washed with hexane to give the desired product (150 mg, 61%) as an off white solid (TLC system: 30% EtOAc-petroleum ether; Rf: 0.35).

Step 2: [3-(4-Chloro-2-fluoro-phenyl)-4-methyl-1-(pyrimidin-2-yl-methyl)-5-(trifluoromethyl)-1H-pyrrol-2-yl]-morpholin-4-yl-methanone Cs₂CO₃ (2 g, 6.15 mmol) was added to a stirred solution of 3-(4-chloro-2-fluorophenyl)-4-methyl-5-(trifluoromethyl)-1H-pyrrole-2-yl)(morpholino)methanone (0.3 g, 0.76 mmol) and freshly prepared 2-chloromethylpyrimidine (0.6 g crude) in MeCN (10 mL) at 0° C. The resulting reaction mixture was then stirred at 80° C. for 16 h. The mixture was cooled, filtered and concentrated and the residue was dissolved in EtOAc (50 mL) and washed with H₂O (50 mL). The organic layer was separated and the aqueous layer was extracted with EtOAc (2×20 mL). The combined organic layer was washed with brine (20 mL), then dried (Na₂SO₄), filtered and evaporated in vacuo to give crude, which was purified by column chromatography (neutral alumina); the product eluted using 15-20% EtOAc in petroleum ether to Step 1: 3-(4-Chloro-2-fluorophenyl)-N-cyclopropyl-N,4-dimethyl-5-(trifluoromethyl)-1H-pyrrole)-2-carboxamide EDCl (0.23 g, 1.24 mmol), HOBt (0.12 g, 0.93 mmol) and DMAP (0.167 g, 1.37 mmol) were successively added to a solution of 3-(4-chloro-2-fluorophenyl)-4-methyl-5-(trifluoromethyl)-1H-pyrrole-2-carboxylic acid (0.2 g, 0.623 mmol) in DCM (10 mL) at 0° C. After stirring for 10 min, a solution of N-cyclopropyl methylamine TFA salt (0.226 g, 1.24 mmol) in DCM (1 mL) was added drop wise at the same temperature and whole stirred at RT for 16 h, diluted with H₂O (20 mL) and extracted with DCM (2×30 mL). The combined organic layers was successively washed with H₂O (20 mL), brine (20 mL), dried (Na₂SO₄) and concentrated in vacuo to get the crude, which was purified by column chromatography (neutral alumina). The product eluted using 10% EtOAc in petroleum ether to give semi-pure compound which was washed with n-hexane to give the desired product (200 mg, 86%) as a white solid (TLC system: 30% EtOAc-petroleum ether; Rf: 0.7).

Step 2: 3-(4-Chloro-2-fluoro-phenyl)-N-cyclopropyl-N,4-dimethyl-1-(pyrimidin-2-yl-methyl)-5-(trifluoromethyl)-1H-pyrrole-2-carboxylic acid amide Cs$_2$CO$_3$ (1.39 g, 4.26 mmol) was added to a solution of 3-(4-chloro-2-fluorophenyl)-N-cycloproyl-N,4-dimethyl-5-(trifluoromethyl)-1H-pyrrole)-2-carboxamide (0.2 g, 0.53 mmol) and freshly prepared 2-chloromethylpyrimidine (0.4 g crude) in MeCN (10 mL) at 0° C. The resulting reaction mixture was stirred at 80° C. for 16 h. The mixture was cooled, filtered and concentrated to residue which was dissolved in EtOAc (20 mL) and washed with H$_2$O (50 mL). The organic layer was separated and the aqueous layer was extracted with EtOAc (2×80 mL). The combined organic layer was washed with brine (50 mL), dried (Na$_2$SO$_4$), filtered and evaporated in vacuo to give crude. The crude was purified by flash column chromatography (silica gel 60-120 mesh); the product eluted using 10% EtOAc in petroleum ether to give the desired product (110 mg, 44%) as a white solid (TLC system: 40% EtOAc petroleum ether; R$_f$: 0.4).

3-(4-Chloro-2-fluoro-phenyl)-N-isopropyl-N,4-dimethyl-1-(pyrimidin-2-yl-methyl)-5-(trifluoromethyl)-1H-pyrrole-2-carboxylic acid amide (Example 064)

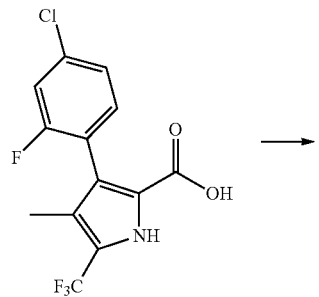

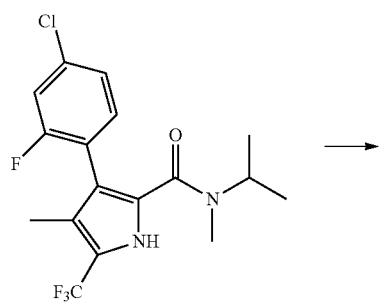

-continued

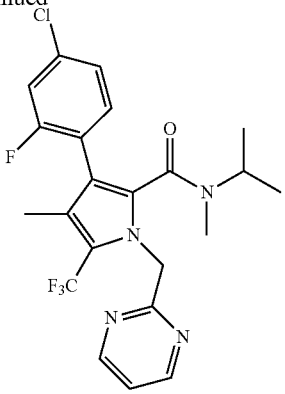

Step 1: 3-(4-Chlorofluorophenyl)-N-isoproyl-N,4-dimethyl-5-(trifluoromethyl)-1H-pyrrole)-2-carboxamide EDCl (0.716 g, 3.73 mmol), HOBt (0.378 g, 2.80 mmol) and DMAP (0.045 g, 0.373 mmol) were successively added to a stirred solution of 3-(4-chloro-2-fluorophenyl)-4-methyl-5-(trifluoromethyl)-1H-pyrrole-2-carboxylic acid (0.6 g, 1.86 mmol) in DCM (10 mL) at 0° C. After stirring for 10 min, a solution of N-isopropyl methylamine (0.38 mL, 3.73 mmol) in DCM (1 mL) was added dropwise at the same temperature and stirred at RT for 16 h. The whole was diluted with H$_2$O (20 mL) and extracted with DCM (2×50 mL). The combined organic layer was successively washed with H$_2$O (20 mL), brine (20 mL), dried (Na$_2$SO$_4$) and concentrated in vacuo to get the crude, which was purified by column chromatography (silica gel; 60-120 mesh); the product eluted using 20% EtOAc in petroleum ether to give semi pure compound which was washed with hexane to give the desired product (500 mg, 70%) as an off white solid (TLC system: 30% EtOAc-petroleum ether; Rf: 0.55).

Step 2: 3-(4-Chloro-2-fluoro-phenyl)-N-isopropyl-N,4-dimethyl-1-(pyrimidin-2-yl-methyl)-5-(trifluoromethyl)-1H-pyrrole-2-carboxylic acid amide Cs$_2$CO$_3$ (3.46 g, 10.63 mmol) was added to a stirred solution of 3-(4-Chloro-2-fluorophenyl)-N-isoproyl-N,4-dimethyl-5-(trifluoromethyl)-1H-pyrrole)-2-carboxamide (0.5 g, 1.32 mmol) and freshly prepared 2-chloromethyl pyrimidine (1 g crude) in DMF (10 mL) at 0° C. The resulting reaction mixture was stirred at 80° C. for 16 h. The reaction mixture was filtered and concentrated to give the residue, which was dissolved in EtOAc (20 mL) and washed with H$_2$O (50 mL). The organic layer was separated and the aqueous layer was extracted with EtOAc (2×15 mL). The combined organic layer was washed with brine (100 mL), then dried (Na$_2$SO$_4$), filtered and evaporated in vacuo to give crude. The crude was purified by flash column chromatography (silica gel 60-120 mesh); the product eluted using 20% EtOAc in petroleum ether to give the desired product (110 mg, 17%) as yellow liquid (TLC system: 40% EtOAc-petroleum ether; Rf: 0.4).

3-(4-Fluorophenyl)-N-isopropyl-N-methyl-1-[(3-methyl-[1,2,4]oxadiazol-5-yl)-methyl]-5-(trifluoromethyl)-1H-pyrrole-2-carboxylic acid amide (Example 065)

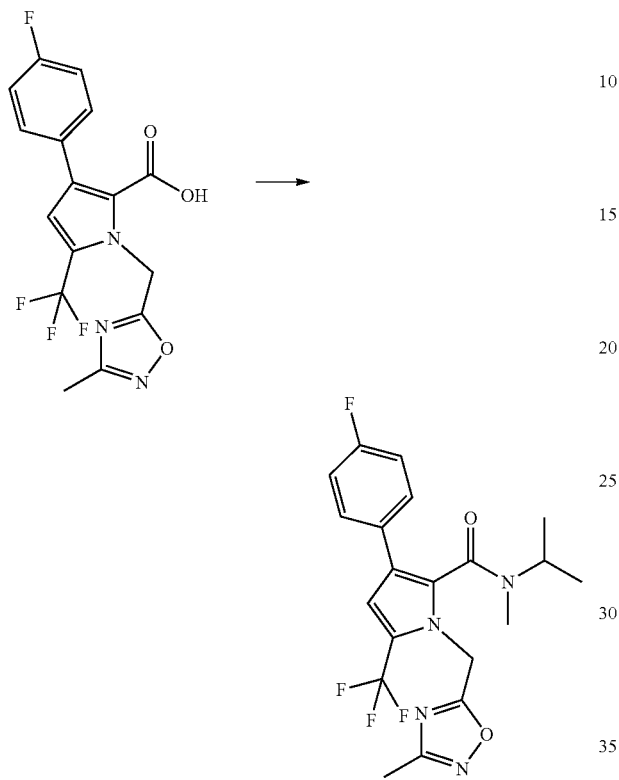

BOP—Cl (0.166 g, 0.65 mmol) was added to a stirred solution of ACI-3 (0.2 g, 0.54 mmol), N-isopropyl methyl amine (0.08 mL, 0.80 mmol) and DIPEA (0.28 mL, 1.62 mmol) in DMF at −40° C., then warmed to RT and stirred for 16 h. The reaction mixture was diluted with H₂O (20 mL) and EtOAc (50 mL). The organic layer was separated and washed with brine (20 mL), dried (Na₂SO₄), filtered and evaporated in vacuo to give crude. The crude was purified by flash column chromatography (silica gel 100-200 mesh; 15% EtOAc in petroleum ether) followed by combiflash purification to give the desired product (110 mg, 47%) as yellow liquid (TLC system: 30% EtOAc-petroleum ether; Rf: 0.5).

3-(4-Chloro-2-fluoro-phenyl)-N,4-dimethyl-N-[(5-methyl-isoxazol-3-yl)-methyl]-1-(pyrimidin-2-yl-methyl)-5-(trifluoromethyl)-1H-pyrrole-2-carboxylic acid amide (Example 066)

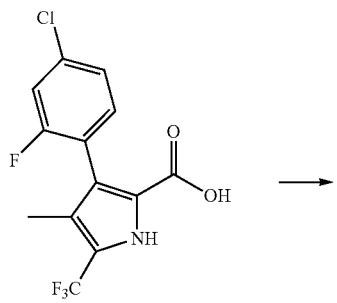

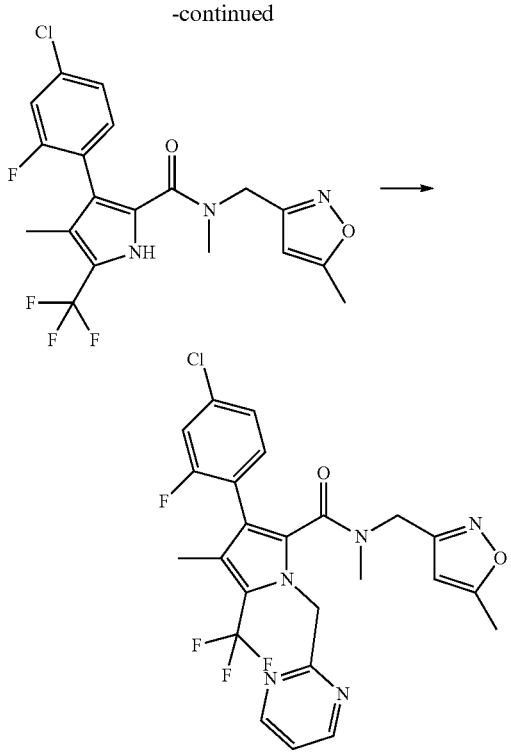

Step 1: 3-(4-chloro-2-fluorophenyl)-N,4-dimethyl-N-((5-methylisoxazol-3-yl)methyl)-5-(trifluoromethyl)-1H-pyrrole-2-carboxamide EDCl (0.77 g, 4.02 mmol), HOBt (0.40 g, 3.03 mmol), and DMAP (0.05 g, 0.4 mmol) were successively added to a stirred solution of 3-(4-chloro-2-fluorophenyl)-4-methyl-5-(trifluoromethyl)-1H-pyrrole-2-carboxylic acid (0.65 g, 2.02 mmol) in DCM (10 mL) at 0° C. After stirring for 30 min N-methyl-(5-methyl isoxazol-3-yl) methylamine (0.5 g, 4.02 mmol) was added at same temperature and then stirred at RT for 16 h. The whole mixture was diluted with H₂O (10 mL) and extracted with DCM (3×30 mL). The combined organic layer was successively washed with H₂O (20 mL), brine (20 mL), dried (Na₂SO₄) and concentrated in vacuo to get the crude, which was purified by column chromatography (silica gel; 60-120 mesh); eluting with 0-35% EtOAc in petroleum ether to give the desired product (0.65 g, 75%) as an off white solid (TLC system: 40% EtOAc-petroleum ether; Rf: 0.7).

Step 2: 3-(4-Chloro-2-fluoro-phenyl)-N,4-dimethyl-N-[(5-methyl-isoxazol-3-yl)-methyl]-1-(pyrimidin-2-yl-methyl)-5-(trifluoromethyl)-1H-pyrrole-2-carboxylic acid amide Cs₂CO₃ (4.25 g, 13.0 5 mmol) was added to a stirred solution of 3-(4-chloro-2-fluorophenyl)-N,4-dimethyl-N-((5-methylisoxazol-3-yl)methyl)-5-(trifluoromethyl)-1H-pyrrole-2-carboxamide (0.7 g, 1.63 mmol) and freshly prepared 2-chloromethylpyrimidine (1.3 g, crude) in MeCN (20 mL) at 0° C. The resulting reaction mixture was then stirred at 80° C. for 16 h. The mixture was diluted with H₂O (20 mL) and extracted with EtOAc (2×50 mL). The combined organic layer was washed with brine (20 mL), then dried (Na₂SO₄), filtered and evaporated in vacuo to give crude, which was purified by column chromatography (100-200 mesh silica gel); the product eluted using 0-70% EtOAc in petroleum ether to give semi-pure compound which was triturated with 20% Et$_2$O in pentane and filtered to give the desired product (0.1 g, 11%) as a brown solid (TLC system: 30% EtOAc-petroleum ether; Rf: 0.2).

3-(4-Chlorophenyl)-N-isopropyl-N,4-dimethyl-1-[(3-methyl-isoxazol-5-yl)-methyl]-5-(trifluoromethyl)-1H-pyrrole-2-carboxylic acid amide (Example 067)

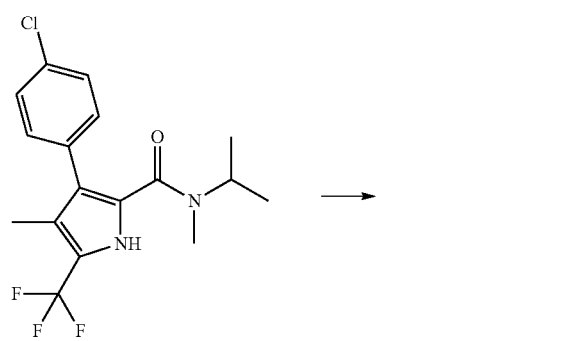

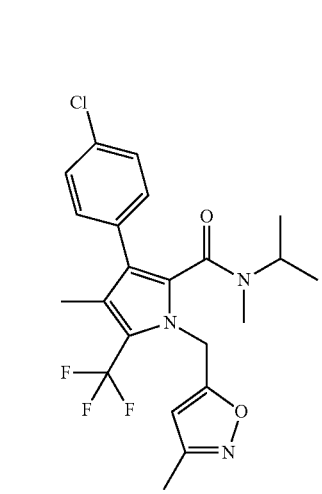

To the stirred solution of 3-(4-chlorophenyl)-N-isopropyl-N,4-dimethyl-5-(trifluoromethyl)-1H-pyrrole-2-carboxamide (200 mg, 0.581 mmol) in MeCN was added Cs$_2$CO$_3$ at 0° C. under N$_2$ atmosphere. The reaction mixture was stirred for 30 min at 0° C. then charged 5-(bromomethyl)-3-methylisoxazole (111 mg, 0.639 mmol). The mixture was warmed to RT and refluxed for 12 h. It was then quenched into ice water (100 mL) and extracted with EtOAc (3×100 mL). The combined organic layer was washed successively with water, brine, dried (Na$_2$SO$_4$) and concentrated to dryness in vacuo. The residue was purified by flash column chromatography (silica gel; 60-120 mesh) and the compound eluted with 20% EtOAc in petroleum ether to give 82 mg (39%) of example 67 as pale yellow liquid. [TLC system: 30% EtOAc-petroleum ether; R$_f$=0.31]

3-(4-Chlorophenyl)-N-isopropyl-N,4-dimethyl-1-[(5-methyl-isoxazol-3-yl)-methyl]-5-(trifluoromethyl)-1H-pyrrole-2-carboxylic acid amide (Example 068)

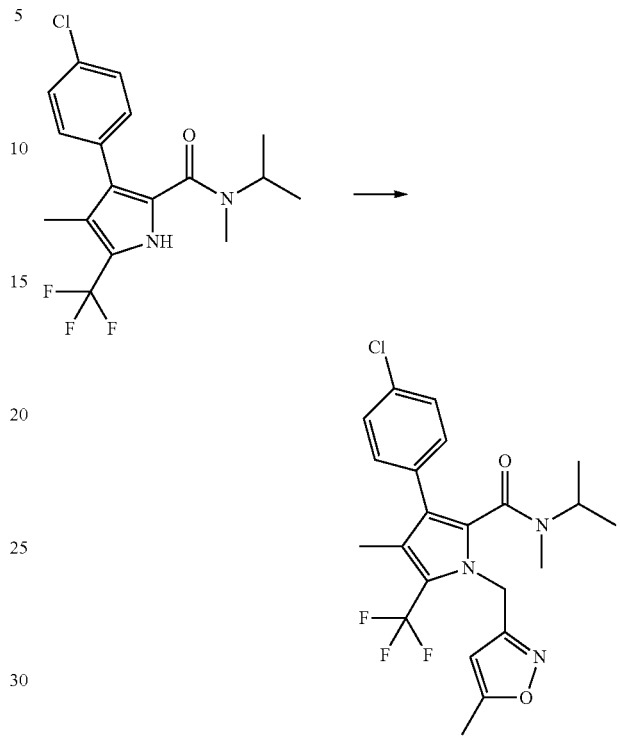

To the stirred solution of 3-(4-chlorophenyl)-N-isopropyl-N,4-dimethyl-5-(trifluoromethyl)-1H-pyrrole-2-carboxamide (200 mg, 0.581 mmol) in MeCN was added Cs$_2$CO$_3$ at 0° C. under inert condition. The reaction mixture was stirred for 30 min at 0° C. then charged with 3-(chloromethyl)-5-methylisoxazole 82 mg, 0.638 mmol). The mixture was warmed to RT and refluxed for 12 h. It was then quenched into ice water (100 mL) and extracted with EtOAc (3×100 mL). The combined organic layer was washed successively with water, brine, dried (Na$_2$SO$_4$) and concentrated to dryness in vacuo. The residue was purified by flash column chromatography (silica gel; 60-120 mesh) and the compound eluted with 30% EtOAc in petroleum ether to give 82 mg (43%) of example 68 as pale yellow liquid [TLC system: 30% EtOAc-petroleum ether; R$_f$=0.29]

3-(4-Chlorophenyl)-N-isopropyl-N,4-dimethyl-1-([1,3,4]thiadiazol-2-yl-methyl)-5-(trifluoromethyl)-1H-pyrrole-2-carboxylic acid amide (Example 069)

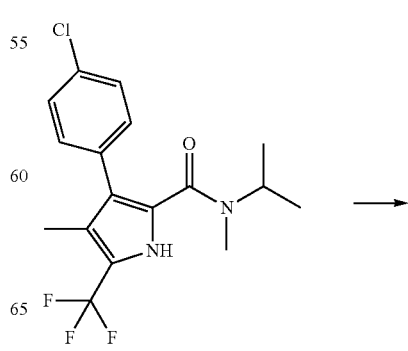

-continued

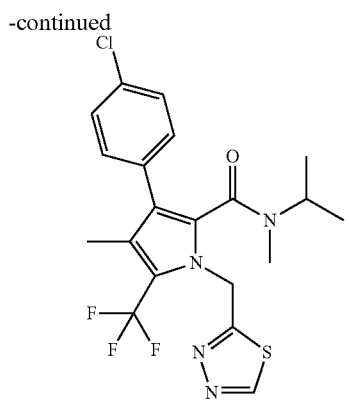

To the stirred solution of 3-(4-chlorophenyl)-N-isopropyl-N,4-dimethyl-5-(trifluoromethyl)-1H-pyrrole-2-carboxamide (200 mg, 0.583 mmol) in MeCN was added $Cs_2CO_3$ at 0° C. under $N_2$ atmosphere. The reaction mixture was stirred for 30 min at 0° C. then charged 2-(bromomethyl)-1,3,4-thiadiazole (114 mg, 0.638 mmol). The mixture was warmed to RT and then refluxed for 12 h. It was then quenched into ice water (100 mL) and extracted with EtOAc (3×100 mL). The combined organic layer was washed successively with water, brine, dried ($Na_2SO_4$) and concentrated to dryness in vacuo. The residue was purified by flash column chromatography (silica gel; 60-120 mesh) and the compound eluted with 20% EtOAc in petroleum ether to give 96 mg (37%) of example 069 as off white solid [TLC system: 30% EtOAc-petroleum ether; $R_f$=0.34]

2. Assay Descriptions and Biological Data 2.1 Fluorescent Assay for CaV2.2 Channels Using Potassium Depolarization to Induce Channel Opening Human CaV2.2 channels were stably expressed in HEK293 cells together with alpha2-delta and beta subunits of voltage gated calcium channels. In addition, an inwardly rectifying potassium channel (Kir2.3) was stably expressed in these cells to augment control of the cell membrane potential by the concentration of extracellular potassium ions. Raise of the extracellular potassium concentration leads to depolarization of the membrane potential and thus regulates the voltage dependent state of CaV2.2 channels. For preparation, cells were seeded in black poly-D-lysine coated 96-well plates (Becton Dickinson, Biocoat 4640) in 100 µL medium [500 mL DMEM/F-12 plus Glutamax (Invitrogen 31331-093) plus 5.5 mL MEM NEAA 100× (Invitrogen 11140-035) plus 50 mL FBS decomplemented (Invitrogen 10270-106) plus 200 µg/mL Geneticin (Invitrogen 10131-027) plus 50 µg/mL Hygromycin B (Invitrogen 10687-010) plus 2 µg/mL Blasticidin (anti-bl5b Invivo-Gen) plus 0.2 µg/mL Puromycin (A 11138-03)] at a cell density of 30.000 cells per well. Plates were incubated at 37° C. (5% $CO_2$) for 20 to 23 h. On the day of experiment medium was discarded and cells were loaded with Fluo 4 by addition of 100 µL of basic assay buffer (10 mM HEPES, 1 mM KCl, 149 mM NaCl, 0.8 mM $CaCl_2$, 1.7 mM $MgCl_2$, 10 mM Glucose, 0.1% BSA, pH 7.4) containing 2 µM Fluo 4 (Molecular Probes; F-14201), 0.01% pluronic acid (Molecular Probes; P-6866) and 2.5 mM probenecid (Molecular Probes; P36400). Cells were incubated in the dark at 25° C. for 60 min. Then dye containing buffer was discarded and 100 µL basic (1 mM KCl) or alternative (30 mM KCl) assay buffer was added. The alternative assay buffer contained altered concentrations of KCl (30 mM) and NaCl (120 mM) and was used in order to promote the inactivated channel state. After that 25 µL of basic or alternative assay buffer with or without test compound were added and cells were incubated again in the dark at 25° C. for 15 min. Fluorescence intensity was measured on a FLIPR 3 instrument (Molecular Devices Corp., Sunnyvale, Calif.) with excitation at 480 nm and emission at 535 nm. After continuously reading fluorescence for 30 sec, 50 µL of basic assay buffer containing 210 mM KCl (NaCl omitted) were added for depolarization. Peak fluorescent signal intensity was determined and the amplitude of the peak signal, normalized to base line, was used to measure channel inhibition by test compounds.

The following table summarizes the inhibitory activity of exemplified compounds according to the present invention.

| Example No. | Activity Category | Example No. | Activity Category | Example No. | Activity Category | Example No. | Activity Category |
|---|---|---|---|---|---|---|---|
| 001 | A | 022 | C | 038 | A | 053 | C |
| 002 | C | 023 | A | 039 | B | 054 | B |
| 003 | C | 024 | C | 040 | B | 055 | C |
| 008 | B | 025 | B | 041 | A | 056 | B |
| 009 | B | 026 | B | 042 | A | 060 | C |
| 010 | B | 027 | C | 043 | B | 061 | A |
| 011 | A | 028 | A | 044 | A | 062 | A |
| 012 | A | 029 | A | 045 | A | 063 | A |
| 013 | B | 030 | A | 046 | A | 064 | A |
| 014 | B | 031 | C | 047 | A | 065 | B |
| 015 | B | 033 | C | 048 | C | 066 | A |
| 016 | B | 034 | B | 049 | B | 067 | A |
| 017 | C | 035 | B | 050 | B | 068 | A |
| 018 | A | 036 | A | 051 | A | 069 | A |
| 019 | B | 037 | A | 052 | C | | |

* %-Inhib (CaV2.2) @3 µM @30 µM KCl:
"A": %-Inhibition >95%;
"B": %-Inhibition >75% up to ≤95%;
"C": %-Inhibition >40% up to ≤75%,
"D": %-Inhibition >30% up to ≤40%.

2.2 Electrophysiological Assessment of Calcium Channel Activity

Patch-clamp recordings were performed using HEK293 cells stably expressing human Cav2.2. Cells were plated in T150 flasks and grown a humidified incubator at 37° C. and under 5% $CO_2$ to approximately 50-60% confluency. Cells were maintained at 30° C. for 48 hrs prior to recording. On the day of the experiment, cells were harvested with TrypLE cell detachment solution (Invitrogen) diluted to 25% with phosphate buffered saline and maintained in 50% cell culture media, 50% NaCl based external saline (in mM, 140 NaCl, 4 KCl, 1 $MgCl_2$, 2 $CaCl_2$, 5 Glucose, 10 HEPES, pH 7.4) up to several hours prior to experiment.

Currents were recorded at room temperature (21-23° C.) using the Patchliner planar array technology (Nanion). Patchliner is a multi-well whole-cell automated patch clamp device that operates asynchronously with fully integrated fluidics. Capacitance and series resistance compensation was automated and no correction for liquid junction potential was employed. Leak was subtracted on-line. Whole-cell patch-clamp recordings were obtained using extracellular saline consisting of (mM): 145 TEA-Cl, 10 $BaCl_2$, 10 HEPES, 10 Glucose. The pH was adjusted to 7.35 with NaOH and the osmolarity was adjusted to 310 mOsm with sucrose. Intracellular solution consisted of (mM): 50 CsCl, 60 CsF, 10 NaCl, 20 EGTA, 5 BAPTA, 10 HEPES. Prior to an experiment, 5 mM MgATP and 0.3 NaGTP were added, the pH was adjusted to 7.2 with CsOH and the osmolarity was adjusted to 290 mOsm with sucrose.

A voltage pulse protocol was utilised to assess compound inhibition. Cells were held at a holding potential of −60 mV and channels were activated using a 10 ms test pulse to +30 mV activated every 10 seconds (0.1 Hz). Increasing concentrations of compound were applied to individual cells with 5 minutes at each test concentration. Compounds were prepared in DMSO as 10 mM stock solutions and subsequent 1:3 serial dilutions performed. Final dilution of 1:1000 in external solution resulted in a final DMSO concentration of 0.1%. For each cell, current responses were normalised to dimethyl sulfoxide vehicle control to generate concentration-response curves. When multiple doses were achieved per cell, IC50 values were calculated from the fits of the Hill equation to the data. The form of the Hill equation used was: Relative current=(100/(1+(IC50/conc)^Slope)). A selection of the foregoing exemplified compounds was tested under these conditions: Several compounds are potent inhibitors (IC50<5 μM) or even very potent inhibitors (IC50<2 μM).

The invention claimed is:

1. A compound of general formula (I),

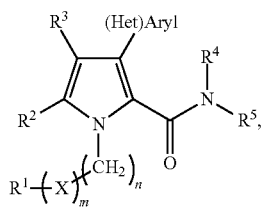

wherein
n represents 0, 1 or 2; m represents 0;
$R^1$ represents heteroaryl;
$R^2$ represents $CH_2F$; $CHF_2$ or $CF_3$;
$R^3$ represents H; methyl, ethyl, iso-propyl or cyclopropyl;
(Het)Aryl represents phenyl, substituted by zero or one or two substituents of the group consisting of $R^6$ and $R^7$, wherein $R^6$ and $R^7$ are each independently of one another selected from the group consisting of F; Cl; CN; $CF_3$; $CH_3$; OH; $OCF_3$; OCH; S(=O)$CH_3$; S(=O)$_2CH_3$; cyclopropyl and O-cylopropyl;
$R^4$ represents H or $C_{1-10}$-alkyl; and
$R^5$ represents H, $C_{1-10}$-alkyl; $C_{3-10}$-cycloalkyl; 3 to 10 membered heterocyclyl, aryl or heteroaryl; or $C_{3-10}$-cycloalkyl; 3 to 10 membered heterocyclyl, aryl or heteroaryl in each case connected via a $C_{1-8}$-alkylene group; or
$R^4$ and $R^5$ together with the nitrogen atom connecting them form a 3 to 10 membered heterocyclyl;
wherein said $C_{1-6}$-alkyl, said $C_{1-10}$-alkyl and said $C_{1-8}$-alkylene in each case may be branched or unbranched and unsubstituted or mono- or poly-substituted;
and wherein said $C_{3-6}$-cycloalkyl, said $C_{3-10}$-cycloalkyl, said 3 to 7 membered heterocyclyl, said 3 to 10 membered heterocyclyl, said aryl and said heteroaryl in each case may be unsubstituted or mono- or polysubstituted;
wherein substituents of "$C_{1-10}$-alkyl" and "$C_{1-8}$-alkylene" are selected from the group consisting of F; Cl; Br; I; $CF_3$; C(=O)—$NH_2$; C(=O)—N(H)($C_{1-6}$-alkyl); C(=O)—N($C_{1-6}$-alkyl)$_2$; OH; O—$C_{1-6}$-alkyl; O—($C_{1-8}$-alkylene)-OH; O—($C_{1-8}$-alkylene)-O—$C_{1-6}$-alkyl; $NH_2$; N(H)($C_{1-6}$-alkyl); N($C_{1-6}$-alkyl)$_2$; N(H)—C(=O)—$C_{1-6}$-alkyl; N(H)—S(=O)$_2$—$C_{1-6}$-alkyl; N($C_{1-6}$-alkyl)-S(=O)$_2$—$C_{1-6}$-alkyl; N(H)—S(=O)$_2$—$NH_2$; SH; S—$C_{1-6}$-alkyl; S(=O)$_2$ $C_{1-6}$-alkyl and S(=O)$_2$—N(H)($C_{1-6}$-alkyl); and wherein substituents of "$C_{3-10}$-cycloalkyl" and "3 to 10-membered heterocyclyl" are selected from the group consisting of F; Cl; Br; I; $NO_2$; $CF_3$; CN; =O; $C_{1-6}$-alkyl; $C_{3-6}$-cycloalkyl or 3 to 7 membered heterocyclyl; $C_{3-6}$-cycloalkyl or 3 to 7 membered heterocyclyl, each bridged via a $C_{1-8}$-alkylene; CHO; C(=O)—$C_{1-6}$-alkyl; $CO_2H$; C(=O)O—$C_{1-6}$-alkyl; $CONH_2$; C(=O)NH—$C_{1-6}$-alkyl; C(=O)N($C_{1-6}$-alkyl)$_2$; OH; O—$C_{1-6}$-alkyl; $OCF_3$; O—($C_{1-8}$-alkylene)-OH; O—($C_{1-8}$-alkylene)-O—$C_{1-6}$-alkyl; O—C(=O)—$C_{1-6}$-alkyl; $NH_2$; NH—$C_{1-6}$-alkyl; N($C_{1-6}$-alkyl)$_2$; NH—C(=O)—$C_{1-6}$-alkyl; SH; alkyl; $SCF_3$; S(=O)$_2$—$C_{1-6}$-alkyl; S(=O)$_2$OH; S(=O)$_2$O—$C_{1-6}$-alkyl and S(=O)$_2$—NH—$C_{1-6}$-alkyl;

wherein substituents of "aryl" and "heteroaryl" are selected from the group consisting of F; Cl; $CF_3$; CN; $C_{1-6}$-alkyl; C(=O)—OH; C(=O)—O—$C_{1-6}$-alkyl; CO—$NH_2$; C(=O)—N(H)$C_{1-6}$-alkyl; C(=O)—N($C_{1-6}$-alkyl)$_2$; OH; O—$C_{1-6}$-alkyl; O—C(=O)—$C_{1-6}$-alkyl; $OCF_3$; $OCHF_2$; $OCH_2F$; $NH_2$; N(H)$C_{1-6}$-alkyl; N($C_{1-6}$-alkyl)$_2$; N(H)—C(=O)—$C_{1-6}$-alkyl; N($C_{1-6}$-alkyl)-C(=O)$C_{1-6}$-alkyl; N(H)—S(=O)$_2$—$C_{1-6}$-alkyl; N($C_{1-6}$-alkyl)-S(=O)$_2$($C_{1-6}$-alkyl); N(H)C(=O)$NH_2$; N(H)C(=O)—N(H)$C_{1-6}$-alkyl; N(H)—C(=O)—N($C_{1-6}$-alkyl)$_2$; N($C_{1-6}$-alkyl)-C(=O)—$NH_2$; N($C_{1-6}$-alkyl)C(=O)—N(H)$C_{1-6}$-alkyl; N($C_{1-6}$-alkyl)-C(=O)—N($C_{1-6}$-alkyl)$_2$; S(=O)$_2C_{1-6}$-alkyl; S(=O)$_2$—$NH_2$; S(=O)$_2$—N(H)$C_{1-6}$-alkyl and S(=O)$_2$—N($C_{1-6}$-alkyl)$_2$;

optionally in the form of an individual stereoisomer or a mixture of stereoisomers,
in the form of the free compound and/or a physiologically acceptable salt and/or a physiologically acceptable solvate thereof.

2. The compound according to claim 1, wherein
m represents 0
and
$R^1$ represents 5- or 6-membered heteroaryl, unsubstituted or mono- or polysubstituted by one or more substituents selected from the group consisting of
F; Cl; $CF_3$; CN; $C_{1-6}$-alkyl; C(=O)—OH; C(=O)—O—$C_{1-6}$-alkyl; CO—$NH_2$; C(=O)—N(H)$C_{1-6}$-alkyl; C(=O)—N($C_{1-6}$-alkyl)$_2$; OH; O—$C_{1-6}$-alkyl; O—C(=O)—$C_{1-6}$-alkyl; $OCF_3$; $OCHF_2$; $OCH_2F$; $NH_2$; N(H)$C_{1-6}$-alkyl; N($C_{1-6}$-alkyl)$_2$; N(H)—C(=O)—$C_{1-6}$-alkyl; N($C_{1-6}$-alkyl)-C(=O)$C_{1-6}$-alkyl; N(H)—S(=O)$_2$—$C_{1-6}$-alkyl; N($C_{1-6}$-alkyl)-S(=O)$_2$($C_{1-6}$-alkyl); N(H)C(=O)$NH_2$; N(H)C(=O)—N(H)$C_{1-6}$-alkyl; N(H)—C(=O)—N($C_{1-6}$-alkyl)$_2$; N($C_{1-6}$-alkyl)-C(=O)—$NH_2$; N($C_{1-6}$-alkyl)C(=O)—N(H)$C_{1-6}$-alkyl; N($C_{1-6}$-alkyl)-C(=O)—N($C_{1-6}$-alkyl)$_2$; S(=O)$_2C_{1-6}$-alkyl; S(=O)$_2$—$NH_2$; S(=O)$_2$—N(H)$C_{1-6}$-alkyl and S(=O)$_2$—N($C_{1-6}$-alkyl)$_2$,
wherein each $C_{1-6}$-alkyl in each case may be branched or unbranched and in each case may be independently unsubstituted or mono- or poly-substituted.

3. The compound according to claim 1, wherein $R^2$ represents $CHF_2$ or $CF_3$.

4. The compound according to claim 1, wherein $R^3$ is selected from the group consisting of H and methyl.

5. The compound according to claim 1, wherein (Het)Aryl is selected from the group consisting of phenyl, 2-fluoro-phenyl, 3-fluoro-phenyl, 4-fluoro-phenyl, 2-chloro-phenyl, 3-chloro-phenyl, 4-chloro-phenyl, 2,4-difluoro-phenyl, 3,4-difluoro-phenyl, 2,4-dichloro-phenyl, 3,4-dichloro-phenyl, 4-chloro-2-fluoro-phenyl, 4-chloro-3-fluoro-phenyl, 2-chloro-4-fluoro-phenyl and 3-chloro-4-fluoro-phenyl.

6. The compound according to claim 1, wherein the compound of general formula (I) is a compound according to general formula (Ia),

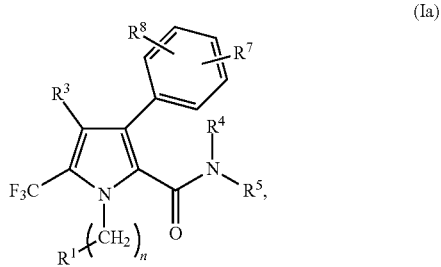

(Ia)

wherein n represents 0 or 1;

$R^3$ represents H or $CH_3$ or cyclopropyl;

$R^7$ and $R^8$ are independently absent or are each independently of one another selected from the group consisting of F; Cl; CN; $CF_3$; $CH_3$, OH; $OCF_3$; and $OCH_3$.

7. The compound according to claim 1, wherein $R^4$ represents

H or a $C_{1-6}$ aliphatic residue, branched or unbranched, unsubstituted or substituted with 1, 2, 3, 4 or 5 substituents independently from one another selected from the group consisting of OH, =O, O—$C_{1-6}$-alkyl, S(=O)—$C_{1-6}$-alkyl, S(=O)$_2$—$C_{1-6}$-alkyl, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, C(=O)—$NH_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl, and N($C_{1-6}$-alkyl)-C(=O)—$C_{1-6}$-alkyl and $R^5$ represents H; or $C_{1-6}$-alkyl, branched or unbranched, unsubstituted or substituted with 1, 2, 3, 4 or 5 substituents independently from one another selected from the group consisting of F, Cl, $CF_3$, CN, OH, =O, $OCF_3$, O—(C=O)$C_{1-6}$-alkyl, S(=O)—$C_{1-6}$-alkyl, S(=O)$_2$—$C_{1-6}$-alkyl, S(=O)$_2$—$NH_2$, S(=O)$_2$—N(H)$C_{1-6}$-alkyl, S(=O)$_2$—N($C_{1-6}$-alkyl)$_2$, $NH_2$, NH($C_{1-6}$-alkyl), N($C_{1-6}$-alkyl)$_2$, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, N(H)—C(=O)—$NH_2$, N(H)—C(=O)—N(H)($C_{1-6}$-alkyl), N(H)—C(=O)—N($C_{1-6}$-alkyl)$_2$, N(H)—C(=O)—O—$C_{1-6}$-alkyl; O—C(=O)—$NH_2$, O—C(=O)—N(H)($C_{1-6}$-alkyl), O—C(=O)—N($C_{1-6}$-alkyl)$_2$, C(=O)—$NH_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl, and N($C_{1-6}$-alkyl)-C(=O)—$C_{1-6}$-alkyl; or $C_{3-6}$-cycloalkyl, unsubstituted or substituted with 1, 2, 3, 4 or 5 substituents independently from one another selected from the group consisting of F, Cl, CN, $CF_3$, =O, $OCF_3$, $C_{1-6}$-alkylen-OH, $C_{1-6}$ alkyl, OH, O—$C_{1-6}$-alkyl, O—(C=O)$C_{1-6}$-alkyl, S(=O)—$C_{1-6}$-alkyl, S(=O)$_2$—$C_{1-6}$-alkyl, S(=O)$_2$—$NH_2$, S(=O)$_2$—N(H) $C_{1-6}$-alkyl, S(=O)$_2$—N($C_{1-6}$-alkyl)$_2$, $NH_2$, NH($C_{1-6}$-alkyl), N($C_{1-6}$-alkyl)$_2$, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, N(H)—C(=O)—O—$C_{1-6}$-alkyl; O—C(=O)—$NH_2$, O—C(=O)—N(H)($C_{1-6}$-alkyl), O—C(=O)—N($C_{1-6}$-alkyl)$_2$, N(H)—C(=O)—$NH_2$, N(H)—C(=O)—N(H) ($C_{1-6}$-alkyl), N(H)—C(=O)—N($C_{1-6}$-alkyl)$_2$, C(=O)—$NH_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl, and N($C_{1-6}$-alkyl)-C(=O)—$C_{1-6}$-alkyl; wherein said $C_{3-6}$-cycloalkyl is optionally connected via $C_{1-6}$-alkylene, branched or unbranched, which in turn may be unsubstituted or substituted with 1, 2, 3, 4 or 5 substituents independently from one another selected from the group consisting of F, Cl, $CF_3$, =O, $OCF_3$, OH, O—$C_{1-6}$-alkyl and $C_{1-6}$-alkylen-OH; or 3-7-membered heterocyclyl, which is unsubstituted or substituted with 1, 2, 3, 4 or 5 substituents independently from one another selected from the group consisting of F, Cl, CN, $CF_3$, =O, $OCF_3$, $C_{1-6}$-alkylen-OH, $C_{1-6}$ alkyl, OH, O—$C_{1-6}$-alkyl, O—(C=O)$C_{1-6}$-alkyl, S(=O)—$C_{1-6}$-alkyl, S(=O)$_2$—$C_{1-6}$-alkyl, S(=O)$_2$—$NH_2$, S(=O)$_2$—N(H)$C_{1-6}$-alkyl, S(=O)$_2$—N($C_{1-6}$-alkyl)$_2$, $NH_2$, NH($C_{1-6}$-alkyl), N($C_{1-6}$-alkyl)$_2$, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, N(H)—C(=O)—O—$C_{1-6}$-alkyl; O—C(=O)—$NH_2$, O—C(=O)—N(H) ($C_{1-6}$-alkyl), O—C(=O)—N($C_{1-6}$-alkyl)$_2$, N(H)—C(=O)—$NH_2$, N(H)—C(=O)—N(H)($C_{1-6}$-alkyl), N(H)—C(=O)—N($C_{1-6}$-alkyl)$_2$, (C=O)$C_{1-6}$-alkyl, C(=O)—$NH_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl, and N($C_{1-6}$-alkyl)-C(=O)—$C_{1-6}$-alkyl, wherein said 3-7-membered heterocyclyl is optionally connected via $C_{1-6}$-alkylene, branched or unbranched, which in turn may be unsubstituted or substituted with 1, 2, 3, 4 or 5 substituents independently from one another selected from the group consisting of F, Cl, $CF_3$, =O, $OCF_3$, OH, O—$C_{1-6}$-alkyl and $C_{1-6}$-alkylen-OH;

or aryl or heteroaryl, which in each case is unsubstituted or substituted with 1, 2, 3, 4 or 5 substituents independently from one another selected from the group consisting of F, Cl, CN, $CF_3$, $OCF_3$, $C_{1-6}$-alkylen-OH, $C_{1-6}$-alkyl, OH, O—$C_{1-6}$-alkyl, O—(C=O)$C_{1-6}$-alkyl, S(=O)—$C_{1-6}$-alkyl, S(=O)$_2$—$C_{1-6}$-alkyl, S(=O)$_2$—$NH_2$, S(=O)$_2$—N(H)$C_{1-6}$-alkyl, S(=O)$_2$—N($C_{1-6}$-alkyl)$_2$, $NH_2$, NH($C_{1-6}$-alkyl), N($C_{1-6}$-alkyl)$_2$, N(H)—S(=O)—$C_{1-6}$-alkyl, N($C_{1-6}$-alkyl)-S(=O)—$C_{1-6}$-alkyl, N(H)—S(=O)$_2$—$C_{1-6}$-alkyl, N($C_{1-6}$-alkyl)-S(=O)$_2$—$C_{1-6}$-alkyl, N(H)—C(=O)—O—$C_{1-6}$-alkyl; O—C(=O)—$NH_2$, O—C(=O)—N(H)($C_{1-6}$-alkyl), O—C(=O)—N($C_{1-6}$-alkyl)$_2$, N(H)—C(=O)—$NH_2$, N(H)—C(=O)—N(H)($C_{1-6}$-alkyl), N(H)—C(=O)—N($C_{1-6}$-alkyl)$_2$, C(=O)—$NH_2$, C(=O)—N(H)($C_{1-6}$-alkyl), C(=O)—N($C_{1-6}$-alkyl)$_2$, C(=O)—O—$C_{1-6}$-alkyl; N(H)—C(=O)—$C_{1-6}$-alkyl, and N($C_{1-6}$-alkyl)-C(=O)—$C_{1-6}$-alkyl, wherein said aryl or heteroaryl is optionally connected via $C_{1-6}$-alkylene, branched or unbranched, which in turn may be unsubstituted or substituted with 1, 2, 3, 4 or 5 substituents independently from one another selected from the group consisting of F, Cl, $CF_3$, =O, $OCF_3$, OH, O—$C_{1-6}$-alkyl and $C_{1-6}$-alkylen-OH.

8. The compound according to claim 1, wherein $R^4$ and $R^5$ together with the nitrogen atom connecting them form a 3-7-membered heterocyclyl, unsubstituted or substituted with 1, 2, 3, 4 or 5 substituents selected from the group consisting of F, Cl, CN, $CF_3$, =O, OH, $C_{1-6}$-alkyl, O—$C_{1-6}$-alkyl, $C_{1-6}$-alkylen-OH, $OCF_3$, $SO_2(C_{1-6}$-alkyl), $SO_2NH_2$, $SO_2N(H)C_{1-6}$-alkyl, $SO_2N(C_{1-6}$-alkyl)$_2$, $C_{1-6}$-alkylen-$SO_2(C_{1-6}$-alkyl), $NH_2$, $NH(C_{1-6}$-alkyl), $N(C_{1-6}$-alkyl)$_2$, (C=O)$C_{1-6}$-alkyl, $C_{3-6}$-cycloalkyl and or 3 to 7 membered heterocyclyl, in each case unsubstituted or mono- or polysubstituted.

9. The compound according to claim 1, wherein
$R^4$ represents H or $C_{1-6}$-alkyl; and
$R^5$ represents
  $C_{3-6}$-cycloalkyl, which is unsubstituted or substituted with 1, 2, 3, 4 or 5 substituents independently from one another selected from the group consisting of F, Cl, $CF_3$, =O, $OCF_3$, OH, O—$C_{1-6}$-alkyl, $C_{1-6}$-alkylen-OH $C_{1-6}$-alkyl, C(=O)—$NH_2$, C(=O)—N(H)($C_{1-6}$-alkyl) and C(=O)—N($C_{1-6}$-alkyl)$_2$; or
  3-7-membered heterocyclyl, which comprises 1 or 2 heteroatoms or heteroatom groups independently from one another selected from the group consisting of O, S, S(=O), S(=O)$_2$, NH and N—$C_{1-6}$-alkyl, and which is unsubstituted or substituted with 1, 2, 3, 4 or 5 substituents independently from one another selected from the group consisting of F, Cl, $CF_3$, $OCF_3$, CN, $C_{1-6}$-alkyl, $C_{1-6}$-alkylen-OH and O—$C_{1-6}$-alkyl; or
  phenyl or heteroaryl, which comprises at least one nitrogen atom, in each case unsubstituted or substituted with 1, 2 or 3 substituents independently from one another selected from the group consisting of F, Cl, CN, $CF_3$, $OCF_3$, $C_{1-6}$-alkylen-OH, $C_{1-6}$-alkyl, OH, O—$C_{1-6}$-alkyl, S(=O)$_2$—$C_{1-6}$-alkyl, S(=O)$_2$—$NH_2$, $NH_2$, $NH(C_{1-6}$-alkyl), $N(C_{1-6}$-alkyl)$_2$, O—C(=O)—$NH_2$, C(=O)—$NH_2$, C(=O)—N(H)($C_{1-6}$-alkyl), C(=O)—N($C_{1-6}$-alkyl)$_2$, and C(=O)—O—$C_{1-6}$-alkyl;
  or a part structure of general formula SF-III

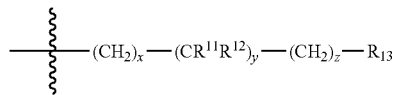

SF-III,
wherein
x represents 0, 1 or 2;
y represents 0, 1 or 2;
z represents 0, 1 or 2;
on the condition that the sum of x, y and z is 1, 2, 3, 4, 5 or 6;
$R^{11}$ and $R^{12}$ are independently from one another selected from H or $C_{1-6}$-alkyl; or
$R^{11}$ and $R^{12}$ together with the carbon atom connecting them form a $C_{3-6}$-cycloalkyl or a 3-7-membered heterocyclyl, which comprises 1 or 2 heteroatoms or heteroatom groups independently from one another selected from the group consisting of O, S, S(=O), S(=O)$_2$, NH and N—$C_{1-6}$-alkyl, wherein said $C_{3-6}$-cycloalkyl or 3-7-membered heterocyclyl may be unsubstituted or substituted with 1, 2, 3, 4 or 5 substituents independently from one another selected from the group consisting of F, Cl, $CF_3$, $OCF_3$, CN, $C_{1-6}$-alkyl and O—$C_{1-6}$-alkyl;

$R^{13}$ is selected from the group consisting of
H, F, Cl, CN, OH, O—$C_{1-6}$-alkyl, O—(C=O)$C_{1-6}$-alkyl, S(=O)—$C_{1-6}$-alkyl, S(=O)$_2$—$C_{1-6}$-alkyl, S(=O)$_2$—$NH_2$, S(=O)$_2$—N(H)$C_{1-6}$-alkyl, S(=O)$_2$—N($C_{1-6}$-alkyl)$_2$, $NH_2$, $NH(C_{1-6}$-alkyl), $N(C_{1-6}$-alkyl)$_2$, N(H)—C(=O)—$C_{1-6}$-alkyl, $N(C_{1-6}$-alkyl)-C(=O)—$C_{1-6}$-alkyl, N(H)—S(=O)—$C_{1-6}$-alkyl, $N(C_{1-6}$-alkyl)-S(=O)—$C_{1-6}$-alkyl, N(H)—S(=O)$_2$—$C_{1-6}$-alkyl, $N(C_{1-6}$-alkyl)-S(=O)$_2$—$C_{1-6}$-alkyl, C(=O)—$NH_2$, C(=O)—N(H)($C_{1-6}$-alkyl), C(=O)—N($C_{1-6}$-alkyl)$_2$, C(=O)—O—$C_{1-6}$-alkyl, N(H)—C(=O)—$NH_2$, N(H)—C(=O)—N(H)($C_{1-6}$-alkyl), N(H)—C(=O)—N($C_{1-6}$-alkyl)$_2$, N(H)—C(=O)—O—$C_{1-6}$-alkyl; O—C(=O)—$NH_2$, O—C(=O)—N(H)($C_{1-6}$-alkyl), and O—C(=O)—N($C_{1-6}$-alkyl)$_2$; or represents $C_{3-6}$-cycloalkyl, which is unsubstituted or substituted with 1, 2, 3, 4, or 5 substituents independently from one another selected from the group consisting of F, Cl, $CF_3$, =O, $OCF_3$, OH, O—$C_{1-6}$-alkyl, $C_{1-6}$-alkylen-OH and $C_{1-6}$-alkyl; or 3-7-membered heterocyclyl, which comprises 1 or 2 heteroatoms or heteroatom groups independently from one another selected from the group consisting of O, S, S(=O), S(=O)$_2$, NH and N—$C_{1-6}$-alkyl, and which is unsubstituted or substituted with 1, 2, 3, 4 or 5 substituents independently from one another selected from the group consisting of F, Cl, $CF_3$, $OCF_3$, CN, $C_{1-6}$-alkyl and O—$C_{1-6}$-alkyl; or phenyl or heteroaryl, which comprises at least one nitrogen atom, in each unsubstituted or substituted with 1, 2 or 3 substituents independently from one another selected from the group consisting of F, Cl, CN, $CF_3$, $OCF_3$, $C_{1-6}$-alkylen-OH, $C_{1-6}$-alkyl, OH, O—$C_{1-6}$-alkyl, S(=O)$_2$—$C_{1-6}$-alkyl, S(=O)$_2$—$NH_2$, $NH_2$, $NH(C_{1-6}$-alkyl), $N(C_{1-6}$-alkyl)$_2$, O—C(=O)—$NH_2$, C(=O)—$NH_2$, C(=O)—N(H)($C_{1-6}$-alkyl), C(=O)—N($C_{1-6}$-alkyl)$_2$, and C(=O)—O—$C_{1-6}$-alkyl;

or $R^4$ and $R^5$ together with the nitrogen atom connecting them form a heterocyclyl, selected from the group consisting of

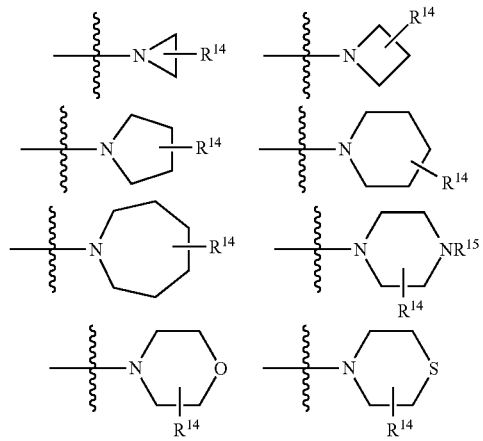

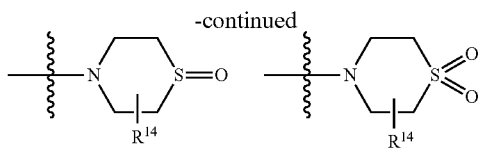

wherein
$R^{14}$ denotes 0, 1, 2, 3 or 4 substituents which are in each case independently of each other selected from the group consisting of F, Cl, $CF_3$, =O, $OCF_3$, OH, O—$C_{1-6}$-alkyl, $C_{1-6}$-alkylen-OH, $C_{1-6}$-alkylen-$SO_2$($C_{1-6}$-alkyl), $SO_2$($C_{1-6}$-alkyl), $C_{1-6}$-alkyl, aryl, heteroaryl, O-aryl and O-heteroaryl, wherein said aryl or said heteroaryl is unsubstituted or substituted with 1, 2, 3, 4 or 5 substituents independently from one another selected from the group consisting of F, Cl, CN, $CF_3$, $OCF_3$, $C_{1-6}$-alkylen-OH, $C_{1-6}$-alkyl, OH, O—$C_{1-6}$-alkyl, $NH_2$, $NH(C_{1-6}$-alkyl), $N(C_{1-6}$-alkyl$)_2$, N(H)—S(=O$)_2$—$C_{1-6}$-alkyl, C(=O)—$NH_2$ or C(=O)—N(H)($C_{1-6}$-alkyl), and C(=O)—N($C_{1-6}$-alkyl$)_2$;
or
$R^{14}$ denotes at least two substituents, wherein two substituents $R^{14}$ stand together for a $C_{1-6}$-alkylen-group, substituted or unsubstituted, wherein optionally one or more C-atoms of the $C_{1-6}$-alkylen-group is replaced by a heteroatom or heteroatom group, selected of O, N—$R^{15}$, S, S(O) and S(O$)_2$, and wherein these two substituents $R^{14}$ are positioned at different carbon atoms of the heterocyclyl, so the $C_{1-6}$-alkylen-group represents a bridge to form a bicyclic heterocyclyl;
or
$R^{14}$ denotes at least two substituents, wherein two substituents $R^{14}$ stand together for a $C_{2-6}$-alkylen-group, substituted or unsubstituted, wherein optionally one or more C-atoms of the $C_{2-6}$-alkylen-group is replaced by a heteroatom or heteroatom group, selected of O, N—$R^{15}$, S, S(O) and S(O$)_2$, and wherein these two substituents $R^{14}$ are positioned at the same carbon atom of the heterocyclyl, so the $C_{2-6}$-alkylen-group forms a spiro-heterocyclyl; and
$R^{15}$ represents H, $C_{1-6}$-alkyl or (C=O)$C_{1-6}$-alkyl.

10. The compound according to claim 1, wherein the compound of general formula (I) is a compound according to general formula (Ia),

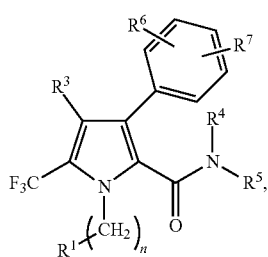

wherein
n is 0 or 1,
$R^1$ represents
pyrrolyl, pyrazolyl, imidazolyl, oxazolyl (1,3-oxazolyl), isoxazolyl (1,2-oxazolyl), thiazolyl (1,3-thiazolyl), isothiazolyl (1,2-thiazolyl), 1,2,4-triazolyl, 1,2,3-triazolyl, tetrazolyl, 1,2,3-oxadiazolyl, 1,2,4-oxadiazolyl, 1,3,4-oxadiazolyl, 1,2,5-oxadiazolyl, 1,2,3-thiadiazolyl, 1,2, 4-thiadiazolyl, 1,3,4-thiadiazolyl, 1,2,5-thiadiazolyl, pyridinyl, pyridin-2-on-1-yl, pyrazinyl, pyrimidinyl, pyridazinyl, 1,2,3-triazinyl, 1,3,5-triazinyl or 1,2,4-triazinyl, in each case unsubstituted or mono- or polysubstituted by one or more substituents selected from F; Cl; CN; $C_{1-6}$-alkyl; $CF_3$; C(=O)—$NH_2$; C(=O)—N(H)($C_{1-6}$-alkyl); C(=O)—N($C_{1-6}$-alkyl$)_2$; OH; O—$C_{1-6}$-alkyl; $NH_2$; N(H)($C_{1-6}$-alkyl); N($C_{1-6}$-alkyl$)_2$; N(H)—C(=O)—$C_{1-6}$-alkyl; S(=O)—$C_{1-6}$-alkyl; S(=O$)_2$—$C_{1-6}$-alkyl and cyclopropyl;

$R^3$ represents H or $CH_3$ or cyclopropyl;
$R^6$ and $R^7$ are independently absent or are each independently of one another selected from the group consisting of F; Cl; CN; $CH_3$; $CF_3$; OH; $OCF_3$ and $OCH_3$;
$R^4$ represents H or $C_{1-6}$-alkyl; and
$R^5$ represents
$C_{3-6}$-cycloalkyl, which is unsubstituted or substituted with 1, 2, 3, 4 or 5 substituents independently from one another selected from the group consisting of F, Cl, $CF_3$, =O, $OCF_3$, OH, O—$C_{1-6}$-alkyl, $C_{1-6}$-alkylen-OH, $C_{1-6}$-alkyl, C(=O)—$NH_2$, C(=O)—N(H)($C_{1-6}$-alkyl) and C(=O)—N($C_{1-6}$-alkyl$)_2$; or
5- or 6-membered heterocyclyl, which comprises 1 or 2 heteroatoms or heteroatom groups independently from one another selected from the group consisting of O, S, S(=O), S(=O$)_2$, NH and N—$C_{1-6}$-alkyl, and which is unsubstituted or substituted with 1, 2, 3, 4 or 5 substituents independently from one another selected from the group consisting of F, Cl, $CF_3$, $OCF_3$, CN, $C_{1-6}$-alkyl, $C_{1-6}$-alkylen-OH and O—$C_{1-6}$-alkyl;
or a part structure of general formula SF-III

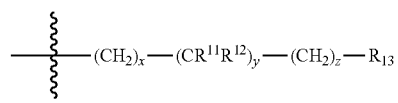

SF-III,
wherein
x represents 1 and y and z each represent 0 or
x and y each represent 1 and z represents 0 or
x and z each represent 1 and y represents 0 or
x, y and z each represent 1;
$R^{11}$ and $R^{12}$ are independently from one another selected from H and $CH_3$;
$R^{13}$ is selected from the group consisting of
H, F, Cl, CN, OH, O—$C_{1-6}$-alkyl, O—(C=O)$C_{1-6}$-alkyl, S(=O)—$C_{1-6}$-alkyl, S(=O$)_2$—$C_{1-6}$-alkyl, $NH_2$, NH($C_{1-6}$-alkyl), N($C_{1-6}$-alkyl$)_2$, N(H)—C(=O)—$C_{1-6}$-alkyl, N(H)—S(=O$)_2$—$C_{1-6}$-alkyl, C(=O)—$NH_2$, C(=O)—N(H)($C_{1-6}$-alkyl), C(=O)—N($C_{1-6}$-alkyl$)_2$, N(H)—C(=O)—$NH_2$, N(H)—C(=O)—N(H)($C_{1-6}$-alkyl), and N(H)—C(=O)—N($C_{1-6}$-alkyl$)_2$,
or represents
$C_{3-6}$-cycloalkyl or
3-7-membered heterocyclyl, which comprises 1 or 2 heteroatoms or heteroatom groups independently from one another selected from the group consisting of O, S, S(=O), S(=O$)_2$, NH and N—$C_{1-6}$-alkyl, and which is unsubstituted or substituted with 1, 2, 3, 4 or 5 substituents independently from one another selected from the group consisting of F, Cl, $CF_3$, $OCF_3$, CN, $C_{1-6}$-alkyl and O—$C_{1-6}$-alkyl; or phenyl or heteroaryl, selected from pyrrolyl, pyrazolyl, imidazolyl, oxazolyl, isoxazolyl, thiazolyl, isothiazolyl, pyridinyl, pyrazinyl, pyrimidinyl and pyridazinyl,
in each unsubstituted or substituted with 1, 2 or 3 substituents independently from one another selected from the group consisting of F, Cl, CN, $CF_3$, $OCF_3$, $C_{1-6}$-alkylen-OH, $C_{1-6}$-alkyl, OH, O—$C_{1-6}$-alkyl, $S(=O)_2$—$C_{1-6}$-alkyl, $S(=O)_2$—$NH_2$, $NH_2$, $NH(C_{1-6}$-alkyl), $N(C_{1-6}$-alkyl$)_2$, O—C(=O)—$NH_2$, C(=O)—$NH_2$, C(=O)—N(H)($C_{1-6}$-alkyl), C(=O)—N($C_{1-6}$-alkyl$)_2$, and C(=O)—O—$C_{1-6}$-alkyl;
or
$R^4$ and $R^5$ together with the nitrogen atom connecting them form a heterocyclyl, selected from the group consisting of

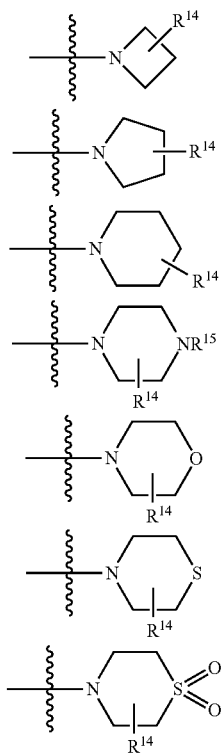

wherein
$R^{14}$ denotes 0, 1 or 2 substituents which are in each case independently of each other selected from the group consisting of F, Cl, $CF_3$, =O, $OCF_3$, OH, O—$C_{1-6}$-alkyl, $C_{1-6}$-alkylen-OH, $C_{1-6}$-alkylen-$SO_2$($C_{1-6}$-alkyl), $SO_2$($C_{1-6}$-alkyl) and $C_{1-6}$-alkyl;
and
$R^{15}$ represents H, $C_{1-6}$-alkyl or (C=O)$C_{1-6}$-alkyl.

11. The compound according to claim 1 selected from the group consisting of 001   3-(4-Chlorophenyl)-1-[(3-ethyl-isoxazol-5-yl)-methyl]-N,4-dimethyl-N-(2-methylsulfonyl-ethyl)-5-(trifluoromethyl)-1H-pyrrole-2-carboxylic acid amide
002   3-(4-Chlorophenyl)-N,4-dimethyl-1-[(1-methyl-1H-imidazol-2-yl)-methyl]-N-(2-methylsulfonyl-ethyl)-5-(trifluoromethyl)-1H-pyrrole-2-carboxylic acid amide
003   3-(4-Chlorophenyl)-N,4-dimethyl-1-[(3-methyl-3H-imidazol-4-yl)-methyl]-N-(2-methylsulfonyl-ethyl)-5-(trifluoromethyl)-1H-pyrrole-2-carboxylic acid amide
004   N-Cyclopropyl-3-(4-fluorophenyl)-N-methyl-1-[(3-methyl-[1,2,4]oxadiazol-5-yl)-methyl]-5-(trifluoromethyl)-1H-pyrrole-2-carboxylic acid amide
005   N-(2-Carbamoyl-2-methyl-propyl)-3-(4-fluorophenyl)-N-methyl-1-[(3-methyl-[1,2,4]oxadiazol-5-yl)-methyl]-5-(trifluoromethyl)-1H-pyrrole-2-carboxylic acid amide
006   4-[3-(4-Fluorophenyl)-1-[(3-methyl-[1,2,4]oxadiazol-5-yl)-methyl]-5-(trifluoromethyl)-1H-pyrrole-2-carbonyl]-piperazin-2-one
007   [3-(4-Fluorophenyl)-1-[(3-methyl-[1,2,4]oxadiazol-5-yl)-methyl]-5-(trifluoromethyl)-1H-pyrrol-2-yl]-morpholin-4-yl-methanone
008   3-(4-Chlorophenyl)-N-(2,2-dimethyl-propyl)-N-methyl-1-[(2-methyl-2H-pyrazol-3-yl)-methyl]-5-(trifluoromethyl)-1H-pyrrole-2-carboxylic acid amide
009   3-(4-Chlorophenyl)-N-(2,2-dimethyl-propyl)-N-methyl-1-[(1-methyl-1H-[1,2,3]triazol-4-yl)-methyl]-5-(trifluoromethyl)-1H-pyrrole-2-carboxylic acid amide
010   3-(4-Chlorophenyl)-N-(2,2-dimethyl-propyl)-N-methyl-5-(trifluoromethyl)-1-[[3-(trifluoromethyl)-[1,2,4]oxadiazol-5-yl]-methyl]-1H-pyrrole-2-carboxylic acid amide
011   3-(4-Chlorophenyl)-N-(2,2-dimethyl-propyl)-N-methyl-1-[(3-methyl-[1,2,4]oxadiazol-5-yl)-methyl]-5-(trifluoromethyl)-1H-pyrrole-2-carboxylic acid amide
012   3-(4-Chlorophenyl)-N-(2,2-dimethyl-propyl)-N-methyl-1-[(5-methyl-[1,2,4]oxadiazol-3-yl)-methyl]-5-(trifluoromethyl)-1H-pyrrole-2-carboxylic acid amide
013   3-(4-Chlorophenyl)-N-(2,2-dimethyl-propyl)-N-methyl-1-[(1-methyl-1H-[1,2,4]triazol-3-yl)-methyl]-5-(trifluoromethyl)-1H-pyrrole-2-carboxylic acid amide
014   3-(4-Chlorophenyl)-N-(2,2-dimethyl-propyl)-N-methyl-1-[(5-methyl-[1,3,4]oxadiazol-2-yl)-methyl]-5-(trifluoromethyl)-1H-pyrrole-2-carboxylic acid amide
015 3-(4-Chlorophenyl)-N,4-dimethyl-1-[(3-methyl-[1,2,4]oxadiazol-5-yl)-methyl]-N-(2-methylsulfonyl-ethyl)-5-(trifluoromethyl)-1H-pyrrole-2-carboxylic acid amide
016   [3-(4-Chlorophenyl)-4-methyl-1-[(2-methyl-2H-pyrazol-3-yl)-methyl]-5-(trifluoromethyl)-1H-pyrrol-2-yl]-morpholin-4-yl-methanone
017 [3-(4-Chlorophenyl)-4-methyl-1-[(1-methyl-1H-[1,2,3]triazol-4-yl)-methyl]-5-(trifluoromethyl)-1H-pyrrol-2-yl]-morpholin-4-yl-methanone
018   [3-(4-Chlorophenyl)-4-methyl-1-[(3-methyl-[1,2,4]oxadiazol-5-yl)-methyl]-5-(trifluoromethyl)-1H-pyrrol-2-yl]-morpholin-4-yl-methanone
019 [3-(4-Chlorophenyl)-4-methyl-1-[(1-methyl-1H-[1,2,4]triazol-3-yl)-methyl]-5-(trifluoromethyl)-1H-pyrrol-2-yl]-morpholin-4-yl-methanone
020 3-(4-Chlorophenyl)-N,4-dimethyl-N-(2-methylsulfonyl-ethyl)-1-(1H-tetrazol-5-yl-methyl)-5-(trifluoromethyl)-1H-pyrrole-2-carboxylic acid amide
021 [3-(4-Chlorophenyl)-4-methyl-1-[(1-methyl-1H-imidazol-2-yl)-methyl]-5-(trifluoromethyl)-1H-pyrrol-2-yl]-(1,1-dioxo-[1,4]thiazinan-4-yl)-methanone
022 [3-(4-Chlorophenyl)-4-methyl-1-[(1-methyl-1H-imidazol-4-yl)-methyl]-5-(trifluoromethyl)-1H-pyrrol-2-yl]-(1,1-dioxo-[1,4]thiazinan-4-yl)-methanone
023   [3-(4-Chlorophenyl)-4-methyl-1-[(1-methyl-1H-pyrazol-4-yl)-methyl]-5-(trifluoromethyl)-1H-pyrrol-2-yl]-morpholin-4-yl-methanone 024 [3-(4-Chlorophenyl)-4-methyl-1-([1,3,4]thiadiazol-2-yl-methyl)-5-(trifluoromethyl)-1H-pyrrol-2-yl]-morpholin-4-yl-methanone
025 3-(4-Chlorophenyl)-N-(2,2-dimethyl-propyl)-N-methyl-1-[(1-methyl-1H-imidazol-2-yl)-methyl]-5-(trifluoromethyl)-1H-pyrrole-2-carboxylic acid amide
026 3-(4-Chlorophenyl)-N-(2,2-dimethyl-propyl)-N-methyl-1-[(3-methyl-3H-imidazol-4-yl)-methyl]-5-(trifluoromethyl)-1H-pyrrole-2-carboxylic acid amide
027 3-(4-Chlorophenyl)-N-(2,2-dimethyl-propyl)-N-methyl-1-[(4-methyl-4H-[1,2,4]triazol-3-yl)-methyl]-5-(trifluoromethyl)-1H-pyrrole-2-carboxylic acid amide
028 [3-(4-Chlorophenyl)-1-[(5-chloro-pyridin-3-yl)-methyl]-4-methyl-5-(trifluoromethyl)-1H-pyrrol-2-yl]-morpholin-4-yl-methanone
029 3-(4-Chlorophenyl)-N-(2,2-dimethyl-propyl)-1-[(5-fluoro-pyridin-2-yl)-methyl]-N-methyl-5-(trifluoromethyl)-1H-pyrrole-2-carboxylic acid amide
030 3-(4-Chlorophenyl)-N-(2,2-dimethyl-propyl)-N-methyl-1-[(5-methyl-pyrazin-2-yl)-methyl]-5-(trifluoromethyl)-1H-pyrrole-2-carboxylic acid amide
031 (2,2-Dimethyl-morpholin-4-yl)-[3-(4-fluorophenyl)-1-(pyrimidin-2-yl-methyl)-5-(trifluoromethyl)-1H-pyrrol-2-yl]-methanone
032 N-Cyclopropyl-3-(4-fluorophenyl)-1-(pyrimidin-2-yl-methyl)-5-(trifluoromethyl)-1H-pyrrole-2-carboxylic acid amide
033 3-(4-Chlorophenyl)-N-(2,2-dimethyl-propyl)-N-methyl-5-(trifluoromethyl)-1-[[2-(trifluoromethyl)-pyrimidin-4-yl]-methyl]-1H-pyrrole-2-carboxylic acid amide
034 3-(4-Chlorophenyl)-N-(2,2-dimethyl-propyl)-N-methyl-1-[(2-methyl-pyrimidin-5-yl)-methyl]-5-(trifluoromethyl)-1H-pyrrole-2-carboxylic acid amide
035 3-(4-Chlorophenyl)-N-(2,2-dimethyl-propyl)-N-methyl-1-[(5-methyl-pyrimidin-2-yl)-methyl]-5-(trifluoromethyl)-1H-pyrrole-2-carboxylic acid amide
036 3-(4-Chlorophenyl)-N-(2,2-dimethyl-propyl)-N-methyl-1-[(4-methyl-pyrimidin-2-yl)-methyl]-5-(trifluoromethyl)-1H-pyrrole-2-carboxylic acid amide
037 3-(4-Chlorophenyl)-N-(2,2-dimethyl-propyl)-N-methyl-1-(pyrimidin-2-yl-methyl)-5-(trifluoromethyl)-1H-pyrrole-2-carboxylic acid amide
038 3-(4-Chlorophenyl)-1-[(5-fluoro-pyridin-2-yl)-methyl]-N,4-dimethyl-N-(2-methylsulfonyl-ethyl)-5-(trifluoromethyl)-1H-pyrrole-2-carboxylic acid amide
039 3-(4-Chlorophenyl)-N,4-dimethyl-N-(2-methylsulfonyl-ethyl)-1-(pyrimidin-2-yl-methyl)-5-(trifluoromethyl)-1H-pyrrole-2-carboxylic acid amide
040 [3-(4-Chlorophenyl)-4-methyl-1-(pyrimidin-2-yl-methyl)-5-(trifluoromethyl)-1H-pyrrol-2-yl]-(2,2-dimethyl-morpholin-4-yl)-methanone
041 [3-(4-Chlorophenyl)-1-[(6-methoxy-pyridin-2-yl)-methyl]-4-methyl-5-(trifluoromethyl)-1H-pyrrol-2-yl]-morpholin-4-yl-methanone
042 [3-(4-Chlorophenyl)-4-methyl-1-[(5-methyl-pyrazin-2-yl)-methyl]-5-(trifluoromethyl)-1H-pyrrol-2-yl]-morpholin-4-yl-methanone
043 [3-(4-Chlorophenyl)-4-methyl-1-[(2-methyl-pyrimidin-5-yl)-methyl]-5-(trifluoromethyl)-1H-pyrrol-2-yl]-morpholin-4-yl-methanone
044 [3-(4-Chlorophenyl)-1-[(5-fluoro-pyridin-2-yl)-methyl]-4-methyl-5-(trifluoromethyl)-1H-pyrrol-2-yl]-morpholin-4-yl-methanone
045 [3-(4-Chlorophenyl)-4-methyl-1-[(5-methyl-pyrimidin-2-yl)-methyl]-5-(trifluoromethyl)-1H-pyrrol-2-yl]-morpholin-4-yl-methanone
046 [3-(4-Chlorophenyl)-4-methyl-1-[(4-methyl-pyrimidin-2-yl)-methyl]-5-(trifluoromethyl)-1H-pyrrol-2-yl]-morpholin-4-yl-methanone
047 [3-(4-Chlorophenyl)-4-methyl-1-(pyrimidin-2-yl-methyl)-5-(trifluoromethyl)-1H-pyrrol-2-yl]-morpholin-4-yl-methanone
048 3-(4-Chlorophenyl)-N-cyclopropyl-4-methyl-1-(pyrimidin-2-yl-methyl)-5-(trifluoromethyl)-1H-pyrrole-2-carboxylic acid amide
049 3-(4-Chlorophenyl)-N-(2,2-dimethyl-propyl)-N,4-dimethyl-1-pyrazin-2-yl-5-(trifluoromethyl)-1H-pyrrole-2-carboxylic acid amide
050 [3-(4-Chlorophenyl)-4-methyl-1-pyrazin-2-yl-5-(trifluoromethyl)-1H-pyrrol-2-yl]-(3,3-difluoro-azetidin-1-yl)-methanone
051 [3-(4-Chlorophenyl)-4-methyl-1-pyrazin-2-yl-5-(trifluoromethyl)-1H-pyrrol-2-yl]-(3-hydroxy-3-methyl-azetidin-1-yl)-methanone
052 [3-(4-Chlorophenyl)-4-methyl-1-(pyrimidin-5-yl-methyl)-5-(trifluoromethyl)-1H-pyrrol-2-yl]-morpholin-4-yl-methanone
053 3-[[3-(4-Chlorophenyl)-4-methyl-2-(morpholine-4-carbonyl)-5-(trifluoromethyl)-1H-pyrrol-1-yl]-methyl]-1H-pyridin-2-one
054 6-[[3-(4-Chlorophenyl)-4-methyl-2-(morpholine-4-carbonyl)-5-(trifluoromethyl)-1H-pyrrol-1-yl]-methyl]-1H-pyridin-2-one
055 1-[2-[3-(4-Chlorophenyl)-4-methyl-2-(morpholine-4-carbonyl)-5-(trifluoromethyl)-1H-pyrrol-1-yl]-ethyl]-1H-pyridin-2-one
056 1-[[3-(4-Chlorophenyl)-4-methyl-2-(morpholine-4-carbonyl)-5-(trifluoromethyl)-1H-pyrrol-1-yl]-methyl]-1H-pyridin-2-one
060 [3-(4-Chlorophenyl)-4-methyl-1-(1H-[1,2,4]triazol-3-yl-methyl)-5-(trifluoromethyl)-1H-pyrrol-2-yl]-morpholin-4-yl-methanone
061 3-(4-Chlorophenyl)-N-isopropyl-N,4-dimethyl-1-(pyrimidin-2-yl-methyl)-5-(trifluoromethyl)-1H-pyrrole-2-carboxylic acid amide
062 [3-(4-Chloro-2-fluoro-phenyl)-4-methyl-1-(pyrimidin-2-yl-methyl)-5-(trifluoromethyl)-1H-pyrrol-2-yl]-morpholin-4-yl-methanone
063 3-(4-Chloro-2-fluoro-phenyl)-N-cyclopropyl-N,4-dimethyl-1-(pyrimidin-2-yl-methyl)-5-(trifluoromethyl)-1H-pyrrole-2-carboxylic acid amide
064 3-(4-Chloro-2-fluoro-phenyl)-N-isopropyl-N,4-dimethyl-1-(pyrimidin-2-yl-methyl)-5-(trifluoromethyl)-1H-pyrrole-2-carboxylic acid amide
065 3-(4-Fluorophenyl)-N-isopropyl-N-methyl-1-[(3-methyl-[1,2,4]oxadiazol-5-yl)-methyl]-5-(trifluoromethyl)-1H-pyrrole-2-carboxylic acid amide
066 3-(4-Chloro-2-fluoro-phenyl)-N,4-dimethyl-N-[(5-methyl-isoxazol-3-yl)-methyl]-1-(pyrimidin-2-yl-methyl)-5-(trifluoromethyl)-1H-pyrrole-2-carboxylic acid amide
067 3-(4-Chlorophenyl)-N-isopropyl-N,4-dimethyl-1-[(3-methyl-isoxazol-5-yl)-methyl]-5-(trifluoromethyl)-1H-pyrrole-2-carboxylic acid amide
068 3-(4-Chlorophenyl)-N-isopropyl-N,4-dimethyl-1-[(5-methyl-isoxazol-3-yl)-methyl]-5-(trifluoromethyl)-1H-pyrrole-2-carboxylic acid amide and
069 3-(4-Chlorophenyl)-N-isopropyl-N,4-dimethyl-1-([1,3,4]thiadiazol-2-yl-methyl)-5-(trifluoromethyl)-1H-pyrrole-2-carboxylic acid amide optionally in the form of a single stereoisomer or a mixture of stereoisomers, in the form of the free compound and/or a physiologically acceptable salt or solvate thereof.

12. A pharmaceutical composition comprising at least one compound according to claim 1.

* * * * *